(12) United States Patent
Abramovitch et al.

(10) Patent No.: US 11,717,508 B2
(45) Date of Patent: Aug. 8, 2023

(54) COMPOUNDS, COMPOSITIONS, AND METHODS FOR INHIBITING BACTERIAL GROWTH

(71) Applicant: Board of Trustees of Michigan State University, East Lansing, MI (US)

(72) Inventors: Robert Abramovitch, East Lansing, MI (US); Huiqing Zheng, Lansing, MI (US); Christopher J. Colvin, East Lansing, MI (US); Benjamin K. Johnson, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 375 days.

(21) Appl. No.: 16/339,896

(22) PCT Filed: Oct. 5, 2017

(86) PCT No.: PCT/US2017/055244
§ 371 (c)(1),
(2) Date: Apr. 5, 2019

(87) PCT Pub. No.: WO2018/067769
PCT Pub. Date: Apr. 12, 2018

(65) Prior Publication Data
US 2020/0046678 A1    Feb. 13, 2020

Related U.S. Application Data

(60) Provisional application No. 62/404,492, filed on Oct. 5, 2016.

(51) Int. Cl.
| | |
|---|---|
| A61K 31/357 | (2006.01) |
| A61K 31/167 | (2006.01) |
| A61K 31/381 | (2006.01) |
| A61K 31/4184 | (2006.01) |
| A61K 31/42 | (2006.01) |
| A61K 31/473 | (2006.01) |
| A61K 31/496 | (2006.01) |
| A61K 31/133 | (2006.01) |
| A61K 31/4409 | (2006.01) |
| A61K 31/4965 | (2006.01) |

(52) U.S. Cl.
CPC .......... *A61K 31/357* (2013.01); *A61K 31/167* (2013.01); *A61K 31/381* (2013.01); *A61K 31/4184* (2013.01); *A61K 31/42* (2013.01); *A61K 31/473* (2013.01); *A61K 31/496* (2013.01); *A61K 31/133* (2013.01); *A61K 31/4409* (2013.01); *A61K 31/4965* (2013.01)

(58) Field of Classification Search
CPC .. A61K 31/357; A61K 31/167; A61K 31/366; A61K 31/381; A61K 31/415; A61K 31/4184; A61K 31/42; A61K 31/4409; A61K 31/473; A61K 31/496; A61K 45/06; A61K 31/133; A61K 31/4965
See application file for complete search history.

(56) References Cited

U.S. PATENT DOCUMENTS

2014/0163078 A1    6/2014  Steyn et al.
2016/0194299 A1    7/2016  Chatterjee et al.

FOREIGN PATENT DOCUMENTS

CN          102526493 A   *  3/2021
WO     WO 2015/115865     *  6/2015

OTHER PUBLICATIONS

CN102526493A (Year: 2012).*
WO 2015/115865—English translation, publication date: Jun. 8, 2015 (Year: 2015).*
Converse et al., "Role of the dosR-dosS two-component regulatory system in *Mycobacterium tuberculosis* virulence in three animal models," Infect Immun, 77(3):1230-1237 (2009).
International Search Report and Written Opinion for International Application No. PCT/PCT/US2017/55244 dated Jan. 9, 2018.
Miller et al., "Design, synthesis, and study of a mycobactin—artemisinin conjugate that has selective and potent activity against tuberculosis and malaria," J Am Chem Soc, 133(7):2076-2079 (2011).

* cited by examiner

*Primary Examiner* — Umamaheswari Ramachandran
(74) *Attorney, Agent, or Firm* — Foley Hoag LLP

(57) ABSTRACT

The present disclosure provides, among other things, compounds, compositions, and methods useful in inhibiting bacteria, such as *Mycobacterium tuberculosis*. These compositions and methods find many uses in medicine and research, e.g., treating subjects afflicted with active or latent bacterial infections.

8 Claims, 28 Drawing Sheets

B

**HC101A
(Artemisinin)**

| Name | Structure | GFP FI (EC50, µM) | Eukaryotic cytotoxicity (EC50, µM) BMDM | THP-1 | J774 |
|---|---|---|---|---|---|
| HC101A (Artemisinin) | 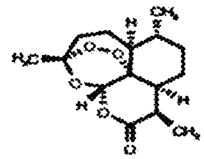 | 1.2 | >400 | >400 | >400 |
| HC101B (Artesunate) | 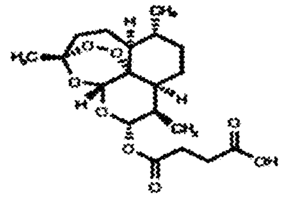 | 1.9 | 160.0 | 33.9 | 0.7 |
| HC101C (Dihydroartemisinin) | 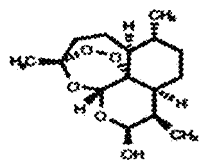 | 3.7 | 100 | 18.8 | 0.4 |
| HC102A | 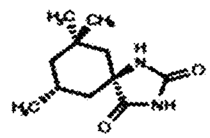 | 12.4 | >400 | >400 | >400 |
| HC103A | 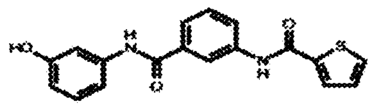 | 3.7 | >160 | 112 | 152 |
| HC103B | 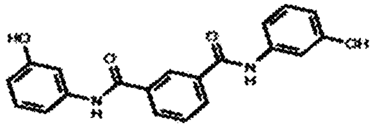 | 5.0 | 179.8 | 91.1 | 204.6 |
| HC104A | 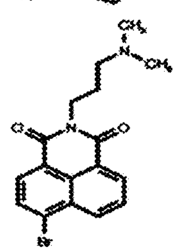 | 2.8 | 72.7 | 16.3 | 84.8 |
| HC105A | 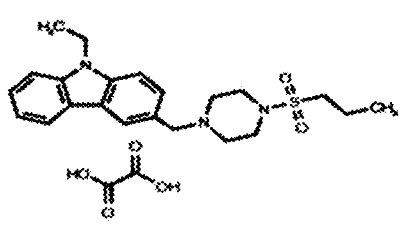 | 12.7 | 235.8 | 90.5 | 57.2 |
| HC106A | 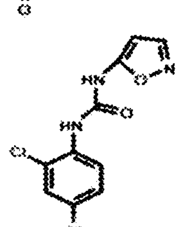 | 6.9 | 88 | 88 | 90 |

COMPOUNDS, COMPOSITIONS, AND METHODS FOR INHIBITING BACTERIAL GROWTH

CROSS REFERENCE TO RELATED APPLICATIONS

This application is a § 371 national-stage application based on PCT/US17/55244, filed Oct. 5, 2017 which claims priority to U.S. Provisional Application No. 62/404,492, filed Oct. 5, 2016, the contents of each of which are incorporated herein by reference in their entirety.

STATEMENT OF GOVERNMENT SUPPORT

This invention was made with government support under AI105867 awarded by the National Institutes of Health. The government has certain rights in the invention.

BACKGROUND

*Mycobacterium tuberculosis* (Mtb) causes tuberculosis (TB) and is responsible for nearly two million deaths annually. In addition, a substantial proportion of the millions of people living with HIV/AIDS worldwide are co-infected with Mtb. Multi-drug resistant (MDR) tuberculosis as well as extensively drug-resistant (XDR) tuberculosis have evolved, which further restricts treatment options for patients and threatens TB control and prevention efforts. Mtb can persist in the host for decades without causing disease symptoms (Gengenbacher, M. et al. *FEMS Microbiol Rev* 36, 514-32 (2012)). Mtb non-replicating persistence (NRP) is characterized by a gradual slowing of metabolic activity upon encountering pressures from the host immune system, including hypoxia, acidic pH or starvation (Boshoff, H. I. et al. *Nat Rev Microbiol* 3, 70-80 (2005); Wayne, L. G. et al. *Annu Rev Microbiol* 55, 139-63 (2001); Baker, J. J. et al. *Mol Microbiol* 94, 56-69 (2014); Betts, J. C. et al. *Mol Microbiol* 43, 717-31 (2002)). Thus, a fundamental challenge of current TB therapy is the long course of treatment. New drugs that shorten the course of therapy could revolutionize TB control.

SUMMARY

The disclosure is based, at least in part, on the discovery and characterization of new chemical compounds (e.g., anti-virulence compounds or inhibitors) that inhibit a two-component regulatory system (e.g., DosRST two-component regulatory system) signaling and persistence. Said compounds reduce expression of DosRST regulon genes, inhibit Mtb persistence-associated physiologies, and directly inhibit the DosS/T sensor kinases. These observations indicate, among other things, that such inhibitors are useful for treating infections by bacteria in which the two-component regulatory system (e.g., DosRST) is conserved.

One of skill in the art would appreciate that there are several benefits to the use of the instantly-disclosed inhibitors and methods. For example, current treatment schedules for tuberculosis infection involve a regimen of at least four compounds (isoniazid, rifampicin, ethambutol, and pyrazinamide) coadministered over a prolonged period (e.g., 6-9 months). The instantly disclosed compounds and compositions, when used alone or in combination with one or more additional agents (e.g., isoniazid, rifampicin, ethambutol, and pyrazinamide), are believed to effectively treat an infection in a shorter period of time, e.g., less than 8 weeks (e.g., less than 7 weeks, 6 weeks, 5 weeks, 4 weeks, 3 weeks, or 2 weeks) or between 2 to 4 weeks. Thus, the instantly disclosed compounds and compositions offer the opportunity for increased patient compliance. The compounds and compositions are also useful for treating immunocompromised subjects (e.g., subjects afflicted with an HIV infection) and/or subjects with latent bacterial infections. Moreover, the compositions and methods described herein are useful for treating drug-resistant bacterial infections, such as infections with MDR and/or XDR tuberculosis.

One aspect of the invention relates to a method for inhibiting growth of one or more bacterial cells in which an at least two-component regulatory system is conserved, said two-component regulatory system comprises one or more sensor histidine kinase and a cognate response regulator, the method comprising contacting the one or more bacterial cells with an effective amount of a compound that inhibits the at least two component regulatory system to thereby inhibit the growth of the one or more bacterial cells. In some embodiments, the compound that inhibits is selected from any of the compounds set forth in Section II infra.

Another aspect of the invention relates to a method for preventing or reducing the likelihood of a productive bacterial infection in a subject, the method comprising administering to a subject an effective amount of a compound that inhibits an at least two-component regulatory system, said two-component regulatory system comprises one or more sensor histidine kinase and a cognate response regulator, to thereby prevent or reduce the likelihood of a productive bacterial infection in the subject, wherein the subject has been identified as being at risk of developing an infection with bacterial cells in which the at least two-component regulatory system is conserved. In some embodiments, the compound that inhibits is selected from any of the compounds set forth in Section II infra.

Yet another aspect of the invention relates to a method for treating a subject who is infected with bacterial cells in which an at least two-component regulatory system is conserved, said two-component regulatory system comprises one or more sensor histidine kinase and a cognate response regulator, the method comprising administering to the subject an effective amount of a compound that inhibits the at least two-component regulatory system to thereby treat the infection. In some embodiments, the compound that inhibits is selected from any of the compounds set forth in Section II infra.

Still another aspect of the invention relates to a method for ameliorating the signs or symptoms of an infection of a subject by bacterial cells in which the at least two-component regulatory system is conserved, said two-component regulatory system comprises one or more sensor histidine kinase and a cognate response regulator, the method comprising administering to the subject an effective amount of a compound that inhibits the at least two-component regulatory system to thereby ameliorate the signs and symptoms of the infection. In some embodiments, the compound that inhibits is selected from any of the compounds set forth in Section II infra.

In some embodiments, the at least two-component regulatory system comprises a member of an oxygen sensing pathway. In some embodiments, the at least two-component regulatory system comprises a heme-based oxygen sensor. In some embodiments, the heme-based oxygen sensor is selected from the group consisting of *Rhizobium* FixL protein, *E. coli* Dos, *Acetobacter* AxPDEA1, *Halobacterium* HemAT, and *Azetobacter* AvReg. In some embodiments, the at least two-component regulatory system comprises a heme-based redox sensor. In some embodiments, the heme-based redox sensor is selected from the group consisting of *Vibrio* VF_A0071, *Clostridium* SONO, and *Rhodospirillum* CooA. In some embodiments, the heme-based histidine sensor kinase is selected from DosS or DosT, both. In some embodiments, the at least two-component regulatory system comprises DosS and DosT. In some embodiments, the cognate response regulator is DosR. In some embodiments, the at least two-component regulatory system is a DosRST two-component regulatory system. In some embodiments, the at least two-component regulatory system comprises a two-component regulatory system regulon. In some embodiments, the at least two-component regulatory system regulon is a DosRST regulon. In some embodiments, the DosRST regulon comprise a network of at least 50 genes.

In some embodiments, the methods further comprise identifying the subject as having an infection with bacterial cells in which the two component regulatory system is conserved. In some embodiments, the bacteria or bacterial cells are *Mycobacterium*. In some embodiments, the *Mycobacterium* are *Mycobacterium tuberculosis*. In some embodiments, the *Mycobacterium tuberculosis* is multi-drug resistant *Mycobacterium tuberculosis*. In some embodiments, the *Mycobacterium tuberculosis* is extensively drug resistant *Mycobacterium tuberculosis*. In some embodiments, the bacteria or bacterial cells are *Clostridium* or *Bacillus*. In some embodiments, the bacteria or bacterial cells are *C. acetobutylicum* or *B. subtilis*. In some embodiments, the bacteria or bacterial cells are *Escherichia coli, Vibrio cholera*, or *Streptomyces coelicolor*. In some embodiments, the bacteria or bacterial cells are Enterobacteriaceae. In some embodiments, the bacteria or bacterial cells are nontuberculosis mycobacterium (NTM). In some embodiments, the NTM are *M. avium, M. intracellulare, M. kansasii, M. abscessus, M. chelonae, M. fortuitum, M. terrae, M. xenopi*, or *M. simiae*. In some embodiments, the NTM are *M. leprae, M. ulcerans*, or *M. marinum*. In some embodiments, the compound that inhibits the at least two-component regulatory system is an anti-virulence compound or analogs or derivatives thereof. In some embodiments, the anti-virulence compound is selected from the group consisting of HC101A (artemisinin), HC101B, HC101C, HC102A, HC103A, HC103B, HC104A, HC105A, and HC106A, or combinations thereof.

In some embodiments, the compound is any of the compounds set forth in Section II infra. In some embodiments, the compound is orally administered to the subject. In some embodiments, the compound is parenterally administered to the subject. In some embodiments, the compound is administered intravenously. In some embodiments, the compound is administered as an aerosol. In some embodiments, the compound is administered using a nebulizer or inhaler. In some embodiments, the compound is topically administered. In some embodiments, the compound is administered as an eye drop. In some embodiments, the compound is administered as a cream, an ointment, or a lotion. In some embodiments, the compound is present on a bandage or dressing applied to an infected site. In some embodiments, the subject has a lung infection. In some embodiments, the subject has a skin infection. In some embodiments, the subject has an infection of the eye.

One aspect of the invention relates to a method for treating tuberculosis in a subject, the method comprising administering to the subject a compound that inhibits a DosRST two-component regulatory system and/or DosRST regulon in an amount effective to treat tuberculosis. In some embodiments, the compound is an anti-virulence compound or analog or derivative thereof. In some embodiments, the anti-virulence compound is an anti-malarial compound or analog or derivative thereof. In some embodiments, the compound is selected from the group consisting of HC101A (artemisinin), HC101B, HC101C, HC102A, HC103A, HC103B, HC104A, HC105A, and HC106A, or combinations thereof. In some embodiments, the tuberculosis is multidrug-resistant tuberculosis. In some embodiments, the tuberculosis is extensively multidrug-resistant tuberculosis. In some embodiments, the subject is a human.

Another aspect of the invention relates to a method for eliminating dormant *Mycobacterium tuberculosis* cells in a subject afflicted with latent tuberculosis, the method comprising administering to the subject an effective amount of compound that inhibits a DosRST two-component regulatory system and/or DosRST regulon to thereby eliminate dormant *Mycobacterium tuberculosis* cells in the subject and treat latent tuberculosis. In some embodiments, the method further comprises determining that the subject has latent tuberculosis. In some embodiments, the *Mycobacterium tuberculosis* is multi-drug resistant *Mycobacterium tuberculosis*. In some embodiments, the *Mycobacterium tuberculosis* is extensively drug resistant *Mycobacterium tuberculosis*. In some embodiments, the compound that inhibits the at least two-component regulatory system is an anti-virulence compound or analogs or derivatives thereof. In some embodiments, the anti-virulence compound is an anti-malarial compound or analogs or derivatives thereof. In some embodiments, the compound is selected from the group consisting of HC101A (artemisinin), HC101B, HC101C, HC102A, HC103A, HC103B, HC104A, HC105A, and HC106A, or combinations thereof. In some embodiments, the compound is an analog or derivative of HC101A (artemisinin), HC101B, HC101C, HC102A, HC103A, HC103B, HC104A, HC105A, or HC106A. In some embodiments, the effective amount of the compound is between 0.01 and 100 mg/kg body weight of the subject. In some embodiments, the compound is administered in combination with one or more antibiotics. In some embodiments, the compound is administered in combination with one or more of isoniazid, rifampicin, ethambutol, and pyrazinamide. In some embodiments, the compound is administered for less than 6 weeks. In some embodiments, the compound is administered for between 2 to 4 weeks.

Another aspect of the invention relates to a pharmaceutical composition for use in topical treatment of an infection with bacterial cells in which a DosRST two-component regulatory system or DosRST regulon is conserved, wherein the pharmaceutical composition comprises the compounds according to any of the compounds set forth in Section II infra. In some embodiments, the compound is formulated as an eye drop. In some embodiments, the compound is formulated as an ointment, a lotion, a cream, or a gel. In some embodiments, the compound is selected from the group consisting of HC101A (artemisinin), HC101B, HC101C, HC102A, HC103A, HC103B, HC104A, HC105A, and HC106A, or combinations thereof. In some embodiments, the compound is an analog or derivative of HC101A (artemisinin), HC101B, HC101C, HC102A, HC103A, HC103B, HC104A, HC105A, or HC106A.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating bacterial infections, will be apparent from the following description, the examples, the drawings, and from the claims.

BRIEF DESCRIPTION OF THE DRAWINGS

FIG. 14 depicts GFP fluorescence inhibition and eukaryotic cytotoxicity by DosR regulon inhibitors. FIG. 14 includes $EC_{50}$ calculation of GFP fluorescence inhibition and eukaryotic cytotoxicity by DosR regulon inhibitors. For reporter fluorescence $EC_{50}$ determination, CDC1551(hspX': GFP) reporter was treated with compounds over an 8 point dose response curve ranging from 400 µM to 0.65 M. Following 6 days of treatment, GFP florescence and optical density were measured. In all cases, no inhibition of growth was observed at the reported $EC_{50}$ for inhibition of GFP fluorescence. For eukaryotic cytotoxicity, macrophage cells including bone marrow derived macrophage (BMDM), THP-1 and J774, were tested with serial dilutions of DosR regulon inhibitors over an 8 point dose response curve ranging from 400 µM to 0.65 M. Macrophages were incubated for 3 days and viability was determined using CellTiter-Glo (Promega) luminescent cell viability assay.

Figure 1A:
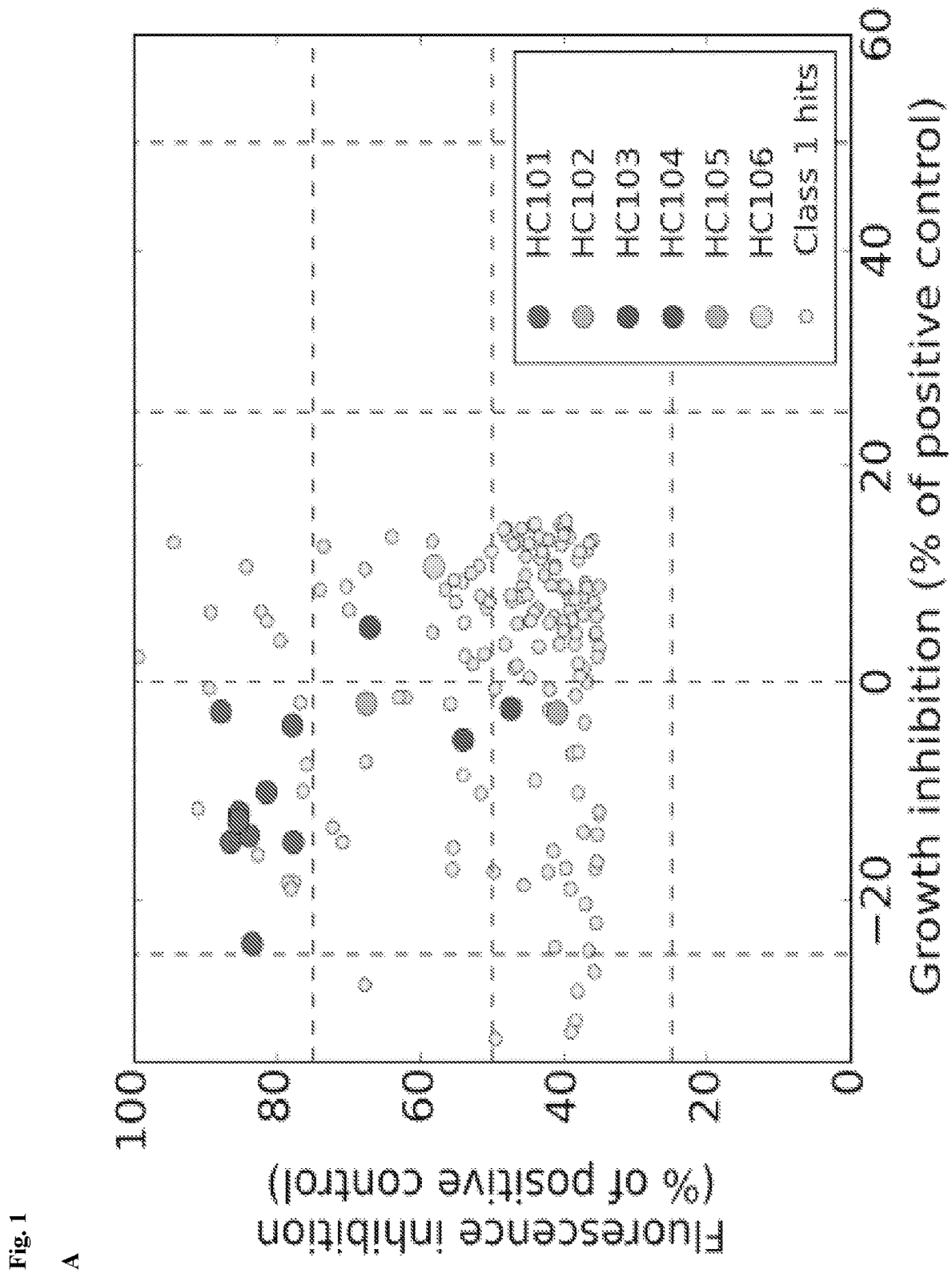
FIG. 1 includes three panels, A-C, and depicts identification of inhibitors of the DosRST pathway. Panel A shows scatter plot of primary screening data showing compounds that inhibit CDC1551 (hspX':GFP) reporter GFP fluorescence with limited impact on Mtb growth. Six distinct classes of compounds (HC101-HC106) are highlighted. Panel B shows structures of compounds confirmed to selectively inhibit CDC1551(hspX':GFP) reporter fluorescence. Panel D shows dose response curves for artemisinin (Art, HC101A), HC102A and HC103A inhibition of GFP fluorescence. Dose response curves for other characterized molecules are presented in FIG. 7.

Note that for every figure containing a histogram, the bars from left to right for each discreet measurement correspond to the figure boxes from top to bottom in the figure legend as indicated.

DETAILED DESCRIPTION

The present disclosure provides, among other things, compounds, compositions, and methods useful for inhibiting bacteria, such as *Mycobacterium tuberculosis*. These compositions and methods find many uses in medicine and research, e.g., treating subjects afflicted with active or latent bacterial infections. While in no way intended to be limiting, exemplary compositions and methods are elaborated on below.

I. Two-Component Regulatory Systems

As used herein, a two-component regulatory system refers to any two-component system that may be involved in oxygen and redox sensing pathways. Such two-component regulatory systems are conserved in many types of bacteria, such as *Escherichia coli* and *M. tuberculosis*. Such bacteria or bacterial cells are also amenable to treatment with the inhibitors, and analogs or derivatives thereof, described herein. In some embodiments, the two-component regulatory system comprises a heme-based oxygen sensor or kinases (e.g., DosS, DosT, or both). Heme-based oxygen sensors are conserved across all kingdoms of life and fall within six distinct classes of sensors (Fahrana A et al. *Antioxid Redox Signal.* 17(9): 1232-1245 (2012)). Related bacterial heme-based sensors include: *Rhizobium* FixL protein, *E. coli* Dos, *Acetobacter* AxPDEA1, *Halobacterium* HemAT, and *Azetobacter* AvReg. Heme-based redox sensors include: *Vibrio* VF_A0071, *Clostridium* SONO and *Rhodospirillum* CooA. In some embodiments, the two-component regulatory system comprises the DosRST two-component regulatory system or DosRST regulon. Many bacteria have evolved conserved domains in the histidine kinase and response regulator proteins (Capra, E J et al. *Annu Rev Microbiol.* 66:325-47 (2012)) and it is possible that inhibitors targeting DosRST may also target domains conserved in other bacterial two-component regulator proteins.

The DosRST two-component regulatory system plays an important role in Mtb NRP physiology (Boon, C. et al. *J Bacteriol* 184, 6760-7 (2002)) and may promote the survival of Mtb during NRP. It is composed of two heme-based histidine sensor kinases, DosS and DosT, and the response regulator DosR, and strongly regulates the expression of approximately 50 genes known as the DosRST regulon (Roberts, D. M. et al. *J Biol Chem* 279, 23082-7 (2004); Park, H. D. et al. *Mol Microbiol* 48, 833-43 (2003); Voskuil, M. I. et al. *J Exp Med* 198, 705-13 (2003); Galagan, J. E. et al. *Nature* 499, 178-83 (2013)). Mtb can sense host stimuli, including nitric oxide (NO), carbon monoxide (CO) and oxygen ($O_2$), through DosS and DosT (Ioanoviciu, A. et al. *Biochemistry* 48, 5839-48 (2009)), with DosS acting as an oxygen and redox sensor and DosT acting as an oxygen sensor (Roberts, D. M. et al. *J Biol Chem* 279, 23082-7 (2004); Voskuil, M. I. et al. *J Exp Med* 198, 705-13 (2003); Ioanoviciu, A. et al. *Biochemistry* 48, 5839-48 (2009); Vos, M. H. et al. *Biochemistry* 51, 159-66 (2012); Kumar, A. et al. *Proc Natl Acad Sci USA* 104, 11568-73 (2007); Ohno, H. et al. *Cell Microbiol* 5, 637-48 (2003)). During hypoxia-driven NRP, DosT is associated with initiating expression of the DosR regulon in response to hypoxia and DosS promotes sustained expression of the DosR regulon (Honaker, R. W. et al. *Infect Immun* 77, 3258-63 (2009)).

dosR mutants have reduced survival during hypoxia in vitro (Leistikow, R. L. et al. *J Bacteriol* 192, 1662-70 (2010)) and reduced virulence in rabbits, guinea pigs, non-human primates, and C3HeB/FeJ mice (Converse, P. J. et al. *Infect Immun* 77, 1230-7 (2009); Gautam, U.S. et al. *Am J Respir Cell Mol Biol* 52, 708-16 (2015); Mehra, S. et al. *Am J Respir Crit Care Med* 191, 1185-96 (2015)), animal models that generate hypoxic granulomas where DosR-dependent persistence is predicted to be required for survival. Additionally, disruption of a DosR regulated gene, tgs1, results in enhanced sensitivity of Mtb to antibiotics in vitro and during mouse infection (Baek, S. H. et al. *PLoS Biol* 9, e1001065 (2011)). Therefore, chemical inhibition of the DosR regulon may stop the establishment and survival of persistent, drug-tolerant Mtb in the granuloma.

II. Compounds that Inhibit Two-Component Regulatory Systems and/or their Regulon The disclosure features, among other things, in vitro and in vivo methods for inhibiting the growth or viability of bacteria, such as *Mycobacterium tuberculosis*, using compounds that inhibit (e.g., inhibitors) a two-component regulatory system and/or its regulon, such as the DosRST two-component regulatory system and/or the DosRST regulon. As used herein, "inhibition of the two-component regulatory system," "inhibition of the DosRST two-component regulatory system," or "inhibition of the DosRST regulon," or similar grammatical terms and phrases, includes direct and indirect inhibition of the DosS, DosT, DosRST regulon, any combination thereof. For example, an inhibitor of the DosRST can be one that directly binds to DosS protein or DosT protein, or both, and inhibits the activity of the protein. In some embodiments, the inhibitor can be one that inhibits the expression or stability of DosS or DosT protein. In some embodiments, the inhibitor inhibits a protein regulator, signaling pathway component, and/or upstream and/or downstream genes of the DosRST regulon. As used herein, the term "inhibiting" and grammatical equivalents thereof refer to a decrease, limiting, and/or blocking of a particular action, function, or interaction. In one embodiment, the term refers to reducing the level of a given output or parameter to a quantity which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control. A reduced level of a given output or parameter need not, although it may, mean an absolute absence of the output or parameter. The disclosure does not require, and is not limited to, methods that wholly eliminate the output or parameter.

In some embodiments, the inhibitors (e.g., artemisinin, HC102A, and HC103A) can inhibit the induction of the core DosRST regulon. In some embodiments, the inhibitors (e.g., HC102A, and HC103A) show strong specificity for the intended target of the DosRST regulon. In some embodiments, the In some embodiments, the inhibitor inhibits the ability of the two component regulatory system, such as DosRST and its regulon, to enhance or repress the expression of a target gene, such as any of those described in the Tables 2-3 provided herein. In some embodiments, the inhibitor can inhibit Mtb persistence associated physiologies, including but not limited to triacylglycerol synthesis, survival, and antibiotic tolerance. In some embodiments, HC101A (artemisinin) can disable the hem-based DosS/T sensor kinases by oxidizing ferrous heme and generating heme-artemisinin adducts. In some embodiments, an HC103A inhibitor can inhibit DosS and DosT autophosphorylation activity without targeting the sensor kinase heme.

In certain aspects, provided herein are compounds (e.g., inhibitors) having the structure of Formula I, or a pharmaceutically acceptable salt thereof:

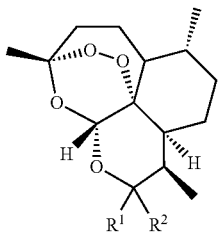

Formula I wherein

R$^1$ and R$^2$ are, independently for each occurrence, H or —OR$^3$, or R$^1$ and R$^2$ together with the carbon to which they are bound form a carbonyl moiety; and R$^3$ is, independently for each occurrence, H or optionally substituted alkyl, cycloalkyl, heterocyclyl, acyl, aryl, or heteroaryl.

In some embodiments, R$^1$ is H and R$^2$ is —OR$^3$. In some embodiments, R$^3$ is

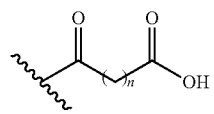

and n is an integer from 1-6 (e.g., 2, 3, 4). In some embodiments, R$^3$ is

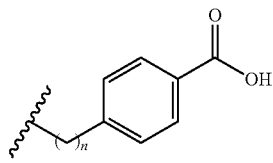

and n is an integer from 1-6 (e.g., 1, 2, 3, 4). 37. In some embodiments, wherein R$^3$ is lower alkyl (e.g., methyl, ethyl).

In certain embodiments, the compound is

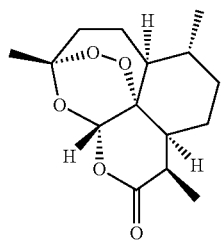 [SMILES: C[C@@H]1CC[C@H]2[C@@H](C)C(=O)O[C@@H]3O[C@]4(C)CC[C@@H]1[C@]32OO4]

or a pharmaceutically acceptable salt thereof.

In certain aspects, provided herein are compounds (e.g., inhibitors) having the structure of Formula II, or a pharmaceutically acceptable salt thereof:

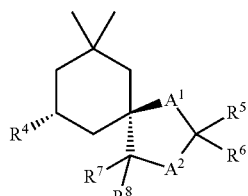

Formula II wherein

A$^1$ is O, NH, or CH$_2$;
A$^2$ is O, NH, or CH$_2$;
R$^4$ is H, halo, or optionally substituted alkyl;
R$^5$ and R$^6$ are H or —OR$^9$, or R$^5$ and R$^6$ together with the carbon to which they are bound form a carbonyl moiety;
R$^9$ is, independently for each occurrence, H or optionally substituted alkyl, cycloalkyl, heterocyclyl, acyl, aryl, or heteroaryl;
R$^7$ and R$^8$ are H or —OR$^{10}$, or R$^5$ and R$^6$ together with the carbon to which they are bound form a carbonyl moiety; and
R$^{10}$ is, independently for each occurrence, H or optionally alkyl, cycloalkyl, heterocyclyl, acyl, aryl, or heteroaryl.

In some embodiments, A$^1$ is NH. In some embodiments, A$^2$ is NH. In some embodiments, R$^4$ is lower alkyl (e.g., methyl). In some embodiments, R$^5$ and R$^6$ together with the carbon to which they are bound form a carbonyl moiety.

In some embodiments, wherein R$^7$ and R$^8$ together with the carbon to which they are bound form a carbonyl moiety.

In certain embodiments, the compound is

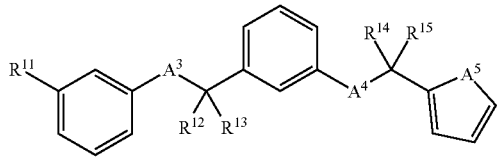

or a pharmaceutically acceptable salt thereof.

In certain aspects, provided herein are compounds (e.g., inhibitors) having the structure of Formula III, or a pharmaceutically acceptable salt thereof:

Formula III wherein

A$^3$ is O, NH, or CH$_2$;
A$^4$ is O, NH, or CH$_2$;
A$^5$ is O, NH, S or CH$_2$;
R$^{11}$ is H, halo, hydroxyl, or optionally substituted alkyl or alkoxy;
R$^{12}$ and R$^{13}$ are H or —OR$^{16}$, or R$^{12}$ and R$^{13}$ together with the carbon to which they are bound form a carbonyl moiety;
R$^{14}$ and R$^{15}$ are H or —OR$^{17}$, or R$^{14}$ and R$^{15}$ together with the carbon to which they are bound form a carbonyl moiety; and $R^{16}$ and $R^{17}$ are, independently for each occurrence, H or optionally substituted alkyl, cycloalkyl, heterocyclyl, acyl, aryl, or heteroaryl.

In some embodiments, $A^3$ is NH. In some embodiments, $A^4$ is NH. In some embodiments, $A^5$ is S. In some embodiments, $R^{11}$ is hydroxyl. In some embodiments, $R^{12}$ and $R^{13}$ together with the carbon to which they are bound form a carbonyl moiety. In some embodiments, $R^{14}$ and $R^{15}$ together with the carbon to which they are bound form a carbonyl moiety.

In certain embodiments, the compound is

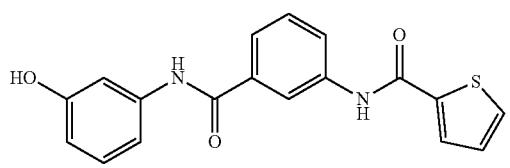 [SMILES: O=C(Nc1cccc(O)c1)c1cccc(NC(=O)c2cccs2)c1]

or a pharmaceutically acceptable salt thereof.

In certain aspects, provided herein are compounds (e.g., inhibitors) having the structure of Formula IV, or a pharmaceutically acceptable salt thereof:

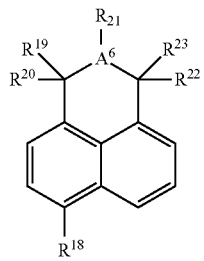

Formula IV wherein $A^6$ is N or CH;

$R^{18}$ is H, halo, or optionally substituted alkyl or alkoxy;

$R^{21}$ is H or optionally substituted alkyl, cycloalkyl, heterocyclyl, acyl, aryl, or heteroaryl;

$R^{19}$ and $R^{20}$ are H or $-OR^{24}$, or $R^{19}$ and $R^{20}$ together with the carbon to which they are bound form a carbonyl moiety;

$R^{22}$ and $R^{23}$ are H or $-OR^{25}$, or $R^{22}$ and $R^{23}$ together with the carbon to which they are bound form a carbonyl moiety; and $R^{24}$ and $R^{25}$ are, independently for each occurrence, H or optionally substituted alkyl, cycloalkyl, heterocyclyl, acyl, aryl, or heteroaryl.

In some embodiments, $A^6$ is NH. In some embodiments, wherein $R^{18}$ is halo (e.g., Br).

In some embodiments, $R^{19}$ and $R^{20}$ together with the carbon to which they are bound form a carbonyl moiety. In some embodiments, $R^{22}$ and $R^{23}$ together with the carbon to which they are bound form a carbonyl moiety. In some embodiments, wherein $R^{21}$ is optionally substituted alkyl. In some embodiments, $R^{21}$ is aminoalkyl. In some embodiments, $R^{21}$ is

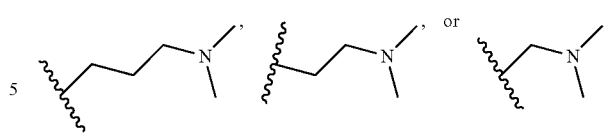

In certain embodiments, the compound is

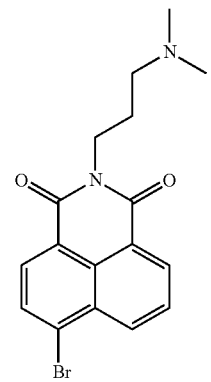

or a pharmaceutically acceptable salt thereof.

In certain aspects, provided herein are compounds (e.g., inhibitors) having the structure of Formula V, or a pharmaceutically acceptable salt thereof:

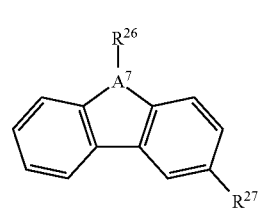

Formula V wherein $A^7$ is N or CH;

$R^{26}$ is H or optionally substituted alkyl, cycloalkyl, heterocyclyl, acyl, aryl, or heteroaryl; and $R^{27}$ is H or optionally substituted alkyl, cycloalkyl, heterocyclyl, or alkoxy.

In some embodiments, $A^7$ is N. In some embodiments, wherein $R^{26}$ is lower alkyl (e.g., ethyl). In some embodiments, $R^{27}$ is aminoalkyl. In some embodiments, $R^{27}$ is

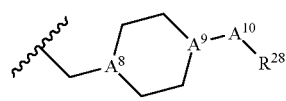

$A^8$ is N or CH;

$A^9$ is N or CH;

$A^{10}$ is $CH_2$, $SO_2$, S=O or S; and $R^{28}$ is optionally substituted alkyl, cycloalkyl, aryl or heteroaryl;

In certain embodiments, the compound is

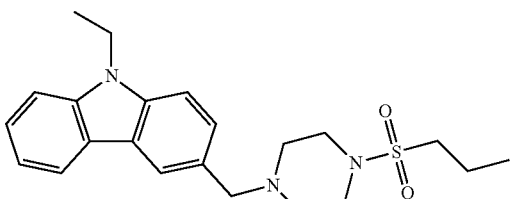

or a pharmaceutically acceptable salt thereof.

In certain aspects, provided herein are compounds (e.g., inhibitors) having the structure of Formula VI, or a pharmaceutically acceptable salt thereof:

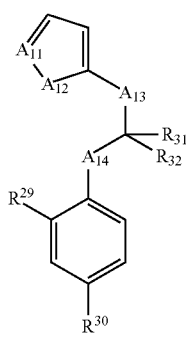

Formula VI wherein
$A^{11}$ is N or CH;
$A^{12}$ is O, NH or $CH_2$;
$A^{13}$ is O, NH or $CH_2$;
$A^{14}$ is O, NH or $CH_2$;
$R^{29}$ is H, halo, or optionally substituted alkyl or alkoxy;
$R^{30}$ is H, halo, or optionally substituted alkyl or alkoxy;
$R^{31}$ and $R^{32}$ are H or —$OR^{33}$, or $R^{31}$ and $R^{32}$ together with the carbon to which they are bound form a carbonyl moiety; and
$R^{33}$ is H or optionally substituted alkyl, cycloalkyl, heterocyclyl, acyl, aryl, or heteroaryl.

In some embodiments, wherein $A^{11}$ is N.
In some embodiments, $A^{12}$ is O. In some embodiments, $A^{13}$ is NH. In some embodiments, $A^{14}$ is NH. In some embodiments, $R^{29}$ is halo. In some embodiments, $R^{29}$ is Cl. In some embodiments, $R^{30}$ is halo (e.g., Cl).

In certain embodiments, the compound is

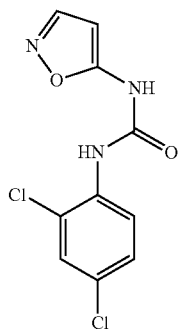 [SMILES: O=C(Nc1ccno1)Nc1ccc(Cl)cc1Cl]

or a pharmaceutically acceptable salt thereof.

In certain aspects, provided herein are compounds (e.g., inhibitors) having the structure of Formula VII, or a pharmaceutically acceptable salt thereof:

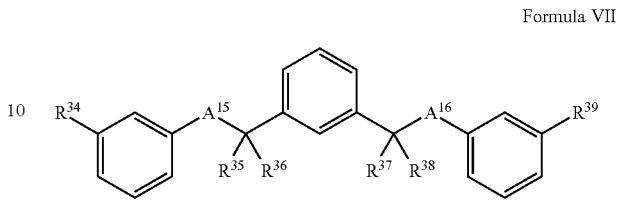

Formula VII wherein
$A^{15}$ is O, NH, or $CH_2$;
$A^{16}$ is O, NH, or $CH_2$;
$R^{34}$ and $R^{39}$ are each, independently for each occurrence H, halo, hydroxyl, or optionally substituted alkyl or alkoxy;
$R^{35}$ and $R^{36}$ are H or —$OR^{39}$, or $R^{35}$ and $R^{36}$ together with the carbon to which they are bound form a carbonyl moiety;
$R^{37}$ and $R^{38}$ are H or —$OR^{40}$, or $R^{37}$ and $R^{38}$ together with the carbon to which they are bound form a carbonyl moiety; and
$R^{39}$ and $R^{40}$ are, independently for each occurrence, H or optionally substituted alkyl, cycloalkyl, heterocyclyl, acyl, aryl, or heteroaryl.

In some embodiments, $A^{15}$ is NH. In some embodiments, $A^{16}$ is NH. In some embodiments, $R^{34}$ is hydroxyl. In some embodiments, $R^{39}$ is hydroxyl. In some embodiments, $R^{35}$ and $R^{36}$ together with the carbon to which they are bound form a carbonyl moiety. In some embodiments, $R^{37}$ and $R^{38}$ together with the carbon to which they are bound form a carbonyl moiety.

In certain embodiments, the compound is

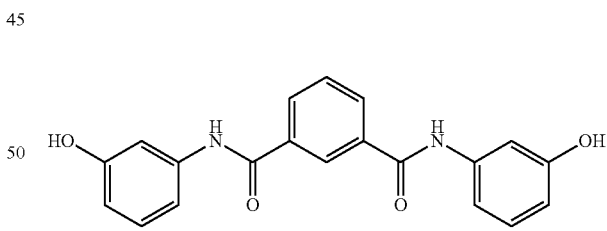

or a pharmaceutically acceptable salt thereof.

Exemplary compounds (e.g., inhibitors) of Formula I-VII are depicted in Table 1. The compounds of Table 1 may be depicted as the free base or the conjugate acid. Compounds may be isolated in either the free base form, as a salt (e.g., a hydrochloride salt) or in both forms. In the chemical structures shown below, standard chemical abbreviations are sometimes used.

TABLE 1
Exemplary compounds of Formulas I-VII
| Ex. | Structure | Name |
|---|---|---|
| 1 | 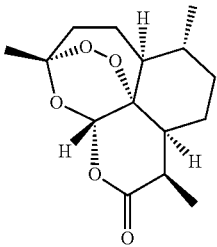 [SMILES: C[C@@H]1CC[C@H]2[C@@H](C)C(=O)O[C@@H]3O[C@]4(C)CC[C@@H]1[C@]32OO4] | HC101A |
| 2 | 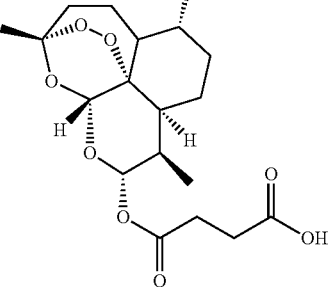 | HC101B |
| 3 | 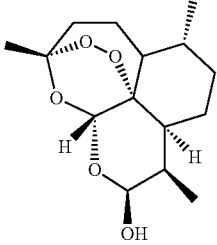 [SMILES: C[C@H]1[C@@H](O)O[C@@H]2O[C@]3(C)CCC4[C@H](C)CC[C@@H]1[C@]42OO3] | HC101C |
| 4 | 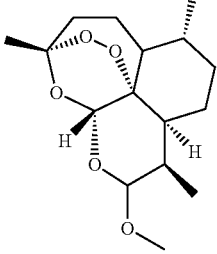 | |
| 5 | 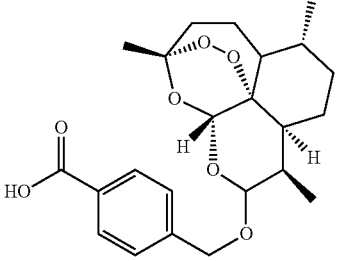 | |
| 6 | 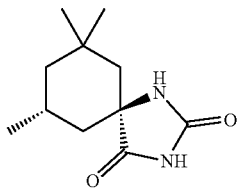 | HC102A |

TABLE 1-continued

Exemplary compounds of Formulas I-VII

| Ex. | Structure | Name |
|---|---|---|
| 7 | 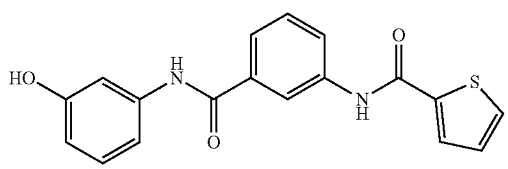 [SMILES: O=C(Nc1cccc(O)c1)c1cccc(NC(=O)c2cccs2)c1] | HC103A |
| 8 | 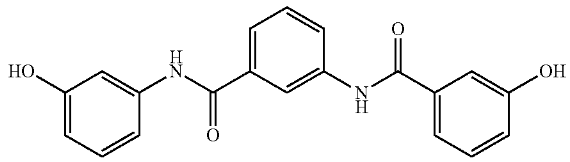 [SMILES: O=C(Nc1cccc(C(=O)Nc2cccc(O)c2)c1)c1cccc(O)c1] | HC103B |
| 9 | 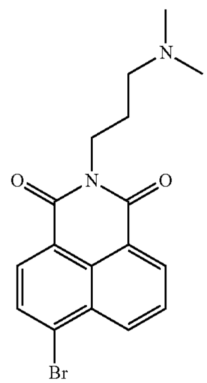 [SMILES: CN(C)CCCN1C(=O)c2cccc3c(Br)ccc(c23)C1=O] | HC104A |
| 10 | 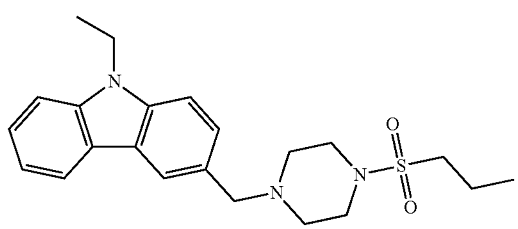 [SMILES: CCCS(=O)(=O)N1CCN(Cc2ccc3c(c2)c2ccccc2n3CC)CC1] | HC105 |
| 11 | 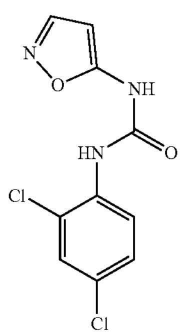 [SMILES: O=C(Nc1ccno1)Nc1ccc(Cl)cc1Cl] | HC106 |

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. The compounds of the invention have more than one stereocenter. Consequently, compounds of the invention may be enriched in one or more diastereomer. For example, a compound of the invention may have greater than 30% de, 40% de, 50% de, 60% de, 70% de, 80% de, 90% de, or even 95% or greater de.

1. Pharmaceutical Compositions

In certain embodiments, the present invention provides pharmaceutical compositions comprising a compound of one of Formulas I-VII and a pharmaceutically acceptable carrier.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention (e.g., compound of formula I-VII) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I-VII. As another example, the salt may comprise less than one inorganic or organic acid molecule per molecule of base, such as two molecules of compound of Formulas I-VII per molecule of tartaric acid.

In further embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benethamine, benzathine, betaine, calcium hydroxide, choline, decanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

2. Definitions

The term "acyl" is art-recognized and refers to a group represented by the general formula hydrocarbylC(O)—, preferably alkylC(O)— or optionally substituted alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, —OCF$_3$, ethoxy, propoxy, tert-butoxy and the like.

The term "cycloalkyloxy" refers to a cycloakyl group having an oxygen attached thereto.

The term "alkoxyalkyl" refers to an alkyl group substituted with an alkoxy group and may be represented by the general formula alkyl-O-alkyl.

The term "alkylaminoalkyl" refers to an alkyl group substituted with an alkylamino group.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkys, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. Co alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

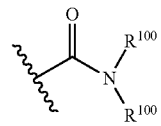

wherein each $R^{100}$ independently represent a hydrogen or hydrocarbyl group, or two $R^{100}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

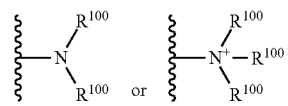

wherein each $R^{100}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

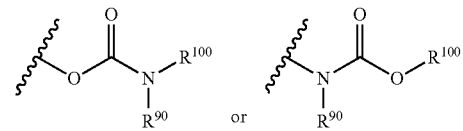

wherein $R^{90}$ and $R^{100}$ independently represent hydrogen or a hydrocarbyl group, such as an alkyl group, or $R^{90}$ and $R^{100}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings.

Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group $-OCO_2-R^{10}$, wherein $R^{10}$ represents a hydrocarbyl group.

The term "carboxy", as used herein, refers to a group represented by the formula $-CO_2H$.

The term "ester", as used herein, refers to a group $-C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical.

Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The term "heteroalkylamino", as used herein, refers to an amino group substituted with a heteroalkyl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Heterocyclyl groups can also be substituted by oxo groups. For example, "heterocyclyl" encompasses both pyrrolidine and pyrrolidinone.

The term "heterocycloalkyl", as used herein, refers to an alkyl group substituted with a heterocycle group.

The term "heterocycloalkylamino", as used herein refers to an amino group substituted with a heterocycloalkyl group.

The term "hydrocarbyl", as used herein, refers to a group that is bonded through a carbon atom that does not have a $=O$ or $=S$ substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a $=O$ substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "oxo" refers to a carbonyl group. When an oxo substituent occurs on an otherwise saturated group, such as with an oxo-substituted cycloalkyl group (e.g., 3-oxo-cyclobutyl), the substituted group is still intended to be a saturated group. When a group is referred to as being substituted by an "oxo" group, this can mean that a carbonyl moiety (i.e., —C(═O)—) replaces a methylene unit (i.e., —CH$_2$—).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

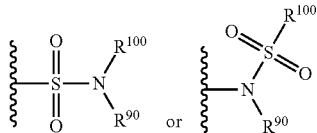

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{100}$, wherein R$^{100}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{100}$, wherein R$^{100}$ represents a hydrocarbyl.

The term "thioalkyl", as used herein, refers to an alkyl group substituted with a thiol group.

The term "thioester", as used herein, refers to a group —C(O)SR$^{100}$ or —SC(O)R$^{100}$ wherein R$^{100}$ represents a hydrocarbyl.

The term "thioether", as used herein, is equivalent to an ether, wherein the oxygen is replaced with a sulfur.

The term "urea" is art-recognized and may be represented by the general formula

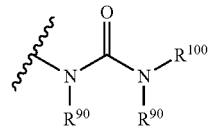

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

III. Applications

As elaborated on in more detail below, the compounds (e.g., inhibitors) described herein are useful in a number of in vitro and in vivo applications. For example, the compounds (e.g., inhibitors) described herein can be used to treat bacterial infections, such as *Mycobacterium tuberculosis* infections.

Methods for Treatment

Also featured herein are therapeutic methods for treating subjects with a variety of infections, such as tuberculosis infections. The methods comprise administering to the subject an inhibitor of a two-component regulatory system (e.g., DosRST), such as any of those described herein, in an amount effective to treat the infection. In some embodiments, the bacteria infecting the subject are identified as expressing one or both of DosS or DosT, DosRST, or DosRST regulon.

In some embodiments, the methods include receiving the results of a test determining that the bacteria infecting the subject are identified as bacteria in which the two-component regulatory system (e.g., DosRST) is conserved and, in view of this information, ordering administration of an effective amount of one or more of the inhibitors described herein to the subject. For example, a physician treating a subject can request that a third party (e.g., a CLIA-certified laboratory) to perform a test to determine whether the bacteria infecting the subject are bacteria in which the two-component regulatory system (e.g., DosRST) is conserved. The laboratory may provide such information, or, in some embodiments, provide an expression score or value, or a positive or negative result. If the bacteria have the conserved two-component regulatory system (e.g., DosRST), or if the bacteria are identified as tuberculosis, the physician may then administer to the subject one or more of the inhibitors described herein. Alternatively, the physician may order the administration of the inhibitor to the subject, which administration is performed by another medical professional, e.g., a nurse.

In some embodiments, the method can include: requesting a test, or the results of a test, which determines that the bacteria infecting the subject are *Mycobacterium tuberculosis* or bacteria in which the two-component regulatory system (e.g., DosRST) is conserved; and administering or ordering administration of an effective amount of an inhibitor described herein to the subject.

A "subject," as used herein, can be any mammal. For example, a subject can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant).

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment.

The term "preventing" is art-recognized, and when used in relation to a condition, is well understood in the art, and includes administration of a composition which reduces the frequency of, or delays the onset of, symptoms of a medical condition in a subject relative to a subject which does not receive the composition. For example, treatment with an inhibitor described herein may delay the onset of, and/or reduce the severity of symptoms upon onset of, a *Myobacterium tuberculosis* infection in a subject who has been exposed to *Myobacterium tuberculosis*. Exposure to a bacterial infection, such as *Myobacterium tuberculosis*, can be, e.g., close quarters exposure to an infected individual or exposure to bodily fluids (e.g., sputum, saliva, etc.) from an infected individual.

As used herein, "latent tuberculosis" refers to the presence of *Myobacterium tuberculosis* in one or more cells of the infected individual (e.g., has a positive tuberculosis skin test), but the individual does not have an active infection (exhibits one or more signs or symptoms of a TB infection, such as cough, fever, night sweats, weight loss, fatigue, flu-like symptoms, chest pain, shortness of breath, blood in the sputum, etc.).

As used herein, "MDR tuberculosis" or "multi-drug resistant tuberculosis" refers to a form of tuberculosis that is resistant to two or more of the primary drugs (isoniazid and rifampicin) used for the treatment of tuberculosis. As used herein, "XDR tuberculosis" or "extensively multi-drug resistant tuberculosis" refers to a form of tuberculosis resistant to at least isoniazid and rifampicin among the first-line anti-TB drugs, is resistant to any fluoroquinolone and at least one of three injectable second-line drugs, such as amikacin, kanamycin or capreomycin.

The inhibitor compositions can be administered to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

As used herein the term "effective amount" or "therapeutically effective amount", in an in vivo setting, means a dosage sufficient to treat, inhibit, or alleviate one or more symptoms of the disorder being treated or to otherwise provide a desired pharmacologic and/or physiologic effect (e.g., modulate (e.g., enhance) an immune response to an antigen.

The precise dosage will vary according to a variety of factors such as subject-dependent variables (e.g., age, immune system health, etc.), the disease, and the treatment being effected.

Suitable human doses of any of the compounds described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

Toxicity and therapeutic efficacy of such compositions can be determined by known pharmaceutical procedures in cell cultures or experimental animals (e.g., animal models of infection). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such compounds lies generally within a range of circulating concentrations of the compounds that include the $ED_{50}$ with little or no toxicity. The dosage may vary within this range depending upon the dosage form employed and the route of administration utilized. A therapeutically effective dose can be estimated initially from cell culture assays. A dose can be formulated in animal models to achieve a circulating plasma concentration range that includes the $IC_{50}$ (i.e., the concentration of the inhibitor which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration is desired, cell culture or animal modeling can be used to determine a dose required to achieve a therapeutically effective concentration within the local site. Suitable dosages are described herein.

In some embodiments of any of the methods described herein, an agent can be administered to a mammal in conjunction with one or more additional therapeutic agents. For example, in some embodiments, it may be advantageous to administer an inhibitor described herein in combination with at least one additional pharmaceutical (or therapeutic) agent (e.g., first-line or second-line antituberculosis drugs, and for patients with HIV or AIDS an HIV/AIDS drug). The inhibitor may be administered either simultaneously with, or before or after, one or more other therapeutic agent(s). Alternatively, the compound of the present invention may be administered separately, by the same or different route of administration, or together in the same pharmaceutical composition as the other agent(s).

Suitable additional TB agents include first-line drugs (such as isoniazid, rifampicin, pyrazinamide, ethambutol and combinations thereof); second-line drugs (such as streptomycin, kanamycin, amikacin, capreomycin, ofloxacin, levofloxacin, moxifloxacin, cycloserine, para-aminosalicylic acid, ethionamide, prothionamide, thioacetazone and combinations thereof); and other antituberculosis drugs (such as clofazimine, amoxicillin with clavulanate, imipenem, linezolid, clarithromycin, thioridazine and combinations thereof). Other potential additional TB agents include compounds such as bicyclic nitroimidazoles (e.g., (S)-6,7-dihydro-2-nitro-6-[[4-(trifluoromethoxy)phenyl]methoxy]-5H-imidazo[2,1-b][1,3]oxazine (PA-824) and TBA-354, available from TB Alliance), bedaquiline (TMC-207), delamanid (OPC67683), oxazolidinone, 2-[(2S)-2-methyl-1,4-dioxa-8-azaspiro[4.5]decan-8-yl]-8-nitro-6-trifluoromethyl-4H-1,3-benzothiazin-4-one (BTZ043), imidazopyridines (e.g., Q201, available from Quro Science Inc.), and combinations thereof.

Suitable therapeutic agents for adjunct therapy include human immunodeficiency virus (HIV) drugs, immunotherapeutic agents, (e.g., anti-interleukin 4 neutralizing antibodies, high-dose intravenous immunoglobulin, 16a-bromoepiandrosterone (HE2000), RUTI® vaccine, DNA vaccine with HSP65, Ag85, MPT-64, and MPT-83, dzherelo (plant extracts from the Ukraine), cytokines (such as Interleukin 2, Interleukin 7, Interleukin 15, Interleukin 27, Interleukin 12, Interferon γ), immunosuppressive agents (such as corticosteroids, thalidomide, and etanercept)), steroids, anti-inflammatory agents (e.g. prednisone), and other agents well-known to those of skill in art for use in improving the quality of care for patients being treated for the diseases, conditions, or disorders described herein.

Suitable HIV/AIDS drugs include non-nucleoside reverse transcriptase inhibitors (NNRTIs), such as efavirenz (Sustiva), etravirine (Intelence) and nevirapine (Viramune); Nucleoside reverse transcriptase inhibitors (NRTIs), such as Abacavir (Ziagen), and the combination drugs emtricitabine and tenofovir (Truvada), and lamivudine and zidovudine (Combivir); Protease inhibitors (PIs), such as atazanavir (Reyataz), darunavir (Prezista), fosamprenavir (Lexiva) and ritonavir (Norvir); Entry or fusion inhibitors, such as enfuvirtide (Fuzeon) and maraviroc (Selzentry); and Integrase inhibitors, such as Raltegravir (Isentress).

Methods for diagnosing a subject has having tuberculosis are well known in the art and include, e.g., chest x-ray, testing of a sputum sample, tuberculin skin test, or a blood test (e.g., to test for the presence of microbial DNA or circulating anti-TB antibodies).

Likewise, methods for determining whether bacteria express DosS, DosT, DosRST, and/or DosRST regulon are known in the art and include, e.g., protein (e.g., Western blot, dot blot, or other immunoassays) and nucleic acid (e.g., RT-PCR) detection techniques.

The International Standards for Tuberculosis Care describes a widely accepted level of care that all practitioners, public and private, should follow in dealing with people who have, or are suspected of having, tuberculosis. The Standards are intended to facilitate the effective engagement of all care providers in delivering high-quality care for patients of all ages, including those with sputum smear-positive, sputum smear-negative, and extrapulmonary tuberculosis; tuberculosis caused by drug resistant *Mycobacterium tuberculosis* complex (*M. tuberculosis*) organisms; and tuberculosis combined with human immunodeficiency virus (HIV) infection, all of which are amenable to treatment using one or more of the inhibitors described herein.

Another aspect of the disclosure is a product comprising an inhibitor described herein and at least one other therapeutic agent (or pharmaceutical agent) as a combined preparation for simultaneous, separate or sequential use in therapy to treat a subject having sputum smear-positive, sputum smear-negative, and extrapulmonary tuberculosis; tuberculosis caused by drug resistant *Mycobacterium tuberculosis* complex (*M. tuberculosis*) organisms; or tuberculosis combined with human immunodeficiency virus (HIV) infection.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Example 1. Materials and Methods

Bacterial Strains and Growth Conditions

Mtb strains CDC1551 and Erdman were used as indicated. CDC1551(ΔdosR) and Erdman(ΔdosR) mutants were constructed using gene replacement by homologous recombination (Sander, P., B, S. & Bottger, E. Gene Replacement in *Mycobacterium tuberculosis* and *Mycobacterium bovis* BCG Using rpsL as a Dominant Negative Selectable Marker, 93-104 (Humana Press, Totowa, N.J., 2001)) using methods as previously described (Abramovitch, R. B. et al. *Mol Microbiol* 80, 678-94 (2011)). Deletions were confirmed by PCR and transcriptional profiling. All strains were cultured at 37° C. and 5% $CO_2$ in standing, vented tissue culture flasks in 7H9 Middlebrook medium supplemented with 10% OADC and 0.05% Tween-80. For dosToverexpression strains, the dosTgene was cloned under the control of the strong hsp60 promoter in the pVV16 vector and transformed into CDC1551. dosT (G85L) and dosT(G115L) mutants were generated using the QuickChange site directed mutagenesis approach (Agilent) in pVV16 and confirmed by sequencing.

High-Throughput Screening Assay and Data Analysis

The HTS was conducted against two compound collections, the 211,655 compound ICCB-Longwood collection and the 328,633 compound NIH Molecular Libraries Program (MLP) collection, both provided by the ICCB at Harvard Medical School. The compounds were arrayed in 384-well clear bottom, black sided microtiter plates (Corning) at a final screening concentration of ~10 µM. Two columns of each plate were left blank for positive and negative controls of 0.3 µM rifampicin and DMSO alone, respectively. The *M. tuberculosis* CDC1551 (hspX':GFP) fluorescent reporter was grown to mid- to late-log phase in vented T-150 standing flasks in Middlebrook 7H9 (OADC) medium (buffered to pH 7.0 with 100 mM MOPS). The cultures were then re-suspended in 7H9 (OADC) pH 7.0 medium and dispensed into the 384-well assay plates utilizing a Cy-Bio Selma liquid handler robot to an OD595 of 0.05. The plates were then placed in a Ziploc bag with a moistened paper towel (to limit evaporation) and incubated for 6 days at 37° C. Fluorescence and optical density (OD) readings were made on an EnSpire plate reader (Perkin Elmer, Inc.) at excitation and emission wavelengths of 488 and 509 nm as a top read, with the OD being taken at 595 nm as a bottom read.

Data analysis was performed utilizing an in-house developed computational tool written in Python. Raw fluorescence and optical density measurements were exported from the EnSpire plate reader (Perkin Elmer, Inc.) in plate format as comma-separated files. Measurements were then normalized as a function of percent inhibition compared to the negative (DMSO) control (see equation below).

$$NPI_{ijk} = \left\{ \frac{\beta_{ijk} - \bar{\mu}_{nk}}{\bar{\mu}_{nk} - \bar{\mu}_{pk}} \times 100 \,\middle|\, \exists \, Z'_{jk} \geq 0.5; Z'_{jk} = 1 - \frac{3\sigma(\mu_{njk}) + 3\sigma(\mu_{pjk})}{\mu_{njk} - \mu_{pjk}} \right\}$$

Figure 7:
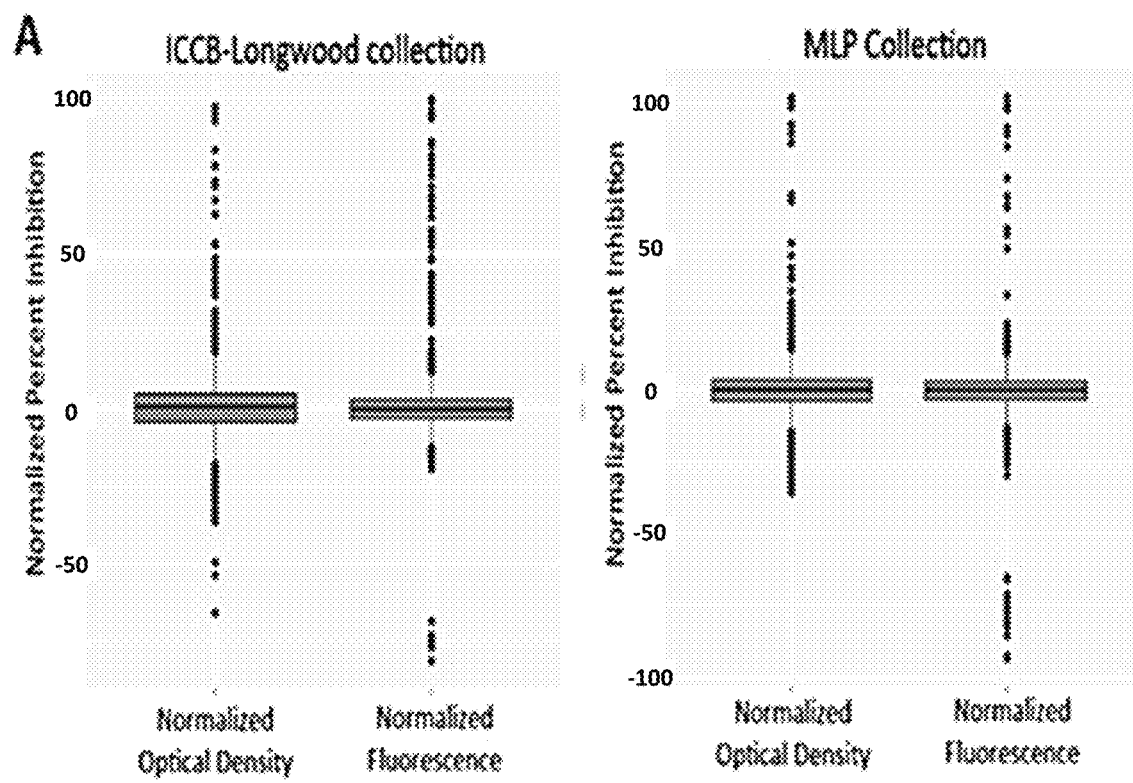
FIG. 7 includes three panels, A-C, and depicts statistical analysis of HTS controls. Panel A shows box plots showing the variation of DMSO control wells (negative control) from the screens of the ICCB-Longwood and Molecular Libraries Program (MLP) collections. Boxes show the 25 and 75% quartiles and the whiskers are 1.5× the interquartile range (approximately 3 standard deviations away from the mean). The dots are considered "outliers". Panel B shows table with the means and standard deviations from the DMSO controls. Along with the Z-factor of 0.9, tight clustering of the control wells around 0% inhibition for both fluorescence and optical density support robustness of the screen. Panel C shows FDR p-values plotted vs. the fluorescence inhibition to growth inhibition ratios shows that the chosen 1.5-fold cut-off ratio (red line) is significant ($p<0.0003$).
Figure 7:
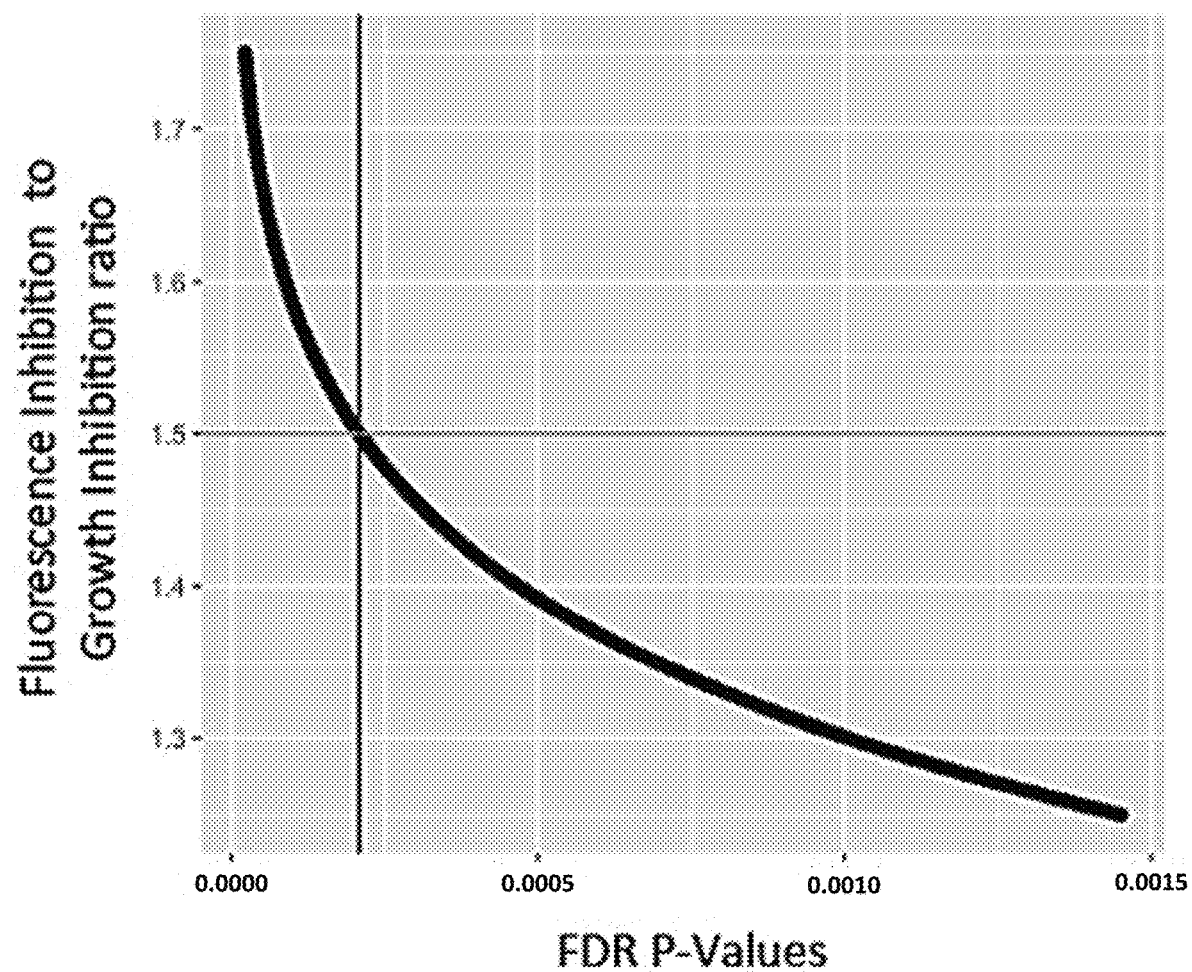

The normalized percent inhibition (NPI) for fluorescence or optical density was calculated by subtracting the overall mean of the negative controls within the run ($\bar{\mu}_{nk}$) from the measured value ($\beta$), divided by the dynamic range and multiplied by 100. The overall means for the positive and negative controls within the run ($\bar{\mu}_{nk}, \bar{\mu}_{pk}$) are determined if there exists at least one plate in the run with a Z' greater than or equal to 0.5[60]. ijk represents the ith value in the jth plate within the kth run. a represents the standard deviation. Potential inhibitors of the DosRST regulon were defined as compounds with greater than 35% fluorescence inhibition, limited growth inhibition, and at least 1.5-fold selectivity in the fluorescence to growth inhibition ratio. To determine the statistical significance of the 1.5 fold selectivity cutoff, Z-scores were calculated for each experimental compound fluorescence inhibition:growth inhibition ratio relative to the negative controls and P-values were derived by testing against the null distribution. Due to the high number of tests, each P-value was false-discovery rate corrected (FIG. 7, Panel C). These "class 1" compounds may be directly or indirectly inhibiting DosRST signaling. The Z-factors of the screens were 0.90 and 0.89 for the ICCB-L and MLP library screens, respectively (Zhang, J. H. et al. *J Biomol Screen* 4, 67-73 (1999)).

For GFP quenching assays, the CDC1551 (hspX':GFP) reporter was grown under GFP-inducing conditions, aliquoted into 96 well plates, treated with a dose response of HC101A-HC106A and then the plates were immediately read for GFP fluorescence. GFP quenchers cause an inhibition of GFP fluorescence and none of the compounds exhibited GFP quenching activity. Cytotoxicity assays were conducted against three eukaryotic cells, primary C57Bl/6 murine derived macrophages (BMDMs), THP-1 and J774 cells. Macrophages were prepared as previously described (Johnson, B. K. et al. *Methods Mol Biol* 1285, 329-41 (2015)) and seeded in white, opaque, 96 well plates (Corning) and treated for three days with the compounds treated with a 8-point dose response curve ranging from 400 M to 0.65 M. Following 3 days, viability was determined using the CellTiter-glo luminescent cell viability assay (Promega). Percent inhibition was normalized to a triton X-100 positive control and a DMSO negative control. $EC_{50}$s were calculated using the GraphPad Prism software package (version 6). Each experiment included two technical replicates per plate and two biological replicates and error bars represent the standard deviation of the biological replicates. The experiment was repeated at least twice.

$EC_{50}$ determinations for HC101A-HC106 compounds were performed in clear bottom, black, 96 well plates (Corning), following methods similar to those described above for the HTS. Briefly, 200 µL of the CDC1551(hspX': GFP) reporter was inoculated into each well at an initial OD of 0.05. The cells were treated for 6 days with compounds using an 8-point dose response curve ranging from 400 µM to 0.65 M. The plates were then read for GFP fluorescence and optical density and percent inhibition was normalized to a rifampin positive control and DMSO negative control. $EC_{50}$s were calculated using the GraphPad Prism software package (version 6). Each experiment included two technical replicates per plate and two biological replicates and error bars represent the standard deviation of the biological replicates. The experiment was repeated at least twice.

Transcriptional Profiling and Data Analysis

CDC1551 or CDC1551(ΔdosR) cultures were treated with 40 µM artemisinin, HC102A, HC103A or DMSO (as a negative control) and grown at 37° C. without shaking in T-25 vented, standing tissue culture flasks in 8 mL of 7H9 medium seeded at an initial OD of 0.1. The experiments were performed with two biological replicates. Following 6 days of incubation, total bacterial RNA was extracted and sequenced as described by Baker, Johnson and Abramovitch (Baker, J. J. et al. *Mol Microbiol* 94, 56-69 (2014). RNA-seq data was analyzed using the SPARTA software package (Johnson, B. K. et al. *BMC Bioinformatics* 17, 66 (2016)v). The transcriptional profiling data have been submitted to the NCBI GEO database (accession no. GSE76566).

Real Time PCR Assays

For the NO and vitamin C sensitivity assays, CDC1551 was seeded at an initial density of 0.6 OD and treated with 80 µM DHA, HC102A, or HC103A for 24 hours, and then induced with 50 µM DETA-NONOate or 2 mM vitamin C for 2 hours. After treatment, total bacterial RNA was extracted as previously described (Rohde, K. H. et al. *Cell Host Microbe* 2, 352-64 (2007)). Transcripts of representative genes from the dosR regulon, including dosR, hspX, and tgs1, were quantified by RT-PCR using gene-specific primers as previously described (Abramovitch, R. B. et al. *Mol Microbiol* 80, 678-94 (2011)). The experiment included three biological replicates and error bars represent the standard deviation from the mean. The experiment was repeated twice with similar results. For the artemisinin resistance assays, CDC1551 was seeded at an initial density of 0.1 and treated with 0.025 µM-20 µM artemisinin for six days at 37° C. Total RNA was extracted and RT-PCR quantification of DosR-regulated genes (dosR, hspX and tgs1) was conducted as described above. The experiment was repeated with three biological replicates with similar results. $EC_{50}$s were calculated using the GraphPad Prism software package (version 6).

Triacylglycerol Accumulation Analysis

CDC1551 cultures were seeded at a density of 0.1 OD in 8 mL of 7H9 medium and treated with 40 μM of artemisinin, HC102A, HC103A or DMSO. The cultures were radiolabeled by addition of 80 μCi of [1,2-$^{14}$C] sodium acetate to the culture, which was then grown at 37° C. in vented, standing, T-25 tissue culture flasks. Total lipid was extracted after 6 days incubation and analyzed in thin-layer chromatography (TLC), as previously described (Abramovitch, R. B. et al. *Mol Microbiol* 80, 678-94 (2011)). Total extractable lipid $^{14}$C incorporation was determined in scintillation counter, and 20,000 cpm was loaded for analysis in a 100-cm$^2$ high-performance TLC silica gel 60 aluminum sheet. To analyze triacylglycerol (TAG), the lipids were resolved in hexane-diethyl ether-acetic acid (80:20:1 [vol/vol/vol]) solvent system. The TLC was exposed to a phosphor screen for three days, imaged on a Typhoon imager and quantified by ImageJ (Schneider, C. A. et al. *Nat Methods* 9, 671-5 (2012)). The experiment was repeated with two biological replicates with similar results.

NRP Survival and Antibiotic Tolerance Assays

The hypoxic shift down assay was used as a model for NRP and performed as previously described (Mak, P. A. et al. *ACS Chem Biol* 7, 1190-7 (2012)). CDC1551 or Erdman cultures were pelleted and resuspended in Dubos medium at OD of 0.25, and inoculated in 24-well plates (1 mL/well). In the experiments presented in FIG. 3, Panel B, cells were treated with 40 μM artemisinin, HC102A or HC103A or equal volume of DMSO, and incubated in an anaerobic chamber (BD GasPak™) for 12 days. Cultures become anaerobic within 48 hours incubation as indicated by methylene blue turning to colorless, and consequently day 0 is considered after 48 hours of incubation. Bacteria were plated on solid medium to enumerate CFUs at day 0 and day 10. Percent viability was determined by comparing surviving bacteria at day 10 relative to day 0. Experimental conditions were examined with three biological replicates and error bars represent the standard deviation from the mean. The dose response experiments (FIG. 3, Panel C and FIG. 10, Panel B) were performed as described above with Mtb CDC1551 using an 8-point dose response covering 1-100 μM and a DMSO control. CFUs were enumerated at day 10 and day 15 and percent viability was determined relative to the DMSO control at day 10 or day 15. The INH tolerance assays (FIG. 3, Panel D and FIG. 10, Panel C) were performed as described above with the following modifications. Mtb Erdman was pretreated with 20 or 40 μM artemisinin, HC102A or HC103A for 2 days in the hypoxic shift down assay and then the anaerobic chamber was opened and the cells were treated again with 20 or 40 μM artemisinin, HC102A or HC103A (for a total treatment of 40 or 80 μM). The cells were also treated with 1, 5 or 25 M INH or a DMSO control. The cells were incubated in the anaerobic chamber for 10 or 15 days and CFUs were enumerated by plating on solid medium. To quantify INH tolerance, percent viability at 1, 5 and 25 μM INH was measured relative to the 0 μM INH control (DMSO control). These experiments were repeated at least twice with similar results.

DosS and Dos T Protein Purification

The dosS (Rv3132c) and dosT(Rv2027c) genes were amplified from Mtb genomic DNA by PCR and cloned into the expression vector pET15b (Novagen Darmstadt, Germany). The DosS E87L and G117L substitutions and DosT G85L and G115L mutants were generated using the Quick-Change site directed mutagenesis approach (Agilent) and confirmed by sequencing. The resulting constructs were confirmed by DNA sequencing. DosS/T protein expression in *E. coli* BL21(DE3) and purification via Co$^{2+}$ column were performed as previously described (Podust, L. M. et al. *Biochemistry* 47, 12523-31 (2008)). Briefly, the His6-DosS or His6-DosT were expressed in *E. coli* BL21(DE3) supplemented with hemin (30 mg/L) and induced by isopropyl 1-thio-β-D-galactopyranoside (IPTG, 1 mM) at 18° C. for 20 h. Cell pellet was suspended in lysis buffer (50 mM sodium phosphate (pH 7.6), 10% glycerol, 200 mM sodium chloride, 1% Triton X-100, 0.5 mg/mL lysozyme, 0.1 mg/mL PMSF). The cell suspension was incubated with shaking at 37° C. for 0.5 h and then sonicated. Soluble extract was applied to a Co$^{2+}$ column (Clontech) and washed with washing buffers (with or without 20 mM imidazole in 50 mM sodium phosphate (pH 7.6), 10% glycerol, 500 mM sodium chloride). The recombinant proteins were eluted with 200 mM imidazole in the same buffer. The fractions containing the purified proteins were pooled together and dialyzed in 20 mM Tris-HCl, pH 7.5.

UV-Visible Spectroscopy Assay and Mass Spectrometry

The absorption spectra of DosS (7.5 μM) and DosT (7.5 μM or 16.9 μM) were analyzed in a stoppered quartz cuvette by a DU800 spectrophotometer (Beckman Coulter). All reagents were degassed with argon in a sealed cuvette or vial prior to use. Proteins were also degassed, and then treated with 400 μM dithionite (DTN). The UV-Visible spectra were recorded before and after DTN treatment. Lastly, different concentration of artemisinin or equal volume of DMSO was added to the reaction. The kinetic changes in the absorption spectra were recorded for 2 h. For mass spectroscopy (MS) analysis, the proteins were subjected to pepsin digestion at 37° C. for 30 min after the assay, and then analyzed by liquid chromatography MS (LC-MS). Sample analysis was carried out on Waters Xevo G2-XS QTof mass spectrometer (Milford, Mass., USA) with an electrospray ionization positive mode. The parameters were: capillary voltage, 3 kV; sampling cone, 40 V; source temperature, 100° C.; desolvation temperature, 350° C.; cone gas flow, 25 L/Hr; desolvation gas flow, 600 L/Hr. Chromatographic separation was done in Waters ultra-performance liquid chromatograph (ACQUITY UPLC) system equipped with a Waters BEH C18 column (1.7 μM, 100×2.1 mm). The column temperature was kept at 30° C. Solvents were (A) 0.1% (vol) folic acid in water, and (B) acetonitrile. The flow rate was 0.2 mL/min with following gradient: A/B=99/1 to A/B=70/30 in 8 minutes, then A/B=1/99 for 10 minutes, and A/B=99/1 for last 2 minutes. The acquisition mass range was 200-2,000 Da. The retention time for heme and heme-artemisinin adducts was between 10-11 min. The experiment was repeated with at least two biological replicates with similar results.

DosS and DosT Autophosphorylation Assay

The in vitro phosphorylation assays were performed as previously described (Roberts, D. M. et al. *J Biol Chem* 279, 23082-7 (2004)). Briefly, 4 μL reaction contained 0.2 μg/μL purified DosS or DosT protein, 100 mM Tris-HCl, pH 8.0, 50 μM KCl$_2$, 5 μM MgCl$_2$ and 2.5 μCi/μL [γ-$^{32}$P] ATP (6000 Ci/mmol, PerkinElmer Life Science). The proteins were treated with a 9 or 10 point dose response curve of HC102A or HC103A and the reaction was incubated at RT for 1 hour. All aliquots were analyzed in 4-12% gradient SDS-PAGE (Bio-Rad), and blotted to PVDF membrane. The blot was exposed to phosphor screen overnight and quantified by ImageJ (Schneider, C. A. et al. *Nat Methods* 9, 671-5

(2012)). The experiment was repeated with three biological replicates with similar results.

Chemical Synthesis of HC102A (CCG-232500) and HC103A (CCG-257424)

Powdered samples of commercially sourced HC102A and HC103A were analyzed by mass spectroscopic and combustion analysis and found to have a molecular formula consistent with the reported structures. 2D-NMR analysis confirmed HC102A to be the racemic (5S,9R)-7,7,9-trimethyl-1,3-diazaspiro[4.5]decane-2,4-dione (alpha) isomer. For HC102A synthesis (generating a compound designated CCG-232500), a mixture of 3,3,5-trimethylcyclohexan-1-one (1.1 g, 7.6 mmol) was treated with sodium cyanide (0.92 g, 18.8 mmol), and carbonic acid, diammonia salt (3.6 g, 37.5 mmol). EtOH (10 mL) and water (10 mL) were added and the resulting mixture was heated to 55° C. for 6 hours. The mixture was cooled and then diluted with cold water, treated with conc. HCl (2 mL) and filtered. The collected solid was washed with water (2x) and triturated in hot methanol. The resulting solid was collected by filtration and dried under high vacuum overnight at room temp. (5S,9R)-7,7,9-trimethyl-1,3-diazaspiro[4.5]decane-2,4-dione was obtained as a white solid (0.53 g, 2.5 mmol, 32%). HPLC system A ($t_R$=5.6 min). $^1$HNMR (400 MHz, DMSO-d6) δ 10.63 (s, 1H), 8.09 (s, 1H), 1.83 (d, J=9.3 Hz, 1H), 1.44 (dd, J=13.3, 7.1 Hz, 2H), 1.32 (dd, J=32.7, 13.7 Hz, 2H), 1.14 (t, J=12.9 Hz, 1H), 0.96 (s, 3H), 0.92-0.62 (m, 7H). ESI-MS m/z 209.1 (M−H+). For HC103A synthesis (generating a compound designated CCG-257424), first 3-amino-N-(3-hydroxyphenyl)benzamide was synthesized. To a solution of 3-aminobenzoic acid (1 g, 7.3 mmol), 3-aminophenol (0.88 g, 8.0 mmol) and HOBT (1.3 g, 8.7 mmol) in dry DMF cooled to 0° C. was added EDC (1.6 g, 8.75 mmol). The resulting solution was allowed to warm to room temperature and stirred overnight. The reaction was diluted with water and washed with satd. NaHCO$_3$, satd. NaCl solution and dried over MgSO$_4$. After filtration, the organic layer was concentrated in vacuo and purified by flash chromatography. (CombiFlash, CH$_2$Cl$_2$/MeOH gradient). 3-amino-N-(3-hydroxyphenyl)benzamide was obtained as an amorphous solid (0.24 g, 7.29 mmol, 14.4% yield). $^1$H NMR (400 MHz, DMSO-d6) (Rotomers) δ 10.18 (m, J=51.4, 10.6 Hz, 1H), 9.90 (s, 1H), 9.35 (m, 2H), 8.25 (s, 1H), 7.95 (m, 1H), 7.83-7.34 (m, 2H), 6.82-6.32 (m, 2H). 5.2 (s, 2H). To synthesize CGC257424, to a solution of 3-amino-N-(3-hydroxyphenyl)benzamide (0.2 g, 0.87 mmol), EDC (0.20 g, 1.1 mmol), and HOBT (0.16 g, 1.0 mmol) in dry DMF cooled to 0° C. was added thiophene-2-carboxylic acid (0.12 g, 0.96 mmol) followed by catalytic DMAP. The resulting solution was allowed to warm to room temperature and stir overnight. The reaction was diluted with water and washed with satd. NaHCO$_3$, satd. NaCl solution and dried, MgSO$_4$. The organic layer was filtered and concentrated in vacuo. Flash chromatography (CH$_2$Cl$_2$/MeOH) was used to obtain N-(3-((3-hydroxyphenyl)carbamoyl)phenyl)thiophene-2-carboxamide as a white solid (0.06 g, 0.17 mmol, 20.2% yield). HPLC system A ($t_R$=5.8 min). $^1$H NMR (400 MHz, DMSO-d6) δ 10.04 (s, 1H), 9.62 (s, 1H), 8.91 (s, 1H), 8.13 (t, J=1.9 Hz, 1H), 8.02-7.90 (m, 2H), 7.59 (d, J=17.2 Hz, 2H), 7.50 (dd, J=4.9, 1.2 Hz, 1H), 7.38-7.29 (m, 2H), 7.11-6.97 (m, 2H), 6.47 (dt, J=8.3, 1.4 Hz, 1H). ESI-MS m/z 339.0 (M+H+).

Starting materials were purchased from Fisher, Sigma-Aldrich Lancaster, Fluka or TCI-America and were used without purification. All reaction solvents were purchased from Fisher and used as received. Reactions were monitored by TLC using precoated silica gel 60 F254 plates. Silica gel chromatography was performed by flash chromatography using silica gel (220-240 mesh) obtained from Silicycle or via MPLC on a CombiFlash instrument. NMR spectra were recorded on a Varian 400 MHz spectrometer. Chemical shifts are reported in δ (parts per million), by reference to the hydrogenated residues of deuterated solvent as internal standard CDCL$_3$: δ=7.28 ($^1$H NMR). Mass spectra were recorded on a Micromass LCT time-of-flight instrument utilizing the electrospray ionization mode. The purity of the compounds was assessed via analytical rpHPLC with a gradient of 10% acetonitrile/water to 90% acetonitrile/water over 6 minutes ("System A", C18 column, 3.5 um, 4.6×100 mm, 254 nm µ).

Structural Modeling of DosT and the G85L and G115L Substituted Proteins

Modeling of DosT was performed using the Molecular Operating Environment (MOE) software (Montreal, Canada). The structure for DosT (2VZW) was downloaded from the RCSB protein data bank. For DosT images, all of Chain B and its associated water molecules were deleted. For Chain A, all water molecules and the acetic acid were deleted. Heavy atoms were fixed and hydrogen atoms relaxed with energy minimization to a gradient of 0.001. Good parameters do not exist for the heme group. Sets were defined for the protein, heme, iron, and oxygen (O$_2$ ligand). Carbon atoms making up the heme were colored yellow. The iron atom of the heme was colored green as a large sphere. The oxygen atoms of the oxygen group were hidden from view in all of the remaining MOE files and pictures. Residues 85 and 115 were labeled and colored purple with heavy bonds. A "Molecular Surface" was created on the protein only. The surface was colored by electrostatics using Posson-Boltzmann to compute the electrostatic field. The iron atom of the heme can be seen down the narrow gorge.

Example 2. Results

Identification and Validation of DosRST Regulon Inhibitors

A whole-cell phenotypic high throughput screen was conducted to identify small molecule inhibitors of DosRST. The CDC15 51 (hspX':GFP) fluorescent reporter strain was previously reported to exhibit DosR-dependent GFP fluorescence that is induced by hypoxia and NO (Tan, S. et al. *PLoS Pathog* 9, e1003282 (2013)). Notably, the reporter is strongly induced under conditions of mild hypoxia (e.g. 2% O$_2$) where Mtb is capable of robust growth (Tan, S. et al. *PLoS Pathog* 9, e1003282 (2013)). dosR mutant strains grow well in rich medium until oxygen is almost fully consumed (Boon, C. et al. *J Bacteriol* 184, 6760-7 (2002); Leistikow, R. L. et al. *J Bacteriol* 192, 1662-70 (2010)), therefore, discovery of compounds that inhibit hypoxia-inducible reporter fluorescence, but leave growth unaffected, may be inhibitors of the DosRST pathway. To discover inhibitors of the DosRST regulon, the CDC1551(hspX': GFP) reporter strain was used to screen a 540,288 compound library. The reporter strain was grown in rich medium with individual compounds (at a screening concentration of ~10 µM) in 384-well plates and incubated for 6 days. Growth of Mtb causes the consumption of oxygen and promotes hypoxic conditions at the bottom of the well. GFP fluorescence and growth (as measured by optical density) were measured after 6 days incubation. For analysis of hits, fluorescence and growth inhibition were normalized at 100% or 0% inhibition based on rifampin and DMSO controls, respectively. The Z-factor for the screen was 0.9 and the variation of controls was limited (FIG. 7, Panels A and B) supporting that the screen was robust. Hits were then distinguished based on their ability to specifically inhibit reporter fluorescence or as general inhibitors of Mtb growth. Putative DosRST pathway inhibitors were defined as compounds that exhibit >1.5 fold higher fluorescence inhibition as compared to growth inhibition (p<0.0003, FIG. 7, Panel C) with at least 35% fluorescence inhibition (Class 1 inhibitors, FIG. 1, Panel A). Fresh powders of several putative DosRST inhibitors were obtained and tested in secondary assays to confirm activity, and exclude compounds with GFP quenching activity and eukaryotic cytotoxicity. Six distinct scaffolds named HC101-HC106 (FIG. 1, Panel B) were confirmed as inhibitors of reporter fluorescence, while exhibiting no GFP quenching activity and limited eukaryotic cytotoxicity (e.g. $EC_{50}$>70 µM for eukaryotic cytotoxicity in murine bone marrow derived macrophages, FIG. 14).

Figure 1:
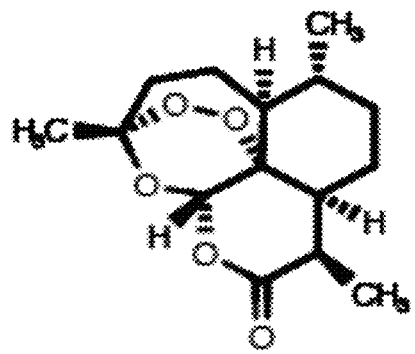
Figure 1:
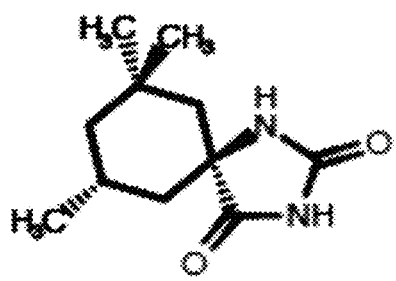
Figure 1:
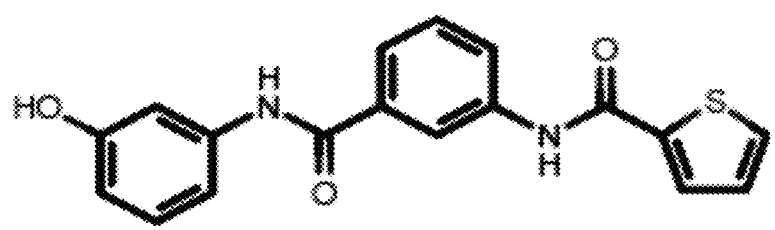
Figure 1:
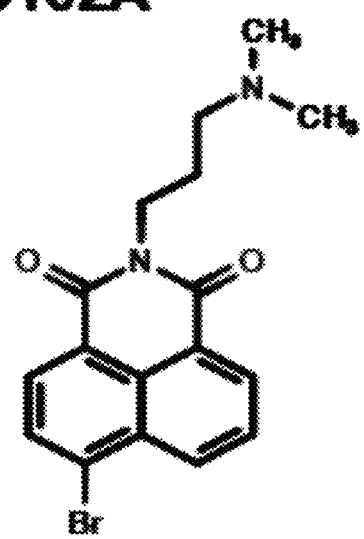
Figure 1:
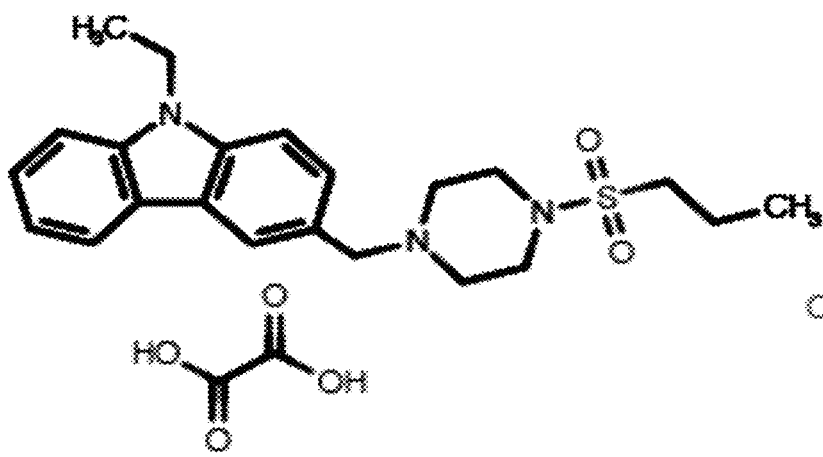
Figure 1:
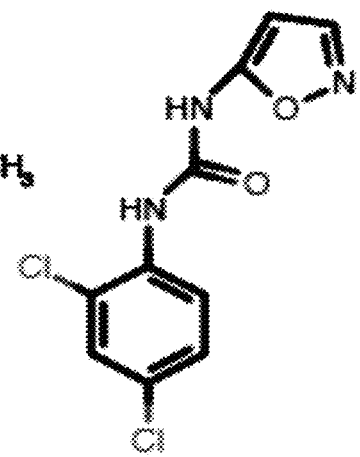
Figure 1C:
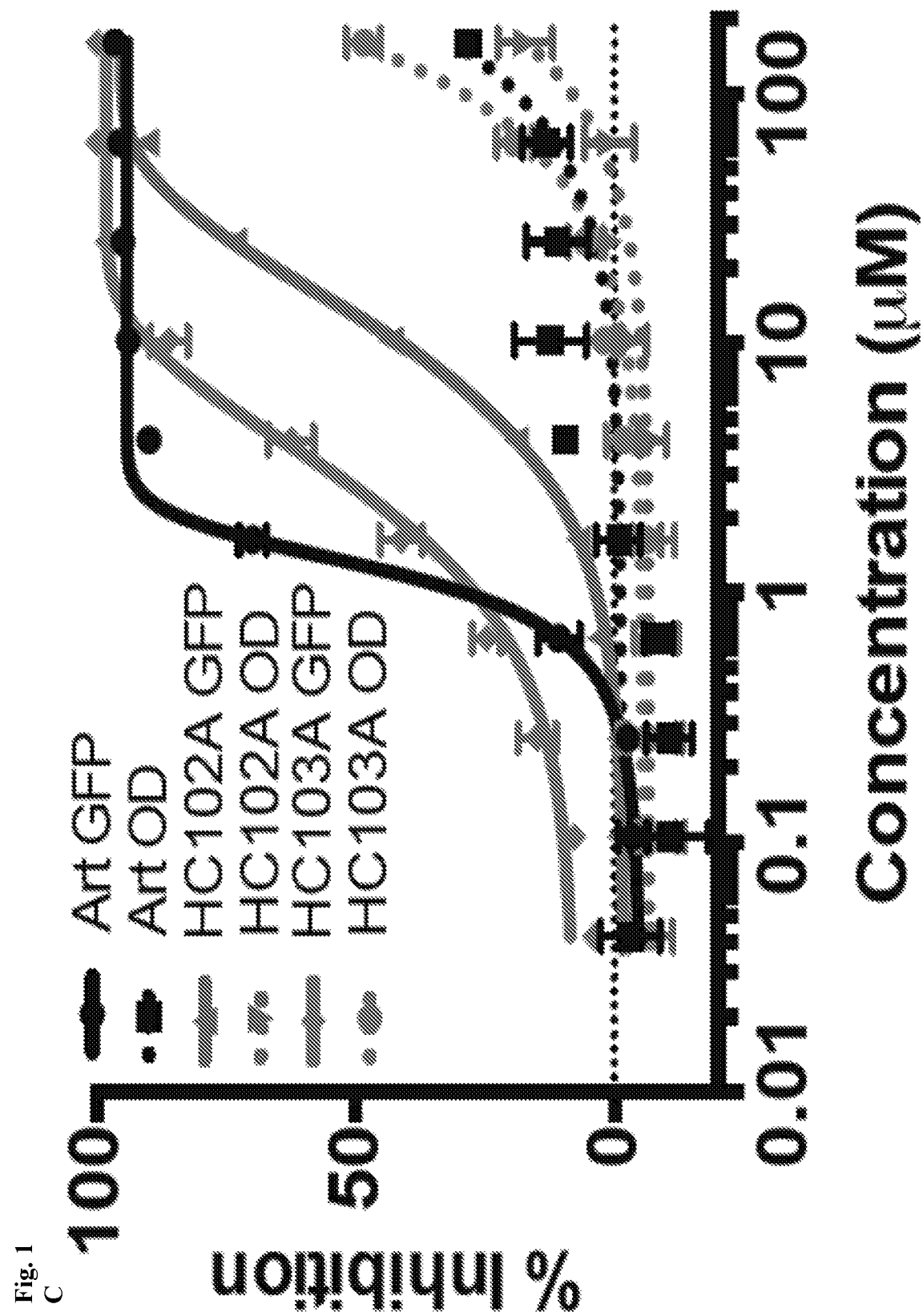
Figure 8:
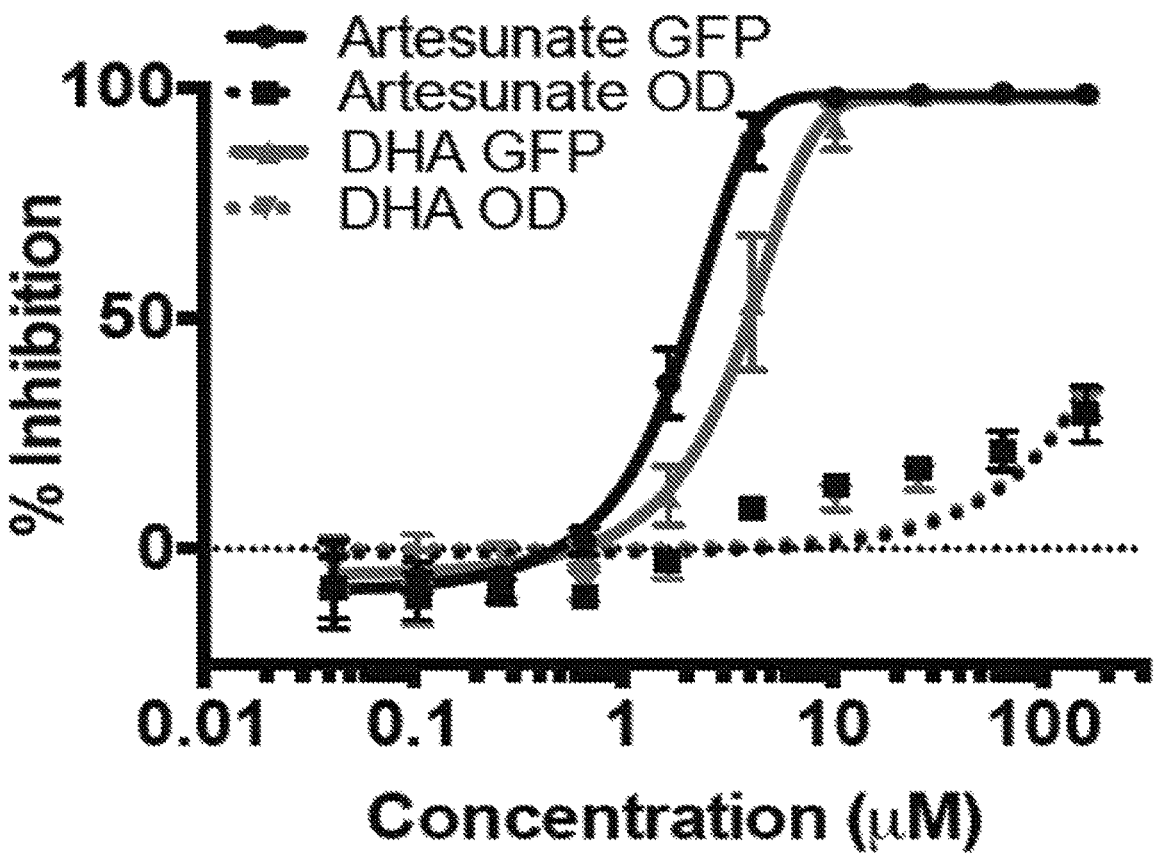
FIG. 8 includes four panels, A-D, and depicts identification of inhibitors of the DosRST pathway. Dose response curves of GFP fluorescence inhibition of CDC1551(hspX': GFP) reporter treated with DosRST regulon inhibitor compounds. Panel A shows Artemisinin analogs, artesunate and dihydroartemisinin (DHA). Panel B shows HC103B and HC104A-HC106A. Panel C shows HC102A generated by organic synthesis (CCG-2323500). Panel D shows HC103A generated by organic synthesis (CCG-257424). Error bars represent the standard deviation and experiments were repeated at least twice with similar results.
Figure 8:
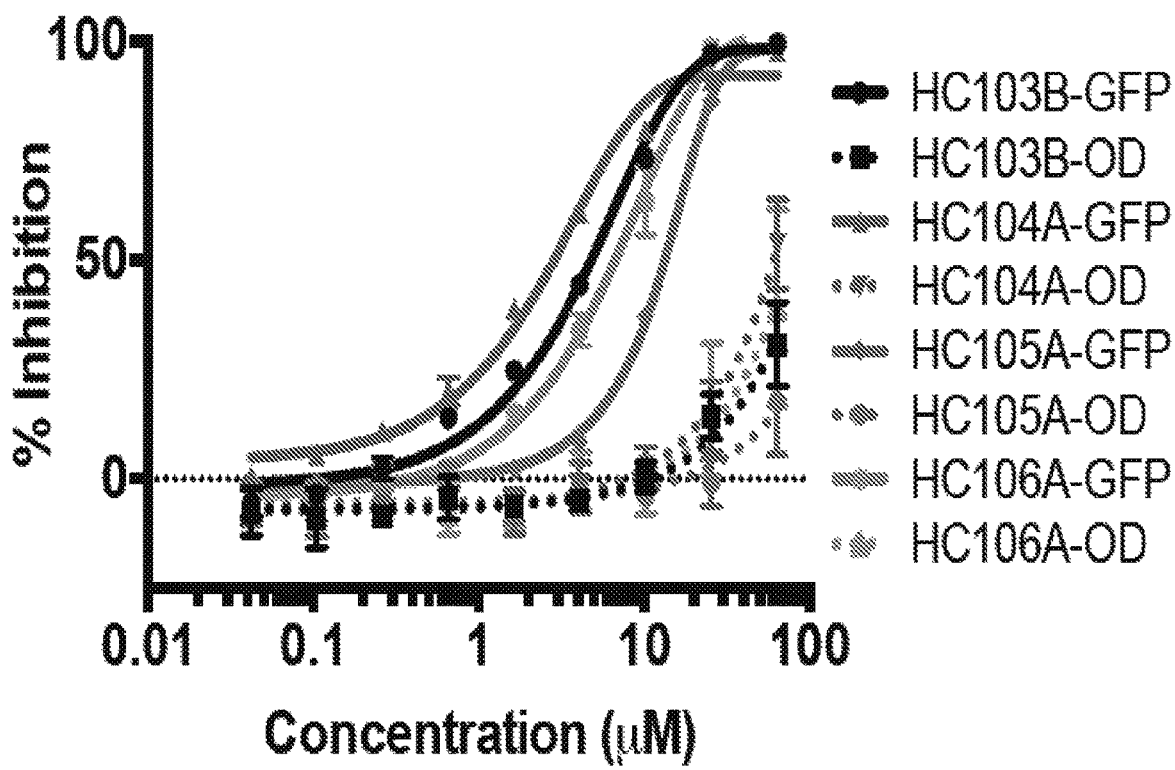
Figure 8:
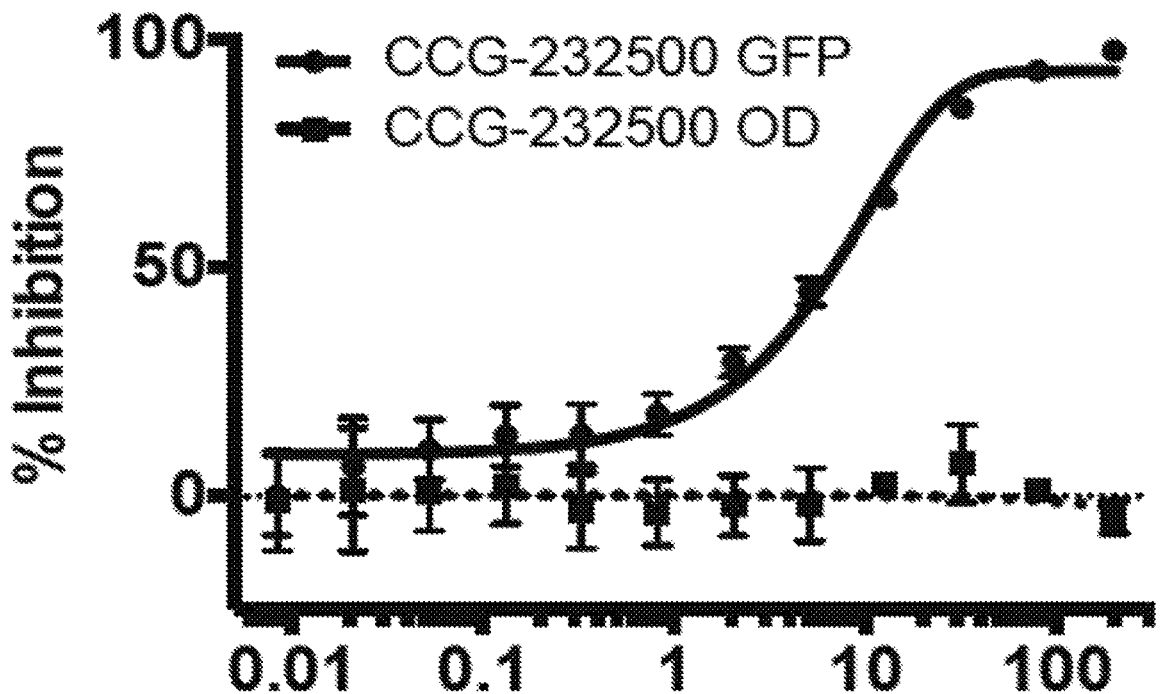
Figure 8:
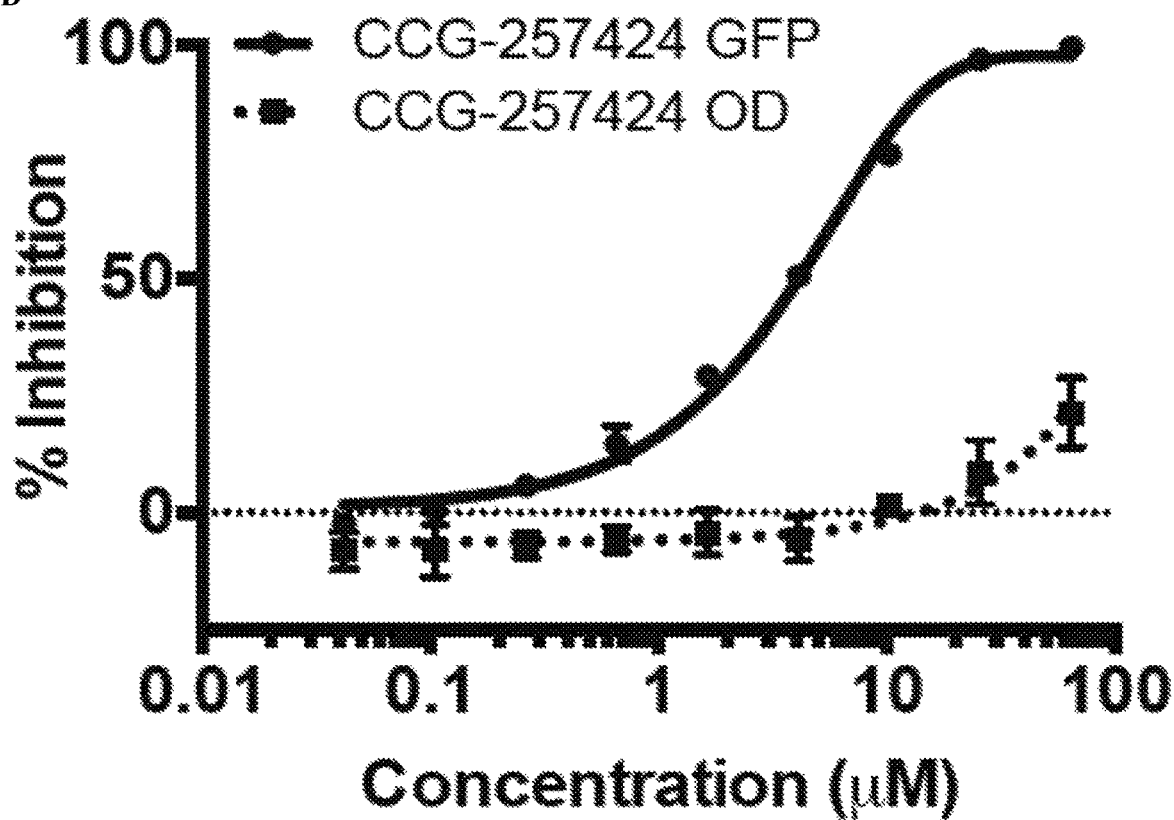

The most frequently identified scaffold from the primary screen was the first-line antimalarial natural product artemisinin (HC101A) and its analogs artemether, artesunate and dihydroartemisinin (DHA, FIG. 1, Panel A). This scaffold was identified as nine independent hits in the screen. Artemisinin and its analogs inhibit CDC1551(hspX':GFP) reporter fluorescence with an $EC_{50}$ ranging from 1.2-3.7 µM (FIG. 1, Panel C; FIG. 8, Panel A; and FIG. 14), while the growth inhibition $EC_{50}$ is >80 µM, indicating a limited impact on growth. HC102A (diazospiro[4.5]decane small molecule (7,7,9-trimethyl-1,3-diazaspiro[4.5]decane-2,4-dione)) was isolated as a singleton and inhibits dosR-dependent GFP fluorescence with an $EC_{50}$ of 12.4 µM, while not inhibiting Mtb growth (e.g. a growth inhibition $EC_{50}$>80 M). HC103A (N-[3-[(3 hydroxyphenyl)carbamoyl]phenyl] thiophene-2-carboxamide) and the analog HC103B inhibit dosR-dependent GFP fluorescence with an $EC_{50}$ of 2.7 µM and 5.0 M, respectively (FIG. 1, FIG. 8, Panel B) while not inhibiting growth (e.g. a growth inhibition $EC_{50}$>80 M). HC104A (6-bromo-2-[3-(dimethylamino)propyl]benzo[de] isoquinoline-1,3-dione), HC105A (9-ethyl-3-[(4-propylsulfonylpiperazin-1-yl)methyl]carbazole; oxalic acid) and HC106A (1-(2,4-dichlorophenyl)-3-(1,2-oxazol-5-yl)urea) inhibit dosR-dependent GFP fluorescence with $EC_{50}$ of 2.8 M, 12.7 µM and 6.9 µM respectively, while not inhibiting Mtb growth (e.g. a growth inhibition $EC_{50}$>80 M; FIG. 8, Panel B; FIG. 14). Artemisinin, HC102A and HC103A were selected for proof-of-concept follow-up experiments characterizing their ability to inhibit dosRST signaling. Both HC102A and HC103A were regenerated by organic synthesis and confirmed to have the activity of the commercially sourced compounds, thus confirming the assigned structures as the active structures (FIG. 8, Panels C and D).

The DosRST regulon is strongly induced by hypoxia and nitric oxide and composed of ~50 genes that are directly regulated by DosR (Park, H. D. et al. *Mol Microbiol* 48, 833-43 (2003)). An additional >100 genes are also differentially expressed in a dosR mutant, possibly due to weak binding by DosR or indirect consequences of misregulated DosR regulon genes (Galagan, J. E. et al. *Nature* 499, 178-83 (2013)). To investigate the inhibitory mechanism of the compounds, RNAseq-based transcriptional profiling was undertaken on CDC1551 treated with 40 µM artemisinin, HC102A, HC103A or a DMSO control. The cultures were grown in standing flasks where growth causes the consumption of oxygen, and following six days of treatment RNA was isolated, sequenced and analyzed (Johnson, B. K. et al. *BMC Bioinformatics* 17, 66 (2016)) (Tables 2-4; Tables 2-4 are provided here; Table 4 is not provided).

Table 2A depicts downregulated gene expression tables of DMSO treated DosR mutant compared to DMSO treated WT (>2 fold, p<0.05). Table 2B depicts upregulated gene expression tables of DMSO treated DosR mutant compared to DMSO treated WT (>2 fold, p<0.05). Table 2C depicts downregulated gene expression tables of WT Mtb treated with HC101A compared to DMSO (>2 fold, p<0.05). Table 2D depicts upregulated gene expression tables of WT Mtb treated with HC101A compared to DMSO (>2 fold, p<0.05). Table 2E depicts downregulated gene expression tables of WT Mtb treated with HC102A compared to DMSO (>2 fold, p<0.05). Table 2F depicts upregulated gene expression tables of WT Mtb treated with HC102A compared to DMSO (>2 fold, p<0.05). Table 3A depicts downregulated gene expression tables of DosR mutant treated with HC101A compared to DMSO (>2 fold, p<0.05). Table 3B depicts upregulated gene expression tables of DosR mutant treated with HC101A compared to DMSO (>2 fold, p<0.05). Table 3C depicts downregulated gene expression tables of DosR mutant treated with HC102A compared to DMSO (>2 fold, p<0.05). Table 3D depicts upregulated gene expression tables of DosR mutant treated with HC102A compared to DMSO (>2 fold, p<0.05). Table 3E depicts downregulated gene expression tables of DosR mutant treated with HC103A compared to DMSO (>2 fold, p<0.05). Table 2F depicts upregulated gene expression tables of DosR mutant treated with HC103A compared to DMSO (>2 fold, p<0.05).

Figure 2:
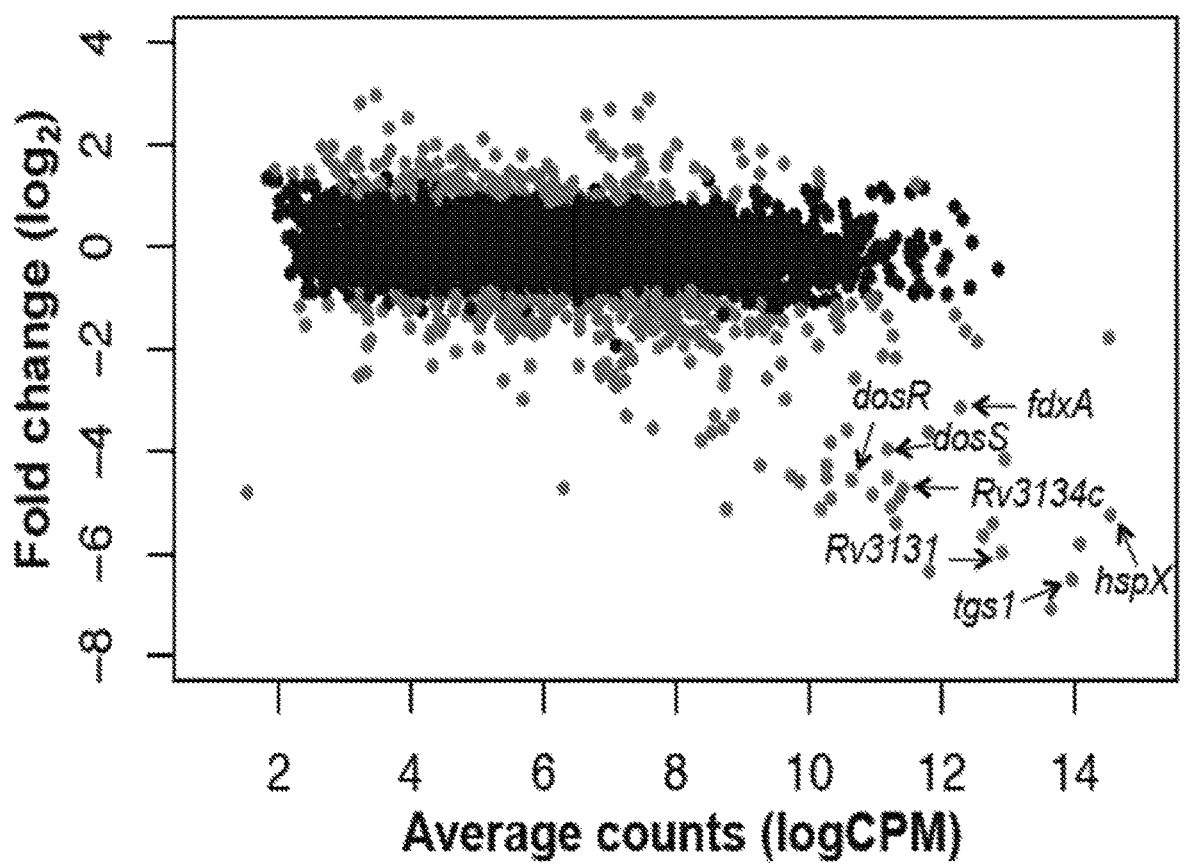
FIG. 2 includes three panels, A-C, and depicts that transcriptional profiling shows that artemisinin, HC102A and HC103A inhibit the core genes of the DosRST regulon during hypoxia. Panel A shows Mtb differential gene expression in response to artemisinin. Genes in red have a p-value<0.05. Indicated gene names include characterized DosR regulated genes. Panel B shows Venn diagram showing genes that are downregulated (>2-fold, p<0.05) in CDC1551 treated with artemisinin, HC102A or HC103A relative to a DMSO treated CDC1551 control. Also shown are genes downregulated (>2-fold, p<0.05) in a DMSO treated CDC1551(ΔdosR) mutant strain relative to a DMSO treated CDC1551 control. Panel C shows Venn diagram showing genes that are downregulated (>2-fold, p<0.05) in a CDC1551((ΔdosR) mutant strain treated with artemisinin, HC102A or HC103A relative to a DMSO treated CDC1551 (ΔdosR) control. The limited genes modulated by HC102A and HC103A support that these compounds are highly specific for the DosR regulon.
Figure 2:
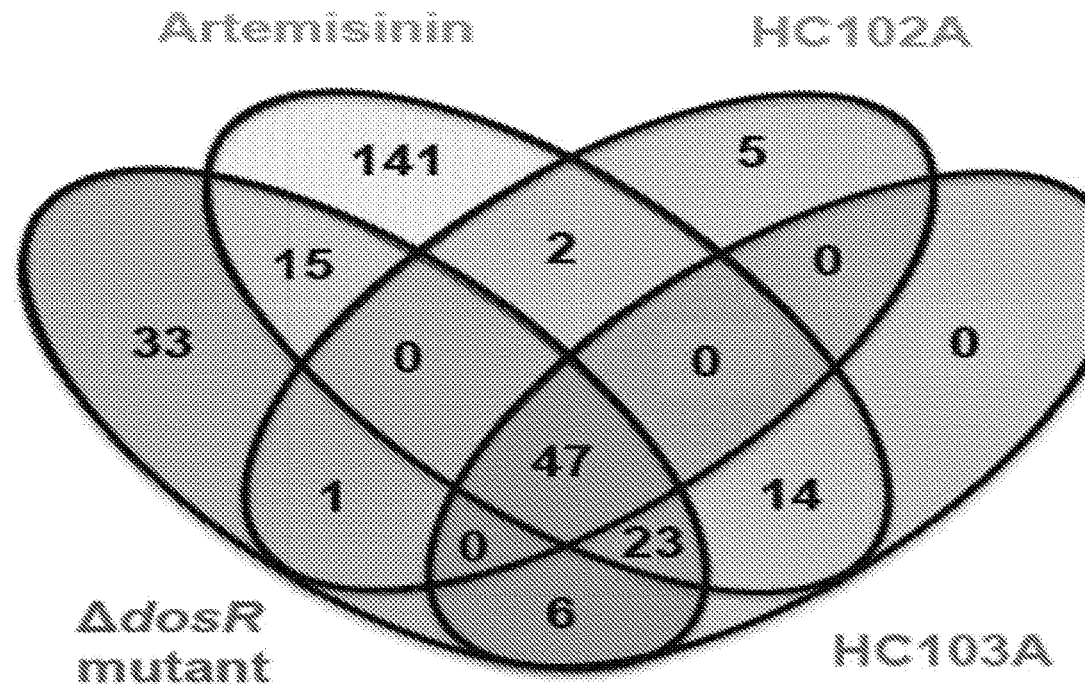
Figure 2:
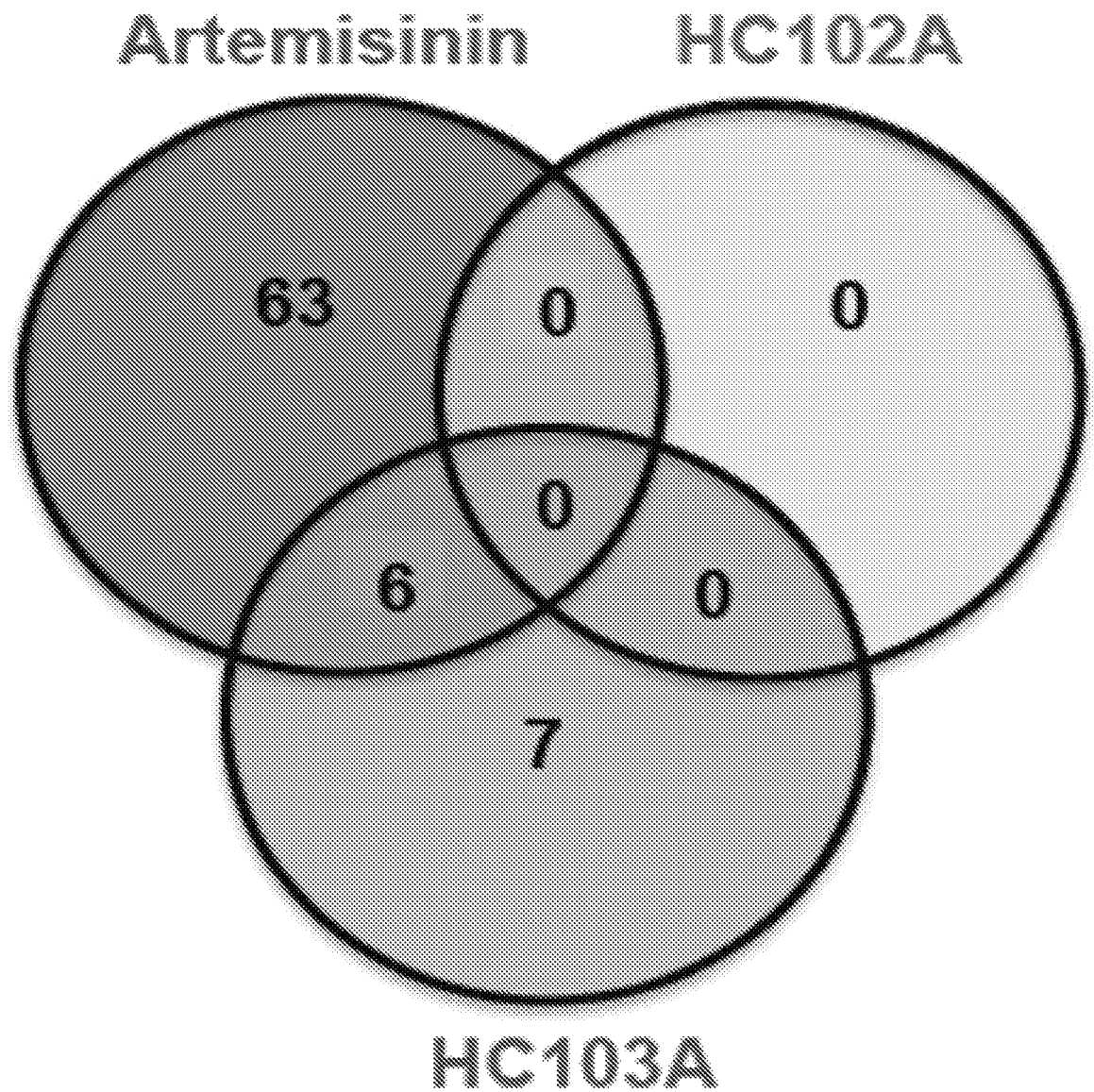
Figure 9:
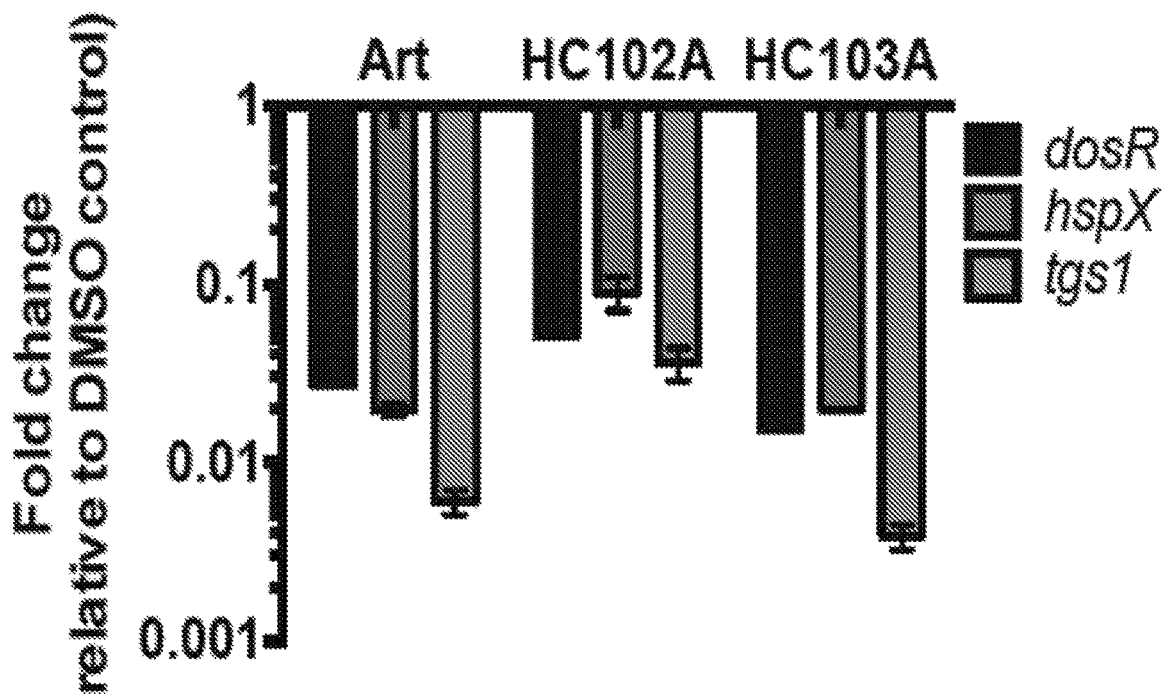
FIG. 9 includes four panels, A-D, and depicts transcriptional profiling shows Artemisinin, HC102A and HC103A inhibit the core genes of the DosRST regulon during hypoxia. Panel A shows inhibition of DosR regulon under hypoxic conditions by the DosR regulon inhibitors. Mtb treated with compounds of interest was grown at 37° C. without shaking for 6 days, and total RNA was extracted for RT-PCR quantification. RT-PCR shows three highly induced DosR regulon genes (dosR, hspX and tgs1) under hypoxia were repressed by the DosR regulon inhibitors. Error bars represent the standard deviation. Panel B shows NO and VitaminC assays. Mtb cells were pre-treated with compounds of interest for 24 hours, and total RNA was extracted after inducing with NO or vitamin C for 2 hours. HC102A and HC103A inhibited the induction of DosR regulon by NO and vitamin C, but DHA had a little effect. In all cases, the difference in the drug treated samples compared to DMSO treated samples in response to vitamin C or NO is significant with a p-value<0.001 based on T-test, except those marked as non-significant (n.s.). Error bars represent the standard deviation. Mtb differential gene expression in response to HC102A (Panel C) and HC103A (Panel D). Genes in red have a p-value<0.05, and indicated gene names are DosR regulated genes. The transcriptional analysis from different assays collectively support that DosR pathway is the target of artemisinin, HC102A and HC103A. Experiments were repeated at least twice with similar results.
Figure 9:
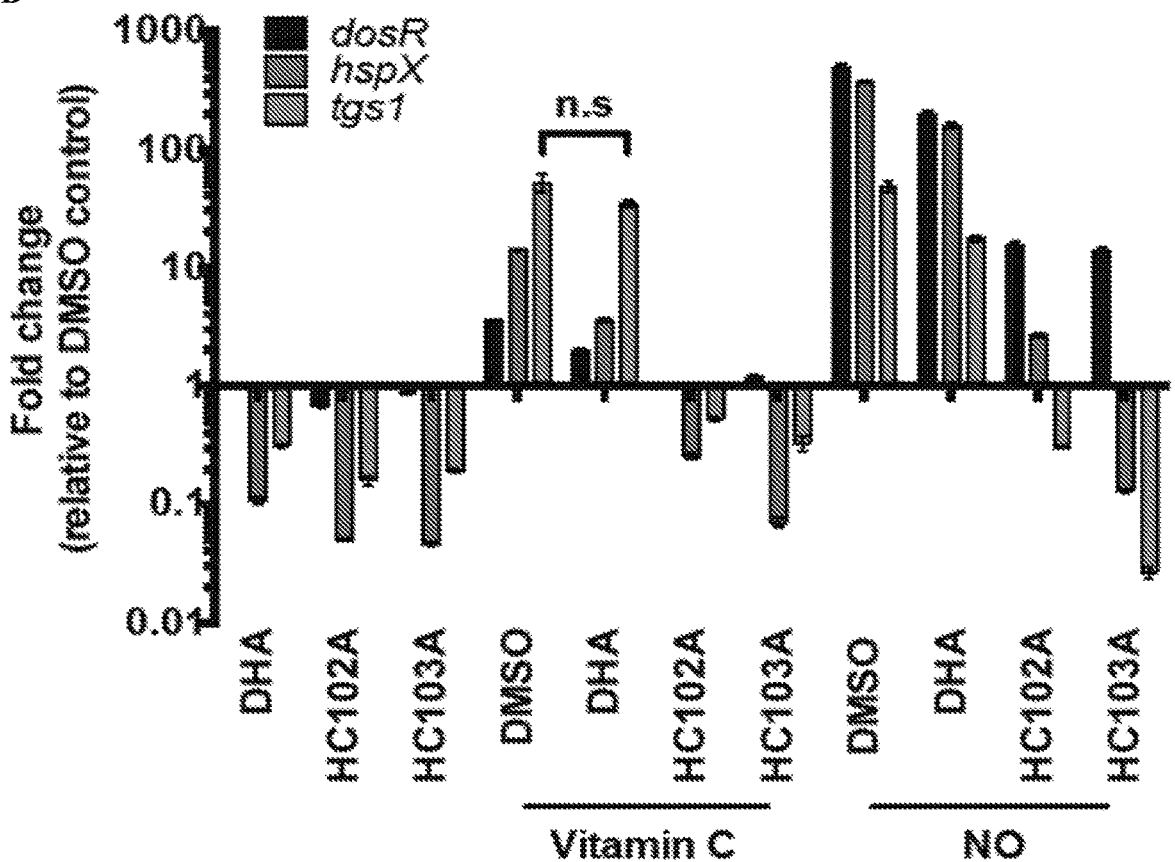
Figure 9:
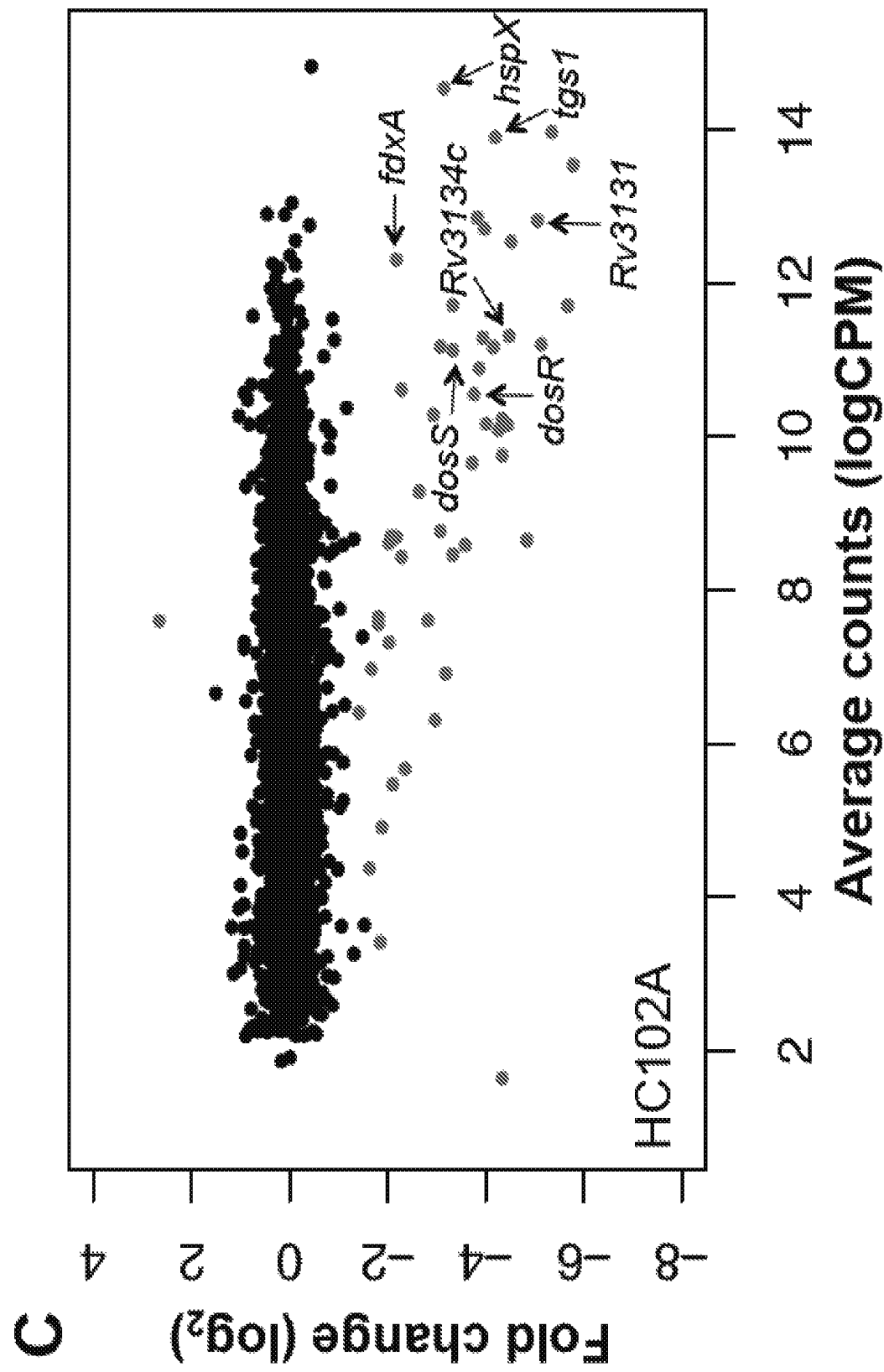
Figure 9:
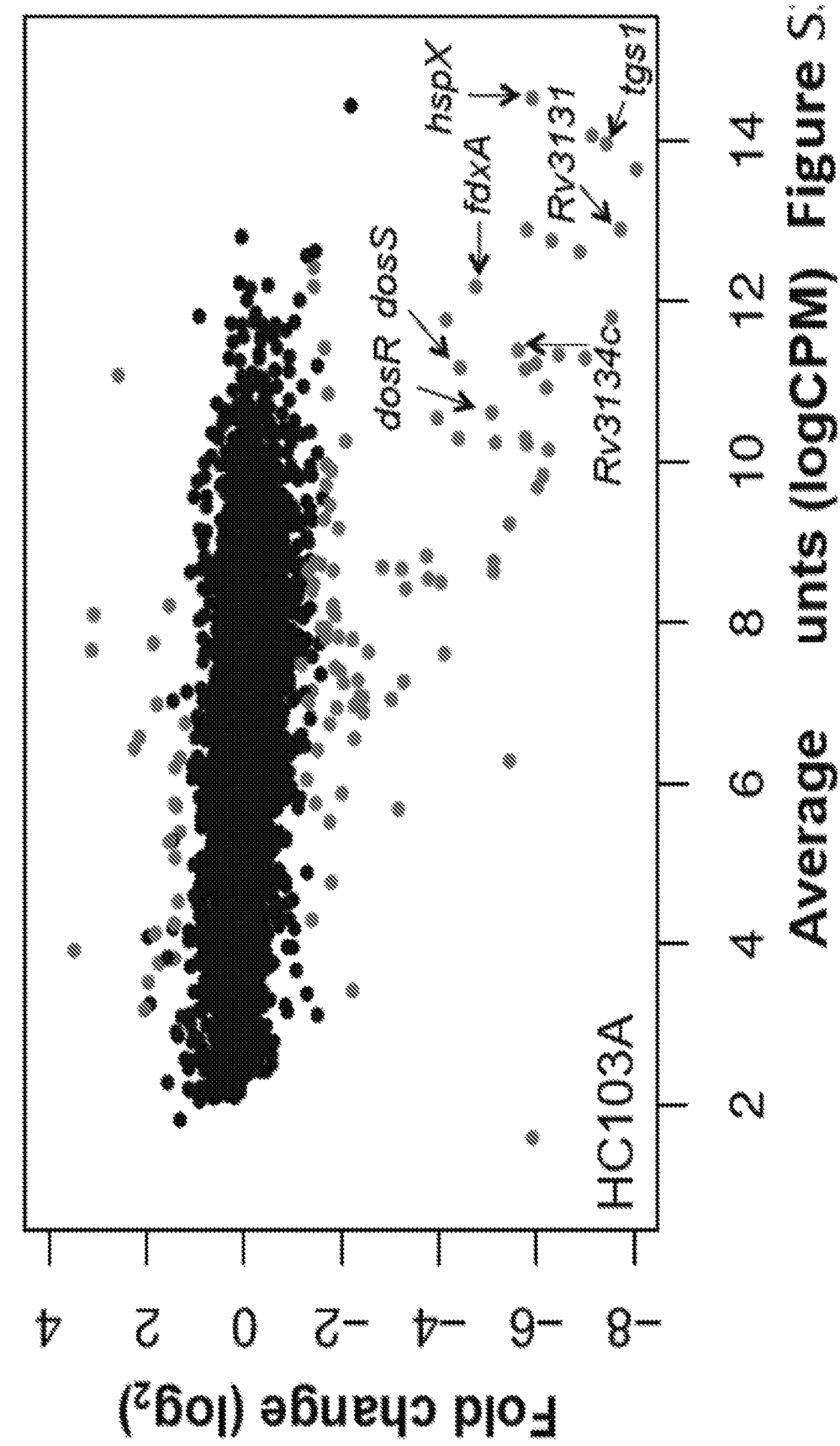

Artemisinin caused the strong downregulation of well-characterized DosR regulon genes, including hspX, fdxA, tgs1, and dosRS (Park, H. D. et al. *Mol Microbiol* 48, 833-43 (2003)) (FIG. 2, Panel A). Real-time PCR confirms the RNA-seq data with hspX, tgs1 and dosRS showing 51-, 166-, and 37-fold inhibition by artemisinin, respectively (FIG. 9, Panel A). Artemisinin inhibited 85 genes (>2-fold, p<0.05) that are also repressed in the CDC1551 (ΔdosR) mutant, accounting for greater than two-thirds of the 125 downregulated genes in the CDC1551(ΔdosR) mutant (FIG. 2, Panel B, Table 2). Notably, artemisinin also inhibited 157 genes that are not modulated in the CDC1551(ΔdosR) mutant, suggesting the drug is also impacting DosRST-independent targets. HC102A and HC103A also inhibited DosRST regulon genes, however, in contrast to artemisinin, HC102A and HC103A showed greater specificity for inhibition of the DosRST regulon; for example, 48 out of 55 genes downregulated by HC102A and 76 out of 90 genes downregulated by HC103A are also downregulated in the CDC1551(ΔdosR) mutant (FIG. 2, Panels B and C, FIG. 9, Panels C and D, Table 2). These transcriptional profiles demonstrate that artemisinin, HC102A and HC103A inhibit induction of the core DosRST regulon.

To further assess the specificity of the compounds for inhibition of the DosRST pathway, a CDC1551 (ΔdosR) mutant was treated with the compounds of interest, with the hypothesis that compounds specific for the DosRST pathway will not modulate gene expression in the CDC1551 (ΔdosR) mutant. The CDC1551(ΔdosR) mutant treated with HC102A or HC103A, exhibited only 0 and 13 downregulated genes, respectively, confirming the on-target specificity of HC102A and HC103A (FIG. 2, Panel C, Table 3). In contrast, the CDC1551(ΔdosR) mutant treated with artemisinin exhibited 69 downregulated genes (FIG. 2, Panel C, Table 3), confirming substantial off-target activity for artemisinin. Overall, these data further support that artemisinin, HC102A and HC103A function to inhibit the core DosRST regulon, with HC102A and HC103A showing strong specificity for the intended target of the DosRST regulon.

The DosRST pathway is also induced by NO and vitamin C (Voskuil, M. I. et al. *J Exp Med* 198, 705-13 (2003);

Kumar, A. et al. *Proc Natl Acad Sci USA* 104, 11568-73 (2007); Taneja, N. K. et al. *PLoS One* 5, e10860 (2010)) and it was examined if the inhibitors could suppress induction of the DosR pathway by these stimuli. CDC1551 was pretreated with DHA, HC102A or HC103A for 1 day prior to induction with NO or vitamin C. As markers for the DosR regulon, the expression of three strongly DosR regulated genes (dosR, tgs1 and hspX) was monitored by real-time PCR. dosR, hspX and tgs1, were strongly upregulated when Mtb was treated with vitamin C or DETA-NONOate (FIG. 9, Panel B). For example vitamin C caused a 4-, 14- and 52-fold induction of dosR, hspX and tgs1, respectively, and NO caused an 491-, 373-, and 47-fold induction of dosR, hspX and tgs1, respectively. Pre-treatment with HC102A or HC103A strongly inhibited the induction of dosR, hspX and tgs1 transcripts in response to both vitamin C and DETA-NONOate. For example, in HC102A and HC103A pretreated cells the tgs1 transcript following treatment with DETA-NONOate is repressed 3-fold and 50-fold, respectively, whereas tgs1 is induced >47-fold in the DMSO pretreated cells. Similarly, in vitamin C treated cells, the tgs1 transcript is repressed 2-fold and 3-fold and in HC102A and HC103A pretreated cells, respectively, while induced >50 fold in the DMSO treated cells. Notably, DHA only weakly inhibited the induction of the DosR regulated genes by NO or vitamin C. In DHA pretreated cells, the dosR, hspX and tgs1 transcripts remain induced by both Vitamin C and DETA-NONOate treatments. Notably, the magnitude of the induction of the transcripts in response to DETA-NONOate is significantly reduced ~2-fold in DHA pretreated cells compared to the DMSO treatment, demonstrating partial inhibition of NO-dependent DosRST signaling by DHA. These data support that HC102A and HC103A act as broad inhibitors of the DosRST regulon in response to both hypoxia and redox environmental cues. In contrast, artemisinin likely acts by a mechanism that is distinct from HC102A and HC103A, given its limited effectiveness to inhibit redox-mediated stimulation of the DosRST regulon.

Artemisinin, HC102A and HC103A Disrupt Persistence-Associated Physiologies

Figure 10:
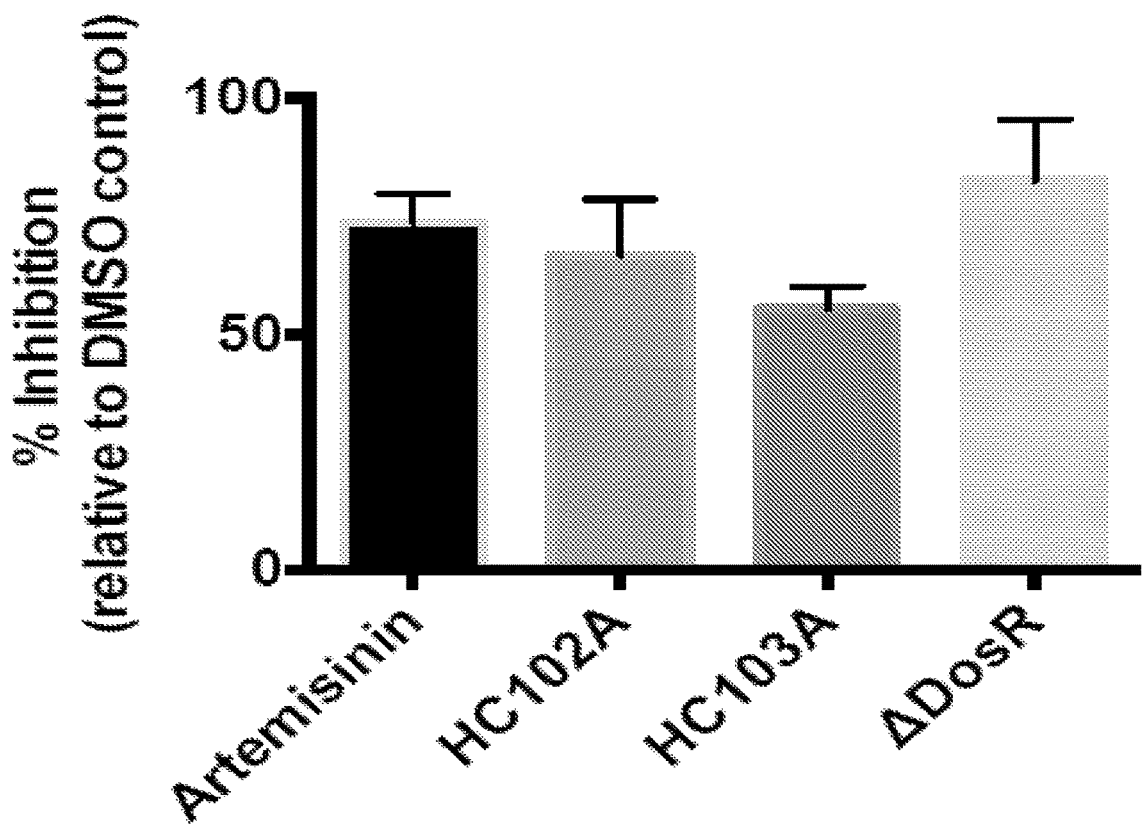
FIG. 10 includes four panels, A-D, and depicts Artemisinin, HC102A and HC103A inhibit TAG synthesis, survival and isoniazid tolerance during NRP. Panel A shows quantification of TAG accumulation for Mtb treated with compounds of interest shows that DosRST regulon inhibitors repress TAG synthesis to the level similar to zdosR mutant. Error bars represent the standard deviation. Panel B shows dose dependent inhibition of Mtb survival during NRP following 15 days of treatment. Percent viability was calculated relative to the viable bacteria in the DMSO control at Day 15. Error bars represent the standard deviation of the mean. Panel C shows fifteen days of treatment with artemisinin, HC102A or HC103A, with or without INH, significantly reduces bacterial survival (p-value<0.05 based on a T-test) during NRP relative to the respective DMSO controls. Panel D shows fifteen days of treatment with artemisinin, HC102A and HC103A reduces isoniazid tolerance during NRP. To quantify INH tolerance, percent viability at 1, 5 and 25 µM INH was measured relative to the 0 µM INH control (DMSO control). Significant differences (marked with an asterisks, p<0.05 based on a T-test) were calculated relative to the respective DMSO control sample. For example, cells treated with 5 µM INH and artemisinin, HC102A and HC103A are significantly different from the DMSO control treated with 5 µM INH. Experiments were repeated at least twice with similar results.
Figure 10:
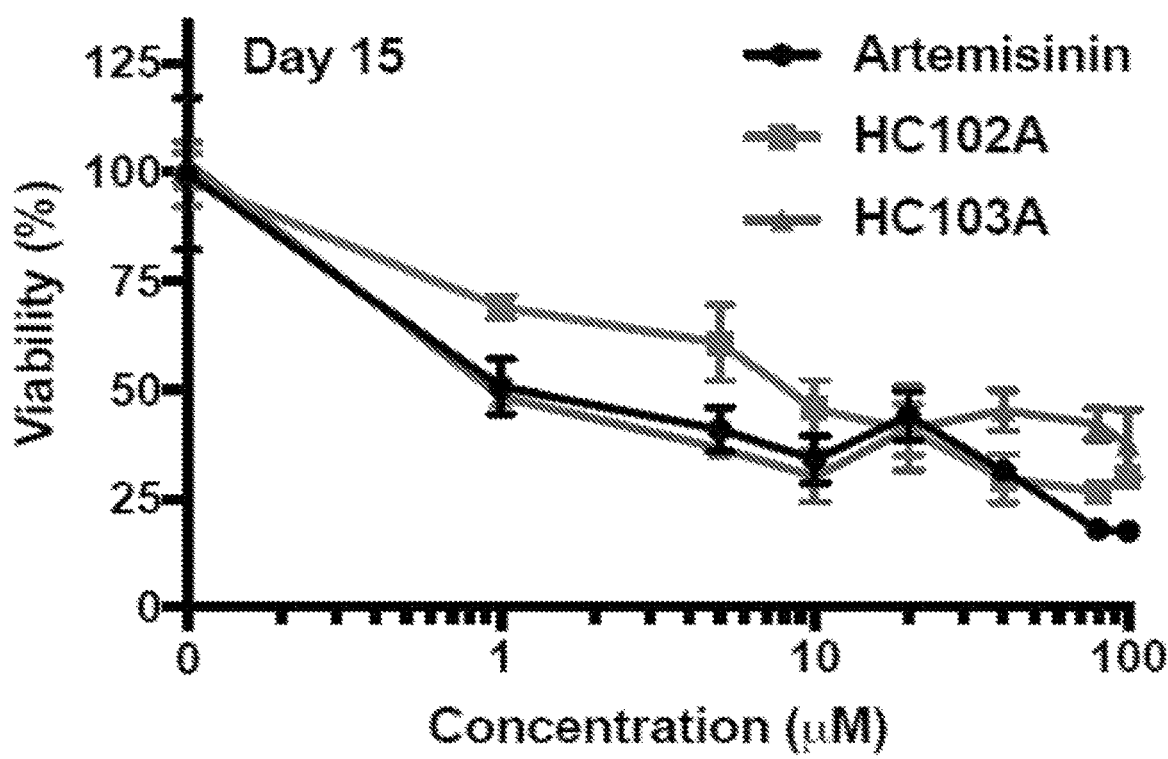
Figure 10:
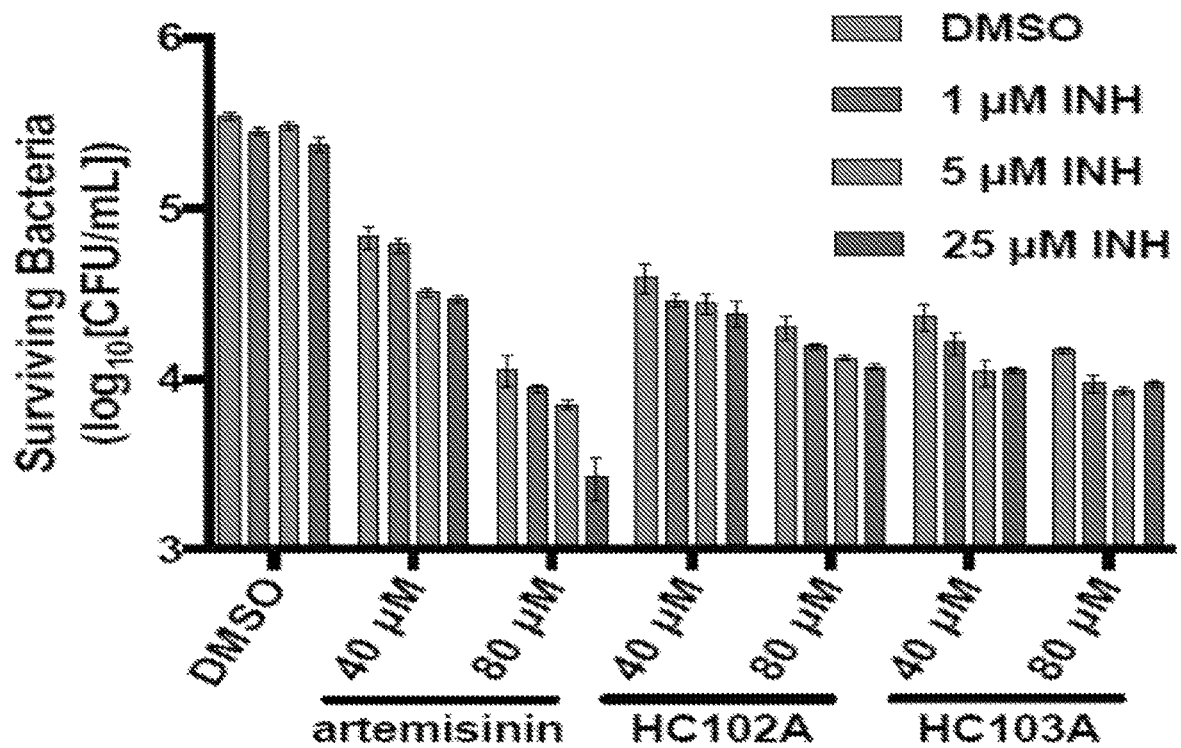
Figure 10:
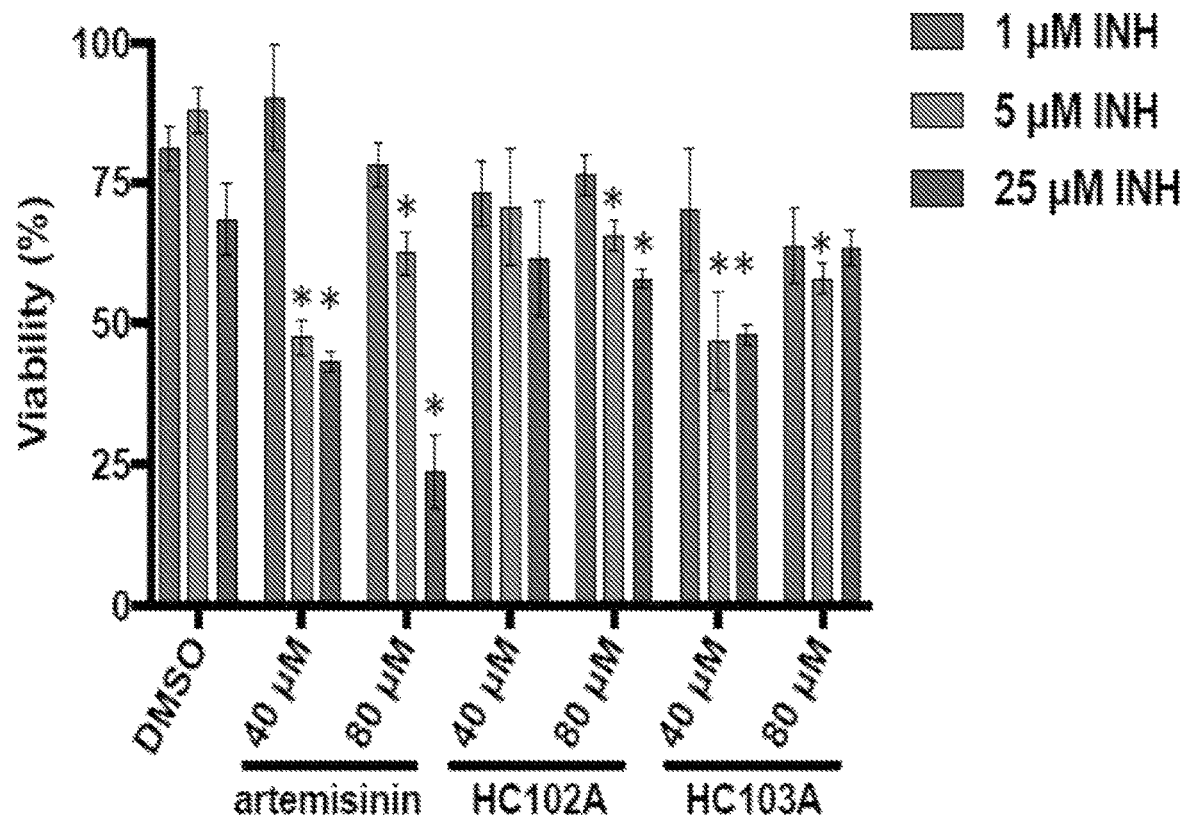

DosRST is required for several persistence-associated physiologies during hypoxia, including triacylglycerol (TAG) synthesis (Wayne, L. G. et al. *Annu Rev Microbiol* 55, 139-63 (2001); Mehra, S. et al. *Am J Respir Crit Care Med* 191, 1185-96 (2015); Johnson, B. K. et al. *BMC Bioinformatics* 17, 66 (2016)) and survival (Leistikow, R. L. et al. *J Bacteriol* 192, 1662-70 (2010)). It was hypothesized that artemisinin, HC102A or HC103A may target these physiologies and compared the activity of the inhibitors to a CDC1551 (ΔdosR) mutant. Transcriptional profiling data in CDC1551 showed that the tgs1 gene, which encodes for the TAG synthase involved in last step of TAG synthesis, is downregulated ~100 fold by artemisinin and ~20 and ~180 fold by HC102A and HC103A, respectively (FIG. 2; FIG. 8, Panel A; Table 2). Therefore, it was hypothesized that CDC1551 treated with artemisinin, HC102A or HC103A would be defective in TAG accumulation. To test this hypothesis, $^{14}$C-labeled lipids were isolated from CDC1551 (ΔdosR) mutant and WT CDC1551 treated with inhibitors or equal volume of DMSO. The lipids were analyzed by thin layer chromatography and quantified. TAG accumulated in the DMSO-treated cells, whereas it was reduced 82% in the CDC1551(ΔdosR) mutant (FIG. 3, Panel A; FIG. 10, Panel A). Treatment with artemisinin, HC102A and HC103A caused a 74%, 67% and 56% reduction in TAG accumulation, respectively (FIG. 3, Panel A; FIG. 10, Panel A), thus providing functional evidence that the inhibitors are impacting persistence-associated lipid metabolism.

Figure 3:
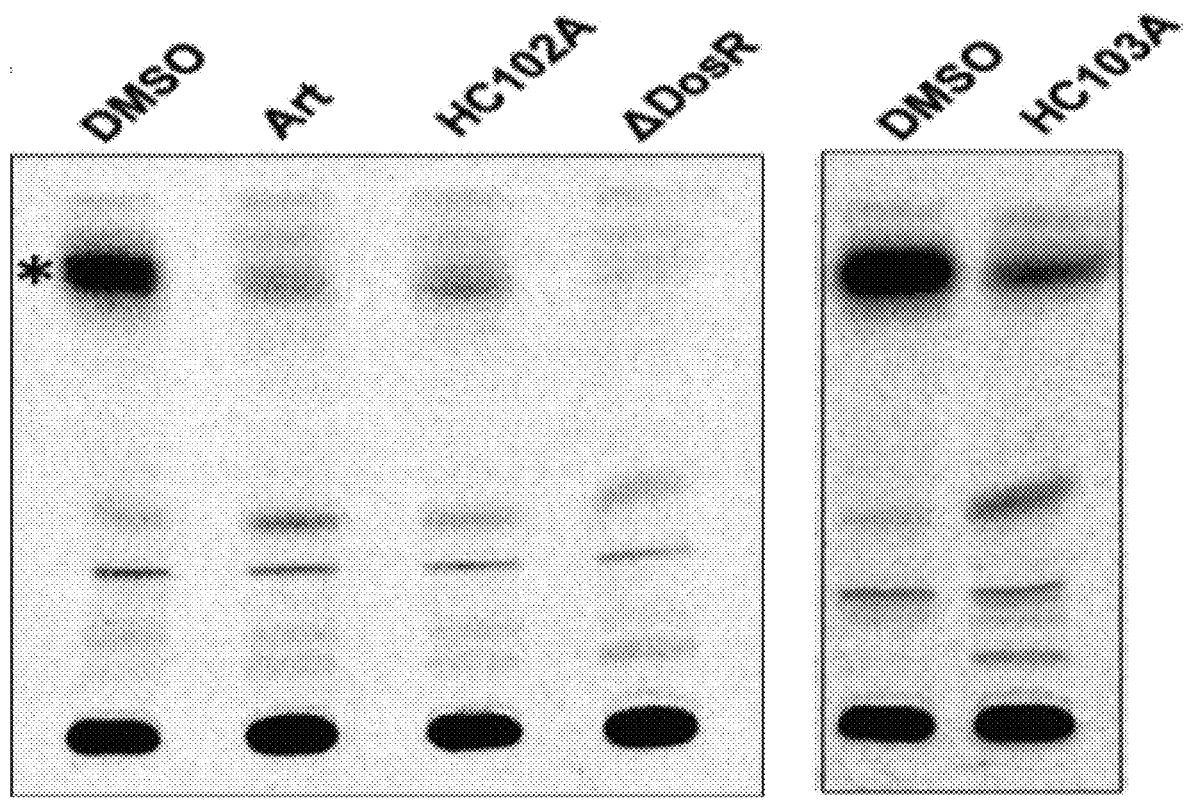
FIG. 3 includes five panels, A-E, and depicts that Artemisinin, HC102A and HC103A inhibit TAG synthesis, survival and isoniazid tolerance during NRP. Panel A shows inhibition of TAG accumulation. CDC1551 treated with compounds of interest (at a concentration of 40 µM) and the CDC1551 (ΔdosR) mutant were radiolabelled with $^{14}$C acetate for 6 days and total lipids extracted and analyzed by TLC. The inhibitors reduce TAG accumulation by 60-70% similar to the CDC1551(ΔdosR) mutant control. The asterisk indicates the position of TAG on the TLC. Panel B shows inhibition of survival during NRP. CDC1551 and Erdman strains were treated with 40 µM of the compounds of interest and NRP was induced using the hypoxic shift down persistence model. Following 10 days of treatment, CFUs were determined and percent survival calculated relative to the WT control at day 0. Error bars represent the standard deviation of the mean. Differences between artemisinin, HC102A and HC103A treated samples as compared to the DMSO treated samples, in both strains, are significant with a p-value<0.05 based on a T-test (marked with an asterisk). Panel C shows dose dependent inhibition of Mtb survival during NRP at day 10. Percent viability was calculated relative to viable bacteria in the DMSO control at day 10. Error bars represent the standard deviation of the mean. Panel D shows ten days of treatment with artemisinin, HC102A or HC103A, with or without INH, significantly reduces bacterial survival (p-value<0.05 based on a T-test) during NRP relative to the respective DMSO controls. Panel E shows ten days of treatment with artemisinin, HC102A and HC103A reduces isoniazid tolerance during NRP. To quantify INH tolerance, percent viability at 1, 5 and 25 µM INH was measured relative to the 0 µM INH control (DMSO control). Significant differences (marked with an asterisk, p<0.05 based on a T-test) were calculated relative to the respective DMSO control sample. For example, cells treated with 5 µM INH and artemisinin, HC102A or HC103A are significantly different from the DMSO control treated with 5 µM INH. Experiments were repeated at least twice with similar results.
Figure 3:
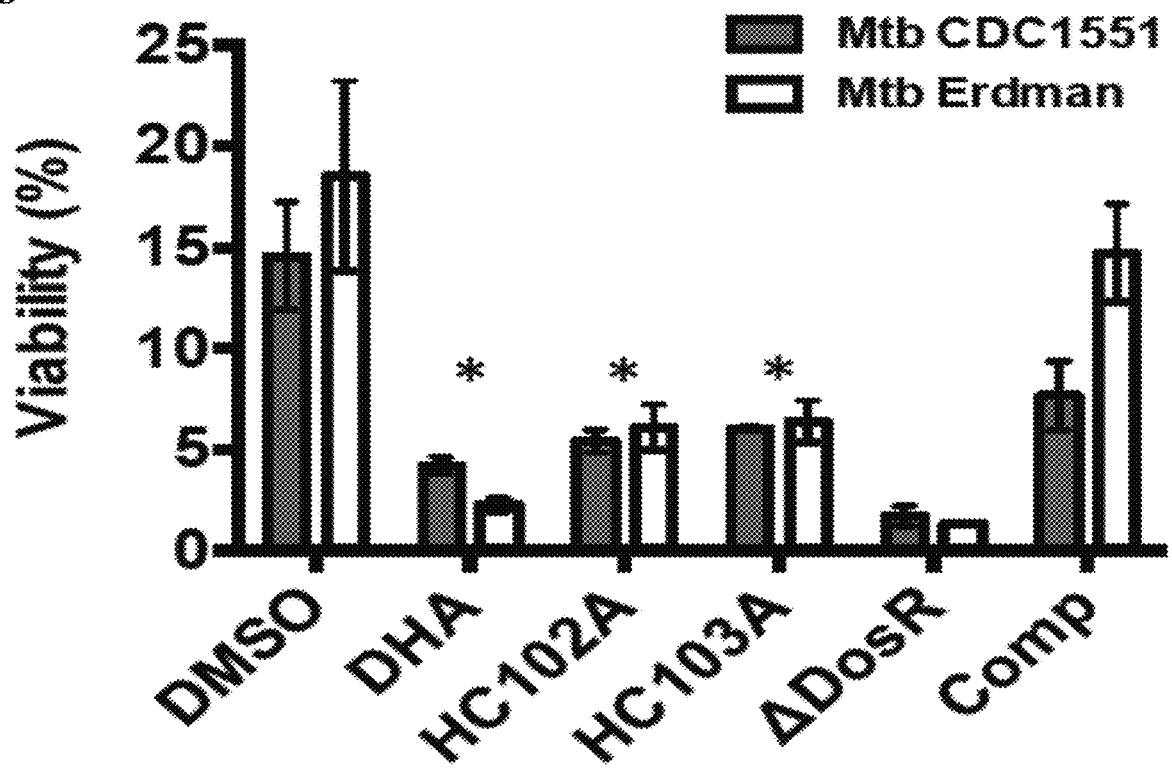
Figure 3:
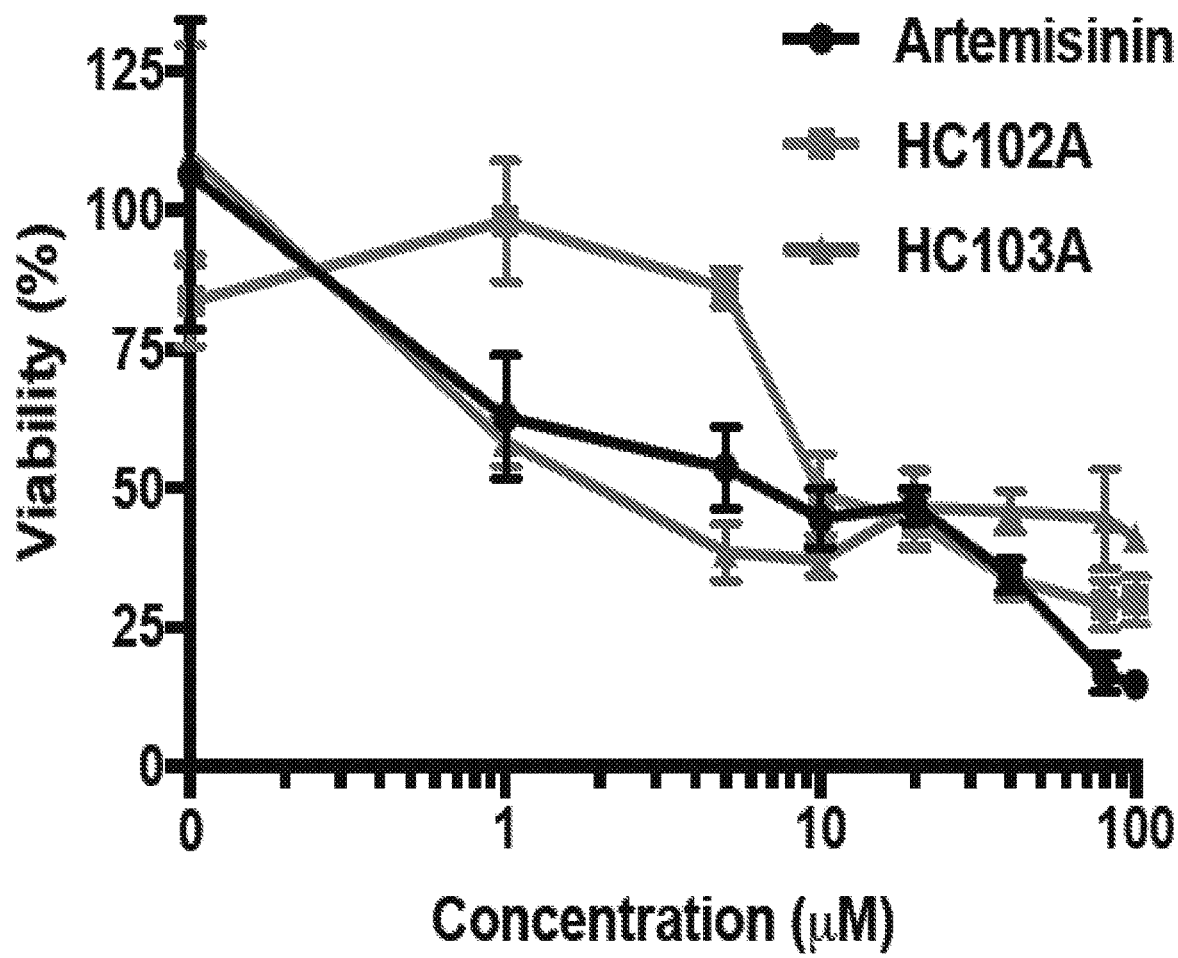
Figure 3:
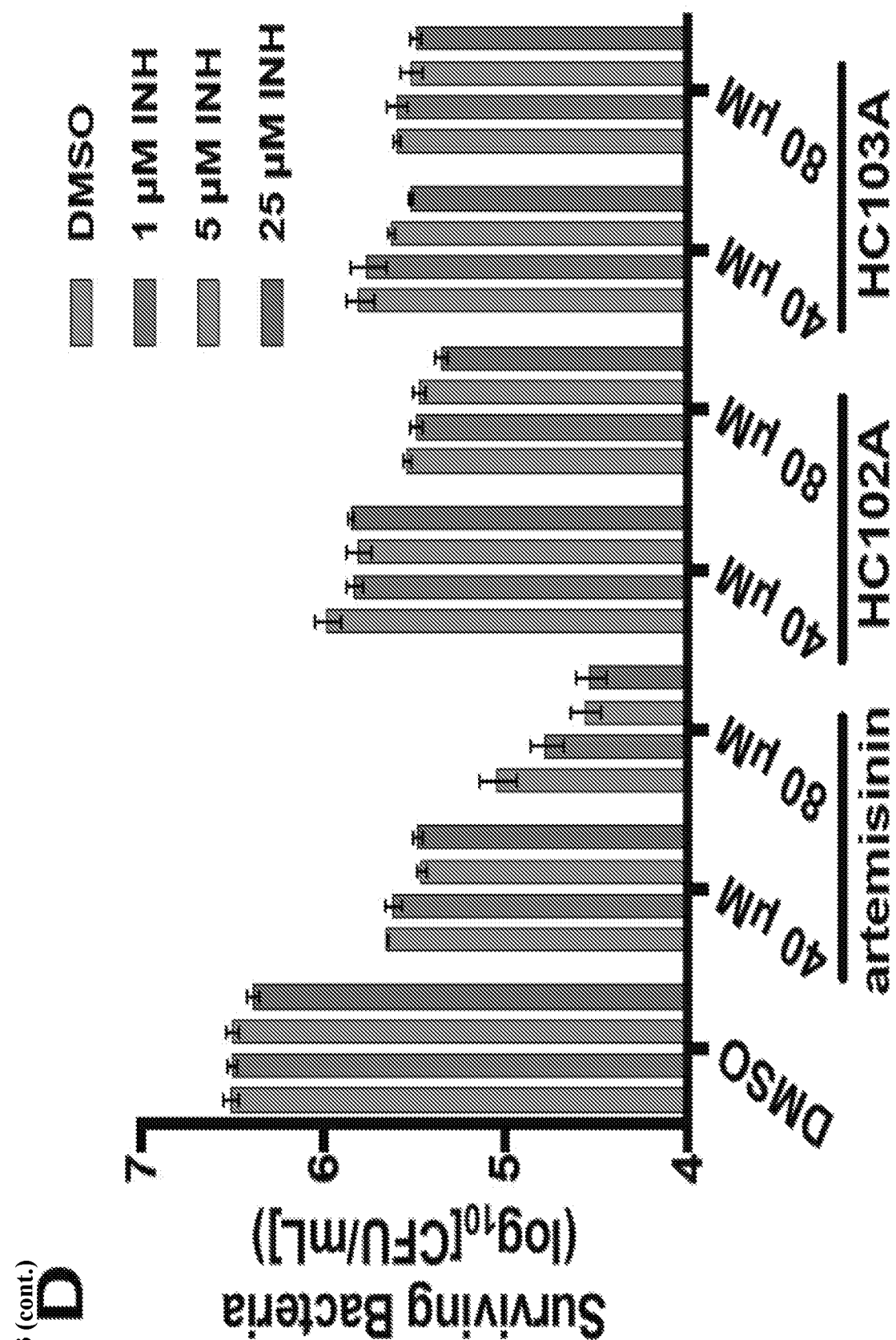
Figure 3:
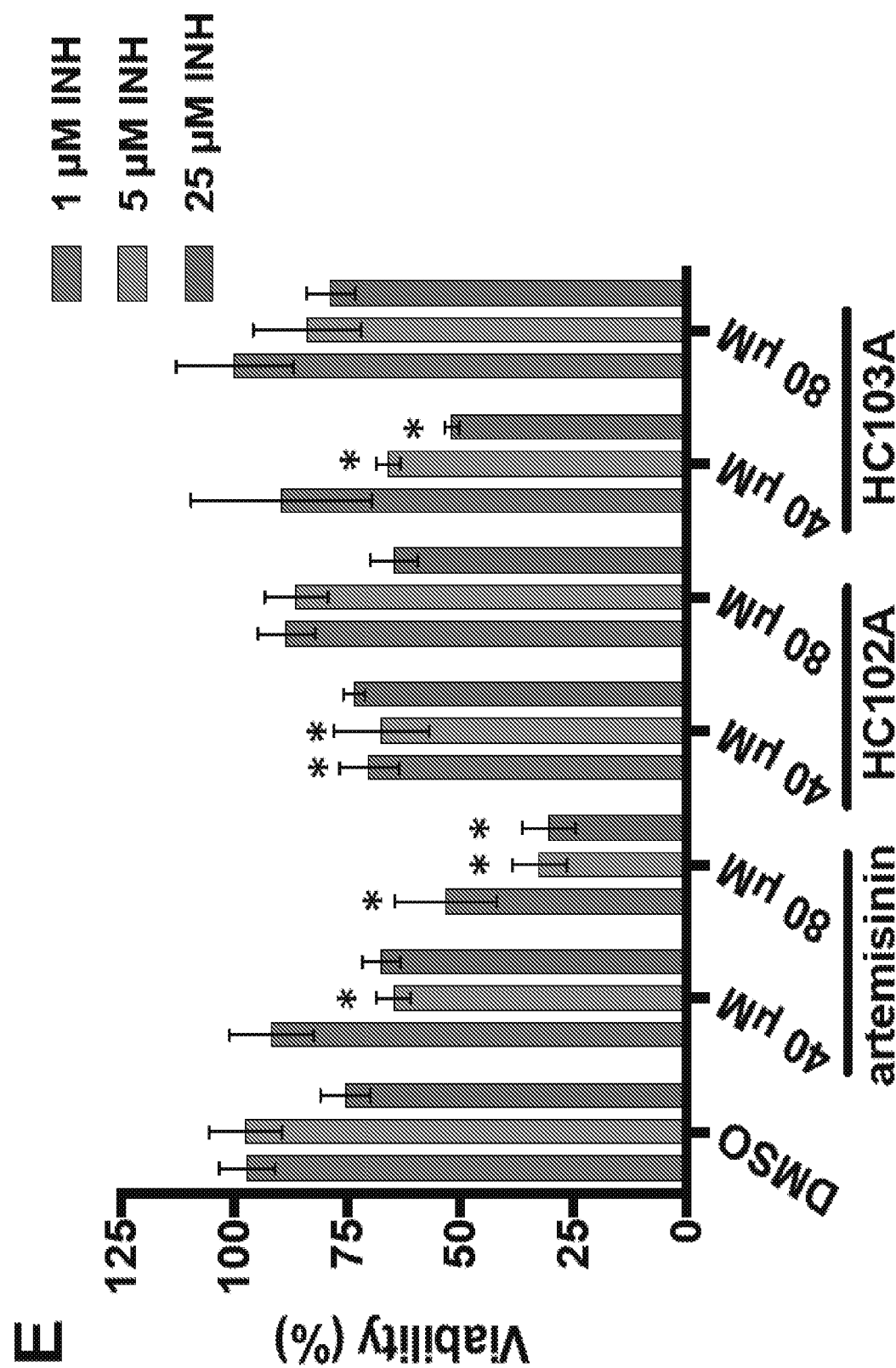

During NRP, the ΔdosR mutant has previously been shown to exhibit reduced intracellular survival as compared to WT bacteria (Leistikow, R. L. et al. *J Bacteriol* 192, 1662-70 (2010)). Using the hypoxic shift down model of NRP (Mak, P. A. et al. *ACS Chem Biol* 7, 1190-7 (2012)), the impact of DHA, HC102A or HC103A on survival during NRP was examined. Following 10 days of incubation in the hypoxic shift down assay, CDC1551 treated with 40 µM DHA, HC102A or HC103A, exhibited significantly reduced survival (70-80% reduction) as compared to the DMSO control (FIG. 3, Panel B). This reduction in survival is comparable to the CDC1551(ΔdosR) mutant relative to the DMSO treated WT control. The survival defect of the CDC1551 (ΔdosR) mutant was partially complemented in the CDC1551(ΔdosR) complemented strain, indicating that the observed survival defect is dosR-dependent. The impact of the inhibitors in the Mtb Erdman strain was also examined, to ensure the observed physiologies are not unique to CDC1551 strain. Although minor differences between CDC1551 and Erdman existed, it was observed that the inhibitors also significantly inhibited survival during NRP in the Erdman strain (FIG. 3, Panel B). The function of the inhibitors was examined in the hypoxic shift down assay in a 8 point dose response covering 1 µM-100 µM and percent viability relative to the DMSO treated control was examined following 10 days and 15 days treatment. Artemisinin, HC102A and HC103A exhibited dose dependent inhibition of viability in the hypoxic shift down model with all three compounds causing an ~50% reduction of viability at 10 µM following 10 or 15 days of incubation (FIG. 3, Panel C and FIG. 10, Panel B). Together, these data support that treatment of Mtb with these inhibitors copies the Mtb ΔdosR mutant phenotypes and reduces survival during NRP.

The DosR regulated gene tgs1 has previously been shown to be required for Mtb tolerance to isoniazid (INH) during hypoxia (Baek, S. H. et al. *PLoS Biol* 9, e1001065 (2011)). Because artemisinin, HC102A and HC103A strongly inhibit tgs1 gene expression, it was hypothesized these compounds may sensitize Mtb to INH. Using the hypoxic shift down assay, Mtb Erdman was pretreated with either 20 µM or 40 µM of artemisinin, HC102A or HC103A and following two days, the cells were treated again with the experimental inhibitors (for a combined treatment of 40 µM or 80 µM) in addition to INH over a dose response (1 µM, 5 µM, 25 µM INH or a DMSO control). Following 10 and 15 days of INH treatment in the hypoxic shift down assay surviving bacteria were enumerated (FIG. 3, Panel D and FIG. 10, Panel C). At day 10, treatment with artemisinin, HC102A or HC103A alone at M or 80 µM causes a significant reduction of survival ranging from a 3-fold to 30-fold decrease in surviving bacteria (FIG. 3, Panel D). Ten days post INH treatment, INH alone had minimal impact on Mtb survival, with ~100% viability at 1 µM and 5 µM INH and ~75% viability at 25 µM INH (FIG. 3, Panel E), supporting that Mtb is tolerant to INH in the hypoxic shift down assay. Treatment with 40 µM artemisinin, HC102A or HC103A caused a significant ~30% reduction of Mtb viability in the presence of 5 µM INH (FIG. 3, Panel E) relative to cultures not treated with INH, supporting that the inhibitors inhibit INH tolerance. At day 15, similar trends were observed in reduction of Mtb survival and antibiotic tolerance in cultures treated with artemisinin, HC102A or HC103A (FIG. 10, Panels C and D). Notably, at day 15, treatment with 40 M artemisinin or HC103A caused a ~50% reduction of Mtb viability when treated with 5 µM INH (FIG. 10, Panel D), suggesting that the function of artemisinin and HC103A may be enhanced during longer periods of NRP. These data support that artemisinin, HC102A and HC103A reduce survival and INH tolerance during NRP.

Artemisinin Directly Modulates DosS/T Activity by Targeting Sensor Kinase Heme

Artemisinin is a first-line drug for treating malaria (O'Neill, P. M. et al. *Molecules* 15, 1705-21 (2010); Krishna, S. et al. *Trends Pharmacol Sci* 29, 520-7 (2008)) and the mechanism of action has been extensively studied (Taneja, N. K. et al. *PLoS One* 5, e10860 (2010); Mak, P. A. et al. *ACS Chem Biol* 7, 1190-7 (2012)). Evidence suggests that reductive cleavage of the artemisinin endoperoxide bridge is initiated by ferrous iron ($Fe^{2+}$) under reduced conditions, and generates a C4-centered radical (Meshnick, S. R. et al. *Microbiol Rev* 60, 301-15 (1996)). The radical form of artemisinin can alkylate heme and results in artemisinin-heme adduct formation (Selmeczi, K. et al. *FEBS Lett* 556, 245-8 (2004); Robert, A. et al. *Acc Chem Res* 35, 167-74 (2002)). Thus, it has been suggested that heme is both the trigger and target of artemisinin (Zhang, S. et al. *Bioorg Med Chem* 16, 7853-61 (2008); Meunier, B. et al. *Acc Chem Res* 43, 1444-51 (2010)). Because DosS/T are also heme-containing proteins, it was hypothesized that artemisinin interacts similarly with the heme in DosS/T leading to artemisinin-mediated inhibition of the DosRST regulon. Biochemical data suggests DosS is a redox sensor that autoxidizes quickly under aerobic conditions (Ioanoviciu, A. et al. *Biochemistry* 46, 4250-60 (2007)), whereas, DosT is a hypoxia sensor and has high affinity and sensitivity to $O_2$ (Cho, H. Y. et al. *FEBS Lett* 585, 1873-8 (2011)). Both kinases sense environmental cues via heme, and are inactive when the heme group exists as either the Met ($Fe^{3+}$) form (in the case of DosS) or the oxy ($Fe^{2+}$—$O_2$) form (in the case of DosT) in the presence of $O_2$; the kinases are activated when DosS is in ferrous form and DosT is in the deoxy form (Kumar, A. et al. *Proc Natl Acad Sci USA* 104, 11568-73 (2007); Ioanoviciu, A. et al. *Biochemistry* 46, 4250-60 (2007); Podust, L. M. et al. *Biochemistry* 47, 12523-31 (2008); Cho, H. Y. et al. *J Biol Chem* 284, 13057-67 (2009); Sousa, E. H. et al. *Protein Sci* 16, 1708-19 (2007)).

Figure 4:
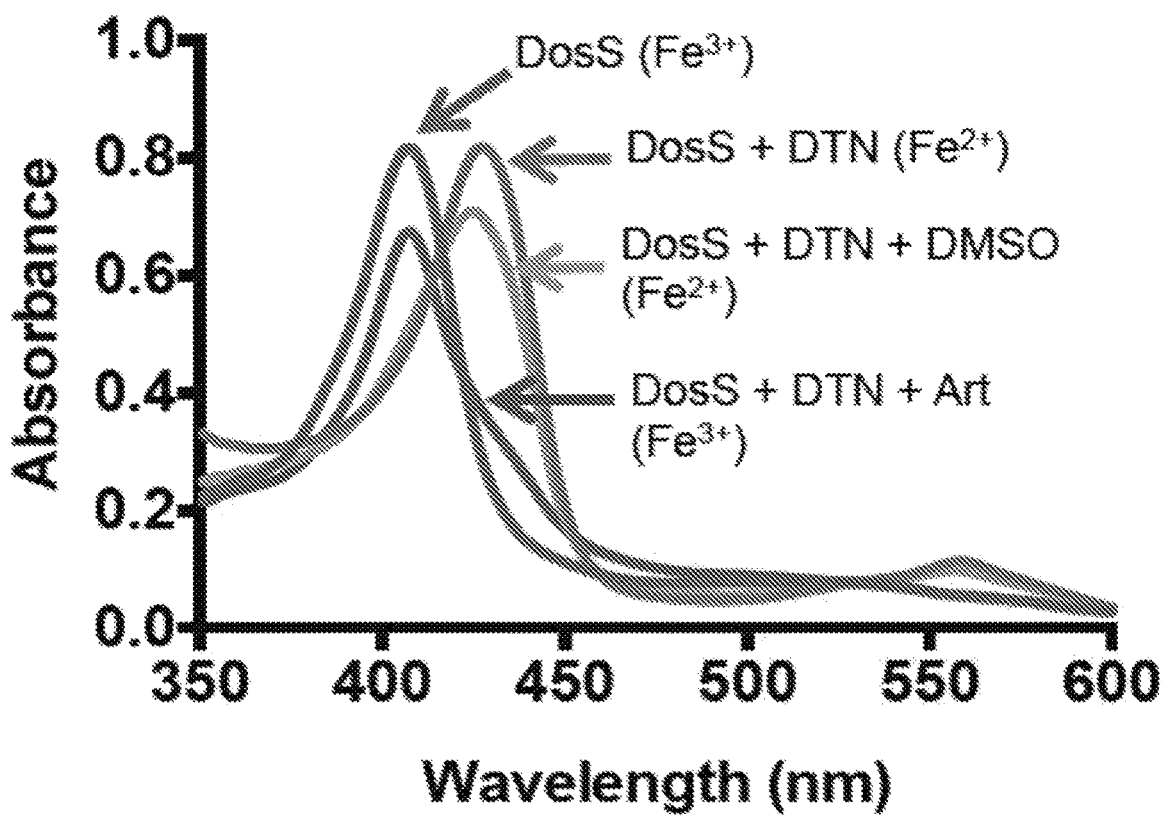
FIG. 4 includes three panels, A-C, and depicts that Artemisinin directly inhibits DosS and DosT by targeting sensor kinase heme. UV-visible spectra of DosS (Panel A) and DosT (Panel B) showing treatment with dithionite (DTN) reduces the heme (the "on" state for the kinases) and that artemisinin oxidizes the heme (the "off" state of the kinases). Panel C shows MS spectra showing the presence of peaks at ~898 Da that are present in artemisinin treated DosS samples, but absent in DMSO treated samples. This mass is the approximate combined mass of heme (616.487 Da) and artemisinin (282.332 Da) and is consistent with the formation of heme-artemisinin adducts. Experiments were repeated at least twice with similar results.
Figure 4:
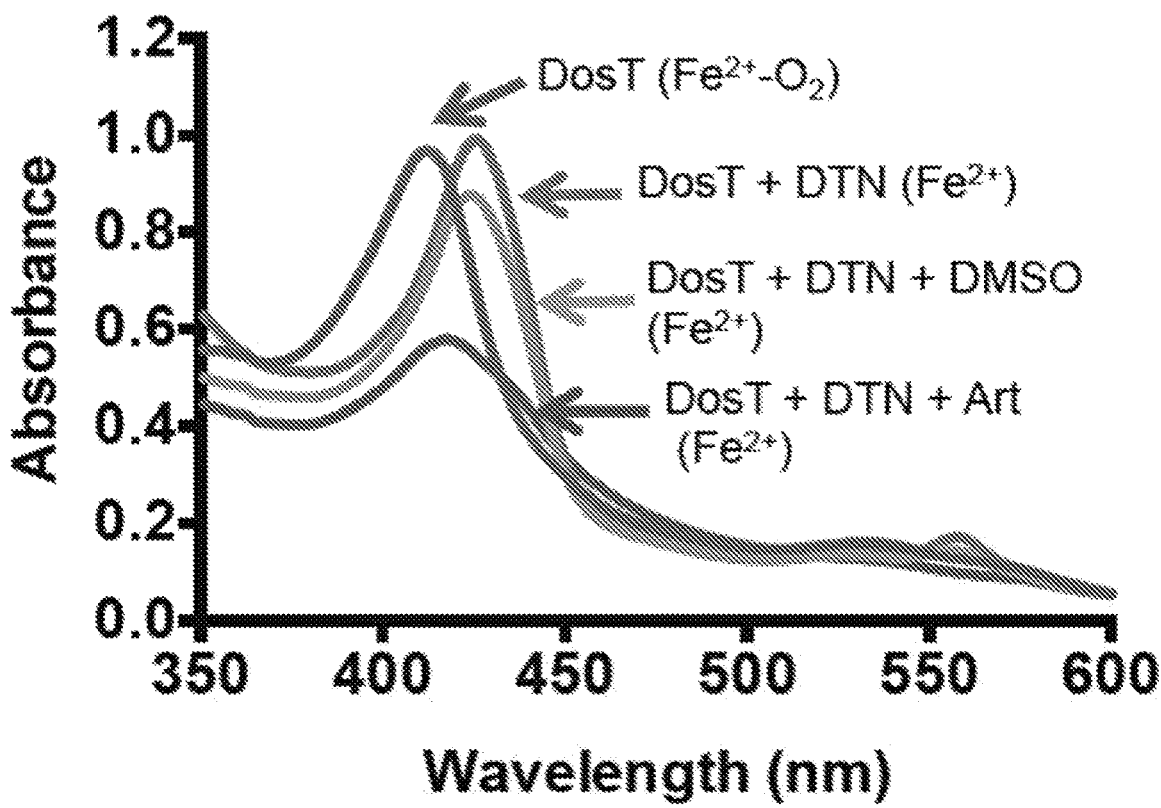
Figure 11:
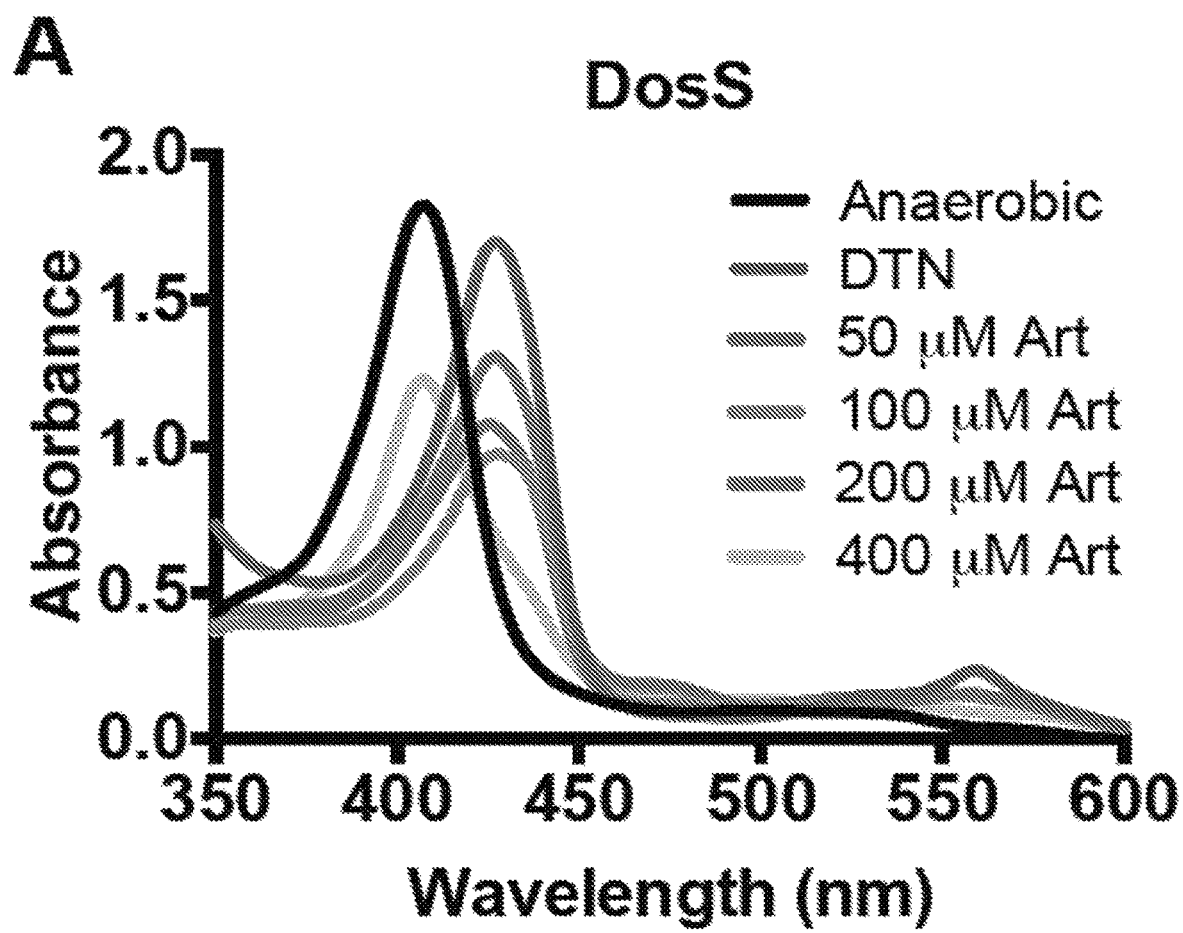
FIG. 11 includes two panels, A-B, and depicts artemisinin directly modulates DosS and DosT (G85L) heme in a dose-dependent manner. UV-visible spectra of DosS (Panel A) and DosT (G85L) (Panel B) treated with different concentrations of artemisinin. Artemisinin modulated DosT heme at a lower concentration (50 µM, FIG. 5, Panel D) than DosS heme (400 µM), supporting that DosT is more sensitive to artemisinin. DosT (G85L) exhibits a similar profile to WT DosT (FIG. 5, Panel D).
Figure 11:
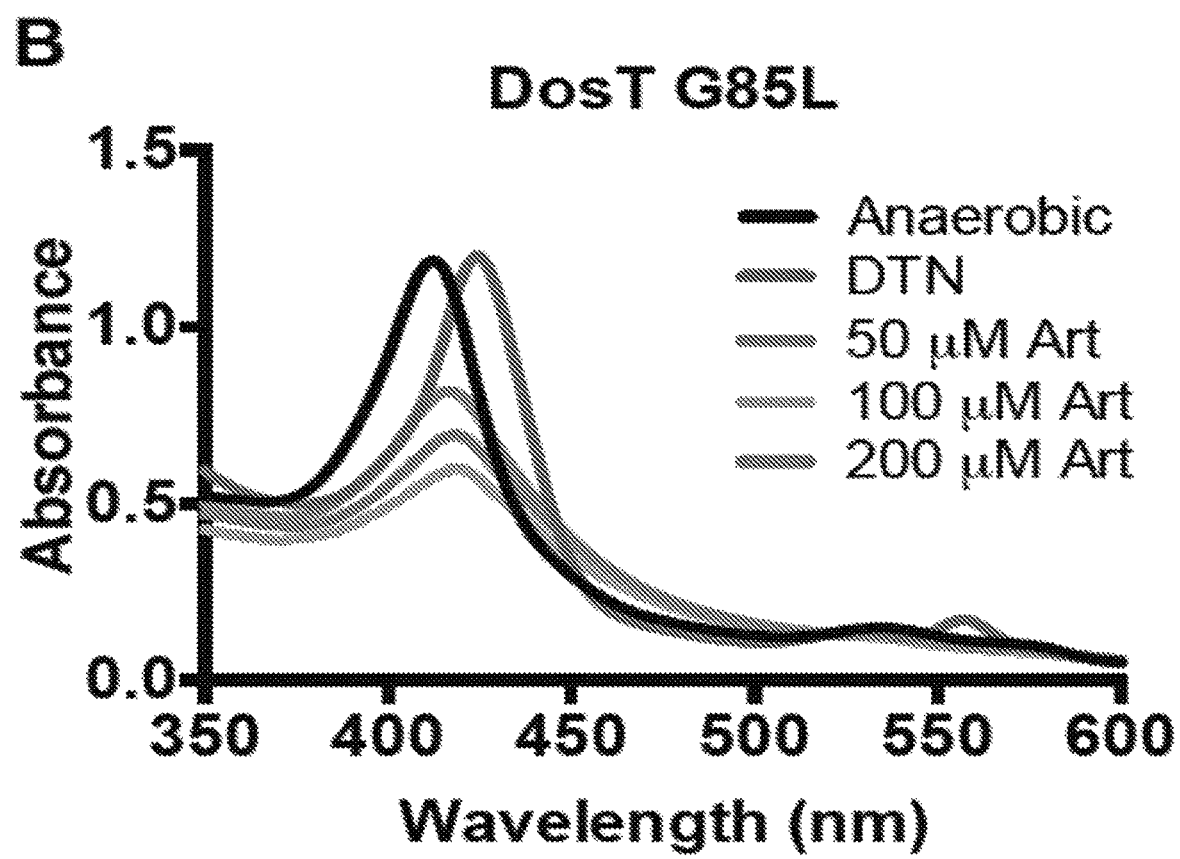

A UV-Visible spectroscopy assay was employed to determine the interaction between DosS/T and artemisinin (Kumar, A. et al. *Proc Natl Acad Sci USA* 104, 11568-73 (2007)). DosS and DosT, purified under aerobic conditions, have Soret peaks at 409 nm and 412 nm, respectively (Kumar, A. et al. *Proc Natl Acad Sci USA* 104, 11568-73 (2007)) (FIG. 4, Panels A and B). Reduction of the heme by dithionite (DTN) shifts the DosS/T Soret peaks to 430 nm. Treatment of DosS with artemisinin (purged of $O_2$) causes the Soret peak of DosS to gradually shift back to the original oxidized Soret peak. This supports that artemisinin can function to modulate DosS redox status. Notably, treatment of DosT with artemisinin reduces the amplitude of the Soret peak, a response that has previously been shown to be associated with artemisinin-mediated degradation of heme (Zhang, S. et al. *Bioorg Med Chem* 16, 7853-61 (2008); Messori, L. et al. *Bioorg Med Chem* 14, 2972-7 (2006)). The position of the peaks did not shift to the oxidized state in the DMSO treated proteins. Dose-response studies further show that artemisinin inhibits DosT at 50 μM (FIG. 5, Panel D), whereas artemisinin only causes the shift of the reduced Soret peak of DosS at a much higher concentration of 400 μM (FIG. 11, Panel A). This suggests that DosT is more sensitive to artemisinin than DosS and may explain why the artemisinins had weaker activity for the inhibition of the DosR pathway when stimulated by NO or vitamin C. Because the DosS/T kinases are active in the reduced form and inactive in the oxidized form (Kumar, A. et al. *Proc Natl Acad Sci USA* 104, 11568-73 (2007)), these data are consistent with artemisinin inhibiting DosS/T kinases by modulating their redox status (e.g. DosS at high concentrations) or causing degradation of the heme (e.g. DosT). To test the hypothesis that artemisinin can alkylate heme carried by the sensor kinase, DosS reaction samples treated with artemisinin or DMSO were subjected to LC-MS analysis. Molecules with masses of ~898 Da were identified in the artemisinin treated sample that are absent in the DMSO treated sample (FIG. 4, Panel C). This molecular weight corresponds to the sum of the masses of artemisinin (282 Da) and heme (616 Da), supporting that artemisinin alkylates the sensor kinase heme to form heme-artemisinin adducts (Robert, A. et al. *Chem Commun (Camb)*, 414-5 (2002); Kannan, R. et al. *Chem Biol* 9, 321-32 (2002)). In a previous study, a structure of the artemisinin-alkylated heme with a mass of 898.3 was shown to involve alkylation of the heme at the a, J3, or 6 positions with the iron in the ferric state (Robert, A. et al. *Chem Commun (Camb)*, 414-5 (2002)). The molecules observed in this study with a mass of 838 Da were also previously shown to be heme-artemisinin adducts that have lost an acetic acid molecule during mass spectrometry (Robert, A. et al. *Chem Commun (Camb)*, 414-5 (2002)). Notably, adducts of DosS peptides were not observed. Together, these findings support a mechanism of action where artemisinin directly targets the heme to inactivate the DosS and DosT sensor kinases. The UV-visible spectra and mass spectrometry data support differing mechanisms for DosS and DosT inactivation by artemisinin, with DosS alkylated-heme remaining intact but in the ferric state (Robert, A. et al. *Chem Commun (Camb)*, 414-5 (2002)) and the DosT heme being degraded by artemisinin (Zhang, S. et al. *Bioorg Med Chem* 16, 7853-61 (2008); Messori, L. et al. *Bioorg Med Chem* 14, 2972-7 (2006)). In both cases, these heme-artemisinin interactions would result in disabling the sensor functions of DosS/T.

Figure 5:
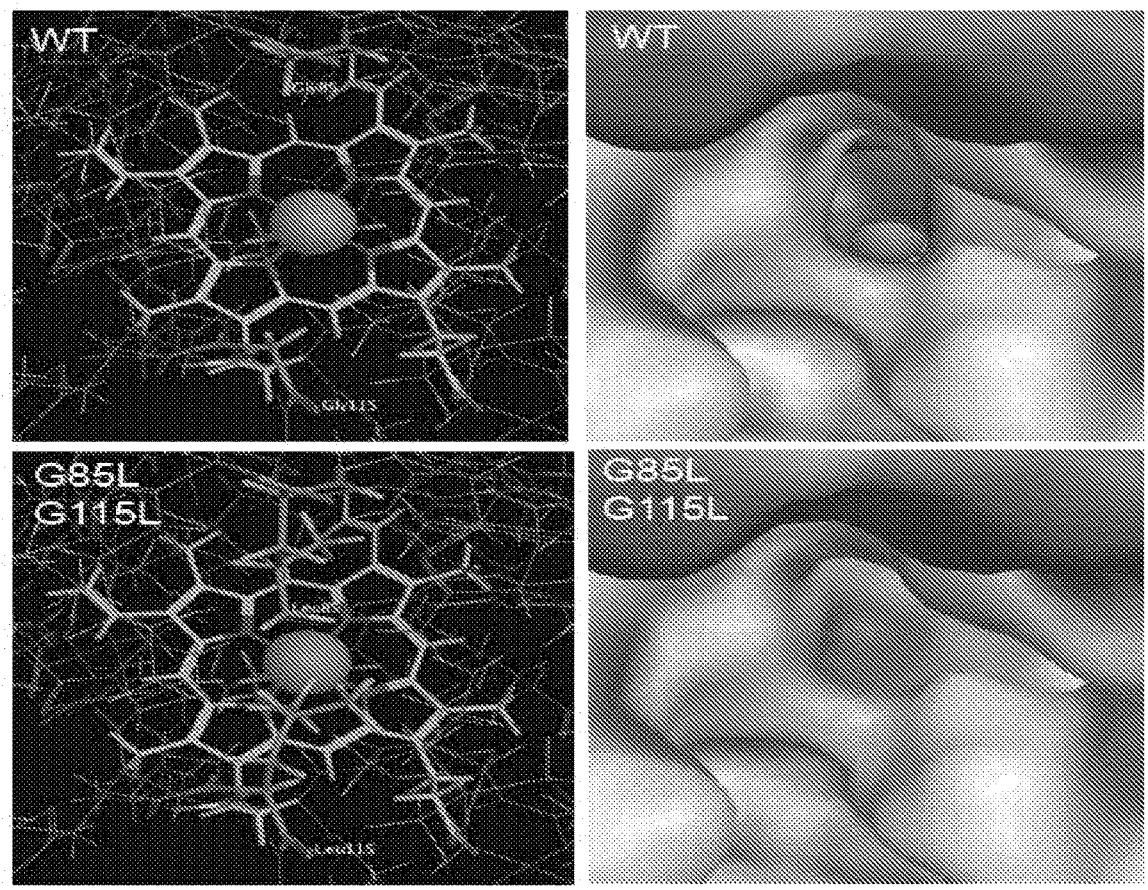
FIG. 5 includes six panels A-F and depicts amino acid substitutions in DosS or DosT promote resistance to artemisinin. Panel A shows molecular modeling indicates a channel exists in DosS and DosT through which artemisinin may access the heme. In WT DosT, the heme (colored yellow) and iron (green ball) is accessible to artemisinin via a channel. G85L and G115L substitutions are predicted to block this channel and access to the heme. Panel B and C show UV visible spectra show that the DosS (G87L) and DosS (G117L) proteins can be reduced by the addition of dithionite (DTN) but are resistant to oxidation by artemisinin (Art). Panel D and E show WT DosT exhibits a dose-dependent decrease in the amplitude of the Soret peak at 430 nm (left side of Panel D) and a loss of the peak at 560 nm (magnified in right side of Panel D). In contrast, DosT (G115L) exhibits resistance to artemisinin because it does not exhibit a dose-dependent decrease in the 430 nm peak (left side of Panel E) and the 560 nm peak is maintained at treatments of 50 and 100 µM artemisinin (right side of phosphorylation with an $IC_{50}$ of ~5 µM. Experiments were repeated at least twice with similar results.
Figure 5:
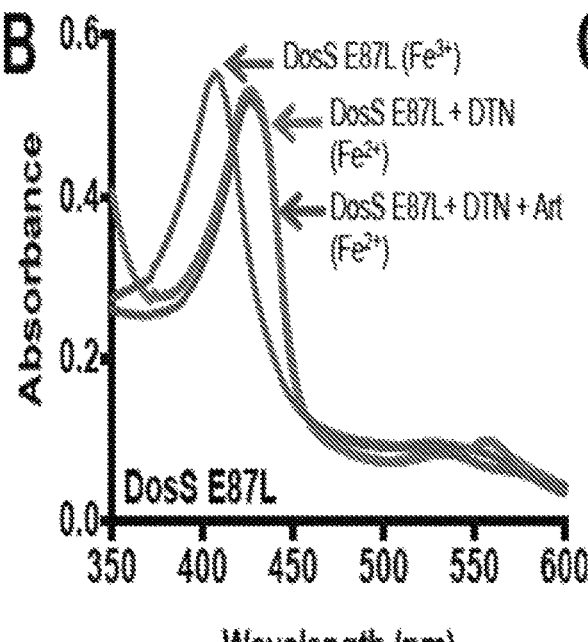
Figure 5:
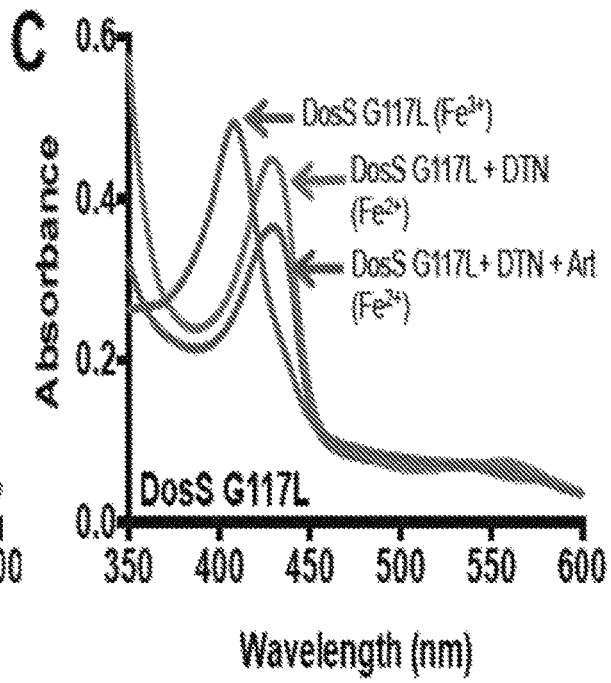
Figure 5:
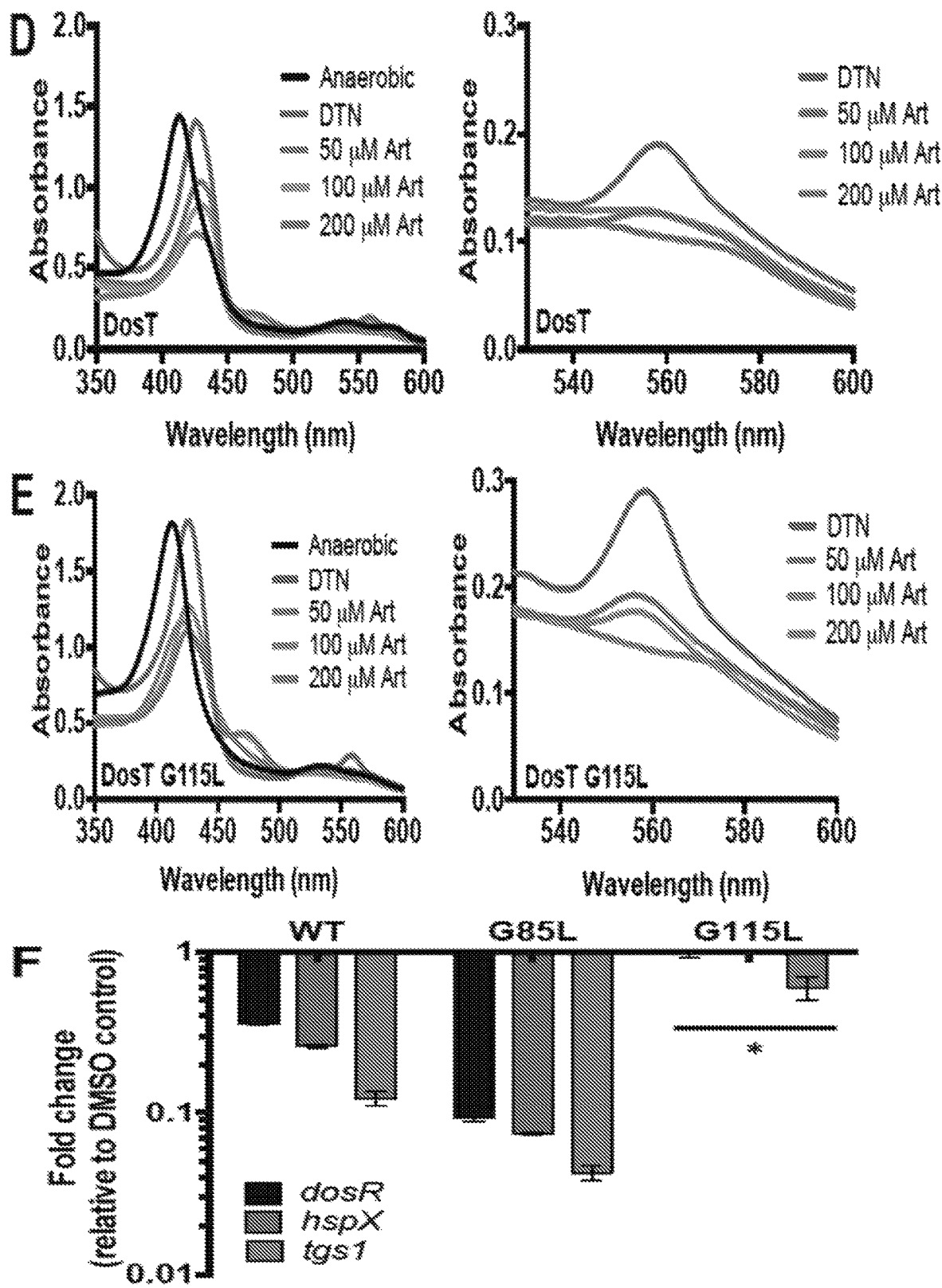

Molecular modeling of DosS and DosT structures (Podust, L. M. et al. *Biochemistry* 47, 12523-31 (2008); Cho, H. Y. et al. *J Biol Chem* 284, 13057-67 (2009)) shows that the kinases have a channel through which the artemisinin may access and dock to the heme (FIG. 5, Panel A). To test this model, amino acid substitutions were generated along the channel in DosS/T, including E87L and G117L in DosS or G85L and G115L in DosT, that are predicted to limit the ability of artemisinin to access the heme based on modeling conducted in this study and published studies (Cho, H. Y. et al. *FEBS Lett* 585, 1873-8 (2011)). In the UV-visible spectroscopy assay, DosS (E87L) and DosS (G117L) exhibited similar overall spectra as WT DosS under aerobic conditions and treatment with DTN caused the Soret peak to shift to the reduced position (FIG. 5, Panels B and C); thus, the heme in both mutant proteins retains the ability to respond to reduction by DTN. Notably, the DosS (E87L) and DosS (G117L) proteins were resistant to oxidation by 400 μM artemisinin and the major Soret peak (430 nm) did not shift to the oxidized position following 60 minutes of treatment (FIG. 5, Panels B and C). The analogous mutations of DosT, G85L and G115L, also exhibited similar overall spectrum as WT DosT under aerobic conditions, as well as in responding to DTN treatment (FIG. 5, Panels D and E and FIG. 11, Panel B). However, the lower peak at 560 nm of deoxy-DosT (G115L) was maintained when treated with 100 μM artemisinin as compared to WT DosT and DosT (G85L) (FIG. 5, Panels D and E and FIG. 11, Panel B). The 560 nm peak is generated by merging two lower peaks at 538 nm and 575 nm together after DTN treatment, and is another signature of reduced penta-coordinated high-spin heme (Sivaramakrishnan, S. et al. *Biosensors (Basel)* 3, 259-282 (2013)). This peak is highly sensitive to oxygen or artemisinin treatment and disappears immediately upon exposure to oxygen or artemisinin (Kumar, A. et al. *Proc Natl Acad Sci USA* 104, 11568-73 (2007); Zhang, S. et al. *Bioorg Med Chem* 16, 7853-61 (2008); Messori, L. et al. *Bioorg Med Chem* 14, 2972-7 (2006)). Additionally, the Soret peak in the G115L mutant is not reduced in a dose-dependent manner, as compared to the WT and G85L mutants (FIG. 5, Panels D and E and FIG. 11, Panel B), further supporting the DosT (G115L) protein exhibits artemisinin resistance.

Figure 12:
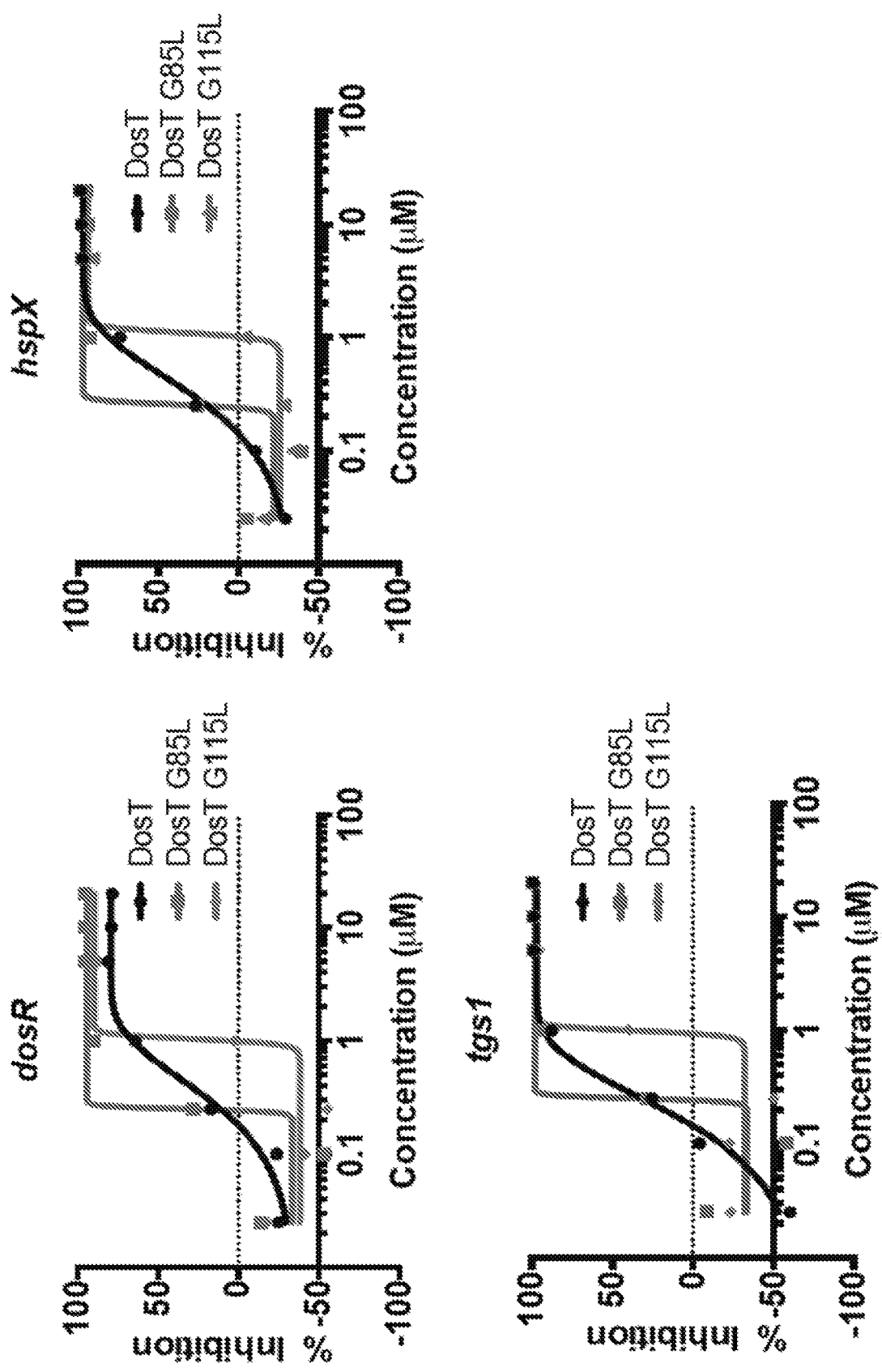
FIG. 12 depicts substitutions in the DosT provide resistance to artemisinin. Mtb was transformed with a replicating plasmid that overexpresses WT dosT, dosT (G85L) or dosT (G15L). Cells were treated with 0.025 µM-20 µM artemisinin, and total RNA was extracted after 6 days incubation at 37° C. RT-PCR quantification of DosR-regulated genes (dosR, hspX and tgs1) shows that strains expressing DosT (G115L) exhibited $EC_{50}$ for artemisinin-mediated inhibition of DosR regulon genes of 1.0-1.6 M, which is ~5-fold more resistant than WT DosT or DosT (G85L) with $EC_{50}$ of 0.2-0.3 µM.

The UV-visible spectroscopy data collectively support that DosS E87L and G117L and DosT G115L substitutions may limit artemisinin from fully accessing the heme, thereby providing resistance to artemisinin. To test this hypothesis in whole cells of Mtb, CDC1551 was transformed with a replicating plasmid overexpressing the WT dosT, dosT (G85L) or dosT (G115L) genes and determined if artemisinin resistance is observed. The strains were grown in standing flasks to stimulate the DosRST regulon and expression of DosRST regulon genes (dosR, hspX, tgs1) was examined by real-time PCR following 6 days of treatment with artemisinin over a dose response curve (FIG. 12). Strains expressing WT dosT or dosT (G85L) exhibited $EC_{50}$ for artemisinin-mediated inhibition of DosR regulon genes of 0.2-0.3 M whereas, dosT (G115L) exhibited $EC_{50}$ of 1.0-1.6 µM. (FIG. 5, Panel F and FIG. 12). Therefore, the DosT (G115L) protein provides ~5 fold resistance to artemisinin and nearly full resistance at 1 µM artemisinin (FIG. 5F). These biochemical and biological data support that artemisinin modulates the DosRST signaling by directly targeting the heme sensor carried by DosS and DosT histidine kinases.

HC103A Inhibits DosS and DosT Autophosphorylation

Figure 6:
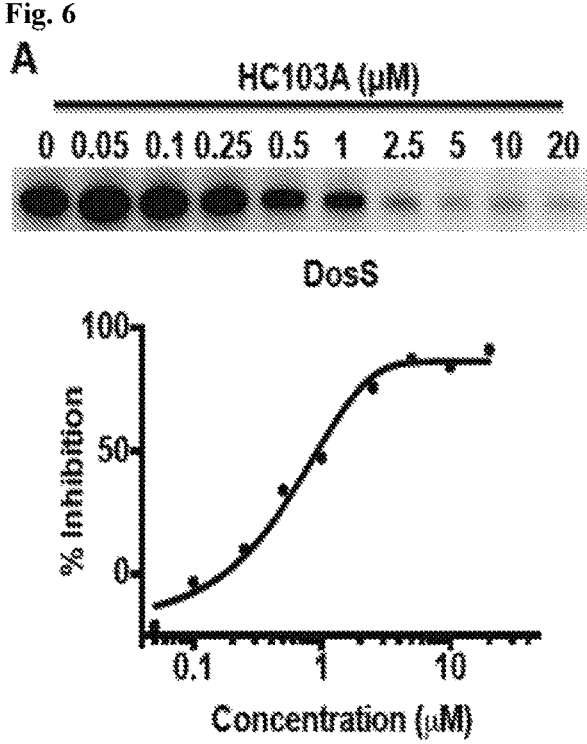
Figure 6:
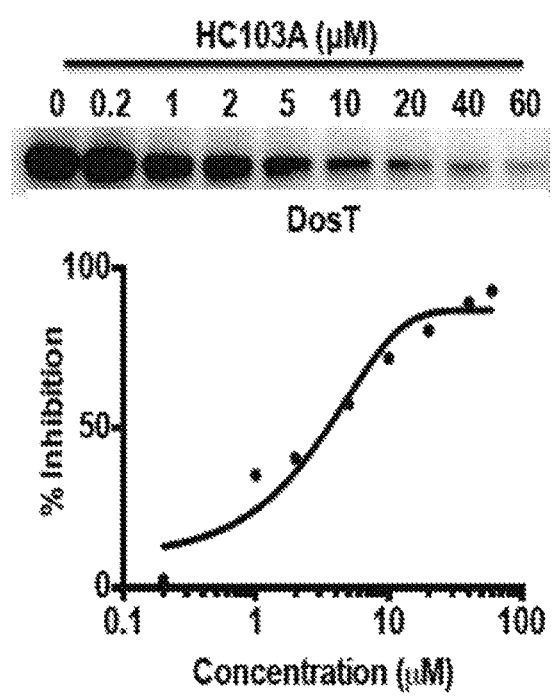
Figure 6:
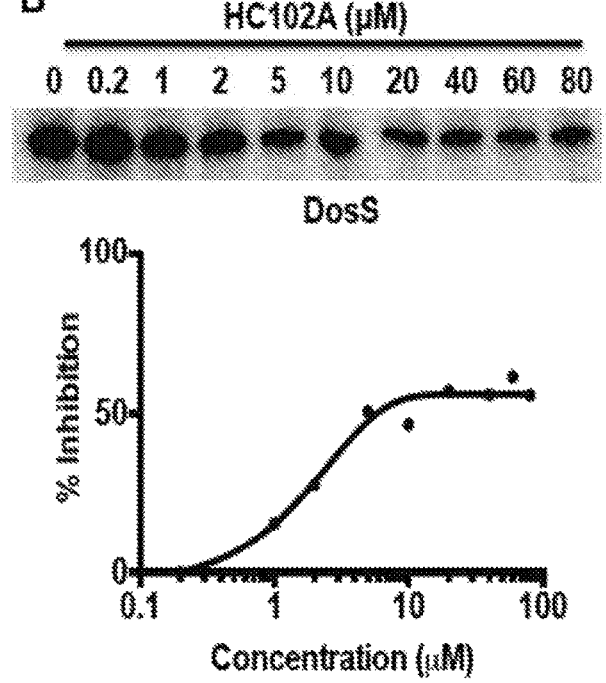
Figure 6:
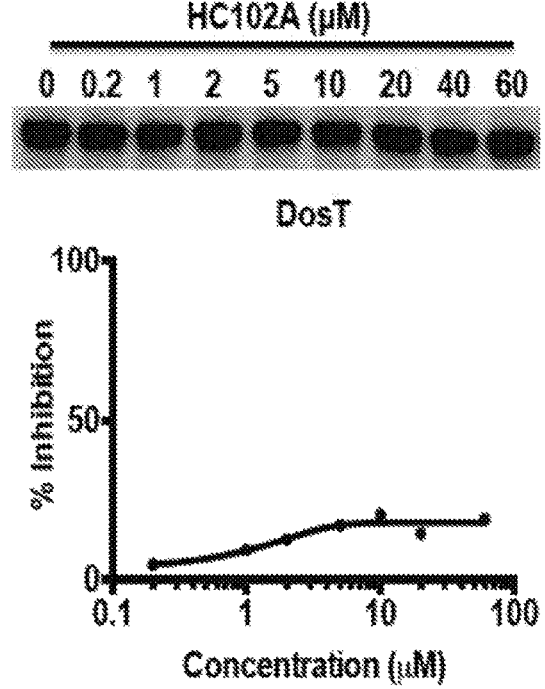
Figure 13:
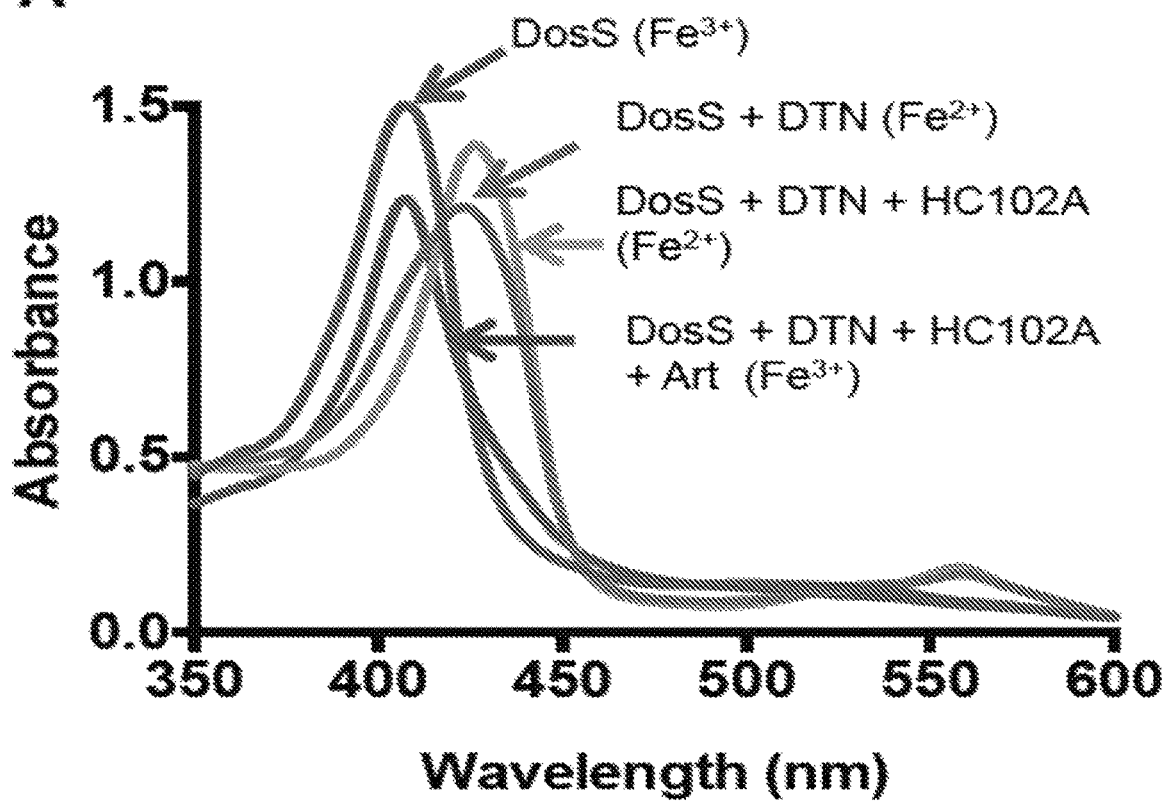
FIG. 13 includes two panels, A-B, and depicts HC102A and HC103A do not modulate DosS redox. DosS treated with HC102A (Panel A) or HC103A (Panel B) shows a similar overall spectrum as DMSO control. This indicates that HC102A and HC103A has no effect in modulating redox status of DosS, and may inhibit DosR regulon by distinct mechanism.
Figure 13:
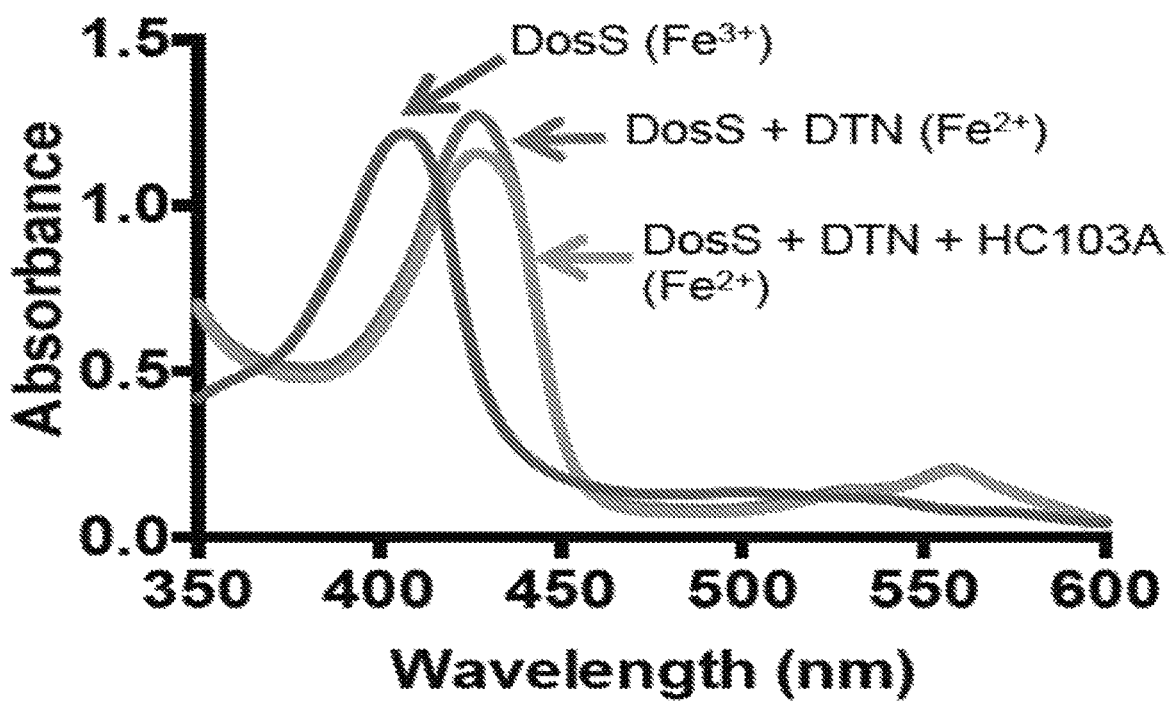

UV-Visible spectroscopy studies showed that HC102A and HC103A have no impact on the redox status of DosS or DosT heme (FIG. 13), suggesting these compounds function by a mechanism that is distinct from artemisinin. Given the strong specificity with which these compounds inhibit the DosRST regulon, it was hypothesized that HC102A and HC103A may directly inhibit DosS/T autophosphorylation activity. To test this hypothesis, in vitro phosphorylation assays were performed as previously described (Roberts, D. M. et al. *J Biol Chem* 279, 23082-7 (2004)). DosS and DosT were quickly phosphorylated within 30 seconds of initiating the assay by adding [$\gamma$-$^{32}$P] ATP. The amount of phosphorylated protein increased over time consistent with previous reports (Roberts, D. M. et al. *J Biol Chem* 279, 23082-7 (2004); Saini, D. K. et al. *Microbiology* 150, 865-75 (2004); Saini, D. K. et al. *FEBS Lett* 565, 75-80 (2004)). DosS treated with HC102A and HC103A showed decreased autophosphorylation activity (FIG. 6). Inhibition of DosS autophosphorylation activity increased in a dose-dependent manner with $IC_{50}$s of 1.9 µM and 0.5 µM for HC102A and HC103A, respectively. Notably, differences in maximal inhibition were observed, with ~60% and ~90% for HC102A and HC103A, respectively. DosT treated with HC103A also showed a dose-dependent inhibition of autophosphorylation and an $IC_{50}$ of ~5 µM (FIG. 6). These findings support that HC103A functions by directly modulating DosS and DosT kinase activity.

DISCUSSION

In this study a CDC1551(hspX':GFP) fluorescent reporter strain was used as a synthetic phenotype for the targeted discovery of several compounds that inhibit the DosRST pathway. Biochemical studies of three prioritized compounds revealed distinct mechanisms of action, with artemisinin oxidizing and alkylating the heme group in the sensor kinases, and HC103A inhibiting sensor kinase autophosphorylation activity, without modulating heme redox status. Treatment of Mtb with these compounds copies several phenotypes of a CDC1551 (ΔdosR) mutant, including: downregulation of the core DosRST regulon, reduced TAG synthesis, and decreased survival during NRP. These findings provide proof-of-concept data that the high throughput screen successfully identified inhibitors of the DosRST regulon and support further studies characterizing additional putative DosRST regulon inhibitors, including HC104-HC106, as well as uncharacterized putative hits from the primary screen. Several new chemical inhibitors of Mtb during NRP have been recently described. One promising target is the direct inhibition of ATP homeostasis by targeting the components of the electron transport chain or ATP synthase (Mak, P. A. et al. *ACS Chem Biol* 7, 1190-7 (2012); Koul, A. et al. *J Biol Chem* 283, 25273-80 (2008); Pethe, K. et al. *Nat Med* 19, 1157-60 (2013); Li, W. et al. *Antimicrob Agents Chemother* 58, 6413-23 (2014)). However, the approach of targeting the DosRST top-level regulators has the potential to inhibit multiple physiologies required for establishing or maintaining NRP and this multifactorial approach may broadly limit persistence in heterogeneous NRP-inducing environments. Using homology modeling, Gupta et al. reported the discovery of a DosR regulon inhibitor that specifically inhibits DosR binding to target DNA (Gupta, R. K. et al. *J Med Chem* 52, 6324-34 (2009)). Additionally, a screen for small molecules that modulate Esx-1 export, identified inhibitors that indirectly modulate the DosR regulon (Rybniker, J. et al. *Cell Host & Microbe* 16, 538-548 (2014)). However, the newly discovered compounds represent novel inhibitors of the DosRST regulon with distinct mechanisms of action.

Both HC102A and HC103A appear to be remarkably specific for inhibiting the DosRST pathway. Indeed, no genes were downregulated (>2-fold, p<0.05) in the CDC1551 (ΔdosR) mutant treated with HC102A, supporting that only DosR controlled pathways are targeted by HC102A. HC103A treatment of the CDC1551(ΔdosR) caused downregulation (>2-fold, p<0.05) of 13 genes. Several genes fell into related classes including: four arginine biosynthesis genes (argC, argB, argJ and argF), two acyl-(ACP) desaturases (desA1 and desA2), two ferroredoxins (fdxC and frB), three PE-PPE genes (Rv0160c, Rv1386 and Rv1387), and an orphan response regulator (Rv0260c). This finding suggests that although HC103A is highly specific for the DosRST pathway other targets likely exist. It is notable that no inhibitors that target multiple two component regulatory pathways were identified. For example, HC101-HC106 were not identified in a similar screen aimed at finding inhibitors of the PhoPR regulon (Johnson, B. K. et al. *Antimicrob Agents Chemother* 59, 4436-45 (2015)). Inhibitors targeting all sensor histidine kinases would not be identified from this screen because at least one, MtrAB, is essential for growth (Zahrt, T. C. et al. *J Bacteriol* 182, 3832-8 (2000)).

In contrast to HC102A and HC103A, artemisinin exhibits significant off-target activities, with 69 genes differentially regulated in the CDC1551(ΔdosR) mutant treated with artemisinin. Given that artemisinin has a reactive endoperoxide bridge, it is perhaps surprising that there are not a greater number of genes that are differentially regulated, as one might expect artemisinin to react with any proteins carrying reduced iron. The downregulated genes do not match genes regulated by ROS (Boshoff, H. I. et al. *J Biol Chem* 279, 40174-84 (2004)), suggesting that artemisinin is not promoting Fenton reactions and acting as an indiscriminate oxidant. Miller and colleagues have shown that when artemisinin is delivered into Mtb as a mycobactin-artemisinin conjugate it causes an intracellular burst of reactive oxygen via Fenton reactions that kills Mtb (Miller, M. J. et al. *J Am Chem Soc* 133, 2076-9 (2011)). Based on this finding, it is tempting to speculate that artemisinin alone cannot fully access the Mtb cytoplasm and is thus modulating membrane-associated proteins, such as DosS/T. Other membrane proteins that may interact with artemisinin (e.g. heme-bearing cytochromes) may be resistant to artemisinin if the heme is buried in the protein and not accessible to artemisinin. Structural analysis of the heme-embedded GAF domain of DosST shows that DosT has a wider channel than DosS that could potentially provide greater accessibility to artemisinin (Podust, L. M. et al. *Biochemistry* 47, 12523-31 (2008); Cho, H. Y. et al. *J Biol Chem* 284, 13057-67 (2009)). This is supported by the data herein that DosT is more sensitive to artemisinin than DosS and is consistent with artemisinins having limited ability to inhibit NO-mediated stimulation of the DosR regulon. Alternatively, DosS may be less sensitive to artemisinin than DosT due to differences in autooxidation rates, where DosS is more quickly oxidized to the ferric state in the presence of oxygen (Kim, M. J. et al. *J Bacteriol* 192, 4868-75 (2010)). Autooxidized DosS in the ferric form would not react with artemisinin, resulting in the observed insensitivity. Collectively, it was shown herein that this channel is susceptible to drugs with artemisinin as a proof-of-concept, therefore structure-based synthesis of compounds that block the heme-bearing channel of DosS and DosT may promote the development of additional novel inhibitors of Mtb persistence. The discovery that artemisinin inhibits Mtb persistence raises interesting questions about the use of artemisinin to treat malaria in individuals co-infected with malaria and Mtb.

INCORPORATION BY REFERENCE

The contents of all references, patent applications, patents, and published patent applications, as well as the Figures, cited throughout this application are hereby incorporated by reference.

EQUIVALENTS

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

TABLE 2A

Downregulated gene expression tables of DMSO treated DosR mutant compared to DMSO treated WT

| Gene | Counts per million (CPM) | | | | WT DMSO/ DosR DMSO Fold change | log2 Fold change | logCPM | Adjusted p-value | Rv number | Gene name | Annotated function |
|---|---|---|---|---|---|---|---|---|---|---|---|
| | WT_DMSO1 | WT_DMSO2 | DosR_DMSO1 | DosR_DMSO2 | | | | | | | |
| MT0038 | 22.1279311 | 12.8686451 | 3.512558319 | 5.150881219 | 0.250393046 | -1.997733597 | 3.38036778 | 0.009459706 | Rv0033 | Rv0033 | possible acyl carrier protein |
| MT0040 | 92.32688494 | 82.9955313 | 27.09687846 | 33.27469268 | 0.344561457 | -1.537166766 | 5.87356991 | 0.001918959 | Rv0035 | fadD34 | acyl-CoA synthase |
| MT0075 | 45.01889431 | 42.6544978 | 20.43018614 | 12.6711678 | 0.379012439 | -1.399682898 | 4.90648668 | 0.034764592 | Rv0079 | Rv0079 | hypothetical protein |
| MT0086 | 1,308.98 | 2,581.54 | 9.032292821 | 4.120704975 | 0.003412235 | -8.195067471 | 9.93012145 | 4.85E-33 | Rv0079 | Rv0079 | hypothetical protein |
| MT0087 | 357.0990261 | 867.404516 | 2.652339955 | 1.442246741 | 0.003414974 | -8.193909753 | 8.26182025 | 4.86E-32 | Rv0080 | Rv0080 | formate hydrogenlyase subunit 4 |
| MT0091 | 130.8600063 | 129.7837755 | 71.11138475 | 45.01870186 | 0.445692815 | -1.165828315 | 6.55623613 | 0.04586184 | Rv0084 | hycD | acyl-CoA synthase |
| MT0175 | 278.8882351 | 151.387319 | 70.8246453 | 68.30068497 | 0.3240725 | -1.625611493 | 7.14732831 | 0.004118518 | Rv0166 | fadD5 | cell invasion protein |
| MT0176 | 259.8124324 | 253.179748 | 87.74227312 | 73.03949569 | 0.31357103 | -1.673135816 | 7.3935147 | 0.000781511 | Rv0169 | mce1 | part of mce1 operon |
| MT0178 | 564.2622431 | 404.422476 | 144.9467943 | 189.9644994 | 0.345884196 | -1.531638997 | 8.34634202 | 0.006937962 | Rv0170 | Rv0170 | part of mce1 operon |
| MT0179 | 438.3619455 | 306.967792 | 107.1688712 | 144.6367446 | 0.33804041 | -1.564732317 | 7.95899111 | 0.004663194 | Rv0171 | Rv0171 | part of mce1 operon |
| MT0180 | 462.0159408 | 361.189612 | 116.8463278 | 166.7855339 | 0.344642164 | -1.53682888 | 8.11016007 | 0.005838808 | Rv0172 | Rv0172 | part of mce1 operon |
| MT0181 | 579.1413692 | 479.031699 | 156.9181666 | 257.0289728 | 0.391221237 | -1.353943409 | 8.52243103 | 0.034099178 | Rv0173 | lprK | conserved hypothetical protein |
| MT0182 | 311.3170996 | 282.676417 | 76.84617384 | 122.590973 | 0.335714585 | -1.57469288 | 7.62955686 | 0.004118518 | Rv0459 | Rv0459 | conserved hypothetical protein |
| MT0475 | 28.23218796 | 26.3156563 | 9.964196049 | 8.550462824 | 0.340744223 | -1.553238897 | 4.1725818 | 0.025007583 | Rv0569 | Rv0569 | conserved hypothetical protein |
| MT0595 | 285.7555241 | 177.124609 | 20.00007696 | 15.96773178 | 0.077988598 | -3.680592977 | 6.9516389 | 6.61E-15 | Rv0570 | nrdZ | ribonucleotide reductase, class II |
| MT0596 | 2,911.35 | 1,704.88 | 39.92846906 | 37.1893624 | 0.01671814 | -5.902469967 | 10.195018 | 2.73E-28 | Rv0571c | Rv0571c | conserved hypothetical protein |
| MT0597 | 248.3669508 | 416.423572 | 36.55928047 | 28.84493483 | 0.098381097 | -3.345475053 | 7.50990205 | 9.20E-12 | Rv0572c | Rv0572c | hypothetical protein |
| MT0598 | 202.5850244 | 342.681897 | 10.03588091 | 8.962533322 | 0.034883115 | -4.841327312 | 7.13641696 | 3.27E-22 | | | |
| MT0599 | 568.4589197 | 773.130846 | 17.41942187 | 27.09363521 | 0.033130208 | -4.915708918 | 8.43464209 | 1.32E-21 | | | |
| MT0600 | 973.2474525 | 1,312.17 | 2.15054591 | 1.030176244 | 0.001438969 | -9.44074926 | 9.15876849 | 7.94E-50 | | | |
| MT0601 | 94.23446521 | 88.4900089 | 7.813650139 | 7.932357078 | 0.086361819 | -3.533462557 | 5.61425504 | 4.41E-16 | Rv0573c | Rv0573c | conserved hypothetical protein |
| MT0602 | 380.3715053 | 345.718319 | 13.76349382 | 14.01039692 | 0.038294812 | -4.706707252 | 7.55221244 | 2.87E-24 | Rv0574c | Rv0574c | conserved hypothetical protein |
| MT1095 | 466.5941334 | 486.116683 | 238.0654322 | 156.9988596 | 0.414753404 | -1.269674273 | 8.39570064 | 0.039405387 | Rv1065 | Rv1065 | conserved hypothetical protein |
| MT1296 | 330.3929023 | 458.21052 | 1774.200376 | 115.8948274 | 0.371841482 | -1.427240372 | 8.07907409 | 0.017194468 | Rv1257c | Rv1257c | similar to many dehydrogenases |
| MT1297 | 207.163217 | 217.899417 | 43.94282142 | 42.95834937 | 0.20446722 | -2.290058522 | 6.99533809 | 1.70E-07 | Rv1258c | Rv1258c | probable multidrug resistance pump |
| MT1635 | 1,021.32 | 525.156393 | 345.3776731 | 224.3723859 | 0.368667553 | -1.439607648 | 9.04576691 | 0.036001439 | Rv1599 | hisD | histidinol dehydrogenase |
| MT1657 | 644.7621304 | 536.434531 | 284.08717147 | 171.3183094 | 0.38572261 | -1.374364378 | 8.67544048 | 0.033703938 | Rv1621c | cydD | ABC transporter |
| MT1773 | 155.2770338 | 225.562768 | 89.67776444 | 57.48383441 | 0.386124805 | -1.372860856 | 7.04421147 | 0.022935127 | Rv1732c | Rv1732c | conserved hypothetical protein |
| MT1774 | 1,426.87 | 1,750.86 | 4.372776683 | 2.678458234 | 0.002250709 | -8.795404644 | 9.63579929 | 6.49E-49 | Rv1733c | Rv1733c | possible membrane protein |
| MT1775 | 566.1698234 | 649.505098 | 52.04321102 | 11.43495631 | 0.052343645 | -4.255841806 | 8.3182942 | 3.18E-09 | | | |
| MT1777 | 20.22035084 | 16.3338415 | 5.161310184 | 3.193546356 | 0.231999244 | -2.107807993 | 3.44026242 | 0.003118061 | Rv1735c | Rv1735c | hypothetical protein |
| MT1778 | 107.206011 | 191.872944 | 0.286739455 | 0.721123371 | 0.003281004 | -8.251646766 | 6.22188263 | 1.05E-37 | Rv1736c | | |
| MT1779 | 5,668.95 | 3,546.69 | 10.75272955 | 5.665969341 | 0.001795059 | -9.121752773 | 11.1717362 | 1.05E-44 | Rv1737c | narX | fused nitrate reductase |
| MT1780 | 2,028.90 | 1,469.34 | 53.77184 | 5.562951717 | 0.003534852 | -8.144134574 | 9.77581156 | 3.51E-46 | Rv1738 | narK2 | nitrite extrusion protein |
| MT1823 | 3,772.05 | 4,986.96 | 4.157722092 | 2.472422985 | 0.000768719 | -10.34525576 | 11.0972462 | 4.44E-59 | Rv1773c | Rv1773c | conserved hypothetical protein |
| MT1860 | 659.6412565 | 359.309922 | 211.1570873 | 154.0113485 | 0.359315519 | -1.476676847 | 8.43312551 | 0.022917062 | Rv1812c | Rv1812c | transcriptional regulator (IclR family) |
| MT1861 | 242.64421 | 163.099232 | 62.724557 | 48.93337158 | 0.275812553 | -1.858239976 | 7.00905311 | 0.000243876 | Rv1813c | Rv1813c | probable dehydrogenase |
| MT1882 | 2,999.86 | 1,583.42 | 10.53767496 | 7.726321829 | 0.004002567 | -7.964588879 | 10.1663707 | 2.92E-38 | Rv1834 | Rv1834 | conserved hypothetical protein |
| MT1987 | 80.11837123 | 75.9105469 | 33.34672215 | 33.68676317 | 0.428062862 | -1.224105421 | 5.7946528 | 0.021630684 | Rv1937 | Rv1937 | conserved hypothetical protein similar to ring-hydroxylating dioxygenases |
| MT1988 | 385.7127301 | 97.1655 | 74.7673128 | 59.54418689 | 0.278840296 | -1.842489033 | 7.26040158 | 0.025007583 | Rv1938 | ephB | probable epoxide hydrolase |
| MT2016 | 152.2249053 | 35.7141049 | 29.03236978 | 20.08843676 | 0.263136796 | -1.926115091 | 5.86465135 | 0.021403294 | Rv1964 | Rv1964 | part of mce3 operon |
| | 368.1629916 | 168.159935 | 83.79960562 | 65.82826198 | 0.279600125 | -1.838563087 | 7.41576938 | 0.002724711 | | | |

TABLE 2A-continued

Downregulated gene expression tables of DMSO treated DosR mutant compared to DMSO treated WT

| Gene | Counts per million (CPM) | | | | WT DMSO/ DosR DMSO Fold change | log2 Fold change | logCPM | Adjusted p-value | Rv number | Gene name | Annotated function |
|---|---|---|---|---|---|---|---|---|---|---|---|
| | WT_DMSO1 | WT_DMSO2 | DosR_DMSO1 | DosR_DMSO2 | | | | | | | |
| MT2017 | 303.052625 | 91.2372478 | 40.00015392 | 49.55147733 | 0.227583638 | -2.135531255 | 6.90708944 | 0.002246518 | Rv1966 | mce3 | cell invasion protein |
| MT2018 | 337.6417073 | 108.443638 | 53.69196288 | 58.41099303 | 0.251926888 | -1.988922984 | 7.11488281 | 0.004118518 | Rv1967 | | part of mce3 operon |
| MT2019 | 349.0871889 | 97.5992746 | 62.36583138 | 47.69716009 | 0.247093802 | -2.016869274 | 7.11054156 | 0.007217261 | Rv1968 | | part of mce3 operon |
| MT2020 | 398.6842759 | 112.781384 | 80.21536244 | 41.10403213 | 0.237814764 | -2.072089814 | 7.29639671 | 0.009603969 | Rv1969 | | part of mce3 operon |
| MT2021 | 101.4832702 | 40.0518505 | 27.31193305 | 12.87720305 | 0.286477895 | -1.803504271 | 5.48197442 | 0.016676652 | Rv1970 | lprM | part of mce3 operon |
| MT2022 | 234.6323729 | 74.3200402 | 37.06107451 | 31.11132256 | 0.22160796 | -2.173918395 | 6.54376541 | 0.000935379 | Rv1971 | | part of mce3 operon |
| MT2023 | 317.0398405 | 90.369698 | 50.53782888 | 46.77000147 | 0.239555542 | -2.061567906 | 6.9678295 | 0.004118518 | Rv1992c | ctpG | probable cation transport ATPase |
| MT2048 | 2,083.08 | 798.434362 | 501.077197 | 316.5731597 | 0.283876924 | -1.816662515 | 9.85171079 | 0.011300679 | Rv1992c | | conserved hypothetical protein |
| MT2052 | 40,500.98 | 9,131.10 | 62.65257084 | 89.62533322 | 0.003068089 | -8.34844373 | 13.6032098 | 7.05E-24 | Rv1996 | Rv1996 | probable cation transport ATPase |
| MT2053 | 3,166.58 | 1,679.72 | 29.10405465 | 26.16647659 | 0.011416583 | -6.452725332 | 10.2576158 | 3.48E-30 | Rv1997 | ctpF | conserved hypothetical protein |
| MT2060 | 538.7006675 | 897.190368 | 68.74578425 | 49.55147733 | 0.082406043 | -3.601100429 | 8.60078438 | 3.27E-12 | Rv2003c | Rv2003c | hypothetical protein |
| MT2061 | 2,717.54 | 2,771.24 | 163.4414891 | 230.656461 | 0.071792403 | -3.800025009 | 10.5216697 | 1.07E-15 | Rv2004c | Rv2004c | conserved hypothetical protein |
| MT2062 | 2,440.18 | 2,227.00 | 91.25483144 | 124.9603784 | 0.046320465 | -4.432206465 | 10.2527586 | 2.61E-20 | Rv2005c | Rv2005c | trehalose-6-phosphate phosphatase |
| MT2063 | 602.7953645 | 816.508301 | 94.4806503 | 134.3349822 | 0.16113863 | -2.633625696 | 8.68544794 | 1.81E-07 | Rv2006 | otsB | ferredoxin |
| MT2086 | 7,680.30 | 9,830.05 | 47.45537974 | 62.32566275 | 0.006279929 | -7.317795385 | 12.1047351 | 1.13E-41 | Rv2007c | fdxA | sensor histidine kinase |
| MT2087 | 332.3004826 | 194.620183 | 54.69555097 | 59.64720452 | 0.217342141 | -2.201960166 | 7.31831837 | 1.34E-05 | Rv2027c | Rv2027c | conserved hypothetical protein |
| MT2088 | 792.4088431 | 718.909027 | 4.014352365 | 2.678458234 | 0.004488188 | -7.799651114 | 8.5647231 | 2.00E-42 | Rv2028c | Rv2028c | conserved hypothetical protein |
| MT2089 | 4,892.94 | 2,628.82 | 6.236883138 | 5.87200459 | 0.001615214 | -9.274058907 | 10.8782427 | 1.82E-48 | | | |
| MT2090 | 14,539.96 | 14,668.81 | 6.451637729 | 3.914669727 | 0.000358657 | -11.4451059 | 12.8344686 | 2.19E-69 | Rv2030c | Rv2030c | conserved hypothetical protein |
| MT2091 | 46,354.20 | 44,251.51 | 9.032292821 | 10.91986818 | 0.000220144 | -12.14926404 | 14.4675784 | 3.64E-80 | | | |
| MT2445.1 | 3,999.05 | 5,966.42 | 7.383540957 | 5.355916468 | 0.001286705 | -9.602102615 | 11.2842649 | 4.29E-55 | Rv2032 | Rv2032 | conserved hypothetical protein |
| MT2446 | 74.01411438 | 109.600371 | 18.85311914 | 39.76480301 | 0.31777865 | -1.653936698 | 5.91799559 | 0.00697094 | Rv2378c | mbtG | mycobactin/exochelin synthesis (lysine hydroxylase) |
| MT2447 | 80.88140334 | 101.069471 | 32.04313406 | 46.8730191 | 0.43241396 | -1.209514992 | 6.02582456 | 0.035645827 | Rv2378c | | |
| MT2448 | 228.1466 | 293.231598 | 121.5775288 | 103.8417654 | 0.43210348 | -1.21055124 | 7.54425616 | 0.040809265 | Rv2379c | mbtF | mycobactin/exochelin synthesis (lysine ligation) |
| MT2449 | 633.6981648 | 578.799846 | 213.2624694 | 222.3120334 | 0.359288996 | -1.476783345 | 8.68583436 | 0.008161223 | Rv2380c | mbtE | mycobactin/exochelin synthesis (lysine ligation) |
| MT2489 | 201.1404762 | 170.762583 | 80.71715648 | 33.17167505 | 0.306584243 | -1.705644545 | 6.92070866 | 0.007058523 | Rv2381c | mbtD | mycobactin/exochelin synthesis (polyketide |
| MT2556 | 207.163217 | 308.413708 | 62.86762543 | 62.9437685 | 0.243761345 | -2.036458729 | 7.32357418 | 3.52E-05 | Rv2416c | Rv2416c | conserved hypothetical protein |
| MT2557 | 807.2879692 | 426.255795 | 185.3770574 | 243.4306464 | 0.34782334 | -1.52357335 | 8.69697564 | 0.02170976 | Rv2483c | | possible transferase |
| MT2576 | 1,231.53 | 615.3815 | 271.9006879 | 344.4909359 | 0.33388514 | -1.582576209 | 9.26490002 | 0.014560858 | Rv2484c | | conserved hypothetical protein |
| MT2577 | 1,467.31 | 658.180589 | 394.7685442 | 396.9269068 | 0.372649095 | -1.424110338 | 9.50913273 | 0.042258365 | Rv2502c | | |
| MT2579 | 473.0799063 | 238.865188 | 134.5524891 | 107.7503999 | 0.340574739 | -1.553956663 | 7.89427969 | 0.011759403 | Rv2504c | accD1 | acetyl/propionyl-CoA carboxylase, [beta] subunit |
| MT2600 | 611.1887177 | 294.243739 | 140.6457025 | 153.0841898 | 0.324744749 | -1.622621899 | 8.22465824 | 0.009371108 | Rv2524c | scoA | 3-oxo acid:CoA transferase, [alpha] subunit |
| MT2684 | 59,719.47 | 11,091.04 | 7,787.77 | 4,178.60 | 0.168994642 | -2.564950587 | 14.3368479 | 0.004674557 | Rv2609c | fas | fatty acid synthase |
| MT2686 | 186.9428662 | 175.24492 | 76.98954357 | 79.11753553 | 0.431182006 | -1.213631121 | 7.01540962 | 0.028172861 | Rv2611c | Rv2609c | conserved hypothetical protein |
| MT2687 | 241.8811779 | 186.956833 | 86.38026071 | 86.43178686 | 0.403439086 | -1.309577233 | 7.22971648 | 0.01939155 | Rv2612c | pgsA | conserved hypothetical protein CDP-diacylglycerol-glycerol-3-phosphate |
| MT2695 | 217.0826344 | 190.427029 | 86.52363044 | 80.14771177 | 0.409326843 | -1.288674814 | 7.16285946 | 0.018562405 | | | |
| MT2698 | 364.3478311 | 225.418176 | 134.1940648 | 78.29339453 | 0.360880071 | -1.470408621 | 7.64454318 | 0.02140329 | Rv2623 | Rv2623 | conserved hypothetical protein |
| | 43,651.54 | 22,787.33 | 92.68852871 | 59.64720452 | 0.002294397 | -8.76766896 | 14.0229365 | 1.13E-41 | | | |

TABLE 2A-continued

Downregulated gene expression tables of DMSO treated DosR mutant compared to DMSO treated WT

| Gene | Counts per million (CPM) | | | | Fold change | log2 Fold change | logCPM | Adjusted p-value | Rv number | Gene name | Annotated function |
|---|---|---|---|---|---|---|---|---|---|---|---|
| | WT_DMSO1 | WT_DMSO2 | DosR_DMSO1 | DosR_DMSO2 | WT DMSO/ DosR DMSO | | | | | | |
| MT2699 | 2,493.21 | 1,896.75 | 8.960607958 | 7.417268956 | 0.003745743 | −8.060532534 | 10.10408 | 1.10E-46 | Rv2624c | Rv2624c | conserved hypothetical protein |
| MT2700 | 5,930.29 | 3,801.89 | 12.40148141 | 8.4474452 | 0.002152157 | −8.86000071 | 11.250982 | 1.85E-48 | Rv2625c | Rv2625c | conserved hypothetical protein |
| MT2701 | 13,330.55 | 10,898.30 | 8.315444185 | 9.683656692 | 0.000742957 | −10.39443406 | 12.5652855 | 4.67E-66 | Rv2626c | Rv2626c | conserved hypothetical protein |
| MT2702 | 8,011.07 | 5,842.22 | 21.36208937 | 28.84493483 | 0.003622325 | −8.108868104 | 11.7627405 | 2.04E-46 | Rv2627c | Rv2627c | conserved hypothetical protein |
| MT2703 | 716.4871485 | 928.711319 | 33.19009187 | 31.21434019 | 0.039162393 | −4.674387255 | 8.73761123 | 2.20E-21 | Rv2628 | Rv2628 | hypothetical protein |
| MT2704 | 7,924.47 | 5,007.78 | 327.5998269 | 429.0684056 | 0.058511346 | −4.095139792 | 11.7403054 | 2.59E-16 | Rv2629 | Rv2629 | hypothetical protein |
| MT2707 | 781.7263936 | 580.679536 | 40.57363283 | 39.97083826 | 0.059162822 | −4.079165319 | 8.49131437 | 1.04E-17 | Rv2630 | Rv2630 | hypothetical protein |
| MT2797 | 1,151.80 | 503.323074 | 75.19742198 | 74.89381293 | 0.090752608 | −3.461917083 | 8.81435422 | 2.85E-10 | Rv2631 | Rv2631 | conserved hypothetical protein |
| MT3004 | 738.6150796 | 774.142987 | 373.1914002 | 265.3734004 | 0.422157177 | −1.244147853 | 9.07061229 | 0.042657862 | Rv2725c | hIX | GTP-binding protein |
| MT3210 | 1,541.71 | 986.981701 | 211.3986629 | 180.0748074 | 0.154875364 | −2.690820423 | 9.51028601 | 5.23E-08 | Rv2934 | ppsD | phenolpthiocerol synthesis (pksE) |
| MT3212 | 8.393353177 | 6.07284375 | 0.215054591 | 0.206035249 | 0.031175839 | −4.976434426 | 1.7015864 | 4.50E-09 | | | |
| MT3216 | 16,224.35 | 10,456.71 | 28.6022606 | 30.39019919 | 0.00221177 | −8.820582855 | 12.7064774 | 9.85E-51 | Rv3127 | Rv3127 | conserved hypothetical protein |
| MT3217 | 33,572.27 | 28,005.50 | 9.749140458 | 9.683656692 | 0.000316093 | −11.6273646 | 13.9104897 | 2.79E-76 | Rv3130c | Rv3130c | conserved hypothetical protein |
| MT3218 | 19,054.06 | 10,491.71 | 7.813650139 | 6.593127961 | 0.000489538 | −10.99629141 | 12.8511309 | 8.37E-60 | Rv3131 | Rv3131 | conserved hypothetical protein |
| MT3219 | 5,329.40 | 3,268.20 | 1,468.11 | 1,110.12 | 0.299909861 | −1.737399134 | 11.4477977 | 0.002445427 | Rv3132c | Rv3132c | sensor histidine kinase |
| MT3220 | 3,862.85 | 2,091.66 | 0.071684864 | 0.206035249 | 4.81962E-05 | −14.34072209 | 10.5386559 | 1.04E-64 | Rv3133c | Rv3133c | two-component response regulator |
| MT3233 | 6,333.93 | 3,965.28 | 80.71715648 | 43.67947274 | 0.01209382 | −6.369877033 | 11.3469612 | 8.94E-28 | Rv3134c | Rv3134c | conserved hypothetical protein |
| MT3234 | 146.8836806 | 228.165415 | 73.04687607 | 46.8730191 | 0.319475008 | −1.64622502 | 6.95060923 | 0.003280598 | Rv3145 | nuoA | NADH dehydrogenase chain A |
| MT3235 | 203.7295726 | 202.717308 | 60.78876438 | 79.0145179 | 0.343871913 | −1.540056812 | 7.09060659 | 0.002953587 | Rv3146 | nuoB | NADH dehydrogenase chain B |
| MT3236 | 149.554293 | 161.219542 | 58.27979416 | 57.38081678 | 0.372063645 | −1.426378665 | 6.73366601 | 0.003086323 | Rv3147 | nuoC | NADH dehydrogenase chain C |
| MT3237 | 410.8927896 | 352.224938 | 118.4950796 | 141.6492335 | 0.340987349 | −1.552209882 | 7.99699076 | 0.003086323 | Rv3148 | nuoD | NADH dehydrogenase chain D |
| MT3238 | 188.0874144 | 216.019728 | 63.72784379 | 45.01870186 | 0.269191984 | −1.893292643 | 6.99941876 | 9.87E-05 | Rv3149 | nuoE | NADH dehydrogenase chain E |
| MT3239 | 327.3407739 | 314.920326 | 132.6169978 | 134.0259293 | 0.415231564 | −1.268101979 | 7.82669393 | 0.02130684 | Rv3150 | nuoF | NADH dehydrogenase chain F |
| MT3240 | 718.7762448 | 598.175109 | 264.3737772 | 262.288371 | 0.400013299 | −1.321880526 | 8.84739698 | 0.0218282 | Rv3151 | nuoG | NADH dehydrogenase chain G |
| MT3241 | 507.4163511 | 394.590252 | 124.8750325 | 206.8593898 | 0.367838093 | −1.442857202 | 8.26706742 | 0.018637339 | Rv3152 | nuoH | NADH dehydrogenase chain H |
| MT3244 | 237.6845013 | 191.872944 | 62.86762543 | 102.0904658 | 0.38413039 | −1.38033199 | 7.21234636 | 0.020937675 | Rv3153 | nuoI | NADH dehydrogenase chain I |
| MT3290.1 | 308.2649712 | 401.819828 | 139.7854841 | 167.1976044 | 0.432021639 | −1.210824519 | 7.98994584 | 0.043964462 | Rv3156 | nuoL | NADH dehydrogenase chain L |
| MT3370 | 94.99749732 | 134.903886 | 62.93931029 | 33.27469268 | 0.418167093 | −1.257848558 | 6.34941097 | 0.049623816 | | | |
| MT3402 | 4,292.44 | 2,498.83 | 1,575.49 | 563.1973525 | 0.314961629 | −1.666753016 | 11.1240739 | 0.034099178 | Rv3270 | ctpC | cation transport ATPase |
| MT3427 | 1,123.56 | 907.167183 | 178.0652013 | 186.5649178 | 0.179594079 | −2.477188306 | 9.22454494 | 1.39E-07 | Rv3303c | lpdA | dihydrolipoamide dehydrogenase |
| MT3444 | 239.5920816 | 243.925891 | 66.16512916 | 89.11024509 | 0.32102187 | −1.639256507 | 7.31665292 | 0.001570229 | | | |
| MT3581 | 1,122.04 | 664.976391 | 304.5889857 | 232.6137959 | 0.300775754 | −1.733239819 | 9.18107601 | 0.002930145 | Rv3341 | metA | homoserine o-acetyltransferase |
| MT3582 | 263.2460769 | 206.332096 | 96.41614162 | 72.21535469 | 0.359592374 | −1.475565671 | 7.31465472 | 0.007151511 | Rv3477 | PE | PE-family protein |
| MT3634 | 157.9476461 | 113.938116 | 69.67768748 | 46.97603672 | 0.430319871 | −1.216518632 | 6.59737042 | 0.036554628 | Rv1361c | PPE | PPE-family protein |
| MT3653 | 231.5802445 | 93.1169375 | 50.8962532 | 67.68257922 | 0.366329269 | −1.448787122 | 6.78337768 | 0.033703938 | Rv3531c | Rv3531c | hypothetical protein |
| MT3654 | 340.6938358 | 209.946884 | 120.3588861 | 113.2163692 | 0.424820904 | −1.235073338 | 7.6121441 | 0.046356345 | Rv3549c | Rv3549c | short-chain alcohol dehydrogenase family |
| MT3655 | 235.395405 | 124.204114 | 63.44110434 | 56.35064054 | 0.334121422 | −1.581555612 | 6.89802833 | 0.005251593 | Rv3551 | Rv3551 | possible glutaconate CoA-transferase |
| MT3656 | 475.7505187 | 197.512013 | 94.6957049 | 128.6690129 | 0.332209831 | −1.589833329 | 7.80377476 | 0.020864159 | Rv3552 | Rv3552 | hypothetical protein |
| MT3657 | 127.4263619 | 89.068375 | 45.30483383 | 34.92297467 | 0.37199042 | −1.426662628 | 6.20542704 | 0.007639252 | | | |
| MT3716 | 3,343.61 | 2,173.79 | 623.1565198 | 659.0037432 | 0.232414502 | −2.105228004 | 10.7306738 | 3.65E-06 | Rv3614c | Rv3614c | conserved hypothetical protein |
| MT3717 | 1,445.18 | 1,052.92 | 243.6568516 | 243.7500962 | 0.200760238 | −2.316454534 | 9.54928945 | 1.96E-06 | Rv3615c | Rv3615c | conserved hypothetical protein |
| MT3718 | 4,661.36 | 3,470.05 | 922.7992499 | 692.8965416 | 0.198719299 | −2.331196103 | 11.2503906 | 2.00E-06 | Rv3616c | Rv3616c | conserved hypothetical protein |

TABLE 2A-continued

Downregulated gene expression tables of DMSO treated DosR mutant compared to DMSO treated WT

| Gene | Counts per million (CPM) | | | | WT DMSO/ DosR DMSO Fold change | log2 Fold change | logCPM | Adjusted p-value | Rv number | Gene name | Annotated function |
|---|---|---|---|---|---|---|---|---|---|---|---|
| | WT_DMSO1 | WT_DMSO2 | DosR_DMSO1 | DosR_DMSO2 | | | | | | | |
| MT3907 | 14,047.04 | 4,046.54 | 3,073.85 | 2,453.88 | 0.305527197 | −1.710627283 | 12.5275801 | 0.03595872 | Rv3800c | pks13 | polyketide synthase |
| MT3947 | 91.94536889 | 62.4635357 | 30.32269733 | 13.70134404 | 0.286990675 | −1.800924236 | 5.61822685 | 0.003113511 | Rv3839 | Rv3839 | hypothetical protein |
| MT3953 | 57.99044013 | 42.2207232 | 19.35491319 | 20.19145438 | 0.396619289 | −1.334173252 | 5.1133998 | 0.028946617 | | | |

TABLE 2B

Upregulated gene expression tables of DMSO treated DosR mutant compared to DMSO treated WT

| | Counts per million (CPM) | | | | WT DMSO/ DosR DMSO | | | | Rv | Gene | |
|---|---|---|---|---|---|---|---|---|---|---|---|
| Gene | WT_DMSO1 | WT_DMSO2 | DosR_DMSO1 | DosR_DMSO2 | Fold change | log2 Fold change | logCPM | Adjusted p-value | number | name | Annealed function |
| MT0160 | 38.9146375 | 40.6302165 | 81.57737485 | 108.6835937 | 2.388163199 | 1.255901429 | 6.08932008 | 0.021630684 | | PE | PE-family protein |
| MT0169 | 4.9597087 | 8.82008259 | 54.48049638 | 68.30068497 | 8.551198149 | 3.095126577 | 5.13510505 | 2.74E-09 | Rv0150c | | acyl-CoA dehydrogenase |
| MT0258 | 635.987261 | 642.130931 | 1,818.64 | 1,416.29 | 2.530986008 | 1.339699532 | 10.1407928 | 0.02186282 | Rv0244c | fadE5 | two-component response regulator |
| MT0273 | 11.0639656 | 4.91611161 | 42.36575442 | 25.11630035 | 4.39162198 | 2.134753876 | 4.43365706 | 0.005768789 | Rv0250c | Rv0260c | cytochrome P-450 monooxygenasemonoxygenase |
| MT0342 | 4.19675659 | 3.32560491 | 14.33697273 | 11.12590343 | 3.451503664 | 1.787225016 | 3.15003122 | 0.035554628 | Rv0327c | Rv0327c | |
| MT0458 | 36.2440251 | 52.0529464 | 153.548978 | 79.0145179 | 2.619991667 | 1.389562223 | 6.34004103 | 0.025437098 | Rv0452 | Rv0452 | putative transcriptional regulator |
| MT0483 | 486.814484 | 522.698337 | 1,914.85 | 1,420.61 | 3.303653028 | 1.724062173 | 10.0862308 | 0.001203906 | Rv0457 | aceA | isocitrate lyase |
| MT0484 | 113.310268 | 124.78248 | 379.7864077 | 271.544579 | 2.733913604 | 1.450967652 | 7.80164398 | 0.007217261 | | | |
| MT0491 | 62.5686328 | 62.6081272 | 206.3090376 | 185.8437944 | 3.132456858 | 1.64729454 | 7.02350646 | 0.000800955 | Rv0474 | Rv0474 | transcriptional regulator (PbsX/Xre family) |
| MT0493 | 546.330989 | 416.857346 | 1,555.35 | 1,455.33 | 2.530986008 | 1.644826929 | 9.95739247 | 0.002139956 | Rv0475 | Rv0475 | possible exported protein |
| MT0542 | 21.7464151 | 30.2196272 | 67.74219616 | 111.0529991 | 3.406562009 | 1.768316468 | 5.86990244 | 0.000894459 | Rv0520 | Rv0520 | similar to methyltransferases |
| MT0738 | 236.921469 | 148.929263 | 554.4107355 | 442.1516439 | 2.587204776 | 1.371394247 | 8.43357051 | 0.02817286 | | | |
| MT0908 | 925.17643 | 216.019728 | 3,557.22 | 4,034.17 | 6.745474828 | 2.753920001 | 11.1092014 | 0.000244637 | Rv0885 | Rv0885 | unknown transmembrane protein |
| MT0909 | 135.438198 | 34.2681897 | 701.8665001 | 443.1818201 | 6.784841685 | 2.762315153 | 8.36467109 | 0.000211208 | Rv0886 | fprB | ferredoxin, ferredoxin-NADP reductase |
| MT1087 | 113.310268 | 195.053958 | 515.772594 | 324.2994816 | 2.718228635 | 1.442666809 | 8.16969686 | 0.027414181 | Rv1057 | Rv1057 | conserved hypothetical protein |
| MT1168 | 70.5804699 | 69.1147455 | 131.3266702 | 198.2059093 | 2.358565228 | 1.2379095 | 6.88173624 | 0.032709004 | Rv1135c | PPE | PPE-family protein |
| MT1213 | 31.2843164 | 31.5209509 | 86.30857585 | 76.33605967 | 2.588866752 | 1.372320712 | 5.83404475 | 0.007245332 | Rv1176c | Rv1176c | conserved hypothetical protein |
| MT1232 | 44.2258622 | 29.7858527 | 97.20467512 | 103.0176244 | 2.727487557 | 1.447572615 | 6.11246536 | 0.006669465 | | | |
| MT1252 | 15.7606421 | 23.7130089 | 64.73143189 | 39.97083876 | 2.652043806 | 1.407104606 | 5.19750573 | 0.034099178 | | | |
| MT1259 | 814.155258 | 804.362614 | 1,720.15 | 2,174.70 | 2.406403224 | 1.266878405 | 10.4294001 | 0.033703938 | Rv1221 | sigE | ECF subfamily sigma subunit |
| MT1555.1 | 2.67051237 | 1.15673214 | 11.039469 | 5.665969341 | 4.800819214 | 2.263280609 | 2.52401764 | 0.031759562 | | | |
| MT1567 | 30.5212843 | 57.2582411 | 183.0831418 | 183.9984772 | 4.139077099 | 2.049309122 | 6.84109591 | 5.81E-05 | Rv1517 | Rv1517 | conserved hypothetical protein |
| MT1558 | 15.6421582 | 11.4227299 | 65.01817134 | 76.85114779 | 5.31907375 | 2.411175043 | 5.42891369 | 9.37E-07 | Rv1518 | Rv1518 | involved in exopolysaccharide synthesis |
| MT1577 | 24.0355114 | 18.6523058 | 102.4376702 | 91.27361521 | 4.580236438 | 2.195422074 | 5.90555169 | 1.24E-06 | Rv1526c | Rv1526c | possible rhamnosyl/glycosyl transferase |
| MT1580 | 101.48327 | 114.082708 | 250.0368044 | 428.4502998 | 3.144100998 | 1.652647562 | 7.80907092 | 0.002953587 | Rv1529 | fadD24 | acyl-CoA synthase |
| MT1905 | 38.1516054 | 45.2571451 | 96.12940217 | 113.6284397 | 2.504745813 | 1.324664203 | 6.20907615 | 0.0116618340 | Rv1857 | modA | molybdate binding protein |
| MT1922 | 6.86728896 | 8.38630804 | 29.60584869 | 28.63889958 | 3.766893019 | 1.913375061 | 4.25903931 | 0.003118061 | Rv1873 | Rv1873 | hypothetical protein |
| MT2040 | 55.3198278 | 32.2439085 | 570.3247753 | 79.32357078 | 7.442851069 | 2.895835368 | 7.53450033 | 0.002953587 | Rv1986 | Rv1986 | membrane protein, IYSEAGGA family |
| MT2417 | 8.01183712 | 6.07284375 | 15.84235487 | 28.74191172 | 3.205618031 | 1.68060253 | 3.93265985 | 0.041840399 | | | |
| MT2526 | 114.454816 | 182.763679 | 1,809.18 | 337.2797022 | 7.214264063 | 2.850852231 | 9.25760852 | 0.000876027 | Rv2450c | Rv2450c | conserved hypothetical protein |
| MT2593.2 | 2.67061237 | 3.61478795 | 12.75990573 | 14.01039692 | 4.120891771 | 2.042965574 | 3.16550579 | 0.008030283 | | | |
| MT2792 | 11.0639656 | 22.9900513 | 58.63821847 | 39.76480301 | 2.829958129 | 1.500270824 | 5.0850945 | 0.03351671 | Rv2719c | Rv2719c | conserved hypothetical protein |
| MT2804 | 37.0070572 | 32.9668661 | 69.2475783 | 95.29130256 | 2.356319315 | 1.236535059 | 5.88806015 | 0.028860259 | Rv2735c | Rv2735c | hypothetical protein |
| MT2805 | 23.6539953 | 32.099317 | 83.08275698 | 52.84804131 | 2.419830115 | 1.274905766 | 5.60439534 | 0.035645827 | Rv2736c | recX | regulatory protein for RecA |
| MT2849 | 22.8909632 | 7.95253348 | 61.2905843 | 40.38290876 | 3.492796632 | 1.76249066 | 5.0773488 | 0.026850503 | Rv2779c | Rv2779c | transcriptional regulator (Lrp/AsnC family) |
| MT3010 | 1,991.13 | 718.619844 | 6,831.93 | 2,972.47 | 3.619282173 | 1.855703559 | 11.6116154 | 0.022912631 | Rv2940c | mas | mycoerosic acid synthase |
| MT3110 | 4.9597087 | 3.75937947 | 20.14344669 | 10.71383294 | 3.614771479 | 1.853904445 | 3.40249143 | 0.034099178 | Rv3026c | Rv3026c | some similarityt o acyltransferase Q59501 |
| MT3111 | 45.0188943 | 34.4127813 | 126.8822087 | 86.12273399 | 2.696689768 | 1.431189561 | 6.20517185 | 0.009371108 | Rv3027c | Rv3027c | hypothetical protein |
| MT3132 | 32.0473485 | 29.4966697 | 94.55233517 | 78.19037691 | 2.813307288 | 1.492262985 | 5.88937727 | 0.003086323 | | | |
| MT3133 | 306.357391 | 226.419272 | 761.3649369 | 867.5114149 | 3.058158084 | 1.612662985 | 9.07999842 | 0.000386323 | Rv3048c | nrdG | ribonucleoside-diphosphate small subunit |
| MT3134 | 877.868439 | 237.419272 | 1,977.00 | 2,032.74 | 3.598450575 | 1.847375843 | 10.3240757 | 0.02186282 | Rv3049c | Rv3049c | Probable monooxygenase |
| MT3140 | 1.90758027 | 2.4550558 | 25.37644174 | 10.40478006 | 7.960462609 | 2.992852273 | 3.45187296 | 0.000200867 | Rv3054c | Rv3054c | conserved hypothetical protein |
| MT3247 | 25.1800595 | 18.2185313 | 57.34789093 | 58.10194015 | 2.687723222 | 1.426384579 | 5.33378974 | 0.015676652 | Rv3159c | PPE | PPE-family protein |

TABLE 2B-continued

Upregulated gene expression tables of DMSO treated DosR mutant compared to DMSO treated WT

| Gene | Counts per million (CPM) | | | | WT DMSO/ DosR DMSO Fold change | log2 Fold change | logCPM | Adjusted p-value | Rv number | Gene name | Annealed function |
|---|---|---|---|---|---|---|---|---|---|---|---|
| | WT_DMSO1 | WT_DMSO2 | DosR_DMSO1 | DosR_DMSO2 | | | | | | | |
| MT3248 | 78.210791 | 66.8012813 | 144.3016305 | 213.2464825 | 2.469112207 | 1.3039924 | 6.98017178 | 0.024272786 | | | |
| MT3441 | 83.1704997 | 67.8134219 | 317.4922612 | 207.2714603 | 3.482898672 | 1.800288501 | 7.4071827 | 0.000694534 | Rv3338 | Rv3338 | conserved hypothetical protein |
| MT3513 | 28.613704 | 27.6169799 | 133.2621615 | 43.57645512 | 3.148339387 | 1.65459107 | 5.88456794 | 0.024335692 | | | |
| MT3514 | 63.7131809 | 49.3057076 | 572.6186909 | 314.2037544 | 7.869912383 | 2.976347574 | 7.97166866 | 4.79E-09 | Rv3406 | Rv3406 | putative dioxygenasedioxygenase |
| MT3515 | 64.476713 | 46.4138777 | 217.9936704 | 178.94164136 | 3.596611544 | 1.846638348 | 6.99698457 | 0.000198777 | Rv3407 | Rv3407 | conserved hypothetical protein |
| MT3532.2 | 32.4288646 | 13.5916027 | 89.82113417 | 73.34854856 | 3.624643162 | 1.857838972 | 5.72742878 | 0.002445427 | Rv3424c | Rv3424c | hypothetical protein |
| MT3533 | 109.113591 | 55.9569174 | 238.1371171 | 197.0727154 | 2.650734927 | 1.406392408 | 7.23515869 | 0.028172861 | Rv3429 | PPE | PPE-family protein |
| MT3941 | 27.4691559 | 31.3763594 | 91.2548314 | 72.73044282 | 2.776179349 | 1.473100773 | 5.81881977 | 0.003842811 | Rv3833 | Rv3833 | transcriptional regulator (AraC/XylS family) |
| MT3976 | 96.9050776 | 37.3046116 | 593.5506711 | 79.4265884 | 5.030707225 | 2.330761231 | 7.6634557 | 0.041661275 | Rv3852c | Rv3862c | hypothetical protein |

TABLE 2C

Downregulated gene expression tables of WT Mtb treated with HC101A Compared to DMSO

| Gene | Counts per million (CPM) | | | | WT DMSO/ WT HC101A Fold change | log2 Fold change | logCPM | Adjusted p-value | Rv number | Gene name | Annotated function |
|---|---|---|---|---|---|---|---|---|---|---|---|
| | WT_DMSO1 | WT_DMSO2 | WT_HC101A1 | WT_HC101A2 | | | | | | | |
| MT0037 | 105.768758 | 87.457548 | 35.2352805 | 27.75295477 | 0.326829649 | −1.611339228 | 5.98129424 | 1.29E−05 | Rv0032 | bioF2 | C-terminal similar to B. subtilis BioF |
| MT0038 | 22.6368559 | 13.1260064 | 2.484119968 | 3.490937707 | 0.17223375 | −2.537560218 | 3.2080193 | 1.17E−07 | Rv0033 | | possible acyl carrier protein |
| MT0040 | 94.4503296 | 84.6553669 | 24.97194284 | 29.55660592 | 0.305148266 | −1.712417701 | 5.84686602 | 1.36E−06 | Rv0035 | fadD34 | acyl-CoA synthase |
| MT0062 | 243.541346 | 182.87919 | 104.594525 | 99.66627154 | 0.479854072 | −1.05933236 | 7.29458933 | 0.011192668 | Rv0056 | rpl1 | 50S ribosoma lprotein L9 |
| MT0055 | 97.9629451 | 59.8781863 | 35.16990902 | 29.03296626 | 0.409633748 | −1.287593517 | 5.77070182 | 0.002536411 | | | |
| MT0086 | 1,339.09 | 2,633.17 | 496.301021 | 1,101.39 | 0.40214484 | −1.314212885 | 10.4433477 | 0.044203618 | Rv0079 | | hypothetical protein |
| MT0105 | 21.0756934 | 27.5793617 | 8.52904831 | 7.796425346 | 0.333840825 | −1.582767761 | 3.98651137 | 0.000151741 | Rv0096 | PPE | PPE-family protein |
| MT0106 | 76.4969611 | 67.5473136 | 24.38359863 | 21.52744919 | 0.319546938 | −1.645900232 | 5.54431417 | 3.96E−06 | Rv0097 | | conserved hypothetical protein |
| MT0107 | 37.85819 | 30.529026 | 11.70151248 | 9.89099017 | 0.318098281 | −1.652455521 | 4.43829409 | 4.04E−05 | Rv0098 | | hypothetical protein |
| MT0108 | 78.0581236 | 71.9718102 | 39.35369002 | 32.64026756 | 0.480564612 | −1.057197681 | 5.78167989 | 0.007028674 | Rv0099 | fadD10 | acyl-CoA synthase |
| MT0117 | 383.265387 | 341.423649 | 157.5455032 | 202.6489339 | 0.497275233 | −1.007883515 | 8.08053967 | 0.019433804 | | | |
| MT0122 | 80.7901579 | 47.0471464 | 36.47734058 | 25.54202756 | 0.489225714 | −1.031407486 | 5.54483179 | 0.0338307 | Rv0113 | gmhA | phosphoheptose isomerase |
| MT0124 | 28.1009245 | 8.70150984 | 5.295097827 | 3.898213773 | 0.258135559 | −1.953799204 | 3.34212895 | 0.002071634 | | | |
| MT0175 | 285.302442 | 154.414929 | 67.07123914 | 45.73128396 | 0.257182706 | −1.959134461 | 7.09489141 | 1.29E−05 | Rv0166 | fadD5 | acyl-CoA synthase |
| MT0176 | 265.787911 | 258.243114 | 118.5186711 | 96.69897448 | 0.410752586 | −1.283658436 | 7.52510923 | 0.000954269 | | | |
| MT0178 | 577.239824 | 412.51056 | 178.4644082 | 133.5865496 | 0.315521154 | −1.664191363 | 8.34152685 | 4.81E−05 | Rv0169 | mceI | cell invasion protein |
| MT0179 | 448.44392 | 313.106871 | 123.1600532 | 102.1681102 | 0.296206916 | −1.755322771 | 7.94008087 | 1.25E−05 | Rv0170 | Rv0170 | part of mceI operon |
| MT0180 | 472.641938 | 368.413077 | 185.5877456 | 130.0374296 | 0.319064589 | −1.64545355 | 8.11077899 | 1.61E−05 | Rv0171 | Rv0171 | part of mceI operon |
| MT0181 | 592.461158 | 488.6119 | 183.5633913 | 197.8198034 | 0.35295154 | −1.502457979 | 8.51074265 | 0.000198389 | Rv0172 | Rv0172 | part of mceI operon |
| MT0183 | 318.477144 | 288.32969 | 87.14031361 | 107.6954283 | 0.321272367 | −1.638131198 | 7.64065981 | 1.66E−05 | Rv0173 | lprK | part of mceI operon |
| MT0183 | 971.823639 | 854.960212 | 348.9534839 | 411.6979202 | 0.416464694 | 1.263733899 | 9.3357677 | 0.004816418 | Rv0174 | Rv0174 | part of mceI operon |
| MT0241 | 149.871597 | 167.098486 | 59.55350765 | 72.37877513 | 0.415933405 | −1.265575537 | 6.80398903 | 0.000935573 | Rv0231 | fadE4 | acyl-CoA dehydrogenase |
| MT0244 | 127.625032 | 68.2847297 | 37.26179952 | 30.02206428 | 0.345666501 | −1.5325473 | 6.01420461 | 0.000493148 | Rv0233 | nrdB | ribonucleoside-diphosphate reductase B2 |
| MT0329 | 252.127739 | 246.59194 | 70.60130435 | 95.12805252 | 0.332425853 | −1.588895508 | 7.36939005 | 2.91E−05 | Rv0315 | | probable [beta]−1,3-glucanase |
| MT0417 | 71.0328925 | 58.4033542 | 28.9596091 | 22.92382428 | 0.402402748 | −1.313287937 | 5.47978443 | 0.000697909 | | | |
| MT0423 | 2,729.30 | 844.931353 | 514.0820902 | 411.8724671 | 0.259149552 | −1.948143194 | 10.1333761 | 0.002195753 | Rv0410c | pknG | serine-threonine protein kinase |
| MT0424 | 1,285.23 | 391.862909 | 282.7320753 | 249.9511398 | 0.317858952 | −1.633541373 | 9.10526088 | 0.009921952 | Rv0411c | glnH | putative glutamine binding protein |
| MT0425 | 1,440.17 | 508.227168 | 385.4961961 | 301.2679241 | 0.325693195 | −1.503514353 | 9.3603738 | 0.015307302 | Rv0412c | Rv0412c | unknown probable membrane protein |
| MT0429 | 18.7339497 | 13.1260064 | 5.818070451 | 5.876411807 | 0.375236657 | −1.414127321 | 3.35475139 | 0.002553491 | Rv0416 | Rv0416 | conserved hypothetical protein |
| MT0434 | 71.4231831 | 34.9535226 | 27.78292069 | 21.99290755 | 0.47351635 | −1.078513853 | 5.25314311 | 0.037382435 | | | |
| MT0524 | 472.251648 | 436.107874 | 188.6623744 | 239.3619621 | 0.471342152 | −1.085153389 | 8.3817664 | 0.010449641 | | | |
| MT0595 | 292.327673 | 180.666942 | 36.08511111 | 36.48029904 | 0.153815128 | −2.700730692 | 7.07431352 | 2.35E−12 | Rv0569 | Rv0569 | conserved hypothetical protein |
| MT0596 | 2,978.31 | 1,738.97 | 90.4742641 | 115.6664027 | 0.04371453 | −4.515743287 | 10.2629631 | 5.00E−21 | Rv0570 | nrdZ | ribonucleotide reductase, class II |
| MT0597 | 254.079192 | 424.751667 | 81.5183579 | 88.37890628 | 0.249911923 | −2.00050836 | 7.72578327 | 9.86E−07 | Rv0571c | Rv0571c | conserved hypothetical protein |
| MT0898 | 207.244318 | 349.535226 | 19.08850081 | 37.46939806 | 0.101519613 | −3.300169619 | 7.25271008 | 9.14E−13 | | | |
| MT0599 | 581.533021 | 788.592764 | 38.43848793 | 70.86603545 | 0.0797843 | −3.647751302 | 8.52648178 | 5.13E−16 | Rv0572c | Rv0572c | hypothetical protein |
| MT0600 | 995.631367 | 1,338.41 | 30.4631554 | 87.62253645 | 0.050609577 | −4.30444578 | 9.25695819 | 2.64E−14 | | | |
| MT0601 | 96.4017827 | 90.2597291 | 10.19796618 | 13.26556329 | 0.126045785 | −2.987980224 | 5.67982926 | 1.06E−17 | Rv0573c | Rv0573c | conserved hypothetical protein |
| MT0602 | 389.119746 | 352.632373 | 28.89423752 | 33.92027805 | 0.084759226 | −3.560485768 | 7.6412979 | 1.93E−22 | Rv0574c | Rv0574c | conserved hypothetical protein |
| MT0637 | 62.8367895 | 53.2414415 | 30.13629751 | 24.84840001 | 0.12774903 | −1.072774903 | 5.3997676 | 0.007860746 | Rv0608 | Rv0608 | conserved hypothetical protein |
| MT0735 | 197.877343 | 95.569125 | 74.26211273 | 58.88048256 | 0.455739016 | −1.133720209 | 6.7228957 | 0.025755689 | Rv0708 | rplP | 50S ribosmal protein L16 |
| MT0736 | 288.034476 | 135.094627 | 109.6935081 | 91.92802628 | 0.477963365 | −1.065028053 | 7.27785554 | 0.044117567 | Rv0709 | rpmC | 50S ribosomal protein L29 |
| MT0741 | 355.945044 | 244.232208 | 127.4745773 | 136.8447581 | 0.441087078 | −1.1808646 | 7.75023671 | 0.005505017 | | | |
| MT0741.1 | 335.259641 | 201.904525 | 117.603649 | 110.9536358 | 0.426291462 | −1.229749545 | 7.57354669 | 0.005083875 | Rv0715 | rplX | 50S ribosomal protein L24 |

TABLE 2C-continued

Downregulated gene expression tables of WT Mtb treated with HC101A Compared to DMSO

| Gene | Counts per million (CPM) | | | | WT DMSO/ WT HC101A Fold change | log2 Fold change | logCPM | Adjusted p-value | Rv number | Gene name | Annotated function |
|---|---|---|---|---|---|---|---|---|---|---|---|
| | WT_DMSO1 | WT_DMSO2 | WT_HC101A1 | WT_HC101A2 | | | | | | | |
| MT0742.1 | 168.215256 | 111.054863 | 74.78508535 | 58.99684725 | 0.480685353 | −1.05683525 | 6.67961107 | 0.01145527 | Rv0717 | rpsN | 30S ribosomal protein S14 |
| MT0747 | 157.67741 | 79.345971 | 51.70891828 | 38.1094033 | 0.380875532 | −1.392608485 | 6.33217258 | 0.004200151 | Rv0722 | rpmD | 50S ribosomal protein L30 |
| MT0845 | 2,819.46 | 2,651.60 | 1,309.20 | 1,158.35 | 0.451029246 | −1.148707111 | 10.9542494 | 0.019433804 | Rv0823c | Rv0823c | transcriptional regulator (NifR3/Smm1 family) |
| MT0846 | 8,232.01 | 7,693.31 | 2,534.91 | 2,497.59 | 0.316010048 | −1.661957664 | 12.3549648 | 0.000214157 | Rv0824c | desA1 | acyl-[ACP] desaturase |
| MT0877 | 79.2289955 | 76.8387563 | 32.03207327 | 42.41489314 | 0.477500297 | −1.066426464 | 5.83714388 | 0.007303548 | Rv0854 | Rv0854 | conserved hypothetical protein |
| MT0908 | 945.454749 | 220.339927 | 115.5769501 | 190.5470155 | 0.26263688 | −1.92885858 | 8.51659222 | 0.007959339 | Rv0885 | Rv0885 | unknown transmembrane protein |
| MT0909 | 138.553169 | 34.9535226 | 22.29170813 | 38.69122625 | 0.354064311 | −1.497916665 | 5.83382041 | 0.037486354 | Rv0886 | fprB | ferredoxin, ferredoxin-NADP reductase |
| MT0911 | 39.4193529 | 31.1189589 | 8.106075685 | 5.527318036 | 0.194605368 | −2.361376587 | 4.31727681 | 6.29E−09 | Rv0888 | Rv0888 | possible membrane protein |
| MT1002 | 1,675.13 | 581.526327 | 418.3127283 | 235.2892015 | 0.28976904 | −1.787024636 | 9.50356257 | 0.005414793 | Rv0974c | accD2 | acetyl/propionyl-CoA carboxylase, [beta] subunit |
| MT1019 | 92.889167 | 82.7380851 | 34.58156482 | 43.40399216 | 0.445023322 | −1.168047152 | 5.97317663 | 0.002584789 | Rv0990c | Rv0990c | hypothetical protein |
| MT1020 | 1,013.19 | 948.317089 | 343.0046703 | 416.0615924 | 0.387022077 | −1.369512232 | 9.40821284 | 0.001896362 | | | |
| MT1056 | 1,408.95 | 630.933205 | 332.8609104 | 384.9560624 | 0.384956024 | −1.377234448 | 9.46130025 | 0.016187653 | Rv1037c | Rv1037c | conserved hypothetical protein |
| MT1095 | 477.325426 | 495.838577 | 232.5920749 | 199.4489077 | 0.443913856 | −1.171648353 | 8.45447392 | 0.004923309 | Rv1065 | Rv1065 | conserved hypothetical protein |
| MT1106 | 157.67741 | 161.936573 | 66.48289493 | 91.17165645 | 0.493273578 | −1.019540082 | 6.89366645 | 0.015307302 | Rv1076 | lipU | probable esterase |
| MT1126 | 7,609.50 | 5,962.16 | 2,656.44 | 2,736.08 | 0.397351627 | −1.331511844 | 12.210737 | 0.005787145 | Rv1094 | acyl-(ACP) desaturase | |
| MT1214 | 1,812.90 | 2,122.28 | 754.7148692 | 847.8905857 | 0.407223683 | −1.296106627 | 10.4345882 | 0.000593149 | Rv1177 | fdxC | ferredoxin 4Fe-4S |
| MT1233 | 751.69973 | 233.7609 | 121.1989058 | 83.31704651 | 0.207804107 | −2.266703925 | 8.20692286 | 0.000103204 | Rv1195 | PE | PE-family protein |
| MT1234 | 798.144314 | 248.361738 | 155.7804706 | 129.2810597 | 0.272740166 | −1.874440914 | 8.37107001 | 0.001548013 | Rv1196 | PPE | PPE-family protein |
| MT1235 | 435.95462 | 181.256874 | 78.8649553 | 84.42251021 | 0.328412061 | −1.606420982 | 7.66840469 | 0.002536411 | | | |
| MT1236 | 385.778003 | 113.857044 | 78.31515057 | 44.97491413 | 0.246852707 | −2.018277629 | 7.26756526 | 0.001410479 | | | |
| MT1314 | 458.201186 | 368.560561 | 209.2544215 | 172.8014155 | 0.462415968 | −1.112736877 | 8.23619081 | 0.007536006 | Rv1277 | Rv1277 | hypothetical protein |
| MT1322 | 613.536852 | 648.631191 | 175.0650862 | 138.7647739 | 0.248626068 | −2.00798418 | 8.61874959 | 4.05E−07 | Rv1284 | Rv1284 | conserved hypothetical protein |
| MT1385 | 149.871597 | 118.72399 | 26.14863124 | 81.16430159 | 0.400178018 | −1.321286172 | 6.54248787 | 0.033990726 | | | |
| MT1414.1 | 19.5145309 | 15.7807043 | 7.648474638 | 6.865510824 | 0.416439762 | −1.263820269 | 3.57480341 | 0.005205549 | | | |
| MT1430 | 70.2523112 | 140.109057 | 44.54878785 | 57.71683676 | 0.483835603 | −1.047411161 | 6.28928669 | 0.039370591 | Rv1386 | PE | PE-family protein |
| MT1431 | 606.121133 | 560.731193 | 210.3657383 | 246.3438375 | 0.391483328 | −1.352977226 | 8.66246816 | 0.001641323 | Rv1387 | PPE | PPE-family protein |
| MT1454 | 12.8795904 | 7.37416088 | 4.118409421 | 4.7709482 | 0.458242826 | 1.1258158 | 2.75702763 | 0.045909218 | Rv1439c | Rv1439c | hypothetical protein |
| MT1585.1 | 1,469.44 | 796.261892 | 142.6407834 | 232.7873628 | 0.165785388 | −2.592611235 | 9.36314818 | 1.36E−07 | | | |
| MT1586 | 217.782165 | 67.5473136 | 48.50571095 | 45.14946101 | 0.329836934 | −1.600175139 | 6.54160975 | 0.007230989 | Rv1535 | Rv1535 | hypothetical protein |
| MT1600 | 28.4912151 | 17.4030197 | 9.740365138 | 9.134620333 | 0.420024644 | −1.251454118 | 3.94969202 | 0.008075386 | Rv1550 | fadD11 | acyl-CoA synthase, N-term |
| MT1627 | 53.8601053 | 19.6152679 | 14.6432335 | 15.5346728 | 0.418123259 | −1.257999797 | 4.63177606 | 0.038713875 | | | |
| MT1638 | 569.824302 | 231.253685 | 205.0052689 | 158.6049355 | 0.454639521 | −1.137204993 | 8.17997361 | 0.047745648 | Rv1602 | hisH | amidotransferase |
| MT1672 | 624.464989 | 234.20335 | 192.0616965 | 153.5430758 | 0.403109649 | −1.310755778 | 8.22756611 | 0.02413631 | Rv1654 | argB | acetylglutamate kinase |
| MT1693 | 520.647684 | 197.922478 | 1744.113704 | 139.2302322 | 0.437297282 | −1.193313713 | 8.00459605 | 0.039763779 | Rv1655 | argD | acetylornithine aminotransferase |
| MT1694 | 564.360234 | 168.130868 | 117.5380974 | 85.87706759 | 0.278189896 | −1.845858074 | 7.8590386 | 0.002584789 | Rv1656 | argF | ornithine carbamoyltransferase |
| MT1725 | 37.4678993 | 26.9894288 | 12.48597142 | 11.63645902 | 0.378651434 | −1.401057704 | 4.41802284 | 0.000897781 | Rv1685c | Rv1685c | conserved hypothetical protein |
| MT1726 | 99.5241076 | 64.3026829 | 24.4758281 | 27.98568395 | 0.324307005 | −1.624567907 | 5.73029344 | 3.15E−05 | Rv1686c | Rv1686c | probable transmembrane protein |
| MT1727 | 73.7649268 | 54.2738241 | 20.06907448 | 22.45836592 | 0.334373509 | −1.58046754 | 5.38275784 | 3.48E−05 | Rv1687c | Rv1687c | probable ABC transporter |
| MT1736 | 284.521861 | 300.128348 | 131.2661288 | 161.0485929 | 0.499910619 | −1.000257923 | 7.77378636 | 0.017572545 | | | |
| MT1774 | 1,459.69 | 1,785.87 | 105.1354073 | 15.1354073 | 0.044553172 | −4.488328032 | 9.72484599 | 4.34E−16 | Rv1733c | Rv1733c | possible membrane protein |
| MT1775 | 579.191277 | 662.494613 | 38.24237319 | 49.68768003 | 0.070829072 | −3.819514543 | 8.37108765 | 1.03E−23 | | | |
| MT1776 | 20.6854028 | 16.6656036 | 2.810977859 | 3.781849183 | 0.179446818 | −2.478371755 | 3.32331401 | 9.89E−09 | Rv1735c | Rv1735c | hypothetical protein |
| MT1777 | 109.671664 | 195.71023 | 2.810977859 | 8.610979677 | 0.037504115 | −4.736807275 | 6.29019257 | 1.56E−17 | | | |
| MT1778 | 5,799.33 | 3,617.62 | 80.0148115 | 197.1797982 | 0.029443155 | −5.085928898 | 11.2415403 | 2.20E−18 | Rv1736c | narX | fused nitrate reductase |
| MT1779 | 2,075.57 | 1,498.72 | 39.51517633 | 104.7863135 | 0.040420307 | −4.62877591 | 9.85761264 | 1.76E−17 | Rv1737c | narK2 | nitrite extrusion protein |
| MT1780 | 3,858.80 | 5,086.70 | 117.0804964 | 274.2131559 | 0.043746244 | −4.514697042 | 11.1879313 | 8.97E−17 | Rv1738 | Rv1738 | conserved hypothetical protein |

TABLE 2C-continued

Downregulated gene expression tables of WT Mtb treated with HC101A Compared to DMSO

| Gene | Counts per million (CPM) | | | | WT DMSO/ WT HC101A | | log2 Fold change | logCPM | Adjusted p-value | Rv number | Gene name | Annotated function |
|---|---|---|---|---|---|---|---|---|---|---|---|
| | WT_DMSO1 | WT_DMSO2 | WT_HC101A1 | WT_HC101A2 | Fold change | | | | | | |
| MT1797 | 58.5435927 | 48.5219786 | 11.30928301 | 15.5346728 | 0.252153196 | -1.987627585 | 5.02178996 | 2.38E-07 | Rv1760 | Rv1760 | conserved hypothetical protein |
| MT1809 | 133.869582 | 74.4790249 | 57.13475925 | 39.44759609 | 0.466037561 | -1.101481858 | 6.23546713 | 0.025279872 | Rv1760 | Rv1760 | |
| MT1822 | 26.9300526 | 15.7807043 | 12.15911353 | 7.27278689 | 0.463755812 | -1.108562733 | 3.89280495 | 0.043686606 | Rv1773c | Rv1773c | transcriptional regulator (IdR family) |
| MT1823 | 674.812479 | 366.495796 | 189.5775765 | 111.2445483 | 0.289154101 | -1.790089532 | 8.8844375 | 0.000256213 | Rv1791 | PE | PE-family protein |
| MT1840 | 382.094515 | 306.027676 | 169.3777589 | 147.3757535 | 0.46069087 | -1.118129088 | 7.96894214 | 0.007433984 | Rv1812c | Rv1812c | probable dehydrogenase |
| MT1850 | 248.224833 | 166.361069 | 69.35924437 | 114.0954807 | 0.443450499 | -1.173155026 | 7.21617316 | 0.014375115 | Rv1813c | Rv1813c | conserved hypothetical protein |
| MT1851 | 3,068.86 | 1,615.09 | 65.63306442 | 173.7323332 | 0.051121904 | -4.289914622 | 10.262847 | 8.10E-13 | Rv1834 | Rv1834 | conserved hypothetical protein |
| MT1932 | 81.9610298 | 77.4286892 | 28.50200805 | 25.48384526 | 0.339094111 | -1.560242365 | 5.71719585 | 9.58E-06 | | | |
| MT1942 | 497.620538 | 648.926157 | 219.8446172 | 285.675059 | 0.440721541 | -1.182060681 | 8.68887422 | 0.011431961 | | | |
| MT1943 | 142.846366 | 155.152345 | 74.52359904 | 69.70238955 | 0.483622049 | -1.048048074 | 6.78351419 | 0.00717373 | | | |
| MT1955 | 127.625032 | 133.914762 | 65.43694968 | 61.14959217 | 0.483777053 | -1.047585756 | 6.59421867 | 0.00720848 | | | |
| MT1959 | 220.514199 | 167.983385 | 88.57848833 | 104.4372197 | 0.497762522 | -1.006470485 | 7.17743577 | 0.01939937 | Rv1904 | Rv1904 | conserved hypothetical protein |
| MT1986 | 153.384213 | 126.393117 | 62.82208655 | 65.5132643 | 0.459643027 | -1.121414242 | 6.66386585 | 0.004050835 | Rv1918c | PPE | PPE-family protein |
| MT1987 | 313.403366 | 78.4610717 | 47.52513728 | 27.86913936 | 0.192984535 | -2.373442854 | 6.84111617 | 0.000324511 | Rv1936 | Rv1936 | similar alkanal monooxygenase alpha chain |
| MT1988 | 394.583815 | 99.1087222 | 66.35215178 | 34.03664254 | 0.203799426 | -2.294778105 | 7.19360922 | 0.000883361 | Rv1937 | Rv1937 | similar to ring-hydroxylating dioxygenases |
| MT1989 | 155.725957 | 36.4283547 | 24.12211232 | 13.49829247 | 0.241917397 | -2.343917397 | 5.7897951 | 0.000642266 | Rv1938 | cphB | probable epoxide hydrolase |
| MT2007 | 67.9105675 | 20.0577176 | 13.56265982 | 7.38915148 | 0.242339546 | -2.044898243 | 4.67516663 | 0.002071634 | Rv1939 | Rv1939 | similar nitrilotriacetate monooxygenase component |
| MT2016 | 62.8367895 | 25.5145966 | 22.22633655 | 14.60375607 | 0.422513495 | -1.242930672 | 4.91685218 | 0.03726568 | | | |
| MT2017 | 375.630446 | 171.522982 | 104.4637818 | 57.77501905 | 0.29655925 | -1.753607723 | 7.46055446 | 0.000941593 | Rv1964 | Rv1964 | part of mce3 operon |
| MT2018 | 310.281041 | 93.0619103 | 43.40672785 | 25.54202756 | 0.171463905 | -2.544023187 | 6.85729679 | 2.29E-05 | | | |
| MT2019 | 345.407197 | 110.612413 | 50.33611514 | 26.88022034 | 0.169759242 | -2.558437974 | 7.03575458 | 1.87E-05 | Rv1966 | mce3 | cell invasion protein |
| MT2020 | 357.115916 | 99.551719 | 52.88560669 | 27.86913936 | 0.177281435 | -2.495886634 | 7.04650222 | 9.97E-05 | Rv1967 | Rv1967 | part of mce3 operon |
| MT2021 | 407.853696 | 115.03691 | 57.9192182 | 26.88022034 | 0.162506529 | -2.621430414 | 7.2259919 | 7.31E-05 | Rv1968 | Rv1968 | part of mce3 operon |
| MT2022 | 103.817304 | 40.8528513 | 23.72988285 | 17.45468854 | 0.287327416 | -1.799232438 | 5.4909853 | 0.000554397 | Rv1969 | Rv1969 | part of mce3 operon |
| MT2023 | 240.02873 | 75.8063738 | 37.39254268 | 24.43656395 | 0.196559328 | -2.346963263 | 6.53023751 | 5.05E-06 | Rv1970 | lprM | part of mce3 operon |
| MT2024 | 324.331504 | 92.177011 | 53.53932247 | 31.18571018 | 0.204009759 | -2.29328993 | 6.94552809 | 0.000231201 | Rv1971 | Rv1971 | part of mce3 operon |
| MT2042.1 | 36.2970275 | 22.4174491 | 16.14677979 | 10.41463083 | 0.458782172 | -1.124118764 | 4.36505888 | 0.031292773 | Rv1972 | Rv1972 | conserved hypothetical protein |
| MT2052 | 64.7882426 | 19.87295974 | 29.96388199 | 0.348200966 | -1.522007888 | 5.57400375 | 0.000113121 | | | | |
| MT2053 | 41,432.47 | 9,313.71 | 177.9414355 | 195.376147 | 0.007357233 | -7.086621003 | 13.6412361 | 1.73E-20 | Rv1996 | Rv1996 | conserved hypothetical protein |
| MT2059 | 3,239.41 | 1,713.31 | 70.20907489 | 92.04439087 | 0.032773923 | 4.931307818 | 10.3179607 | 1.93E-22 | Rv1997 | ctpF | probable cation transport ATPase |
| MT2050 | 551.090353 | 915.133365 | 101.8489187 | 119.9137102 | 0.151170782 | -2.725748777 | 8.71859637 | 2.61E-10 | Rv2003c | Rv2003c | conserved hypothetical protein |
| MT2051 | 2,780.04 | 2,826.66 | 233.964878 | 227.90005 | 0.082380416 | -3.601554787 | 10.5658011 | 1.13E-17 | Rv2004c | Rv2004c | hypothetical protein |
| MT2052 | 2,496.30 | 2,271.54 | 149.3086844 | 170.4159424 | 0.068923173 | -3.858867071 | 10.3134888 | 1.08E-19 | Rv2005c | Rv2005c | conserved hypothetical protein |
| MT2053 | 615.659177 | 832.83773 | 122.7678237 | 1,178.54 | 0.179486125 | -2.478055772 | 8.7367092 | 7.32E-10 | Rv2006 | otsB | trehalose-6-phosphate phosphatase |
| MT2079 | 7,856.94 | 10,026.65 | 580.1727557 | 1,736.45 | 0.112720075 | -3.149183619 | 12.2801231 | 7.51E-09 | Rv2007c | fdxA | ferredoxin |
| MT2080 | 37.0776087 | 31.5614086 | 11.24391143 | 1,435.55 | 0.353465499 | -1.500358692 | 4.49040228 | 0.000186055 | Rv2023c | Rv2023c | hypothetical protein |
| MT2086 | 100.304689 | 79.0510046 | 28.30589793 | 12.85828722 | 0.348446653 | -1.521412636 | 5.895632 | 4.81E-05 | | | |
| MT2087 | 339.943128 | 198.512411 | 56.35030033 | 33.92027805 | 0.214609111 | -2.220216767 | 7.33935177 | 3.20E-08 | Rv2027c | Rv2027c | sensor histidine kinase |
| MT2088 | 810.633614 | 733.286558 | 41.77243841 | 58.93866495 | 0.085211169 | -3.552813642 | 8.70509527 | 8.52E-14 | Rv2028c | Rv2028c | conserved hypothetical protein |
| MT2089 | 5,005.48 | 2,681.39 | 91.91243882 | 89.71709907 | 0.034136438 | -4.872543662 | 10.9549642 | 6.68E-19 | | | |
| MT2090 | 14,874.37 | 14,962.17 | 490.6136937 | 170.4159424 | 0.055945122 | -4.159843853 | 12.9430487 | 8.64E-17 | Rv2030c | Rv2030c | conserved hypothetical protein |
| MT2091 | 47,420.31 | 45,136.50 | 697.7762247 | 1,736.45 | 0.026300434 | -5.248769581 | 14.5334016 | 1.86E-20 | | | |
| MT2156 | 4,091.03 | 6,085.75 | 87.33642835 | 255.0711818 | 0.03364996 | -4.893251407 | 11.3600939 | 8.47E-16 | Rv2032 | Rv2032 | conserved hypothetical protein |
| MT2278 | 57.7630115 | 43.5075492 | 20.06907448 | 13.38192788 | 0.332234462 | -1.589726364 | 5.0353742 | 0.000149414 | Rv2107 | PE | PE-family protein |
| MT2304 | 1,279.76 | 1,006.57 | 436.2245407 | 385.9231635 | 0.359672237 | -1.475245294 | 9.60032212 | 0.000981117 | Rv2220 | glnA1 | glutamine synthase class I |
| | 5,107.73 | 2,123.46 | 6266.519477 | 987.3535481 | 0.223236286 | -2.163356548 | 11.1095232 | 0.00018736 | Rv2244 | acpM | acyl carrier protein (meromycolate extension) |

TABLE 2C-continued

Downregulated gene expression tables of WT Mtb treated with HC101A Compared to DMSO

| Gene | Counts per million (CPM) | | | | WT DMSO/ WT HC101A | log2 Fold | logCPM | Adjusted | Rv | Gene | Annotated function |
| | WT_DMSO1 | WT_DMSO2 | WT_HC101A1 | WT_HC101A2 | Fold change | change | | p-value | number | name | |
| --- | --- | --- | --- | --- | --- | --- | --- | --- | --- | --- | --- |
| MT2305 | 5,019.92 | 2,531.55 | 854.7987553 | 1,424.88 | 0.801926853 | −1.727729022 | 11.2263262 | 0.00211661 | Rv2245 | kasA | [beta]-ketoacyl-ACP synthase (meromycolate |
| MT2306 | 2,614.56 | 1,551.26 | 581.8070451 | 834.8577526 | 0.339328292 | −1.559246371 | 10.4480685 | 0.002554128 | | | |
| MT2307 | 2,316.37 | 2,024.21 | 817.0793547 | 1,179.12 | 0.459925909 | −1.120526623 | 10.6289766 | 0.03235796 | Rv2247 | accD6 | acetyl/propionyl CoA carboxylase [beta] subunit |
| MT2329 | 57.372209 | 62.9753339 | 24.2528548 | 26.99658493 | 0.425135813 | −1.234004299 | 5.4076278 | 0.00126386 | Rv2267c | Rv2267c | hypothetical protein |
| MT2391 | 137.772588 | 53.5838912 | 43.01449839 | 2.232991493 | 0.395827325 | −1.337056885 | 6.03162931 | 0.015331014 | Rv2329c | norK1 | probable nitrite extrusion protein |
| MT2399 | 61.6659177 | 60.0255695 | 23.01079549 | 25.0183859 | 0.395100831 | −1.339707215 | 5.38685136 | 0.000296028 | Rv2336 | Rv2336 | hypothetical protein |
| MT2412 | 2,673.88 | 1,182.23 | 901.6048052 | 586.0702587 | 0.385898205 | −1.373707762 | 10.3822627 | 0.024658182 | | | |
| MT2455 | 365.702309 | 179.634559 | 119.2377585 | 92.27712006 | 0.388745837 | −1.36310087 | 7.5548903 | 0.005505017 | | | |
| MT2504 | 293.888835 | 410.888244 | 119.2377585 | 223.4200132 | 0.485828522 | −1.041480905 | 8.03149708 | 0.043287009 | Rv2429 | ahpD | member of AhpC/TSA family |
| MT2556 | 825.854948 | 434.780525 | 303.2587508 | 203.6962152 | 0.402456138 | −1.313096535 | 8.78394075 | 0.015218202 | Rv2483c | Rv2483c | possible transferase |
| MT2559 | 33.1747025 | 29.4966435 | 9.478878825 | 10.00735476 | 0.312652244 | −1.677369221 | 4.30714999 | 1.68E-05 | Rv2485c | lipQ | probable carboxylesterase |
| MT2574 | 537.820472 | 208.688753 | 176.9608619 | 105.2517719 | 0.378646869 | −1.401070595 | 7.99895112 | 0.017713159 | Rv2499c | Rv2499c | putative aldehyde dehydrogenase |
| MT2575 | 1,805.09 | 827.675817 | 668.6205009 | 432.5271819 | 0.418407288 | −1.257020115 | 9.86465534 | 0.03821673 | Rv2500c | fadE19 | acyl-CoA dehydrogenase (aka mmgC) |
| MT2577 | 483.960366 | 243.642275 | 133.6848772 | 116.1900433 | 0.344012239 | −1.539468203 | 7.92540501 | 0.001133528 | Rv25020 | accD1 | acetyl/propionyl-CoA carboxylase, [beta] subunit |
| MT2578 | 621.342664 | 260.455362 | 124.1406268 | 102.2844748 | 0.257166758 | −1.959223924 | 8.10544747 | 8.35E-05 | Rv2503c | scoB | 3-oxo acid:CoA transferase, [beta] subunit |
| MT2579 | 625.24557 | 300.128348 | 157.0225305 | 129.0483306 | 0.309567309 | −1.691674968 | 8.23583645 | 0.000358942 | Rv2504c | scoA | 3-oxo acid:CoA transferase, [alpha] subunit |
| MT2600 | 61,092.97 | 11,312.85 | 13,005.68 | 8,330.13 | 0.294673885 | −1.762808886 | 14.5162761 | 0.040131693 | Rv2524c | fas | fatty acid synthase |
| MT2603 | 23.0271465 | 24.4822141 | 9.086649357 | 11.8691882 | 0.440534032 | −1.182674621 | 4.06514809 | 0.00717373 | Rv2528c | mrr | restriction system protein |
| MT2634 | 895.326678 | 721.045451 | 293.6491288 | 273.6895152 | 0.351103372 | −1.510032242 | 9.09019171 | 0.000438489 | Rv2557 | Rv2557 | conserved hypothetical protein |
| MT2698 | 44.655.49 | 425.7650882 | 425.7650882 | 779.933656 | 0.01758251 | −5.815366693 | 14.0762905 | 6.52E-24 | Rv2623 | Rv2623 | conserved hypothetical protein |
| MT2699 | 2,550.55 | 1,934.68 | 49.48628463 | 78.89519218 | 0.02863648 | −5.126002039 | 10.1692966 | 3.90E-26 | Rv2624c | Rv2624c | conserved hypothetical protein |
| MT2700 | 6,066.68 | 3,877.92 | 78.90349477 | 150.6339621 | 0.023088062 | −5.436709124 | 11.3114209 | 9.02E-24 | Rv2625c | Rv2625c | conserved hypothetical protein |
| MT2701 | 13,637.14 | 11,116.25 | 153.8846949 | 330.649831 | 0.019576871 | −5.674706025 | 12.6228786 | 8.20E-25 | Rv2626c | Rv2626c | conserved hypothetical protein |
| MT2703 | 8,195.320 | 5,959.06 | 62.56060025 | 108.7427096 | 0.012106337 | −6.368093763 | 11.805502 | 2.43E-32 | Rv2627c | Rv2627c | conserved hypothetical protein |
| MT2704 | 732.965781 | 947.284706 | 18.30404187 | 29.03296526 | 0.02819297 | −5.148532072 | 8.75010527 | 5.02E-29 | Rv2628 | Rv2628 | hypothetical protein |
| MT2705 | 8,106.73 | 5,107.93 | 492.2479831 | 567.801018 | 0.080224587 | −3.639811732 | 11.8004038 | 2.16E-15 | Rv2629 | Rv2629 | hypothetical protein |
| MT2707 | 799.705476 | 592.292602 | 73.86988325 | 67.49146234 | 0.101612565 | −3.298849289 | 8.57624072 | 5.23E-17 | Rv2630 | Rv2630 | hypothetical protein |
| MT2708 | 1,178.29 | 513.38908 | 99.10331241 | 69.52784256 | 0.099752969 | −3.325496402 | 8.85461609 | 5.72E-11 | Rv2631 | Rv2631 | conserved hypothetical protein |
| MT2709 | 112.403698 | 75.5114074 | 38.17700161 | 35.49120002 | 0.394162835 | −1.343137987 | 6.01133759 | 0.000703663 | Rv2632c | Rv2632c | conserved hypothetical protein |
| MT2795 | 254.079192 | 135.389594 | 56.80790137 | 62.89506102 | 0.308403524 | −1.697108846 | 6.9772474 | 8.84E-05 | Rv2633c | Rv2633c | hypothetical protein |
| MT2850 | 174.069616 | 142.763755 | 77.87754952 | 74.24060857 | 0.480905382 | −1.056175023 | 6.86581617 | 0.008117818 | Rv2723 | Rv2723 | probable membrane protein, tellurium resistance |
| MT2876 | 1,480.76 | 447.759049 | 463.0922593 | 163.3758847 | 0.324986539 | −1.621548134 | 9.31529438 | 0.043100188 | Rv2780 | ald | L-alanine dehydrogenase |
| MT2889 | 78.4484142 | 58.5508374 | 33.5636272 | 31.0111633 | 0.474839031 | −1.074489567 | 5.63734483 | 0.007298242 | Rv2809 | Rv2809 | hypothetical protein |
| MT2985 | 19.5145309 | 10.9137581 | 6.994758857 | 5.352771151 | 0.418240594 | −1.257595 | 3.32082922 | 0.019433804 | | | |
| MT3056 | 65.5688238 | 50.7342268 | 28.30589332 | 21.46926659 | 0.430254567 | −1.216737588 | 5.35157405 | 0.002845529 | Rv2917 | Rv2917 | conserved hypothetical protein |
| MT3057 | 782.142399 | 661.314748 | 256.0604714 | 203.05621 | 0.318147403 | −1.652232748 | 8.89090713 | 0.000106318 | Rv2978c | Rv2978c | transposase |
| MT3085 | 235.165175 | 211.7859 | 109.1705534 | 89.42618759 | 0.443281521 | −1.173704873 | 7.33191161 | 0.003205818 | Rv2979c | Rv2979c | resolvase |
| MT3118 | 505.597222 | 529.907201 | 240.6981505 | 239.536509 | 0.463285117 | −1.110027758 | 8.56497446 | 0.010203936 | Rv3005c | Rv3005c | conserved hypothetical protein |
| MT3132 | 32.7844119 | 50.4392604 | 10.98242512 | 21.87654296 | 0.392203413 | −1.350326006 | 4.84630937 | 0.010866027 | Rv3033 | Rv3033 | hypothetical protein |
| MT3133 | 32.7844119 | 30.0865764 | 11.37463459 | 6.807328529 | 0.28970782 | −1.787015774 | 4.28495567 | 3.56E-05 | | | |
| MT3135 | 313.403366 | 231.253685 | 113.3543164 | 79.70974431 | 0.354909645 | −1.494476313 | 7.5195057 | 0.000269814 | Rv3048c | nrdG | ribonucleoside-diphosphate small subunit |
| MT3155 | 979.629451 | 373.280024 | 290.2498068 | 251.5802441 | 0.400856616 | −1.31884181 | 8.883772585 | 0.030312812 | Rv3080c | pknK | serine-threonine protein kinase |
| MT3158 | 323.160632 | 313.549321 | 112.8313438 | 148.4230348 | 0.410422716 | −1.284817513 | 7.80655801 | 0.001459159 | Rv3083 | Rv3083 | probable monooxygenase |
| MT3171 | 701.742531 | 435.665425 | 192.3231828 | 192.8743083 | 0.338959558 | −1.560814942 | 8.56803889 | 0.000446334 | Rv3086 | adhD | zinc-containing alcohol dehydrogenase |
| MT3172 | 370.385797 | 255.145966 | 136.2997403 | 149.5284985 | 0.457608238 | −1.127815072 | 7.82690262 | 0.00904192 | Rv3087 | Rv3087 | conserved hypothetical protein |
| MT3173 | 249.005414 | 212.080867 | 98.5149682 | 104.9026781 | 0.441629354 | −1.179092026 | 7.37045764 | 0.002530467 | | | |

TABLE 2C-continued

Downregulated gene expression tables of WT Mtb treated with HC101A Compared to DMSO

| Gene | Counts per million (CPM) | | | | WT DMSO/ WT HC101A Fold change | log2 Fold change | logCPM | Adjusted p-value | Rv number | Gene name | Annotated function |
|---|---|---|---|---|---|---|---|---|---|---|---|
| | WT_DMSO1 | WT_DMSO2 | WT_HC101A1 | WT_HC101A2 | | | | | | | |
| MT3175 | 64.397952 | 66.5149311 | 23.07616707 | 28.33477772 | 0.392688129 | −1.348544109 | 5.49273373 | 0.000307474 | Rv3090 | Rv3090 | hypothetical protein |
| MT3210 | 8.5863936 | 6.19429514 | 0.13074315 | 0.349093771 | 0.035772197 | −4.805017477 | 1.52085904 | 3.48E-14 | Rc3127 | Rv3127 | conserved hypothetical protein |
| MT3212 | 16.597.5 | 10.665.84 | 231.7422444 | 409.079171 | 0.023507189 | −5.410754173 | 12.7677567 | 3.08E-24 | Rv3130c | Rv3130c | conserved hypothetical protein |
| MT3216 | 34,344.40 | 28,565.58 | 221.1520487 | 476.1639032 | 0.011085249 | −6.49521497 | 13.9567337 | 5.67E-30 | Rv3131 | Rv3131 | conserved hypothetical protein |
| MT3217 | 19,492.28 | 10,701.53 | 147.5436518 | 329.9517956 | 0.015816395 | −5.982435365 | 12.904169 | 3.95E-23 | Rv3132c | Rv3132c | sensor histidine kinase |
| MT3218 | 5,451.97 | 3,333.56 | 240.8288937 | 318.5480658 | 0.063680094 | −3.973013716 | 11.1887328 | 4.71E-17 | Rv3133c | Rv3133c | two-component response regulator |
| MT3219 | 3,951.69 | 2,133.49 | 100.9549944 | 149.5866807 | 0.042663798 | −4.550843798 | 10.6293405 | 1.65E-19 | Rv3134c | Rv3134c | conserved hypothetical protein |
| MT3220 | 6,479.60 | 4,044.58 | 145.9093623 | 248.5547647 | 0.037488517 | −4.737407446 | 11.4134083 | 2.23E-18 | | | |
| MT3223 | 32.3941213 | 5.30993583 | 6.929387279 | 3.549120002 | 0.285283537 | −1.809531602 | 3.39081696 | 0.043997396 | | | |
| MT3227 | 2,351.11 | 1,444.89 | 910.3645967 | 765.562639 | 0.441594486 | −1.179205936 | 10.4168658 | 0.02687643 | Rv3140 | fadE23 | acyl-CoA dehydrogenase |
| MT3257 | 61.6659177 | 34.0686233 | 21.96485024 | 19.89834493 | 0.442794803 | −1.175289804 | 5.06730841 | 0.012325698 | | | |
| MT3251 | 55.0309771 | 44.3924485 | 23.99136916 | 24.84384001 | 0.494113328 | −1.017086125 | 5.19091987 | 0.013593095 | | | |
| MT3292 | 45.6640023 | 47.3421128 | 13.98951771 | 21.4692659 | 0.381393779 | −1.390646785 | 4.98044788 | 0.00095557 | | | |
| MT3295 | 244.321927 | 179.487076 | 90.34352094 | 70.80785316 | 0.380903791 | −1.392501447 | 7.18341883 | 0.000617173 | Rv3201c | Rv3201c | probable ATP-dependent DNA helicase |
| MT3296 | 277.496629 | 221.814759 | 96.58456402 | 84.36432792 | 0.36303142 | −1.461833676 | 7.40282326 | 0.000134878 | Rv3202c | Rv3202c | similar to UvrD proteins |
| MT3344 | 857.078197 | 811.747629 | 414.6519199 | 352.8174376 | 0.459919873 | −1.120545557 | 9.24916061 | 0.015218202 | Rv3246c | mtrA | two-component responseregulator |
| MT3409 | 113.964861 | 87.1625816 | 35.2352805 | 51.66587806 | 0.433638273 | −1.205436001 | 6.1556138 | 0.004356979 | Rv3310 | Rv3310 | probable acid phosphastase |
| MT3413 | 11.7087185 | 6.34177836 | 3.20207327 | 2.676288575 | 0.341627838 | −1.549502556 | 2.41021594 | 0.06064645 | | | |
| MT3424 | 83.9124829 | 60.320636 | 29.48258173 | 27.4620433 | 0.397242447 | −1.331908306 | 5.62866332 | 0.000582996 | Rv3323c | gphA | phosphoglycolate phosphatase |
| MT3425 | 81.5707392 | 61.5005017 | 25.6910302 | 25.60020985 | 0.360521927 | −1.471841086 | 5.57695963 | 7.88E-05 | Rv3324c | moaC3 | molybdenum co-factor biosynthesis, protein C |
| MT3426 | 47.6154554 | 51.7666094 | 17.55032609 | 20.36380329 | 0.381929641 | −1.388621205 | 5.08021868 | 0.0002669 | | | |
| MT3427 | 245.102508 | 248.804188 | 54.32378141 | 69.35329578 | 0.2504605 | −1.997344998 | 7.26192473 | 3.37E-08 | | | |
| MT3443 | 2,028.34 | 1,018.81 | 499.4388567 | 496.7604357 | 0.327045269 | −1.612457752 | 9.97943634 | 0.001896362 | Rv3340 | metC | cystathionine [beta]-lyase |
| MT3444 | 1,147.84 | 678.275318 | 300.447773 | 343.7991818 | 0.35298491 | −1.502306948 | 9.26784854 | 0.00182937 | Rv3341 | metA | homoserine o-acetyltransferase |
| MT3449.2 | 7.80581236 | 6.93171123 | 3.726179952 | 2.792750156 | 0.447241796 | −1.160873076 | 2.33003806 | 0.040866137 | | | |
| MT3491 | 92.4998765 | 46.1622471 | 33.50099115 | 20.77107936 | 0.395346484 | −1.3388105 | 5.56024252 | 0.008340803 | Rv3383c | idsB | transfergeranyl, similar geranyl pyrophosphate |
| MT3497 | 149.481307 | 126.245634 | 57.85384662 | 60.7423151 | 0.430920606 | −1.214506008 | 6.61345577 | 0.001470284 | Rv3390 | lpqD | lipoprotein |
| MT3580 | 61.6659177 | 76.3963067 | 28.04440701 | 34.5602833 | 0.45181394 | −1.146199311 | 5.6392313 | 0.003820169 | | | |
| MT3582 | 269.300526 | 210.458551 | 30.26704065 | 41.48397642 | 0.149833433 | −2.738568522 | 7.09230371 | 1.63E-13 | Rv3477 | PE | PE-family protein |
| MT3583 | 161.580316 | 116.216775 | 42.29541103 | 54.51681052 | 0.349621428 | −1.516134485 | 6.53450558 | 0.000142385 | Rv1361c | PPE | PPE-family protein |
| MT3591 | 213.098677 | 161.051674 | 100.3453724 | 79.76792651 | 0.48227584 | −1.052069555 | 7.10750292 | 0.013635153 | Rv3479 | Rv3479 | hypothetical protein |
| MT3608 | 117.087185 | 34.8060393 | 12.15911353 | 12.45101115 | 0.163599442 | −2.611760268 | 5.39463971 | 4.00E-06 | Rv3487c | lipF | probable esterase |
| MT3629 | 164.702641 | 88.9323802 | 69.52073068 | 44.50945576 | 0.451872395 | −1.146012671 | 6.50775355 | 0.025926815 | Rv3504 | fadE26 | acyl-CoA dehydrogenase |
| MT3634 | 264.226748 | 252.491268 | 111.9815133 | 124.5101115 | 0.457832033 | −1.127109688 | 7.55278186 | 0.004274618 | Rv3528c | Rv3528c | hypothetical protein |
| MT3640 | 235.906405 | 94.9791921 | 83.08727577 | 41.13488255 | 0.375502968 | −1.413103785 | 6.81635547 | 0.021245859 | Rv3531c | Rv3531c | hypothetical protein |
| MT3649 | 599.096099 | 239.365262 | 121.0213055 | 125.3246637 | 0.413634417 | −1.273571864 | 8.20425666 | 0.037209726 | Rv3536c | Rv3536c | aromatic hydrocarbon degradation |
| MT3653 | 218.172456 | 148.368117 | 73.54302537 | 59.22957643 | 0.363144104 | −1.46138594 | 6.95243011 | 0.000269435 | Rv3545c | Rv3545c | cytochrome p450 |
| MT3656 | 348.529522 | 214.145632 | 154.2115528 | 107.9863397 | 0.466776412 | −1.099196436 | 7.68206379 | 0.023308096 | Rv3549c | Rv3549c | short-chain alcohol dehydrogenase family |
| MT3715 | 485.692401 | 201.462075 | 154.1461812 | 82.96795284 | 0.345106745 | −1.534885423 | 7.84492555 | 0.008669974 | Rv3552 | Rv3552 | hypothetical protein |
| MT3716 | 114.355151 | 41.1478177 | 36.15048269 | 17.33832394 | 0.346403228 | −1.529479471 | 5.66792251 | 0.016066587 | Rv3612c | Rv3612c | hypothetical protein |
| MT3717 | 3,420.51 | 2,217.26 | 563.3722601 | 375.7412619 | 0.166595834 | −2.585575773 | 10.6818002 | 6.27E-08 | Rv3614c | Rv3614c | conserved hypo- |
| MT3718 | 1,478.42 | 1,073.97 | 308.0962475 | 205.4416841 | 0.201243953 | −2.312989833 | 9.57953024 | 2.60E-07 | Rv3615c | Rv3615c | conserved hypothetical protein |
| MT3722 | 4,768.57 | 3,539.45 | 1,098.37 | 739.7878824 | 0.221264778 | −2.17615428 | 11.3079104 | 3.59E-06 | Rv3616c | Rv3616c | conserved hypothetical protein |
| MT3750.1 | 659.591145 | 206.470126 | 217.0336393 | 163.7249785 | 0.394629365 | −1.341429782 | 8.39014392 | 0.010704637 | | | |
| MT3750.1 | 3,039.58 | 2,447.19 | 1,243.69 | 1,392.01 | 0.480413824 | −1.057650429 | 10.9872494 | 0.039159881 | Rv3648c | cspA | cold shock protein, transcriptional regulator |
| MT3838 | 87.0348078 | 84.9503333 | 37.98088688 | 41.60034101 | 0.463029946 | −1.110822594 | 5.96360915 | 0.003563541 | Rv3733c | Rv3733c | hypothetical protein |

TABLE 2C-continued

Downregulated gene expression tables of WT Mtb treated with HC101A Compared to DMSO

| Gene | Counts per million (CPM) | | | | WT DMSO/ WT HC101A Fold change | log2 Fold change | logCPM | Adjusted p-value | Rv number | Gene name | Annotated function |
|---|---|---|---|---|---|---|---|---|---|---|---|
| | WT_DMSO1 | WT_DMSO2 | WT_HC101A1 | WT_HC101A2 | | | | | | | |
| MT3839 | 313.013076 | 293.786569 | 116.6882669 | 125.790122 | 0.399746804 | -1.322841597 | 7.72558479 | 0.000623369 | Rv3734c | Rv3734c | conserved hypothetical protein |
| MT3857 | 41.7610961 | 29.3491603 | 18.56552818 | 14.77830296 | 0.47377179 | -1.077735798 | 4.67142562 | 0.021245859 | Rv3760 | Rv3760 | conserved hypothetical protein |
| MT3870 | 299.352904 | 369.150494 | 106.0980713 | 166.8086401 | 0.408019558 | -1.293289786 | 7.87602759 | 0.003232032 | Rv3763 | ipqH | 19 kDKD |
| MT3907 | 14.370.11 | 4,127.47 | 2,825.10 | 2,333.05 | 0.278872845 | -1.842320637 | 12.5294487 | 0.006363538 | Rv3800c | pks13 | polyketide synthase |
| MT3908 | 4.858.34 | 1,777.17 | 1,423.79 | 1,165.10 | 0.390224236 | -1.357624713 | 11.1703676 | 0.036285309 | Rv3801c | fadD32 | acyl-CoA synthase |
| MT3932 | 87.8153891 | 36.575838 | 20.91890499 | 22.6329128 | 0.354143925 | -1.497592299 | 5.3476356 | 0.003424009 | Rv3824c | papA1 | PKS-associated protein, unknown function |
| MT3939 | 15.392206 | 21.3850666 | 8.498305154 | 10.24008394 | 0.489918288 | -1.029386947 | 3.80251024 | 0.033759492 | Rv3831 | Rv3831 | hypothetical protein |
| MT3953 | 59.3241739 | 43.0650995 | 21.89944786 7 | 20.94562624 | 0.421809953 | -1.245334956 | 5.15268502 | 0.00207743 | | | |
| MT3959 | 489.424435 | 315.024153 | 131.5929867 | 130.910154 | 0.326744 | -1.61376735 | 8.05317994 | 7.13E-05 | Rv3848 | Rv3848 | probable membrane proteinprot |
| MT3959 | 1,650.93 | 1,190.34 | 200.8868595 | 159.0122126 | 0.126698983 | -2.980523155 | 9.64148554 | 2.87E-12 | Rv3854c | Rv3854c | probable monooxygenase |
| MT3970 | 185.949206 | 169.310734 | 55.04286875 | 47.94221118 | 0.289310529 | -1.789309267 | 6.83158774 | 5.84E-07 | Rv3855 | Rv3855 | putative transcriptional regulator |
| MT3972 | 17.1727872 | 9.73389236 | 7.050130435 | 4.538219019 | 0.444260982 | -1.170520655 | 3.16995054 | 0.040456515 | Rv3857c | Rv3857c | hypothetical protein |
| MT3958 | 3,168.38 | 2,112.11 | 1,252.52 | 1,278.56 | 0.4793938 | 1.060716843 | 10.9308176 | 0.044973745 | Rv3874 | Rv3874 | conserved hypothetical protein |
| MT4005 | 180.704556 | 188.483552 | 97.04806825 | 72.23559381 | 0.458491225 | 1.125033971 | 7.06774704 | 0.005886986 | Rv3890c | Rv3890c | hypothetical protein |

TABLE 2D

Upregulated gene expression tables of WT Mtb treated with HC101A compared to DMSO

| Gene | Counts per million (CPM) | | | | DMSO WT/ HC101A WT Fold change | log2 Fold change | logCPM | Adjusted p-value | Rv number | Gene name | Annotated function |
|---|---|---|---|---|---|---|---|---|---|---|---|
| | WT_DMSO1 | WT_DMSO2 | WT_HC101A1 | WT_HC101A2 | | | | | | | |
| MT0153 | 196.316181 | 299.685898 | 654.8924695 | 893.5055061 | 3.116888797 | 1.540106684 | 9.00107705 | 0.000436841 | Rv0145 | Rv0145 | conserved hypothetical protein |
| MT0154 | 206.854028 | 336.556703 | 857.3482469 | 1,090.63 | 3.578987361 | 1.839551449 | 9.28592322 | 7.32E-05 | Rv0146 | Rv0146 | conserved hypothetical protein |
| MT0213 | 25.368890 | 52.0615758 | 66.94049598 | 102.9826624 | 2.162396313 | 1.112630957 | 5.975215 | 0.033071525 | Rv0203 | Rv0203 | hypothetical protein |
| MT0236 | 16.7824966 | 34.3635897 | 47.7866235 | 71.15694693 | 2.275753662 | 1.186344402 | 5.44602791 | 0.019109561 | Rv0225c | Rv0225c | probable membrane protein |
| MT0247 | 68.6911488 | 75.3639242 | 189.9238607 | 166.9250047 | 2.465713077 | 1.30200493 | 6.97691654 | 0.00058961 | Rv0236c | Rv0236c | possible membrane protein |
| MT0255 | 53.0952241 | 43.360066 | 401.9698338 | 182.9251358 | 6.083941323 | 2.505006239 | 7.42456039 | 1.65 E-08 | Rv0251c | hsp | possible heat shock protein |
| MT0270.2 | 1.95145309 | 4.57197974 | 9.544250403 | 10.7055423 | 2.806463025 | 1.488753052 | 2.91633916 | 0.005185649 | | | |
| MT0298 | 19.9048215 | 26.3994959 | 30.98612802 | 96.98988596 | 2.744589875 | 1.456590583 | 5.48068753 | 0.019260881 | | | |
| MT0342 | 4.2931968 | 3.392114 | 11.37465459 | 8.785526563 | 2.700598295 | 1.43327906 | 2.9303237 | 0.011192668 | Rv0327c | Rv0327c | cytochrome P-450 monooxygenasemonooxygenase |
| MT0382 | 1.95145309 | 2.21224826 | 17.12735345 | 12.04373509 | 6.830401583 | 2.771970402 | 3.23386343 | 6.59E-08 | Rv0366c | Rv0366c | conserved hypothetical protein |
| MT0384 | 1.17087185 | 2.80218113 | 5.295097827 | 6.516417053 | 2.635271 | 1.39795133 | 2.2172623 | 0.02336732 | Rv0368c | Rv0368c | conserved hypothetical protein |
| MT0398 | 24.1980183 | 47.9320457 | 76.28863165 | 92.33530235 | 2.298631885 | 1.200775444 | 5.93736923 | 0.010449641 | Rv0385 | Rv0385 | similar to oxidoreductases |
| MT0426 | 37.85819 | 55.1587234 | 83.80636313 | 112.3500119 | 2.089943741 | 1.063464107 | 6.19468928 | 0.014262803 | Rv0413 | mutT3 | MutT homologue |
| MT0435 | 11.7087185 | 14.4533553 | 33.40487641 | 33.3966374 | 2.514673933 | 1.330371344 | 4.594804 | 0.001805253 | Rv0421c | Rv0421c | hypothetical protein |
| MT0453 | 18.3436586 | 31.5614086 | 42.2954103 | 62.66233184 | 2.053842714 | 1.045333027 | 5.3100483 | 0.033252288 | Rv0437c | psd | putative phosphatidylserine decarboxylase |
| MT0465 | 16.7824966 | 19.3203015 | 34.84305113 | 39.91305445 | 2.053885115 | 1.038355487 | 2.2172623 | 0.019433804 | Rv0449c | Rv0449c | putative dehydrogenase |
| MT0468 | 37.0776087 | 53.0939583 | 320.9090769 | 348.9774061 | 7.352190895 | 2.880135158 | 5.93736923 | 0.010449641 | Rv0452 | Rv0452 | putative transcriptional regulator |
| MT0469 | 12.4892998 | 12.6835767 | 35.43139533 | 28.50932461 | 2.535063932 | 1.342022131 | 4.5325702 | 0.014268928 | Rv0453 | PPE | PPE-family protein |
| MT0502 | 32.0038307 | 53.5652668 | 85.83288205 | 112.1172827 | 2.045184861 | 1.053842714 | 6.21751778 | 0.001805253 | Rv0484c | Rv0484c | oxidoreductase |
| MT0511 | 8.19610298 | 14.4533553 | 26.14863124 | 31.94208002 | 2.471160841 | 1.305188915 | 4.40401589 | 0.005083875 | Rv0492c | Rv0492c | gmc-type oxidoreductase |
| MT0519 | 12.4892998 | 24.1872477 | 38.89608897 | 39.21486691 | 2.059191924 | 1.049067466 | 4.88996359 | 0.034688101 | Rv0499 | Rv0499 | hypothetical protein |
| MT0535 | 2.34174371 | 7.07910944 | 19.5147343 | 18.15287608 | 3.631988279 | 1.860759547 | 3.69041987 | 0.000201488 | Rv0514 | Rv0514 | possible membrane protein |
| MT0556 | 12.8795904 | 10.3238252 | 29.94018277 | 25.77475674 | 2.441383492 | 1.287698931 | 4.35709052 | 0.004070146 | Rv0532 | PE_PGRS | PE_PGRS-family |
| MT0556 | 8.5863936 | 14.1583889 | 26.54086071 | 30.54570494 | 2.424711819 | 1.277813291 | 4.38651659 | 0.000495033 | | | |
| MT0569 | 30.4426682 | 46.75218 | 87.85940097 | 78.13882234 | 2.123534911 | 1.086467827 | 5.94863123 | 0.010221912 | Rv0541c | Rv0541c | unknown membrane protein |
| MT0574 | 10.5378467 | 15.4857378 | 23.86062601 | 30.72025182 | 2.046125087 | 1.032894345 | 4.3914378 | 0.031559747 | | | |
| MT0586 | 28.1009245 | 21.974999 | 57.00401611 | 45.14946101 | 2.051778861 | 1.043889603 | 5.27598414 | 0.017572545 | | | |
| MT0589 | 28.1009245 | 30.2340596 | 201.4752037 | 136.2629352 | 5.771644481 | 2.528983186 | 6.65079751 | 1.50E-11 | Rv0560c | Rv0560c | methyl transferase |
| MT0651 | 96.011492 | 120.346306 | 425.8304598 | 287.0132618 | 3.286878745 | 1.716718236 | 7.86749244 | 2.80E-05 | Rv0563 | htpX | probable (transmembrane) heat shock protein |
| MT0654 | 1.17087185 | 3.392114 | 6.341043076 | 8.087339021 | 2.777796675 | 1.471341804 | 7.46807479 | 0.013593095 | | | |
| MT0679 | 9.36697483 | 19.6152679 | 38.76534582 | 51.14223741 | 2.992689934 | 1.581442812 | 4.94947852 | 0.000812298 | Rv0626 | Rv0626 | conserved hypothetical protein |
| MT0689 | 0.39029062 | 2.35973148 | 4.510638889 | 5.178224265 | 2.851715697 | 1.511830159 | 1.93584468 | 0.018356424 | | | |
| MT0706.1 | 19.9048215 | 24.9246638 | 70.01296015 | 83.549775579 | 3.386082932 | 1.759617308 | 5.66632135 | 1.59E-06 | Rv0660c | Rv0660c | conserved hypothetical protein |
| MT0738 | 137.772588 | 69.7595619 | 521.7305649 | 291.7260277 | 3.939996402 | 1.977828099 | 8.00218591 | 6.45 E-05 | Rv0678 | Rv0678 | hypothetical protein |
| MT0739 | 242.370474 | 151.907714 | 816.1641526 | 730.3623506 | 3.930874669 | 1.974850366 | 8.92602148 | 9.76E-06 | | | |
| MT0754 | 158.457991 | 119.16644 | 344.442845 | 284.3368762 | 2.270233353 | 1.128840597 | 7.8291977 | 0.005158165 | Rv0712 | Rv0712 | conserved hypothetical protein |
| MT0772.1 | 10.9281373 | 21.9749994 | 31.37835749 | 47.06947675 | 2.315280291 | 1.211866859 | 4.85133483 | 0.02108558 | Rv0729 | xylB | xylulose kinase |
| MT0808 | 1.17087185 | 5.8993287 | 12.87820089 | 25.89112133 | 4.880196579 | 2.286939252 | 3.6666453 | 0.000208725 | | | |
| MT0851 | 27.7106339 | 41.2953009 | 265.473978 | 172.3941404 | 6.273762007 | 2.549330802 | 7.00317008 | 3.30E-11 | Rv0784 | Rv0784 | conserved hypothetical protein |
| MT0854 | 67.5202769 | 79.6409375 | 251.7459473 | 276.0749903 | 3.576123661 | 1.838396605 | 7.40955711 | 4.19E-07 | Rv0830 | Rv0830 | conserved hypothetical protein |
| MT0860 | 11.7087185 | 20.9426169 | 39.22294685 | 39.04032002 | 2.327104893 | 1.218536241 | 4.84420804 | 0.008203865 | Rv0832 | PE_PGRS | PE_PGRS-family protein |
| MT0885 | 13.6601716 | 34.9535226 | 55.17361192 | 56.90228462 | 2.244046651 | 1.166102658 | 5.3672368 | 0.028070721 | Rv0838 | lpqR | lipoprotein |
| MT1021 | 35.9067369 | 63.71275 | 98.71108294 | 116.0154965 | 2.131607785 | 1.091194207 | 6.31498285 | 0.020363606 | Rv0862c | Rv0862c | conserved hypothetical protein |
| MT1021 | 3.90290618 | 9.29144271 | 15.16620612 | 27.52022559 | 3.044793671 | 1.506344458 | 3.91105566 | 0.003989351 | Rv0992c | Rv0992c | conserved hypothetical protein |

TABLE 2D-continued

Upregulated gene expression tables of WT Mtb treated with HC101A compared to DMSO

| Gene | Counts per million (CPM) | | | | | DMSO WT/ HC101A WT Fold change | log2 Fold change | logCPM | Adjusted p-value | Rv number | Gene name | Annotated function |
|---|---|---|---|---|---|---|---|---|---|---|---|---|
| | WT_DMSO1 | WT_DMSO2 | WT_HC101A1 | WT_HC101A2 | | | | | | | | |
| MT1034 | 30.4426682 | 33.4786904 | 67.55958334 | 66.32781643 | 2.087643477 | 1.061875353 | 5.65275661 | 0.006175481 | Rv1005c | pabB | p-aminobenzoate synthase |
| MT1054 | 8.19610298 | 11.6511742 | 27.12920491 | 25.30929838 | 2.565416889 | 1.359193288 | 4.24831867 | 0.001734138 | | | hypothetical protein |
| MT1073 | 39.809543 | 37.9031869 | 245.6010189 | 98.38626104 | 4.42899315 | 2.146978756 | 6.73779954 | 1.46 E-05 | Rv1043c | Rv1043c | conserved hypothetical protein |
| MT1087 | 115.916314 | 198.954861 | 368.8918152 | 553.4299912 | 2.919948846 | 1.545943095 | 8.27875796 | 0.000827668 | Rv1057 | Rv1057 | hypothetical protein |
| MT1112 | 9.75726545 | 113562078 | 22.51856602 | 22.98200657 | 2.131270014 | 1.091713382 | 4.12486106 | 0.015850829 | Rv1081c | Rv1081c | hypothetical protein |
| MT1123 | 19.5145309 | 20.0577176 | 41.77243841 | 45.2658256 | 2.195533216 | 1.134571361 | 5.02104076 | 0.005787145 | Rv1091 | PE_PGRS | PE_PGRS-family protein |
| MT1178 | 67.5202769 | 134.504694 | 210.885286 | 239.6528736 | 2.315538464 | 1.211347722 | 7.40373555 | 0.011657439 | | | |
| MT1186 | 17.9533584 | 18.8778519 | 38.37311635 | 38.98213773 | 2.093484779 | 1.065906429 | 4.87422501 | 0.034766654 | Rv1152 | Rv1152 | transcriptional regulator (GntR family) |
| MT1247 | 7.80581236 | 28.1692946 | 35.2352805 | 61.20777446 | 2.596957451 | 1.376822377 | 5.10147795 | 0.034766654 | Rv1209 | Rv1209 | conserved hypothetical protein |
| MT1303 | 88.2056797 | 89.3748298 | 336.5982557 | 191.827027 | 2.97476628 | 1.572776324 | 7.47251288 | 0.000231662 | Rv1265 | Rv1265 | hypothetical protein |
| MT1379 | 62.0562083 | 59.2882535 | 145.5948382 | 101.1208289 | 2.001623231 | 1.001170439 | 6.50202231 | 0.021193865 | Rv1338 | murI | glutamate racemase |
| MT1429 | 26.1494714 | 34.5110729 | 78.77275162 | 83.49159349 | 2.645457172 | 1.403517052 | 5.82759285 | 0.00020113 | Rv1385 | pyrF | orotidine 5'-phosphate decarboxylase |
| MT1446 | 9.75726545 | 9.43892592 | 20.33056079 | 18.38560526 | 2.021213343 | 1.015221609 | 3.92042063 | 0.034281244 | | | |
| MT1514.1 | 19.1242403 | 33.92114 | 43.99507205 | 74.58970234 | 2.197094945 | 1.135597216 | 5.45687431 | 0.025203737 | Rv1468c | PE_PGRS | PE_PGRS-family protein |
| MT1613 | 33.5649932 | 47.6370793 | 93.1544988 | 79.12792136 | 2.099880584 | 1.070307287 | 6.00681164 | 0.009738412 | Rv1562c | glgZ | maltooligosyltrehalose trehalohydrolase |
| MT1619 | 23.4174371 | 42.3276834 | 74.32748431 | 99.14263088 | 2.595110077 | 1.375795735 | 5.92945404 | 0.00197997 | Rv1568 | bioA | adenosylmethionine-8-amino 7-oxononanoate aminotransferase |
| MT1620 | 13.6601716 | 38.9355694 | 44.32192995 | 92.9753076 | 2.557940633 | 1.354982781 | 5.60579953 | 0.033675427 | Rv1569 | bioT | 8-amino-7-oxononanoate synthase |
| MT1621 | 4.68348742 | 9.14395949 | 21.18039131 | 33.3384551 | 3.736178549 | 1.901563402 | 4.19000449 | 8.41E-05 | Rv1570 | bioD | dethiobiotin synthase |
| MT1622 | 1.56116247 | 2.65469792 | 5.818070451 | 11.63645902 | 3.85016715 | 1.94492108 | 2.65113909 | 0.018896362 | Rv1571 | Rv1571 | conserved hypothetical protein |
| MT1645 | 19.1242403 | 41.1003345 | 69.48998753 | 88.32072399 | 2.570978984 | 1.362317817 | 5.79841313 | 0.003964587 | Rv1610 | Rv1610 | possible membrane protein |
| MT1719 | 80.0095767 | 70.2020116 | 162.1215137 | 144.4084565 | 2.045124255 | 1.032188499 | 6.84491956 | 0.010919028 | Rv1679 | fadE16 | acyl-CoA dehydrogenase |
| MT1746 | 4.68348742 | 5.75184549 | 14.6432335 | 10.7637246 | 2.37444345 | 1.247589397 | 3.277647 | 0.017796173 | Rv1706c | PPE | PPE-family protein |
| MT1753 | 62.0562083 | 77.7871389 | 170.9466767 | 129.6883358 | 2.139692787 | 1.097403672 | 6.79526578 | 0.007969339 | Rv1713 | Rv1713 | conserved hypothetical protein |
| MT1758 | 7.02523112 | 7.07919444 | 12.94357246 | 15.65103739 | 2.024987774 | 1.017913198 | 3.5006925 | 0.049024614 | | | |
| MT1836 | 51.5183616 | 33.3312072 | 118.2571848 | 69.99330103 | 2.239340405 | 1.163202695 | 6.1083948 | 0.017688136 | Rv1787 | PPE | PPE-family protein |
| MT1837 | 3.51261556 | 3.68708044 | 18.17329871 | 7.38915148 | 3.518866315 | 1.815110706 | 3.17552499 | 0.004627557 | Rv1788 | PE | PE-family protein |
| MT1888 | 15.2213341 | 14.3058721 | 38.04625846 | 31.94208002 | 2.378402695 | 1.249993003 | 4.68344445 | 0.004200151 | Rv1840c | PE_PGRS | PE_PGRS family protein |
| MT1893 | 61.6659177 | 127.278017 | 230.8924139 | 298.0678979 | 2.781237859 | 1.475727133 | 7.49782011 | 0.002014733 | Rv1845c | Rv1845c | hypothetical protein |
| MT1950 | 53.0795241 | 49.8493275 | 131.9198445 | 75.0551607 | 2.012848292 | 1.009238441 | 5.2897503 | 0.033134083 | | | |
| MT2055 | 7.41552174 | 9.73389236 | 25.56028704 | 19.72379804 | 2.575174209 | 1.364670033 | 4.04417813 | 0.002284789 | | | |
| MT2084 | 27.3203433 | 18.4354022 | 52.03577617 | 50.50223216 | 2.28278274 | 1.19079356 | 5.24020568 | 0.005787631 | Rv2025c | Rv2025c | possible membrane protein |
| MT2094 | 1.95145309 | 5.8893287 | 10.78631039 | 14.72012066 | 2.928455963 | 1.5501402 | 3.2171278 | 0.00508925 | | | |
| MT2112 | 41.3708055 | 53.8313744 | 246.5815926 | 122.4737312 | 3.857035592 | 1.947492459 | 6.87489784 | 1.94E-05 | Rv2052c | Rv2052c | hypothetical protein |
| MT2126 | 17.1727872 | 25.9570463 | 42.75301208 | 62.72051414 | 2.402614999 | 1.264605486 | 5.25402506 | 0.004366979 | Rv2066 | cobI | CobI-CobJ fusion protein |
| MT2159 | 7.80581236 | 9.43892592 | 19.54610185 | 15.88376657 | 2.017464249 | 1.012543108 | 3.79490609 | 0.03961407 | Rv2098c | PE_PGRS | PE_PGRS-family |
| MT2154 | 15.3382546 | 26.2140282 | 26.21400282 | 23.68019411 | 2.067517442 | 1.0478995 | 4.25968596 | 0.037189219 | Rv2104c | Rv2104c | conserved hypo- |
| MT2182.1 | 2.73203433 | 7.5216861 | 11.24391143 | 23.15655346 | 3.11673293 | 1.640034537 | 3.61040594 | 0.007028674 | | | |
| MT2220 | 309.11017 | 447.316599 | 815.183579 | 804.1375008 | 2.138629257 | 1.096686405 | 9.21660886 | 0.02413631 | Rv2162c | PE_PGRS | PE_PGRS-family protein |
| MT2254 | 7.80581236 | 16.0756707 | 39.58054791 | 67.08418627 | 4.302885731 | 2.105304528 | 5.08799787 | 9.81E-06 | Rv2208 | cobS | cobalamin (5'-phosphate) synthase |
| MT2310 | 22.2465552 | 20.2052008 | 36.93494163 | 49.80404462 | 2.052978984 | 1.037718859 | 5.04586575 | 0.001255562 | Rv2250c | Rv2250c | putative transcriptional regulator |
| MT2311 | 161.580316 | 216.35788 | 395.8249054 | 613.532202 | 2.656528778 | 1.414962898 | 8.4428077 | 0.001734138 | Rv2251 | Rv2251 | conserved hypothetical protein |
| MT2334 | 8.5863936 | 17.8454693 | 32.16281643 | 45.09127872 | 2.817302962 | 1.494314714 | 4.75744434 | 0.002409597 | | | |
| MT2389 | 115.916314 | 121.378686 | 252.4650345 | 271.7695005 | 2.207966094 | 1.142718018 | 7.57962372 | 0.003671666 | Rv2327 | Rv2327 | conserved hypothetical protein |
| MT2434 | 1.95145309 | 5.0144294 | 12.09374195 | 9.367349514 | 2.777776241 | 1.473923207 | 2.99599504 | 0.006298485 | | | |
| MT2515 | 8.19610298 | 16.3706372 | 36.47734058 | 45.44037249 | 3.206324692 | 1.580920529 | 4.79717304 | 0.0002669 | Rv2439c | proB | glutamate 5-kinase |
| MT2526 | 117.087185 | 186.418787 | 295.5449045 | 339.493692 | 2.085449997 | 1.060358721 | 7.8805006 | 0.021295236 | Rv2450c | Rv2450c | conserved hypothetical protein |

TABLE 2D-continued

Upregulated gene expression tables of WT Mtb treated with HC101A compared to DMSO

| Gene | Counts per million (CPM) | | | | DMSO WT/ HC101A WT | | | | Rv number | Gene name | Annotated function |
|---|---|---|---|---|---|---|---|---|---|---|---|
| | WT_DMSO1 | WT_DMSO2 | WT_HC101A1 | WT_HC101A2 | Fold change | log2 Fold change | logCPM | Adjusted p-value | | | |
| MT2533 | 8.97668421 | 21.680033 | 29.51332488 | 43.05489839 | 2.289470441 | 1.195013939 | 4.74870605 | 0.0338307 | Rv2458 | Rv2458 | conserved hypothetical protein |
| MT2540 | 25.3688902 | 59.2882535 | 78.5112653 | 119.3318873 | 2.303713508 | 1.203961313 | 6.16345003 | 0.027194856 | Rv2465c | rpi | phosphopentose isomerase |
| MT2608 | 78.0581236 | 110.46493 | 212.0000278 | 258.5039372 | 2.484956519 | 1.313220608 | 7.37372216 | 0.001365742 | Rv2533c | musB | N-utilisation substance protein B |
| MT2615.1 | 1.56116247 | 4.86694618 | 6.733272545 | 12.80010493 | 2.731778008 | 1.449840251 | 2.88124352 | 0.023378291 | | | |
| MT2628 | 0.78058124 | 5.45687905 | 12.15911353 | 11.8691882 | 3.321507788 | 1.731838297 | 3.10280927 | 0.003368674 | | | |
| MT2631 | 21.8562746 | 31.2664421 | 57.85384662 | 50.38586757 | 2.007268018 | 1.005233264 | 5.3651424 | 0.019433804 | | | |
| MT2657 | 597.144546 | 619.282031 | 1,613.24 | 1,665.93 | 2.695545894 | 1.430577473 | 10.1356765 | 0.000148658 | Rv2590 | fadD9 | acyl-CoA synthase |
| MT2668.1 | 33.9952838 | 39.0830527 | 114.661748 | 87.62253645 | 2.75598679 | 1.462568973 | 6.12689548 | 0.000134878 | Rv2591 | PE_PGRS | PE_PGRS-family protein |
| MT2690 | 12.0990092 | 20.9426169 | 37.3271711 | 79.12792136 | 3.448774073 | 1.786083622 | 5.27128487 | 0.000453302 | Rv2615c | PE_PGRS | PE-family protein |
| MT2693 | 17.5630778 | 19.3203015 | 39.09220371 | 41.94943478 | 2.184547266 | 1.127134321 | 4.92172818 | 0.007175485 | | | |
| MT2718 | 8.19610298 | 12.9785231 | 31.83595854 | 47.24402363 | 3.620228381 | 1.856080712 | 4.46680489 | 0.014408261 | Rv2652c | Rv2652c | phiRv2 phage related protein |
| MT2729 | 12.0990092 | 14.7483218 | 31.83595854 | 26.53112657 | 2.143221757 | 1.099781132 | 2.849373253 | 0.003964587 | | | |
| MT2736.1 | 2.73203433 | 3.53959722 | 11.44002617 | 8.029156726 | 2.987385962 | 1.578883642 | 6.04543073 | 7.49E-05 | | | |
| MT2739 | 23.8077277 | 40.1154352 | 97.86125242 | 97.57170891 | 3.005875284 | 1.587785152 | 8.58628718 | 0.021245859 | Rv2720 | lexA | LexA, SOS repressor protein |
| MT2793 | 232.613208 | 269.894288 | 538.0080878 | 493.3276803 | 2.050915155 | 1.03626781 | 5.49025089 | 0.010374701 | Rv2736c | recX | regulatory protein for RecA |
| MT2805 | 24.1980183 | 32.7412743 | 59.03053503 | 60.27685774 | 2.059316609 | 1.049154397 | 5.26775839 | 0.023378291 | Rv2739c | Rv2739c | glycosyltransferase |
| MT2808.1 | 16.392206 | 29.4966435 | 39.28831844 | 64.87325906 | 2.224804255 | 1.153678409 | 7.08920106 | 0.011470854 | Rv2743c | Rv2743c | conserved hypothetical protein |
| MT2814 | 76.4969511 | 98.076397 | 202.2596627 | 164.1322545 | 2.091313814 | 1.064409563 | 7.28787865 | 7.54E-06 | Rv2745c | Rv2745c | putative transcriptional regulator |
| MT2816 | 59.3241739 | 75.5114074 | 296.3293635 | 188.8015477 | 3.583855096 | 1.841512307 | 3.46285068 | 0.001699979 | Rv2762c | Rv2762c | hypothetical protein |
| MT2832 | 2.73203433 | 6.63674475 | 16.56975242 | 14.13829771 | 3.015345533 | 1.592323332 | 5.6469077 | 0.000718899 | Rv2836c | dinF | DNA-damage-inducible protein F |
| MT2902 | 28.8815057 | 28.464261 | 75.11194324 | 64.3496184 | 2.432653335 | 1.282530744 | 6.14685145 | 0.013851196 | Rv2848c | cobB | cobyrinicacid a,c-diamide synthase |
| MT2914 | 50.3474897 | 41.4427841 | 106.9479018 | 81.74612464 | 2.055793601 | 1.046696118 | 10.1526528 | 0.022139378 | | | |
| MT3002 | 817.268554 | 569.28522 | 1,831.19 | 1,282.20 | 2.282482861 | 1.190604027 | 11.6110682 | 0.001196406 | Rv2933 | ppsC | phenolpthiocerol synthesis (pksD) |
| MT3003 | 2,070.49 | 1,694.29 | 4,461.74 | 4,282.33 | 2.322828008 | 1.198258467 | 9.25040831 | 0.002584789 | Rv2946c | pksI | polyketide synthase |
| MT3018 | 366.873181 | 292.754187 | 895.8521064 | 876.7490051 | 2.689153979 | 1.427152355 | 7.01827515 | 0.003955304 | Rv2947c | pks15 | polyketide synthase |
| MT3021.1 | 86.6445172 | 67.8422801 | 202.5865205 | 158.0812958 | 2.343337999 | 1.228565051 | 3.89808912 | 0.034443851 | Rv2972c | Rv2972c | hypothetical protein |
| MT3044 | 5.46406865 | 9.73389236 | 20.85355342 | 19.84016263 | 2.545482494 | 1.347939144 | 3.46325515 | 4.26E-07 | Rv3026c | Rv3026c | some similarity to acyltransferase Q59601 |
| MT3050 | 6.63494051 | 6.48926157 | 16.01603664 | 12.33464656 | 2.151716242 | 1.11217716 | 3.95181228 | 5.05E-05 | Rv3037c | Rv3037c | hypothetical protein |
| MT3110 | 5.07377803 | 3.83456366 | 30.39778382 | 18.15287608 | 5.618510293 | 2.490187651 | 4.61506366 | 0.025279872 | Rv3039c | echA17 | enoyl-CoA hydratase/isomerase superfamily |
| MT3122 | 7.80581236 | 12.9785231 | 33.56636272 | 38.98213773 | 3.359485613 | 1.752528366 | 5.68107454 | 7.46E-06 | Rv3054c | Rv3054c | conserved hypothetical protein |
| MT3124 | 23.0271465 | 42.1802002 | 63.34505918 | 72.72278689 | 2.04970793 | 1.03541835 | 3.47069402 | 0.001656726 | Rv3066 | Rv3066 | putative transcriptional regulator |
| MT3140 | 1.95145309 | 2.5072147 | 26.21400282 | 9.076438038 | 7.635770088 | 2.932773654 | 4.68339085 | 0.000335573 | | | |
| MT3151 | 14.0504523 | 13.8634225 | 39.4190616 | 31.94208002 | 2.556879158 | 1.354383978 | 7.36071869 | 0.046428091 | Rv3167c | Rv3167c | putative transcriptional regulator |
| MT3176.1 | 94.0600389 | 97.1914404 | 246.6469642 | 215.681768 | 2.416055519 | 1.272653607 | 2.97180107 | 0.02515022 | Rv3180c | Rv3180c | hypothetical protein |
| MT3256 | 4.2931968 | 4.71946296 | 10.98242512 | 8.843708858 | 2.159478554 | 1.117348325 | 4.20673149 | 0.011192668 | | | |
| MT3271 | 11.3184279 | 11.9461406 | 22.74930918 | 24.96020461 | 2.041154612 | 1.029385467 | 6.01162539 | 0.015069945 | Rv3199c | Rv3199c | conserved hypothetical protein |
| MT3276 | 38.2484806 | 44.2449653 | 99.49554188 | 72.6696866 | 2.07755312 | 1.054885365 | 6.42254074 | 0.008660259 | Rv3242c | Rv3242c | conserved hypothetical protein |
| MT3293 | 41.7610961 | 56.5149311 | 106.294185 | 124.4568293 | 2.112502714 | 1.079953195 | 3.81930887 | 0.0002669 | Rv3247c | tmk | thymidylate kinase |
| MT3340 | 8.19610298 | 7.96409375 | 18.5001566 | 18.85106362 | 2.316064787 | 1.21167561 | 4.40147904 | 0.000141567 | Rv3269 | Rv3269 | probable heat shock protein |
| MT3345 | 7.02523112 | 12.2411071 | 29.35183857 | 31.59298625 | 3.032604843 | 1.600557523 | 9.6200201 | 0.000797906 | Rv3307 | deoD | probable purine nucleoside phosphorylase |
| MT3369 | 418.781833 | 351.010058 | 1,077.85 | 1,295.49 | 3.084469984 | 1.625022607 | 6.43662874 | 0.00020223 | Rv3308 | pmmB | phosphomannomutase |
| MT3406 | 38.2484806 | 61.7954682 | 94.59267352 | 147.4921181 | 2.398262855 | 1.261989979 | 5.35725334 | 0.00223136 | Rv3384c | PE_PGRS | conserved hypothetical protein |
| MT3407 | 22.6368559 | 24.924658 | 49.22479831 | 63.53506627 | 2.359735275 | 1.238625022 | 4.37117375 | 2.90E-05 | Rv3388 | PE_PGRS | PE_PGRS-family protein |
| MT3492 | 4.2931968 | 10.7662749 | 32.29355958 | 30.48752264 | 3.897635134 | 1.962599043 | 2.82408928 | 0.00223136 | Rv3406 | Rv3406 | putative dioxygenasedioxygenase |
| MT3495 | 4.2931968 | 1.62251539 | 10.39408092 | 9.309167219 | 3.815297509 | 1.93179556 | 4.371117375 | 0.00223136 | | | |
| MT3514 | 65.1785332 | 50.2917772 | 303.5202371 | 96.05896924 | 3.459025162 | 1.794430305 | 7.02099715 | 0.002407018 | | | |

TABLE 2D-continued

Upregulated gene expression tables of WT Mtb treated with HC101A compared to DMSO

| Gene | Counts per million (CPM) | | | | DMSO WT/ HC101A WT Fold change | log2 Fold change | logCPM | Adjusted p-value | Rv number | Gene name | Annotated function |
|---|---|---|---|---|---|---|---|---|---|---|---|
| | WT_DMSO1 | WT_DMSO2 | WT_HC101A1 | WT_HC101A2 | | | | | | | |
| MT3524 | 2.34174371 | 3.09714757 | 6.341043075 | 11.8691882 | 3.223784028 | 1.688755096 | 2.74715203 | 0.005505017 | Rv3415c | Rv3415c | conserved hypothetical protein |
| MT3539 | 12.0990092 | 16.8130868 | 32.94727537 | 32.23299149 | 2.2076827 | 1.142532835 | 4.60893403 | 0.010732372 | Rv3433c | Rv3433c | conserved hypothetical protein |
| MT3548 | 247.834542 | 367.380695 | 589.8477492 | 693.8238693 | 2.083917608 | 1.059298239 | 8.89396797 | 0.033604484 | Rv3443c | rplM | 50S ribosomal protein L13 |
| MT3592 | 2.73203433 | 9.43892592 | 12.551343 | 17.74560001 | 2.296121357 | 1.199198895 | 3.53183797 | 0.04811238 | | | |
| MT3612 | 15.6116247 | 24.1872477 | 51.97040459 | 50.44404987 | 2.517241207 | 1.331843455 | 5.19319801 | 0.001223163 | Rv3507 | PE_PGRS | PE_PGRS-family protein |
| MT3666 | 19.1242403 | 31.7088918 | 54.32378141 | 56.72773774 | 2.141453364 | 1.098590259 | 5.37286514 | 0.012098186 | | | |
| MT3696 | 6.24464989 | 11.3562078 | 21.76873551 | 31.65116854 | 2.905364083 | 1.538718965 | 4.23330711 | 0.001340758 | Rv3590c | PE_PGRS | PE_PGRS-family protein |
| MT3756 | 6.24464989 | 12.2411071 | 22.29170813 | 19.89834493 | 2.172874227 | 1.119604659 | 4.00548733 | 0.024333502 | | | |
| MT3758 | 3.90290518 | 5.78422801 | 9.740365138 | 16.00013116 | 2.287001502 | 1.193457313 | 3.30955767 | 0.034876382 | Rv3658c | Rv3658c | probable transmembrane protein |
| MT3763 | 3.90290518 | 6.63674479 | 11.37465459 | 11.81100591 | 2.078813776 | 1.055760525 | 3.19706184 | 0.048817793 | Rv3662c | Rv3662c | hypothetical protein |
| MT3831 | 6.63494051 | 9.29144271 | 24.90657126 | 26.06566821 | 3.098585585 | 1.631609817 | 4.14886482 | 0.000110601 | Rv3728 | Rv3728 | possible sugar transporter |
| MT3880 | 5.07377803 | 3.98204687 | 9.217392513 | 11.17100066 | 2.319941604 | 1.214088491 | 2.99383814 | 0.034220816 | Rv3771c | Rv3771c | conserved hypothetical protein |
| MT3914 | 71.0328925 | 109.874997 | 201.9328048 | 221.4999976 | 2.32789127 | 1.219023675 | 7.24939738 | 0.004133928 | Rv3807c | Rv3807c | possible membrane protein |
| MT3921 | 5.07377803 | 2.94966435 | 10.32870934 | 13.09101164 | 3.128576963 | 1.645506595 | 3.09822964 | 0.003794215 | | | |
| MT3998 | 121.380382 | 111.497313 | 412.7561442 | 272.1767766 | 2.94323293 | 1.557401723 | 7.84880521 | 0.000176222 | Rv3883c | Rv3883c | probable secreted protease |
| MT4025 | 10.5378467 | 19.9102344 | 35.59288165 | 38.63304396 | 2.353203499 | 1.240743857 | 4.76582909 | 0.008706425 | Rv3906c | Rv3906c | conserved hypothetical protein |

TABLE 2E

Downregulated gene expression tables of WT Mtb treated with HC102A compared to DMSO

| | Counts per million (CPM) | | | | WT DMSO/WT HC102A | | | | | | | |
|---|---|---|---|---|---|---|---|---|---|---|---|---|
| Gene | WT_DMSO1 | WT_DMSO2 | WT_HC102A1 | WT_HC102A2 | Fold change | log2 Fold change | LogCPM | Adjusted p-value | Rv number | Gene name | Annotated function |
| MT0595 | 268.861154 | 166.489022 | 21.37579586 | 25.91548951 | 0.10889336 | −3.199012103 | 6.90534438 | 6.46E−10 | Rv0569 | Rv0569 | conserved hypothetical protein |
| MT0596 | 2,739.23 | 1,602.51 | 102.6525862 | 94.10488838 | 0.045326402 | −4.463504566 | 10.1467857 | 1.17E−11 | Rv0570 | nrdZ | ribonucleotide reductase, class II |
| MT0597 | 233.683395 | 391.419089 | 94.1998 | 81.32304061 | 0.280536264 | −1.833740818 | 7.64431228 | 0.007274158 | Rv0571c | Rv0571c | conserved hypothetical protein |
| MT0598 | 190.608115 | 322.105292 | 57.7062019 | 66.54769365 | 0.242120414 | −2.046203069 | 7.313962 | 0.000631144 | Rv0572c | Rv0572c | hypothetical protein |
| MT0599 | 534.851395 | 726.707593 | 127.4420072 | 180.587574 | 0.244148489 | −2.034169248 | 8.61536498 | 0.003135948 | Rv0572c | Rv0572c | hypothetical protein |
| MT0600 | 915.708663 | 1,233.38 | 129.5552038 | 211.3109145 | 0.158620436 | −2.656349443 | 9.28114862 | 6.40E−05 | | | |
| MT0601 | 88.6632849 | 83.1765564 | 13.81705436 | 19.29003631 | 0.193202634 | −2.371813334 | 5.66671759 | 4.53E−07 | Rv0573c | Rv0573c | conserved hypothetical protein |
| MT0602 | 357.883786 | 324.95939 | 45.10861864 | 51.53781737 | 0.141613201 | −2.819921397 | 7.602328 | 9.79E−08 | Rv0574c | Rv0574c | conserved hypothetical protein |
| MT1096 | 16.5121907 | 20.6582297 | 9.103000518 | 3.811101398 | 0.343643905 | −1.541013723 | 3.63229664 | 0.153219639 | | | |
| MT1385 | 137.840896 | 109.407072 | 56.64992286 | 35.06213287 | 0.371217878 | −1.429661902 | 6.3994683 | 0.031837186 | | | |
| MT1774 | 1,342.51 | 1,645.73 | 109.6423902 | 115.9747472 | 0.075506286 | −3.727259433 | 9.64920275 | 9.78E−10 | Rv1733c | Rv1733c | possible membrane protein |
| MT1775 | 532.697631 | 610.505051 | 172.1442419 | 61.79847498 | 0.20456776 | −2.289349304 | 8.42595935 | 0.004239872 | | | |
| MT1776 | 19.0249154 | 15.3577629 | 5.201714582 | 4.162895374 | 0.274235718 | −1.866511608 | 3.40676192 | 0.00225844 | Rv1735c | Rv1735c | hypothetical protein |
| MT1777 | 100.867948 | 180.351782 | 11.46002744 | 24.0978873 | 0.126516464 | −2.982602952 | 6.3034017 | 1.38E−07 | | | |
| MT1778 | 5,333.80 | 3,333.72 | 234.4835401 | 266.0798857 | 0.055450253 | −4.172662152 | 11.1586863 | 6.00E−11 | Rv1736c | narX | fused nitrate reductase |
| MT1779 | 1,908.95 | 1,381.11 | 72.41762019 | 91.9354922 | 0.049973376 | −4.322696514 | 9.75284262 | 1.17E−11 | Rv1737c | narK2 | nitrite extrusion protein |
| MT1780 | 3,549.40 | 4,687.52 | 337.7863406 | 628.9489954 | 0.117377012 | −3.090778204 | 11.1676891 | 4.29E−06 | Rv1738 | Rv1738 | conserved hypothetical protein |
| MT1839 | 62.1001955 | 42.9473723 | 29.82858205 | 18.93824233 | 0.466011498 | −1.101562543 | 5.25494611 | 0.49861605 | Rv1790 | PPE | PPE-family protein |
| MT1860 | 228.298985 | 153.30581 | 54.94311027 | 65.8441057 | 0.317076728 | −1.657096103 | 6.96750601 | 0.007760235 | Rv1812c | Rv1812c | probable dehydrogenase |
| MT1861 | 2,822.51 | 1,488.34 | 121.346248 | 147.2257786 | 0.062318769 | −4.004189449 | 10.1597254 | 1.18E−09 | Rv1813c | Rv1813c | conserved hypothetical protein |
| MT1882 | 75.3817402 | 71.3524381 | 37.79370751 | 31.48556078 | 0.47231284 | −1.082185339 | 5.75107316 | 0.275155648 | Rv1834 | Rv1834 | conserved hypothetical protein |
| MT2052 | 38.106.55 | 8,582.81 | 561.6226212 | 277.3309171 | 0.017968834 | −5.798359383 | 13.536324 | 2.50E−10 | Rv1996 | Rv1996 | conserved hypothetical protein |
| MT2053 | 2,979.37 | 1,578.86 | 105.0908899 | 117.3819231 | 0.048820109 | −4.356380684 | 10.2218042 | 5.28E−11 | Rv1997 | ctpF | probable cation transport ATPase |
| MT2059 | 506.852463 | 843.317864 | 203.5983598 | 201.1537695 | 0.222651698 | −2.16713948 | 8.68849175 | 0.006801091 | Rv2003c | Rv2003c | conserved hypothetical protein |
| MT2060 | 2,556.88 | 2,604.84 | 661.1866894 | 393.8919876 | 0.204398457 | −2.290543807 | 10.6015696 | 0.001198816 | Rv2004c | Rv2004c | hypothetical protein |
| MT2061 | 2,295.91 | 2,093.28 | 308.4454193 | 262.8487318 | 0.130163441 | −2.9416038 | 10.2756004 | 1.66E−06 | Rv2005c | Rv2005c | conserved hypothetical protein |
| MT2062 | 567.157855 | 767.480415 | 140.7714009 | 181.0566326 | 0.241112783 | −2.052219957 | 8.69310712 | 0.002861277 | Rv2006 | otsB | trehalose-6-phosphate phosphatase |
| MT2063 | 7,226.24 | 9,239.80 | 1,505.73 | 2,151.57 | 0.222112178 | −2.170639598 | 12.2965031 | 0.00225844 | Rv2007c | fdxA | ferredoxin |
| MT2086 | 312.654741 | 182.903406 | 90.78617481 | 84.3132894 | 0.353776498 | −1.499089886 | 7.38546279 | 0.065748479 | Rv2027c | Rv2027c | sensor histidine kinase |
| MT2087 | 745.561307 | 675.741566 | 62.09546782 | 56.16977138 | 0.083223857 | −3.586859038 | 8.5858908 | 3.60E−10 | Rv2028c | Rv2028c | conserved hypothetical protein |
| MT2088 | 4,603.67 | 2,470.97 | 254.0712466 | 225.5585705 | 0.067802631 | −3.882514936 | 10.0823475 | 2.73E−09 | | | |
| MT2089 | 13,680.35 | 13,788.01 | 1,125.52 | 784.7350941 | 0.069543418 | −3.845942215 | 12.8423576 | 4.93E−10 | Rv2030c | Rv2030c | conserved hypothetical protein |
| MT2090 | 43,613.72 | 41,594.39 | 3,874.46 | 5,782.55 | 0.113335288 | −3.141330972 | 14.5335551 | 4.53E−07 | | | |
| MT2091 | 3,762.63 | 5,608.17 | 270.570435 | 336.8427313 | 0.064822017 | −3.947372269 | 11.28433 | 4.32E−10 | Rv2032 | Rv2032 | conserved hypothetical protein |
| MT2698 | 41,070.84 | 21,419.05 | 903.5540782 | 611.3592966 | 0.024242603 | −5.366311566 | 13.9657966 | 2.87E−14 | Rv2623 | Rv2623 | conserved hypothetical protein |
| MT2699 | 2,345.81 | 1,782.86 | 106.235288 | 108.4111767 | 0.051997333 | −4.26541855 | 10.0835172 | 1.38E−11 | Rv2624c | Rv2624c | conserved hypothetical protein |
| MT2700 | 5,579.68 | 3,573.60 | 146.135669 | 111.8704841 | 0.028188487 | −5.148750164 | 11.1996004 | 1.76E−14 | Rv2625c | Rv2625c | conserved hypothetical protein |
| MT2701 | 12,542.44 | 10,243.90 | 447.5100076 | 554.4859373 | 0.043975931 | −4.507142079 | 12.5377788 | 5.37E−13 | Rv2626c | Rv2626c | conserved hypothetical protein |
| MT2702 | 7,537.46 | 5,491.42 | 101.2708808 | 156.724216 | 0.01980729 | −5.6578247 | 11.6973292 | 6.57E−17 | Rv2627c | Rv2627c | conserved hypothetical protein |
| MT2703 | 674.128134 | 872.946114 | 20.64430475 | 33.42042765 | 0.034986572 | −4.837054871 | 8.64298969 | 2.96E−14 | Rv2628 | Rv2628 | hypothetical protein |
| MT2704 | 7,455.97 | 4,707.09 | 540.5719325 | 660.1413945 | 0.098725003 | −3.340440678 | 11.7056884 | 1.12E−07 | Rv2629 | Rv2629 | conserved hypothetical protein |
| MT2705 | 735.510408 | 545.812174 | 71.27974513 | 56.05250672 | 0.099397816 | −3.33064204 | 8.45712957 | 1.63E−08 | Rv2630 | Rv2630 | hypothetical protein |
| MT2707 | 1,083.70 | 478.100642 | 110.861542 | 72.58682356 | 0.117877549 | −3.084639128 | 8.76191316 | 1.10E−05 | Rv2631 | Rv2631 | conserved hypothetical protein |
| MT3168 | 297.219433 | 288.943397 | 100.2955593 | 66.8408553 | 0.285100254 | −1.81045877 | 7.54451932 | 0.005587532 | Rv3083 | Rv3083 | probable monooxygenase |
| MT3169 | 45.5880048 | 49.9351143 | 16.74301881 | 9.205275685 | 0.272400211 | −1.87620276 | 4.90417444 | 0.001146198 | Rv3084 | lipR | probable acetyl-hydrolase |

TABLE 2E-continued

Downregulated gene expression tables of WT Mtb treated with HC102A compared to DMSO

| Gene | Counts per million (CPM) | | | | WT DMSO/WT HC102A | | | | Rv number | Gene name | Annotated function |
| --- | --- | --- | --- | --- | --- | --- | --- | --- | --- | --- | --- |
| | WT_DMSO1 | WT_DMSO2 | WT_HC102A1 | WT_HC102A2 | Fold change | log2 Fold change | LogCPM | Adjusted p-value | | | |
| MT3170 | 28.7168534 | 34.2491703 | 11.7851346 | 8.618952393 | 0.322380984 | −1.633161448 | 4.3696841 | 0.007955648 | Rv3085 | Rv3085 | short chain alcohol dehydrogenase |
| MT3209 | 12.5636234 | 14.9500347 | 5.689375324 | 5.394174287 | 0.400042658 | −1.321774248 | 3.25998407 | 0.179392401 | | | |
| MT3210 | 7.89713469 | 5.70819505 | 0.568937532 | 0.117264658 | 0.049489681 | −4.336728438 | 1.63692637 | 7.67E-09 | | | |
| MT3212 | 15,265.16 | 9,828.83 | 690.1212267 | 898.1886511 | 0.063297395 | −3.981710068 | 12.7034075 | 3.82E-10 | Rv3127 | Rv3127 | conserved hypothetical protein |
| MT3216 | 31,587.46 | 26,323.89 | 1,395.93 | 1,787.99 | 0.054980252 | −4.184942683 | 13.8987023 | 1.54E-11 | Rv3130c | Rv3130c | conserved hypothetical protein |
| MT3217 | 17,927.57 | 9,861.72 | 415.6495058 | 421.6837117 | 0.030133008 | −5.052511151 | 12.8048644 | 3.98E-14 | Rv3131 | Rv3131 | conserved hypothetical protein |
| MT3218 | 5,014.32 | 3,071.96 | 438.9759446 | 364.75172 | 0.099400131 | −3.330608443 | 11.1174312 | 1.84E-07 | Rv3132c | Rv3132c | sensor histidine kinase |
| MT3219 | 3,634.48 | 1,966.07 | 233.8333258 | 174.0207531 | 0.072830384 | −3.779315735 | 10.5518606 | 8.64E-09 | Rv3133c | Rv3133c | two-component response regulator |
| MT3220 | 5,959.47 | 3,727.18 | 264.5559525 | 171.7927246 | 0.045046862 | −4.472429565 | 11.3048235 | 1.54E-11 | Rv3134c | Rv3134c | conserved hypothetical protein |
| MT3947 | 86.5095209 | 58.7128633 | 25.92729612 | 7.680835126 | 0.231430045 | −2.111351925 | 5.46470098 | 0.006563585 | Rv3839 | Rv3839 | hypothetical protein |

TABLE 2F

Upregulated gene expression tables of WT Mtb treated with HC102A compared to DMSO

| Gene | Counts per million (CPM) | | | | WT DMSO/WT HC102A | | | | | | |
|------|---|---|---|---|---|---|---|---|---|---|---|
| | WT_DMSO1 | WT_DMSO2 | WT_HC102A1 | WT_HC102A2 | Fold change | log2 Fold change | logCPM | Adjusted p-value | Rv number | Gene name | Annotated function |
| MT3514 | 59.9464315 | 46.3451074 | 494.4067156 | 167.9816232 | 6.242013606 | 2.642011502 | 7.59224185 | 0.000317734 | Rv3406 | Rv3406 | putative dioxygenasedioxygenase |
| MT3515 | 60.6643578 | 43.6769193 | 191.0817341 | 103.1342671 | 2.83052096 | 1.501067607 | 6.64659687 | 0.059101187 | Rv3407 | Rv3407 | conserved hypothetical protein |

TABLE 2G

Downregulated gene expression tables of WT Mtb treated with HC103A compared to DMSO

| Gene | Counts per million (CPM) | | | | WT DMSO/ WT HC103A fold change | log2 Fold change | logCPM | Adjusted p-value | Rv number | Gene name | Annotated function |
|---|---|---|---|---|---|---|---|---|---|---|---|
| | WT_DMSO1 | WT_DMSO2 | WT_HC103A1 | WT_HC103A2 | | | | | | | |
| MT0086 | 1,344.34 | 2,642.07 | 612.5276035 | 320.9822393 | 0.234129998 | −2.094618305 | 10.2641608 | 0.002403546 | Rv0079 | Rv0079 | hypothetical protein |
| MT0087 | 366.745783 | 887.742741 | 224.6690753 | 124.678515 | 0.278271737 | −1.845433709 | 8.64718864 | 0.011177019 | Rv0080 | Rv0080 | hypothetical protein |
| MT0595 | 293.474991 | 181.277689 | 28.45338011 | 30.13064112 | 0.123647827 | −3.015691208 | 7.04534272 | 4.00E−12 | Rv0569 | Rv0569 | conserved hypothetical protein |
| MT0596 | 2,990.00 | 1,744.85 | 73.80579518 | 59.09242116 | 0.028074924 | −5.154574088 | 10.2471594 | 7.73E−20 | Rv0570 | nrdZ | ribonucleotide reductase, class II |
| MT0597 | 255.076394 | 426.187547 | 71.15907097 | 45.13102495 | 0.170484289 | −2.552289305 | 7.63637259 | 1.57E−07 | Rv0571c | Rv0571c | conserved hypothetical protein |
| MT0598 | 208.057704 | 350.716836 | 38.26407004 | 19.74076487 | 0.103640123 | −3.27034546 | 7.26356337 | 9.61E−11 | | | |
| MT0599 | 583.815402 | 791.258616 | 49.6827945 | 34.61127525 | 0.051279748 | −4.028445826 | 8.50796164 | 9.17E−17 | Rv0572c | Rv0572c | hypothetical protein |
| MT0600 | 999.538986 | 1,342.93 | 44.59182885 | 9.22101517 | 0.023006121 | −5.441838415 | 9.22447285 | 2.48E−12 | | | |
| MT0601 | 96.780137 | 90.5648538 | 11.49434515 | 9.545698803 | 0.112430302 | −3.152897175 | 5.6772449 | 1.09E−16 | Rv0573c | Rv0573c | conserved hypothetical protein |
| MT0602 | 30.64595 | 353.824453 | 26.39162143 | 16.68873872 | 0.057867557 | −4.111101441 | 7.61294181 | 1.23E−19 | Rv0574c | Rv0574c | conserved hypothetical protein |
| MT0846 | 8,264.32 | 7,719.32 | 2,581.69 | 3,416.39 | 0.375267691 | −1.414008011 | 12.4428990 | 0.049685627 | Rv0824c | desA1 | acyl-[ACP] desaturase |
| MT1095 | 479.198816 | 497.514769 | 198.5043159 | 168.5757421 | 0.37580797 | −1.411932431 | 8.39033385 | 0.008693841 | Rv1065 | Rv1065 | conserved hypothetical protein |
| MT1126 | 7,639.36 | 5,982.31 | 2,249.03 | 2,771.69 | 0.358594808 | −1.439892344 | 12.1861135 | 0.042853699 | Rv1094 | desA2 | acyl-[ACP] desaturase |
| MT1322 | 615.94484 | 650.8239 | 223.6860063 | 205.264926 | 0.338601401 | −1.562340153 | 8.72613001 | 0.003978725 | Rv1284 | Rv1284 | conserved hypothetical protein |
| MT1692 | 626.915868 | 234.995078 | 176.2718325 | 60.13140879 | 0.274508805 | −1.865075672 | 8.09465786 | 0.032145592 | Rv1654 | argB | acetylglutamate kinase |
| MT1693 | 522.691105 | 198.591558 | 135.0585555 | 51.68963433 | 0.259191794 | −1.947908054 | 7.81868454 | 0.014293698 | Rv1655 | argD | acetylornithine aminotransferase |
| MT1694 | 566.575215 | 168.699237 | 115.1703135 | 42.01406208 | 0.214013541 | −2.224226011 | 7.79205039 | 0.008693841 | Rv1656 | argF | ornithine carbamoyltransferase |
| MT1774 | 1,465.42 | 1,791.91 | 40.50831149 | 8.961268264 | 0.015211975 | −6.038648635 | 9.68951437 | 5.69E−15 | Rv1733c | Rv1733c | possible membrane protein |
| MT1775 | 581.464467 | 664.734188 | 101.9366925 | 24.15646228 | 0.101154341 | −3.305369861 | 8.41880625 | 2.26E−06 | | | |
| MT1776 | 20.7665886 | 16.721942 | 4.990965658 | 2.922152695 | 0.212249883 | −2.234126628 | 3.41909217 | 3.64E−05 | Rv1735c | Rv1735c | hypothetical protein |
| MT1777 | 110.102099 | 196.371832 | 5.142207042 | 2.013038523 | 0.023219994 | −5.42848861 | 6.28084269 | 1.09E−22 | | | |
| MT1778 | 5,822.09 | 3,629.85 | 122.2786585 | 26.1695008 | 0.01570476 | −5.992654328 | 11.2279303 | 4.16E−13 | Rv1736c | narX | fused nitrate reductase |
| MT1779 | 2,083.71 | 1,503.79 | 36.90289759 | 14.54582675 | 0.01433855 | −6.123957096 | 9.82700111 | 7.71E−21 | Rv1737c | narK2 | nitrite extrusion protein |
| MT1780 | 3,873.95 | 5,103.89 | 133.470521 | 33.11773054 | 0.018553396 | −5.752172919 | 11.1580888 | 5.71E−14 | Rv1738 | Rv1738 | conserved hypothetical protein |
| MT1823 | 677.460959 | 367.734741 | 222.7029373 | 163.7054876 | 0.359999624 | −1.434404289 | 8.48011424 | 0.030780306 | Rv1773c | Rv1773c | transcriptional regulator (IclR family) |
| MT1860 | 249.199057 | 166.923456 | 78.19179531 | 78.70331258 | 0.37778447 | −1.404364695 | 7.15571214 | 0.006966211 | Rv1812c | Rv1812c | probable dehydrogenase |
| MT1851 | 3,080.90 | 1,620.55 | 58.53041544 | 24.74089282 | 0.017712284 | −5.819105922 | 10.222168 | 6.26E−18 | Rv1813c | Rv1813c | conserved hypothetical protein |
| MT1882 | 82.2827076 | 77.6904383 | 28.35775942 | 29.22152695 | 0.350385832 | −1.4723858 | 5.75296114 | 0.000318876 | Rv1834 | Rv1834 | conserved hypothetical protein |
| MT1986 | 314.633401 | 78.7263108 | 72.29338135 | 31.5592491 | 0.254644172 | −1.917874211 | 6.94117308 | 0.036540371 | Rv1936 | Rv1936 | similar alkanal monooxygenase alpha chain |
| MT1987 | 396.132464 | 99.443761 | 83.71210581 | 36.75418723 | 0.243540613 | −2.037765716 | 7.2530058 | 0.021838157 | Rv1937 | Rv1937 | similar to ring-hydroxylating dioxygenases |
| MT1988 | 156.337145 | 36.5515014 | 32.13879401 | 15.97443473 | 0.250792276 | −1.995435178 | 5.87799594 | 0.019514616 | Rv1938 | ephB | probable epoxide hydrolase |
| MT1989 | 68.1771006 | 20.1255231 | 16.33406943 | 8.831394811 | 0.288272345 | −1.794495652 | 4.76511612 | 0.032145592 | Rv1939 | Rv1939 | similar nitrilotriacetate monooxygenase component |
| MT2016 | 378.108533 | 172.102819 | 93.31593367 | 56.94950919 | 0.273586323 | −1.869913983 | 7.44310485 | 0.002131279 | Rv1964 | Rv1964 | part of mce3 operon |
| MT2017 | 311.498822 | 93.3765077 | 44.46496677 | 29.87089421 | 0.184132813 | −2.441181356 | 6.88594958 | 0.000176184 | | | |
| MT2018 | 346.762839 | 110.98634 | 54.82500155 | 33.76709781 | 0.194002689 | −2.365851444 | 7.07787394 | 0.000318876 | Rv1966 | mce3 | cell invasion protein |
| MT2019 | 358.517512 | 99.8877063 | 58.15231198 | 26.29357425 | 0.184609615 | −2.437450404 | 7.06759573 | 0.001388491 | Rv1967 | Rv1967 | part of mce3 operon |
| MT2020 | 409.454426 | 115.425794 | 72.36900204 | 31.88393274 | 0.19897433 | −2.329345774 | 7.28307276 | 0.00283279 | Rv1968 | Rv1968 | part of mce3 operon |
| MT2021 | 104.224763 | 40.9909551 | 29.34082841 | 13.89645948 | 0.299724448 | −1.738291327 | 5.52495651 | 0.014293698 | Rv1969 | Rv1969 | part of mce3 operon |
| MT2022 | 240.97087 | 76.0626386 | 41.74262187 | 24.09152555 | 0.208386864 | −2.262663756 | 6.55893009 | 0.000614941 | Rv1970 | lprM | part of mce3 operon |
| MT2023 | 325.604429 | 92.488617 | 53.3882084 | 33.31254072 | 0.207923317 | −2.265877997 | 6.96231439 | 0.001400244 | Rv1971 | Rv1971 | part of mce3 operon |
| MT2024 | 36.4394848 | 22.4932317 | 12.77989691 | 9.285951897 | 0.379139962 | −1.399197566 | 4.29593002 | 0.022895927 | Rv1972 | Rv1972 | conserved hypothetical protein |
| MT2048 | 2,139.35 | 817.155429 | 531.3866012 | 326.761608 | 0.290344505 | −1.784162363 | 9.89554944 | 0.02467178 | Rv1992c | ctpG | probable cation transport ATPase |
| MT2052 | 41,595.08 | 9,345.20 | 107.0788995 | 83.44369362 | 0.003740546 | −8.062535237 | 13.6416439 | 2.73E−20 | Rv1996 | Rv1996 | conserved hypothetical protein |
| MT2053 | 3,252.13 | 1,719.10 | 57.84982922 | 33.11773054 | 0.018301247 | −5.771914204 | 10.3036166 | 4.69E−20 | Rv1997 | ctpF | probable cation transport ATPase |

TABLE 2G-continued

Downregulated gene expression tables of WT Mtb treated with HC103A compared to DMSO

| Gene | Counts per million (CPM) | | | | WT DMSO/ WT HC103A fold change | log2 Fold change | logCPM | Adjusted p-value | Rv number | Gene name | Annotated function |
|---|---|---|---|---|---|---|---|---|---|---|---|
| | WT_DMSO1 | WT_DMSO2 | WT_HC103A1 | WT_HC103A2 | | | | | | | |
| MT2059 | 553.253253 | 918.226989 | 93.54279574 | 62.92368803 | 0.106281917 | −3.234031939 | 8.66688637 | 2.99E-10 | Rv2003c | Rv2003c | conserved hypothetical protein |
| MT2060 | 2,790.95 | 2,836.22 | 219.6781095 | 144.3543431 | 0.054691641 | −3.950276881 | 10.5476363 | 6.06E-14 | Rv2004c | Rv2004c | hypothetical protein |
| MT2061 | 2,506.10 | 2,279.22 | 138.385865 | 91.75559462 | 0.04809474 | −4.377977065 | 10.2908234 | 1.17E-16 | Rv2005c | Rv2005c | conserved hypothetical protein |
| MT2062 | 619.079419 | 835.653152 | 107.457003 | 97.40508983 | 0.140787855 | −2.828405205 | 869441052 | 1.78E-09 | Rv2006 | otsB | trehalose-6-phosphate phosphatase |
| MT2063 | 7,887.78 | 10,060.54 | 527.756808 | 132.3410487 | 0.086776485 | −4.765072593 | 12.1833835 | 1.97E-10 | Rv2007c | fdxA | ferredoxin |
| MT2086 | 341.277325 | 199.183486 | 73.20082965 | 62.79381457 | 0.252079115 | −1.988051492 | 7.39337895 | 2.99E-05 | Rv2027c | Rv2027c | sensor histidine kinase |
| MT2087 | 813.815161 | 735.765446 | 35.9198285 | 8.701521358 | 0.028784019 | −5.118588124 | 8.63420694 | 2.36E-13 | Rv2028c | Rv2028c | conserved hypothetical protein |
| MT2088 | 5,025.12 | 2,690.46 | 84.09020927 | 21.29924631 | 0.01365854 | −6.194052854 | 10.9318764 | 1.20E-14 | | | |
| MT2089 | 14,932.74 | 15,012.75 | 451.0774265 | 80.39166747 | 0.01747447 | −5.816244714 | 12.8952105 | 1.30E-11 | Rv2030c | Rv2030c | conserved hypothetical protein |
| MT2090 | 47,606.42 | 45,289.09 | 1,309.90 | 213.7067671 | 0.016401187 | −5.930055975 | 14.5267165 | 2.25E-11 | | | |
| MT2091 | 4,107.08 | 6,106.32 | 93.24031297 | 24.61101936 | 0.011537183 | −6.437565232 | 11.3342536 | 1.17E-16 | Rv2032 | Rv2032 | conserved hypothetical protein |
| MT2445.1 | 76.0135489 | 112.170195 | 33.55120785 | 43.89722715 | 0.410508589 | −1.284515686 | 6.05094956 | 0.010996717 | | | |
| MT2556 | 829.096235 | 436.250309 | 246.1453518 | 207.9923351 | 0.359152376 | −1.477332034 | 8.74488432 | 0.029194771 | Rv2483c | Rv2483c | possible transferase |
| MT2557 | 1,264.80 | 629.810486 | 325.1689747 | 280.0721016 | 0.319604679 | −1.645639556 | 9.28539783 | 0.014293698 | Rv2484c | Rv2484c | conserved hypothetical protein |
| MT2574 | 539.931291 | 209.394229 | 131.6556244 | 99.22331817 | 0.308582331 | −1.696272638 | 7.93033342 | 0.011019471 | Rv2499c | Rv2499c | putative aldehyde dehydrogenase |
| MT2576 | 1,506.95 | 673.613095 | 381.7332521 | 270.2666559 | 0.291274429 | −1.741167888 | 9.46570666 | 0.014355782 | | | |
| MT2577 | 485.859797 | 244.465912 | 138.3102453 | 104.8078767 | 0.333354395 | −1.584871345 | 7.92145921 | 0.007362242 | Rv2502c | accD1 | acetyl/propionyl-CoA carboxylase, [beta] subunit |
| MT2578 | 623.781288 | 261.335836 | 136.9490728 | 114.223702 | 0.284123026 | −1.815366642 | 8.14436233 | 0.003449274 | Rv2503c | scoB | 3-oxo acid:CoA transferase, [beta] subunit |
| MT2579 | 627.699512 | 301.142937 | 149.7289697 | 111.0418024 | 0.281045175 | −1.83112605 | 8.21112326 | 0.002131279 | Rv2504c | scoA | 3-oxo acid:CoA transferase, [alpha] subunit |
| MT2698 | 44.830.75 | 23,321.63 | 323.5809402 | 153.3156114 | 0.006997504 | −7.158943883 | 14.0663893 | 1.55E-23 | Rv2623 | Rv2623 | conserved hypothetical protein |
| MT2699 | 2,560.56 | 1,941.23 | 46.27986337 | 12.98734531 | 0.013162362 | −6.24743783 | 10.153358 | 1.61E-17 | Rv2624c | Rv2624c | conserved hypothetical protein |
| MT2700 | 6,090.49 | 3,891.03 | 65.10941563 | 13.96139621 | 0.00792069 | −6.980157945 | 11.2955224 | 2.53E-16 | Rv2625c | Rv2625c | conserved hypothetical protein |
| MT2701 | 13,690.67 | 11,153.83 | 174.8350394 | 34.87102216 | 0.008440262 | −6.888490456 | 12.6124486 | 1.24E-15 | Rv2626c | Rv2626c | conserved hypothetical protein |
| MT2702 | 8,227.49 | 5,979.20 | 50.96834625 | 24.87076627 | 0.005337923 | −7.549505876 | 11.8013664 | 8.53E-29 | Rv2627c | Rv2627c | conserved hypothetical protein |
| MT2703 | 735.8425 | 950.487019 | 26.46724213 | 22.33823393 | 0.028942941 | −5.110644648 | 8.75778035 | 3.83E-24 | Rv2678 | Rv2678 | hypothetical protein |
| MT2704 | 8,138.54 | 5,125.20 | 413.1914599 | 339.4242697 | 0.056745847 | −4.13934138 | 11.7742307 | 6.87E-14 | Rv2629 | Rv2629 | hypothetical protein |
| MT2705 | 802.844133 | 594.294857 | 59.8159672 | 43.0530497 | 0.073654982 | 3.763073086 | 8.54591318 | 3.82E-15 | Rv2630 | Rv2630 | conserved hypothetical protein |
| MT2707 | 1,182.91 | 515.124601 | 74.71324349 | 51.81950779 | 0.074561034 | −3.745434328 | 8.82811081 | 7.33E-11 | Rv2631 | Rv2631 | hypothetical protein |
| MT3171 | 704.496706 | 437.138199 | 246.825938 | 214.6158813 | 0.404459787 | −1.305931823 | 8.64417435 | 0.048905958 | Rv3086 | adhD | zinc-containing alcohol dehydrogenase |
| MT3210 | 8.62009318 | 6.21523506 | 0.226862075 | 0 | 0.016401029 | −5.930069827 | 1.59138092 | 6.06E-13 | | | |
| MT3212 | 16.662.64 | 10,701.89 | 251.2875588 | 90.32698663 | 0.01248603 | −6.323821751 | 12.7757593 | 1.09E-18 | Rv3127 | Rv3127 | conserved hypothetical protein |
| MT3216 | 34,479.20 | 28,662.15 | 290.8371805 | 74.09280499 | 0.00577935 | −7.434874628 | 13.9544872 | 6.82E-20 | Rv3130c | Rv3130c | conserved hypothetical protein |
| MT3217 | 19,568.79 | 10,737.71 | 118.8001058 | 25.13051318 | 0.004748874 | −7.71819819 | 12.8938498 | 1.61E-17 | Rv3131 | Rv3131 | conserved hypothetical protein |
| MT3218 | 5,473.37 | 3,344.83 | 237.9026964 | 168.7056156 | 0.046114017 | −4.438650848 | 11.1103676 | 4.05E-15 | Rv3132c | Rv3132c | sensor histidine kinase |
| MT3219 | 3,967.20 | 2,140.70 | 112.5235894 | 67.0147018 | 0.029397765 | −5.088149713 | 10.6167498 | 5.91E-17 | Rv3133c | Rv3133c | two-component response regulator |
| MT3220 | 6,505.04 | 4,058.25 | 155.1736595 | 61.75482695 | 0.020535938 | −5.605705377 | 11.3952646 | 8.05E-17 | Rv3134c | Rv3134c | conserved hypothetical protein |
| MT3427 | 246.064478 | 249.645275 | 112.372348 | 107.4702824 | 0.443484319 | −1.173045002 | 7.48030878 | 0.030125275 | | | |
| MT3443 | 2,036.30 | 1,022.26 | 593.2443271 | 359.1000978 | 0.31144493 | −1.682951008 | 9.96829767 | 0.022475051 | Rv3340 | metC | cystathionine [beta]-lyase |
| MT3444 | 1,152.35 | 680.568239 | 307.3981121 | 175.4590351 | 0.253523562 | −1.923996132 | 9.17484404 | 0.00228429 | Rv3341 | metA | homoserine o-acetyltransferase |
| MT3608 | 165.34906 | 89.2330177 | 48.09475998 | 42.0789988 | 0.355796739 | −1.490874807 | 6.41567229 | 0.004050376 | Rv3504 | fadE26 | acyl-CoA dehydrogenase |
| MT3634 | 237.836207 | 95.3002709 | 55.2787257 | 43.57254352 | 0.297808555 | −1.747542899 | 5.7400196 | 0.004050376 | Rv3531c | Rv3531c | hypothetical protein |
| MT3655 | 241.754431 | 127.116355 | 77.96493323 | 70.71609521 | 0.404241247 | −1.306711559 | 7.00706704 | 0.033246082 | Rv3551 | Rv3551 | possible glutaconate CoA-transferase |
| MT3656 | 488.602554 | 202.143121 | 108.5156927 | 106.3663581 | 0.311623713 | −1.582123076 | 7.81591006 | 0.007764831 | Rv3552 | Rv3552 | hypothetical protein |

TABLE 2G-continued

Downregulated gene expression tables of WT Mtb treated with HC103A compared to DMSO

| Gene | Counts per million (CPM) | | | | WT DMSO/ WT HC103A fold change | log2 Fold change | logCPM | Adjusted p-value | Rv number | Gene name | Annotated function |
|---|---|---|---|---|---|---|---|---|---|---|---|
| | WT_DMSO1 | WT_DMSO2 | WT_HC103A1 | WT_HC103A2 | | | | | | | |
| MT3716 | 3,433.93 | 2,224.76 | 1,189.74 | 540.013818 | 0.305702713 | −1.709798739 | 10.8503981 | 0.026274113 | Rv3614c | Rv3614c | conserved hypothetical protein |
| MT3717 | 1,484.22 | 1,077.60 | 538.7218083 | 261.0456407 | 0.312225945 | −1.679337655 | 9.71363719 | 0.016305758 | Rv3615c | Rv3615c | conserved hypothetical protein |
| MT3718 | 4,787.29 | 3,551.41 | 1,818.45 | 821.5145276 | 0.316601944 | −1.659257979 | 11.422029 | 0.032145592 | Rv3616c | Rv3616c | conserved hypothetical protein |

TABLE 2H

Upregulated gene expression tables of WT Mtb treated with HC103A compared to DMSO

| Gene | Counts per million (CPM) | | | | WT DMSO/ WT HC103A Fold change | log2 Fold change | logCPM | Adjusted p-value | Rv number | Gene name | Annotated function |
|---|---|---|---|---|---|---|---|---|---|---|---|
| | WT_DMSO1 | WT_DMSO2 | WT_HC103A1 | WT_HC103A2 | | | | | | | |
| MT0169 | 5.09369142 | 9.02688902 | 19.65137986 | 19.54595469 | 2.65424121 | 1.408299485 | 3.82188565 | 0.02422713 | Rv0160c | PE | PE-family protein |
| MT0206 | 29.7785037 | 29.1524121 | 145.191728 | 138.3152276 | 4.812769415 | 2.266857304 | 6.43805492 | 2.94E-09 | Rv0196 | Rv0196 | transcriptional regulator (TetR/AcrR family) |
| MT0207 | 106.183875 | 77.8384201 | 324.1859057 | 345.528322 | 3.650489315 | 1.868089857 | 7.74407444 | 4.88 E-05 | Rv0197 | Rv0197 | conserved hypothetical protein |
| MT0337 | 24.6848123 | 23.0851588 | 71.00782959 | 46.2349493 | 2.459102365 | 1.298131791 | 5.39177723 | 0.014293698 | Rv0322 | udgA | UDP-glucose dehydrogenase/GDP-mannose |
| MT0468 | 37.2231296 | 53.2734434 | 128.9332795 | 95.91154512 | 2.464713661 | 1.301420051 | 6.31646908 | 0.010807249 | Rv0452 | Rv0452 | putative transcriptional regulator |
| MT0491 | 64.2258764 | 64.0761138 | 167.575453 | 130.5877571 | 2.322964768 | 1.215957273 | 6.74652129 | 0.017604747 | Rv0474 | Rv0474 | transcriptional regulator (PbsX/Xre family) |
| MT0585 | 516.813768 | 721.559194 | 2,729.98 | 4,689.54 | 5.989313531 | 2.582390657 | 11.0806573 | 8.14E-06 | Rv0559c | Rv0559c | possible exported |
| MT0586 | 28.211214 | 30.362664 | 6,038.01 | 10,500.79 | 281.967054 | 8.139382793 | 12.0192376 | 4.69E-35 | Rv0560c | Rv0560c | methyl transferase |
| MT0808 | 27.819316 | 41.4349004 | 168.9366255 | 139.873709 | 4.409357079 | 2.140558314 | 6.57959735 | 2.49E-07 | Rv0784 | Rv0784 | conserved hypothetical protein |
| MT0910 | 12.1464949 | 13.0223973 | 40.68393218 | 23.63696846 | 2.542787418 | 1.346410855 | 4.53042946 | 0.035133938 | Rv0887c | Rv0887c | hypothetical protein |
| MT1294 | 5.87733626 | 5.7712897 | 27.37469043 | 11.94835769 | 3.371255322 | 1.753285894 | 3.75644833 | 0.015411127 | Rv1255c | Rv1255c | transcriptional regulator (TetR/AcrR family) |
| MT1608 | 47.4105125 | 34.6277382 | 306.7931466 | 411.3741627 | 8.810245489 | 3.139182219 | 7.65359653 | 7.95E-13 | Rv1557 | mmpL6 | conserved large membrane protein |
| MT1924 | 28.211214 | 49.5738987 | 139.9739005 | 72.46938683 | 2.701976395 | 1.434015071 | 6.19955069 | 0.019618016 | Rv1875 | Rv1875 | conserved hypothetical protein |
| MT2526 | 117.546725 | 187.048979 | 565.3402918 | 307.6702104 | 2.859869289 | 1.51594921 | 8.20640952 | 0.019618016 | Rv2450c | Rv2450c | conserved hypothetical protein |
| MT2792 | 11.3628501 | 23.5291042 | 54.3712774 | 41.55950499 | 2.673772219 | 1.418876566 | 5.07183172 | 0.018868454 | Rv2719c | Rv2719c | conserved hypothetical protein |
| MT2805 | 24.2929899 | 32.8519568 | 90.29110599 | 59.15735789 | 2.588825705 | 1.372297838 | 5.71429378 | 0.00721086 | Rv2736c | recX | regulatory protein for RecA |
| MT3110 | 5.09369142 | 3.84752647 | 19.13203502 | 14.80557365 | 3.905613947 | 1.965549352 | 3.52262207 | 0.001035498 | Rv3026c | Rv3026c | some similarity to acyltransferase Q59601 |
| MT3140 | 1.95911209 | 2.51569038 | 40.68393218 | 10.90937006 | 11.16441708 | 3.480836022 | 3.91758447 | 3.76E-06 | Rv3054c | Rv3054c | conserved hypothetical protein |
| MT3345 | 7.05280351 | 12.2824883 | 32.74375954 | 20.58494232 | 2.667096434 | 1.415259989 | 4.24792745 | 0.031354665 | Rv3247c | tmk | thymidylate kinase |
| MT3513 | 29.3866813 | 28.245214 | 104.8858995 | 49.09216527 | 2.671952469 | 1.417894344 | 5.74663856 | 0.01630758 | | | |
| MT3514 | 65.4343437 | 50.4617894 | 685.0478469 | 289.7476739 | 8.432726886 | 3.07599923 | 8.09771066 | 1.14E-08 | Rv3406 | Rv3406 | putative dioxygenasedioxygenase |
| MT3515 | 66.2179885 | 47.5021537 | 276.7717319 | 112.9249675 | 3.43630065 | 1.781833916 | 6.9856793 | 0.004813941 | Rv3407 | Rv3407 | conserved hypothetical protein |
| MT3723 | 9.0119156 | 5.91927149 | 40.45707011 | 11.42886387 | 3.541646992 | 1.824420421 | 4.12573872 | 0.049772943 | Rv3621c | PPE | PPE-family protein |
| MT3724 | 3.52640176 | 2.95963574 | 20.2663454 | 6.363799202 | 4.15388209 | 2.054460265 | 3.17403054 | 0.02286752 | Rv3622c | PE | PE-family protein |
| MT3846 | 16.8483639 | 21.4573591 | 53.3882084 | 59.48204152 | 2.911687207 | 1.54185538 | 5.27373589 | 0.000789768 | | | |

TABLE 3A

Downregulated gene expression tables of DosR mutant treated with HC101A compared to DMSO

| Gene | Counts per million (CPM) | | | | DosR DMSO/ DosR HC101A Fold change | log2 Fold change | logCPM | Adjusted p-value | Rv number | Gene name | Annotated function |
|---|---|---|---|---|---|---|---|---|---|---|---|
| | DosR_DMSO1 | DosR_DMSO2 | DosR_HC101A1 | DosR_HC101A2 | | | | | | | |
| MT0169 | 64.58870928 | 84.0637388 | 26.44202932 | 29.07142071 | 0.3768729 | −1.407850038 | 5.674321191 | 1.79E-11 | Rv0160c | PE | PE-family protein |
| MT0258 | 2,156.07 | 1,743.15 | 759.8536329 | 1,123.31 | 0.476497164 | −1.069460467 | 10.4975482 | 3.12E-06 | Rv0244c | fadE5 | acyl-CoA dehydrogenase |
| MT0273 | 50.22621998 | 30.93748458 | 15.80072484 | 7.243384284 | 0.276685089 | −1.853638197 | 4.711335163 | 3.79E-15 | Rv0260c | Rv0260c | two-component response regulator |
| MT0292 | 87.78965353 | 32.83937912 | 31.79492794 | 16.54232357 | 0.421264317 | −1.247202377 | 5.408527970 | 6.32E-08 | Rv0280 | PPE | PPE-family protein |
| MT0329 | 315.2948835 | 381.9004243 | 113.2492768 | 189.11106 | 0.421745609 | −1.245555046 | 7.965296850 | 7.73E-11 | Rv0315 | Rv0315 | probable [beta]-1,3-glucanase |
| MT0456 | 13,997.90 | 10,939.82 | 5,842.91 | 4,666.11 | 0.42194445 | −1.244875019 | 13.11333853 | 9.01E-08 | Rv0440 | groEL2 | 50 kD chaperonin 2 |
| MT0483 | 2,270.12 | 1,748.48 | 884.5181272 | 561.0686313 | 0.353704674 | −1.499382811 | 10.41591660 | 1.78E-19 | Rv0467 | aceA | isocitrate lyase |
| MT0484 | 450.2512918 | 334.2262678 | 179.3543501 | 142.8121307 | 0.41241961 | −1.277815164 | 8.112643960 | 7.22E-14 | | | |
| MT0493 | 1,843.92 | 1,791.20 | 790.810155 | 938.1161484 | 0.473889687 | −1.077376829 | 10.38919730 | 1.91E-10 | Rv0475 | Rv0475 | possible exported protein |
| MT0901 | 34.24901295 | 28.65521112 | 18.57391328 | 12.13756285 | 0.48399995 | −1.046921195 | 4.557439690 | 1.50E-05 | Rv0878c | PPE | PPE-family protein |
| MT0908 | 4,335.77 | 4,965.21 | 437.9058027 | 441.3570235 | 0.094762148 | −3.399545287 | 11.313454 | 6.23E-73 | Rv0885 | Rv0885 | PPE-family protein |
| MT0909 | 832.0895428 | 545.4633551 | 103.5753636 | 55.40210142 | 0.112773205 | −3.148503776 | 8.585720630 | 4.33E-77 | Rv0886 | fprB | ferredoxin, ferredoxin-NADP reductase |
| MT0911 | 34.41898323 | 21.6815978 | 9.415942149 | 8.907404998 | 0.330101989 | −1.599016264 | 4.227655570 | 1.31E-10 | Rv0888 | Rv0888 | possible membrane protein |
| MT0915.1 | 27.62017173 | 17.37063683 | 9.86739143 | 9.494706427 | 0.434673077 | −1.201997355 | 4.021213980 | 5.15E-06 | | | |
| MT1019 | 184.0778214 | 157.3500752 | 62.68695732 | 83.49468641 | 0.42444355 | −1.236355380 | 6.930616600 | 5.19E-09 | Rv0990c | Rv0990c | hypothetical protein |
| MT1020 | 1,742.62 | 1,801.09 | 529.4210213 | 1,032.48 | 0.417341957 | −1.260698129 | 10.3179161 | 3.64E-08 | | | |
| MT1224 | 101.1323211 | 61.49459024 | 50.04637745 | 29.85448928 | 0.490463134 | −1.027783396 | 5.926463690 | 5.03E-07 | Rv1187 | rocA | pyrroline-5-carboxylate dehydrogenase |
| MT1233 | 1,072.43 | 189.5554895 | 282.5427572 | 86.52907713 | 0.344705898 | −1.536562112 | 8.672673560 | 1.73E-13 | Rv1195 | PE | PE-family protein |
| MT1385 | 164.3612681 | 49.82963704 | 26.31304381 | 28.69988642 | 0.300795667 | −1.733144309 | 6.076799600 | 1.15E-05 | | | |
| MT1430 | 211.5280229 | 69.22896139 | 77.39130534 | 47.86506642 | 0.498258307 | −1.005030874 | 6.668938870 | 7.89E-05 | Rv1386 | PE | PE-family protein |
| MT1431 | 686.6799618 | 1,329.93 | 317.6913084 | 543.6453556 | 0.434847868 | −1.201417334 | 9.490740340 | 1.16E-15 | Rv1387 | PPE | PPE-family protein |
| MT1484 | 22.26510767 | 16.99025792 | 6.96521748 | 6.851849999 | 0.351511648 | −1.5083556 | 3.741794230 | 2.05E-09 | Rv1439c | Rv1439c | hypothetical protein |
| MT1585.1 | 1,611.23 | 1,599.87 | 293.5065255 | 393.6877242 | 0.211686853 | −2.23995420 | 9.928643220 | 1.01E-41 | | | |
| MT1586 | 245.6070655 | 107.5204382 | 44.69347883 | 38.95766142 | 0.255009473 | −1.971377256 | 6.772875320 | 1.22E-15 | Rv1535 | Rv1535 | hypothetical protein |
| MT1627 | 65.77850129 | 40.70054323 | 22.44347855 | 21.43650214 | 0.420349715 | −1.250337999 | 5.237879410 | 3.25E-07 | | | |
| MT1628 | 830.5598102 | 715.2391413 | 334.3304391 | 332.3147249 | 0.432331395 | −1.209790490 | 9.111686960 | 4.83E-15 | Rv1592c | Rv1592c | conserved hypothetical protein |
| MT1736 | 339.4306643 | 676.5672855 | 181.2891328 | 300.2089135 | 0.486736165 | −1.038788124 | 8.548215070 | 8.49E-10 | | | |
| MT1775 | 61.69921439 | 14.07401962 | 17.80000023 | 12.82274785 | 0.495705695 | −1.012444261 | 4.747583800 | 0.01098138 | | | |
| MT1854 | 34.75892381 | 34.61448069 | 12.83405814 | 20.45766642 | 0.466148949 | −1.101137082 | 4.685900740 | 2.84E-05 | Rv1804c | Rv1804c | conserved hypothetical protein |
| MT1922 | 35.09886438 | 35.24844554 | 11.35072478 | 17.71692643 | 0.402336506 | −1.313525449 | 4.638914020 | 2.55E-07 | Rv1873 | Rv1873 | hypothetical protein |
| MT1969 | 184.2477917 | 195.3879661 | 90.22536347 | 98.56875641 | 0.496989464 | −1.008712826 | 7.151666920 | 1.59E-08 | Rv1918c | PPE | PPE-family protein |
| MT2040 | 676.141804 | 97.63058657 | 79.60861695 | 31.42062642 | 0.191586675 | −2.383930874 | 7.790161210 | 1.24E-14 | Rv1986 | Rv1986 | membrane protein, LYSE/YGGA family |
| MT2166 | 118.809231 | 106.2525085 | 25.86159453 | 35.23808571 | 0.268141469 | −1.898933742 | 6.161606630 | 7.05E-19 | Rv2107 | PE | PE-family protein |
| MT2167 | 117.7894093 | 105.1113718 | 31.60144968 | 38.76189428 | 0.313858093 | −1.671815585 | 6.197252820 | 1.57E-16 | Rv2108 | PPE | PPE-family protein |
| MT2168 | 25.83548371 | 22.18876967 | 9.544927658 | 9.201055713 | 0.390066405 | −1.358208345 | 4.069878050 | 1.54E-08 | | | |
| MT2278 | 1,659.42 | 1,394.85 | 635.8985589 | 701.140022 | 0.438790291 | −1.188396492 | 10.100566 | 1.97E-12 | Rv2220 | glnA1 | glutamine synthetase class I |
| MT2284 | 394.7559929 | 430.0817528 | 197.4768141 | 213.4840692 | 0.498334104 | −1.004814785 | 8.271591510 | 4.03E-09 | Rv2225 | panB | 3-methyl-2-oxobutanoate hydroxymethyltransferase |
| MT2304 | 2,882.27 | 3,978.89 | 831.7630541 | 1,835.61 | 0.364903403 | −1.454413488 | 11.21802880 | 1.93E-11 | Rv2244 | acpM | acyl carrier protein (meromycolate extension) |
| MT2305 | 3,048.08 | 4,168.70 | 1,175.19 | 2,060.94 | 0.436596286 | −1.195628236 | 11.35162050 | 1.14E-09 | Rv2245 | kasA | [beta]-ketoacyl-ACP synthase (meromycolate |
| MT2306 | 1,735.23 | 2,051.25 | 704.1318931 | 1,234.02 | 0.494085354 | −1.017167804 | 10.4830102 | 1.77E-07 | | | |
| MT2391 | 194.1060684 | 118.1710475 | 72.03840672 | 73.99997999 | 0.48031748 | −1.057939782 | 6.842143710 | 3.49E-06 | Rv2329c | narK1 | probable nitrate extrusion protein |
| MT2417 | 18.78171678 | 35.37523851 | 8.835507359 | 16.05290571 | 0.462050215 | −1.113878445 | 4.303601890 | 1.78E-06 | | | |
| MT2503 | 1,013.70 | 1,679.12 | 372.703628 | 897.8860005 | 0.443527623 | −1.172904135 | 9.952488230 | 5.58E-11 | Rv2428 | ahpC | alkyl hydroperoxide reductase |

TABLE 3A-continued

Downregulated gene expression tables of DosR mutant treated with HC101A compared to DMSO

| Gene | Counts per million (CPM) | | | | DosR DMSO/ DosR HC101A Fold change | log2 Fold change | logCPM | Adjusted p-value | Rv number | Gene name | Annotated function |
|---|---|---|---|---|---|---|---|---|---|---|---|
| | DosR_DMSO1 | DosR_DMSO2 | DosR_HC101A1 | DosR_HC101A2 | | | | | | | |
| MT2504 | 415.8521303 | 612.663629 | 163.8760891 | 315.7724014 | 0.450251864 | −1.151195845 | 8.55953127 | 4.65E-11 | Rv2429 | ahpD | member of AhpC/TSA family |
| MT2506 | 448.9765146 | 464.8230264 | 236.2369595 | 203.0105271 | 0.479671999 | −1.05987987 | 8.40239452 | 1.00E-09 | | | conserved hypothetical protein |
| MT2526 | 2,144.86 | 415.1201824 | 892.3862433 | 239.7168664 | 0.489117101 | −1.031748189 | 9.85074083 | 2.90E-09 | Rv2450c | Rv2450c | conserved hypothetical protein |
| MT2698 | 109.8857909 | 73.41312938 | 41.08188458 | 44.83067571 | 0.475570384 | −1.07226922 | 6.07558838 | 5.65E-06 | Rv2623 | Rv2623 | hypothetical protein |
| MT2778 | 93.05873245 | 111.7046062 | 45.20942087 | 56.67458785 | 0.496425032 | −1.010352231 | 6.26154043 | 1.54E-07 | Rv2705c | Rv2705c | transcriptional regulator (Lro/AsnC family) |
| MT2849 | 72.66229794 | 49.70284407 | 26.8934786 | 12.92063143 | 0.314626742 | −1.668286794 | 5.34642958 | 1.82E-13 | Rv2779c | Rv2779c | L-alanine dehydrogenase |
| MT2850 | 3,452.35 | 1,786.13 | 1,263.03 | 369.1189478 | 0.275243597 | −1.861219091 | 10.7463868 | 1.63E-17 | Rv2780 | ald | 3-isopropylmalate dehydratase small subunit |
| MT3065 | 409.9583336 | 29.54276191 | 140.2072482 | 20.16401571 | 0.468314386 | −1.094450737 | 7.23227791 | 2.39E-05 | Rv2987c | leuD | hypothetical protein |
| MT3118 | 48.27156167 | 75.56860985 | 22.05652202 | 33.57406499 | 0.450654957 | −1.149904836 | 5.48777325 | 4.92E-08 | Rv3033 | Rv3033 | |
| MT3132 | 112.0954047 | 96.2358639 | 35.5335077 | 21.04496785 | 0.265633497 | −1.91249101 | 6.0511335 | 1.78E-19 | | | ribonucleoside-diphosphate small subunit |
| MT3133 | 902.6272122 | 1,067.72 | 232.5608725 | 256.0634228 | 0.248616092 | −2.008008413 | 9.26383339 | 1.84E-42 | Rv3048c | nrdG | Probable monooxygenase |
| MT3134 | 2,343.81 | 2,501.88 | 487.3717454 | 585.0501063 | 0.220501526 | −2.181139458 | 10.5309216 | 2.93E-41 | Rv3049c | Rv3049c | conserved hypothetical protein |
| MT3178 | 110.3957018 | 41.58809402 | 44.69347883 | 16.44444 | 0.400684732 | −1.319460558 | 5.74220275 | 1.57E-10 | Rv3094c | Rv3094c | conserved hypothetical protein |
| MT3441 | 375.3992018 | 255.1074548 | 119.763045 | 82.41796713 | 0.320596258 | −1.641170509 | 7.70423005 | 7.19E-21 | Rv3338 | Rv3338 | conserved hypothetical protein |
| MT3481 | 167.1557778 | 70.75047702 | 86.74275473 | 29.16930428 | 0.466099048 | −1.101291528 | 6.47109453 | 2.40E-08 | Rv3371 | Rv3371 | fatty acyl CoA reductase |
| MT3498 | 157.0525457 | 92.68566075 | 73.1992763 | 47.47353213 | 0.487784668 | −1.035683582 | 6.53587331 | 4.31E-08 | Rv3391 | acrA1 | PE-family protein |
| MT3581 | 114.3050184 | 88.88187167 | 30.05362357 | 39.25131214 | 0.339690806 | −1.557705924 | 6.09187099 | 1.75E-11 | Rv3477 | PE | probable esterase |
| MT3591 | 85.91998037 | 32.3322074 | 22.95942058 | 20.555555 | 0.40596188 | −1.30058383 | 5.34500007 | 4.34E-05 | Rv3487c | lipF | hypothetical protein |
| MT3947 | 355.94871582 | 16.86346495 | 12.44710161 | 10.47354214 | 0.45262101 | −1.143624541 | 4.2572301 | 4.84E-05 | Rv3839 | Rv3839 | probable membrane proteinprot |
| MT3963 | 550.0833158 | 592.2499609 | 225.5311623 | 354.9258299 | 0.494260436 | −1.016656568 | 8.7532464 | 6.07E-08 | Rv3848 | Rv3848 | probable monooxygenase |
| MT3969 | 918.2544786 | 1,935.62 | 246.4913075 | 439.3993521 | 0.246822495 | −2.01845421 | 9.78925838 | 1.31E-40 | Rv3854c | Rv3854c | putative transcriptional regulator |
| MT3970 | 182.7180591 | 232.0311343 | 59.4623196 | 89.17193355 | 0.353628242 | −1.499694597 | 7.1180532 | 5.25E-17 | Rv3855 | Rv3855 | hypothetical protein |
| MT3976 | 703.6769906 | 97.75731954 | 184.2557995 | 55.69575213 | 0.382440282 | −1.386693506 | 8.0260941 | 1.78E-07 | Rv3862c | Rv3862c | conserved hypothetical protein |
| MT3978 | 1,992.82 | 1,049.21 | 526.4543546 | 634.3834263 | 0.399484534 | −1.323788446 | 10.0373647 | 5.50E-07 | Rv3864 | Rv3864 | conserved hypothetical protein |
| MT3988 | 3,617.31 | 2,423.90 | 1,214.01 | 1,648.46 | 0.477698917 | −1.06582549 | 11.120268 | 5.37E-05 | Rv3874 | Rv3874 | early secretory antigen target |
| MT3989 | 4,163.17 | 5,549.60 | 1,889.51 | 2,881.50 | 0.48544579 | −1.042617896 | 11.8221611 | 2.87E-07 | Rv3875 | esat6 | |

TABLE 3B

Upregulated gene expression tables of DosR mutant treated with HC101A compared to DMSO

| Gene | Counts per million (CPM) | | | | DosR DMSO/ DosR HC101A Fold change | log2 Fold change | logCPM | Adjusted p-value | Rv number | Gene name | Annotated function |
|---|---|---|---|---|---|---|---|---|---|---|---|
| | DosR_DMSO1 | DosR_DMSO2 | DosR_HC101A1 | DosR_HC101A2 | | | | | | | |
| MT0468 | 182.038178 | 97.25020766 | 461.5101508 | 261.5449028 | 2.609307907 | 1.383667197 | 7.97137994 | 7.91E-16 | Rv0452 | Rv0452 | putative transcriptional regulator |
| MT0530 | 671.4676211 | 626.6108556 | 1,704.93 | 1,028.46 | 2.042497809 | 1.030334531 | 9.97755494 | 7.38E-08 | Rv0509 | hemA | glutamyl-tRNA reductase |
| MT0531 | 272.6232413 | 206.7993334 | 794.5152275 | 398.3861356 | 2.373685343 | 1.247128703 | 8.70902983 | 3.03E-11 | Rv0510 | hemC | porphobilinogen deaminase |
| MT0532 | 568.3806417 | 442.5074638 | 1,631.80 | 832.7934256 | 2.326476251 | 1.21814646 | 9.76361083 | 2.56E-11 | Rv0511 | cysG | uroporphyrin-III c-methyltransferase |
| MT0533 | 234.049086 | 160.3931065 | 601.201457 | 365.6930228 | 2.421877135 | 1.276125677 | 8.41233028 | 1.47E-14 | Rv0512 | hemB | [delta]-aminolevulinic acid dehydratase |
| MT0583 | 136.8260815 | 132.8790321 | 376.895657 | 224.6427964 | 2.162414792 | 1.112643286 | 7.76911036 | 3.39E-07 | Rv0557 | Rv0557 | conserved hypothetical protein |
| MT0586 | 25.92046886 | 18.00460168 | 106.1550738 | 65.09257499 | 3.862908971 | 1.949687681 | 5.75984128 | 1.26E-21 | Rv0560c | Rv0560c | methyl transferase |
| MT0658 | 25.92046886 | 24.85142204 | 75.58550821 | 34.25924999 | 2.029015455 | 1.020779854 | 5.33989547 | 0.000692083 | Rv0630c | recB | exodeoxyribonuclease V |
| MT0705 | 912.8254294 | 389.1276236 | 3,503.44 | 3,550.24 | 3.682762206 | 1.880788246 | 11.1312868 | 7.94E-27 | Rv0676c | mmpL5 | conserved large membrane protein |
| MT0706 | 374.4445435 | 389.1276236 | 1,184.86 | 1,231.08 | 3.163944842 | 1.661724449 | 9.65513029 | 2.79E-30 | Rv0677c | mmpS5 | conserved small membrane protein |
| MT0706.1 | 82.26561919 | 76.05781724 | 272.4818875 | 202.4232257 | 2.973758576 | 1.572287527 | 7.30970488 | 9.70E-18 | Rv0678 | Rv0678 | hypothetical protein |
| MT0772.5 | 69.00793676 | 40.70054323 | 199.9920315 | 58.24072499 | 2.060267909 | 1.042831952 | 6.53007235 | 0.000102935 | Rv0747 | PE_PGRS | PE_PGRS-family protein |
| MT0808 | 121.6987259 | 62.38214103 | 811.834793 | 173.351805 | 4.335232504 | 2.116109369 | 8.19408205 | 2.26E-14 | Rv0784 | Rv0784 | conserved hypothetical protein |
| MT0956 | 154.4180063 | 202.8687513 | 370.5108743 | 355.6110149 | 2.051794886 | 1.036886515 | 8.0826697 | 7.77E-08 | Rv0929 | pstC2 | membrane-bound component of phosphate transport |
| MT1073 | 70.28271391 | 115.5083953 | 209.4079737 | 170.4152978 | 2.097730541 | 1.068829372 | 7.14621936 | 3.97E-05 | Rv1043c | Rv1043c | hypothetical protein |
| MT1123 | 30.0847409 | 12.04533221 | 76.29492851 | 18.20634428 | 2.020723749 | 1.014872106 | 5.11304295 | 0.000164604 | Rv1091 | PE_PGRS | PE_PGRS-family protein |
| MT1296 | 210.3382309 | 142.6420908 | 517.1029052 | 305.0052085 | 2.294968556 | 1.198474387 | 8.20030973 | 6.21E-12 | Rv1257c | Rv1257c | similar to many dehydrogenases |
| MT1297 | 52.09589314 | 52.87266831 | 201.7333359 | 152.3063871 | 3.348797584 | 1.743643176 | 6.84667558 | 4.42E-20 | Rv1258c | Rv1258c | probable multidrug resistance pump |
| MT1303 | 138.1008587 | 104.6041999 | 292.5036269 | 237.2697771 | 2.190933348 | 1.131545596 | 7.59584057 | 1.97E-10 | Rv1265 | Rv1265 | hypothetical protein |
| MT1424 | 103.5119051 | 62.76251994 | 370.4463815 | 97.00261927 | 2.36979857 | 1.244764437 | 7.3118985 | 1.28E-05 | Rv1380 | pyrB | aspartate carbamoyltransferase |
| MT1425 | 255.2953719 | 158.491212 | 782.684058 | 262.425855 | 2.259917715 | 1.176270244 | 8.51235533 | 2.69E-07 | Rv1381 | pyrC | dihydroorotase |
| MT1426 | 45.97696279 | 30.81069161 | 173.5500022 | 47.37564856 | 2.442760358 | 1.285512338 | 6.22648987 | 2.70E-05 | | | |
| MT1427 | 248.0716347 | 170.4097511 | 572.8891378 | 296.3914542 | 2.007479995 | 1.005385611 | 8.33225518 | 7.72E-08 | Rv1383 | car A | carbamoyl-phosphate synthase subunit |
| MT1428 | 538.8058116 | 442.7610497 | 1,369.37 | 816.1532184 | 2.165978513 | 1.115018931 | 9.62956458 | 4.94E-11 | Rv1384 | carB | carbamoyl-phosphate synthase subunit |
| MT1429 | 35.69376039 | 18.25818762 | 136.9826104 | 37.58729142 | 2.871304664 | 1.521706418 | 5.84806679 | 3.05E-09 | Rv1385 | pyrF | orotidine 5'-phosphate decarboxylase |
| MT1620 | 36.79856726 | 9.763058657 | 87.71014605 | 20.65343357 | 2.269157962 | 1.182157042 | 5.29300694 | 2.55E-07 | Rv1569 | bioF | 8-amino-7-oxononanoate synthase |
| MT1836 | 50.84936295 | 40.32016432 | 284.6710181 | 109.7274836 | 3.598432437 | 1.847368571 | 6.95820103 | 6.83E-17 | Rv1787 | PPE | PPE-family protein |
| MT1893 | 140.3104724 | 34.48768772 | 347.744932 | 58.82802642 | 2.083536209 | 1.059034172 | 7.18838382 | 3.55E-07 | Rv1845c | Rv1845c | hypothetical protein |
| MT2126 | 24.6456917 | 18.13139465 | 68.03985594 | 27.11374928 | 2.068388446 | 1.048507151 | 5.12347158 | 0.000180441 | Rv2066 | cobI | CobI-CobJ fusion protein |
| MT2264 | 22.69103339 | 7.607578174 | 65.13768199 | 14.09523428 | 2.402237549 | 1.264378821 | 4.8000351 | 1.25E-06 | Rv2208 | cobS | cobalamin (5' phosphate) synthase |
| MT2615 | 185.012658 | 26.37293767 | 668.7253709 | 48.55025124 | 2.641782364 | 1.401511619 | 7.8627379 | 1.24E-08 | Rv2540c | aroF | chorismate synthase |
| MT2631 | 46.91179937 | 7.987957083 | 100.8021752 | 15.95502214 | 2.089072285 | 1.062862413 | 5.4403404 | 4.03E-06 | | | |
| MT2863 | 54.47547717 | 68.72178951 | 147.5239149 | 103.8544693 | 2.029218701 | 1.020924361 | 6.55383074 | 2.88E-05 | Rv2794c | Rv2794c | conserved hypothetical protein |
| MT3110 | 23.8808254 | 13.18646884 | 98.60942155 | 28.28835214 | 3.057275312 | 1.612246475 | 5.37357044 | 2.51E-09 | Rv3026c | Rv3026c | some similarity to acyltransferase Q59601 |
| MT3293 | 56.60010576 | 70.62368405 | 141.6905815 | 118.6348885 | 2.054631858 | 1.03887992 | 6.60216128 | 1.16E-06 | Rv3199c | Rv3199c | conserved hypothetical protein |
| MT3327 | 811.4381529 | 430.7157176 | 1,566.59 | 1,092.38 | 2.211109757 | 1.14470641 | 9.93018834 | 5.56E-12 | Rv3230c | Rv3230c | similar to various oxygenases |
| MT3492 | 23.54088483 | 4.691339874 | 51.14275428 | 8.907404998 | 2.072623049 | 1.051457755 | 4.49526699 | 6.11E-05 | Rv3384c | Rv3384c | conserved hypothetical protein |
| MT3539 | 17.67690991 | 5.452097692 | 60.35521816 | 7.341267856 | 2.349607525 | 1.232419791 | 4.53755458 | 0.000295271 | Rv3433c | Rv3433c | conserved hypothetical protein |
| MT3696 | 24.73067684 | 4.057375026 | 89.00000114 | 5.481479999 | 2.528782815 | 1.338443136 | 4.9723221 | 8.07E-05 | Rv3590c | PE_PGRS | PE_PGRS-family protein |

TABLE 3C

Downregulated gene expression tables of DosR mutant treated with HC102A compared to DMSO

| Gene | Counts per million (CPM) | | | | DosR DMSO/ DosR HC102A Fold change | log2 Fold change | logCPM | Adjusted p-value | Rv number | Gene name | Annotated function |
| --- | --- | --- | --- | --- | --- | --- | --- | --- | --- | --- | --- |
| | DosR_DMSO1 | DosR_DMSO2 | DosR_HC102A1 | DosR_HC102A2 | | | | | | | |

TABLE 3D

Upregulated gene expression tables of DosR mutant treated with HC102A compared to DMSO

| Gene | Counts per million (CPM) | | | | DosR DMSO/ DosR HC102A Fold change | log2 Fold change | logCPM | Adjusted p-value | Rv number | Gene name | Annotated function |
| --- | --- | --- | --- | --- | --- | --- | --- | --- | --- | --- | --- |
| | DosR_DMSO1 | DosR_DMSO2 | DosR_HC102A1 | DosR_HC102A2 | | | | | | | |

TABLE 3E

Downregulated gene expression tables of DosR mutant treated with HC103A compared to DMSO

| Gene | Counts per million (CPM) | | | | DosR DMSO/ DosR HC103A Fold change | log2 Fold change | logCPM | Adjusted p-value | Rv number | Gene name | Annotated function |
|---|---|---|---|---|---|---|---|---|---|---|---|
| | DosR_DMSO1 | DosR_DMSO2 | DosR_HC103A1 | DosR_HC103A2 | | | | | | | |
| MT0169 | 65.85191614 | 84.53368756 | 32.4408011 | 38.88882855 | 0.475892173 | −1.071293369 | 5.79145216 | 3.88E-05 | Rv0160c | PE | PE-family protein |
| MT0273 | 51.20852953 | 31.11043705 | 19.06256394 | 17.9486901 | 0.460945483 | −1.117331966 | 4.9019279 | 0.002130737 | Rv0260c | Rv0260c | two-component response regulator |
| MT0846 | 4,560.33 | 12,066.90 | 2,264.39 | 5,375.06 | 0.470288699 | −1.088381431 | 12.5666524 | 7.66E-07 | Rv0824c | desA1 | acyl-[ACP] desaturase |
| MT0908 | 4,420.57 | 4,992.97 | 2,165.30 | 1,401.92 | 0.370895088 | −1.430916935 | 11.6640643 | 1.43E-08 | Rv0885 | Rv0885 | unknown transmembrane protein |
| MT0909 | 848.3633039 | 548.5127057 | 412.6517122 | 231.1962225 | 0.453003864 | −1.14240474 | 8.99505899 | 3.98E-10 | Rv0886 | fprB | ferredoxin, ferredoxin-NADP reductase |
| MT1214 | 1,358.72 | 2,946.95 | 704.925834 | 1,378.70 | 0.492649453 | −1.02136664 | 10.6413369 | 1.77E-07 | Rv1177 | fdxC | ferredoxin 4Fe-4S |
| MT1430 | 215.6650254 | 69.61597799 | 63.30105053 | 54.48709495 | 0.476492293 | −1.069475216 | 6.6566741 | 0.010220947 | Rv1386 | PE | PE-family protein |
| MT1690 | 411.2278869 | 71.65600665 | 130.6035722 | 56.83751865 | 0.497858635 | −1.006191942 | 7.39031805 | 0.010220947 | Rv1652 | argC | N-acetyl-[gamma]-glutamyl-phosphate reductase |
| MT1691 | 265.3139043 | 42.45809647 | 81.47439866 | 33.33328161 | 0.484648036 | −1.04499069 | 6.72563835 | 0.01108789 |  |  |  |
| MT1692 | 339.13736811 | 84.0236804 | 128.7695646 | 55.27056951 | 0.496487803 | −1.010169819 | 7.2476763 | 0.000384713 | Rv1654 | argB | acetylglutamate kinase |
| MT1694 | 240.8793775 | 71.14599949 | 79.75154302 | 39.5298532 | 0.425890365 | −1.231446004 | 6.75437876 | 5.96E-06 | Rv1656 | argF | ornithine carbamoyltransferase |
| MT3134 | 2,389.64 | 2,515.87 | 1,202.50 | 892.6624326 | 0.422609861 | −1.242601664 | 10.7732604 | 3.66E-09 | Rv3049c | Rv3049c | Probable monooxygenase |
| MT3573.12 | 587.5550571 | 755.95812 | 280.9921962 | 281.5522697 | 0.422123825 | −1.244261836 | 8.89619806 | 1.03E-10 |  |  |  |

TABLE 3F

Upregulated gene expression tables of DosR mutant treated with HC103A compared to DMSO

| Gene | Counts per million (CPM) | | | | DosR DMSO/ DosR_HC103A Fold change | log2 Fold change | logCPM | Adjusted p-value | Rv number | Gene name | Annotated function |
|---|---|---|---|---|---|---|---|---|---|---|---|
| | DosR_DMSO1 | DosR_DMSO2 | DosR_HC103A1 | DosR_HC103A2 | | | | | | | |
| MT0206 | 48.7824063 | 41.56558393 | 286.383067 | 309.0451045 | 6.590155298 | 2.720312463 | 7.42556003 | 6.04E-41 | Rv0196 | Rv0196 | transcriptional regulator (TetR/AcrR family) |
| MT0207 | 145.3074518 | 107.9940171 | 509.3539316 | 528.2755336 | 4.133856535 | 2.047488321 | 8.33610979 | 1.49E-25 | Rv0197 | Rv0197 | conserved hypothetical protein |
| MT0585 | 689.5388798 | 1,220.83 | 4,246.95 | 5,318.58 | 5.179641056 | 2.372852124 | 11.486527 | 2.23E-30 | Rv0559c | Rv0559c | possible exported |
| MT0586 | 26.42741372 | 18.10525435 | 8,065.19 | 8,969.64 | 384.8522776 | 8.588160975 | 12.0601627 | 8.66E-197 | Rv0560c | Rv0560c | methyl transferase |
| MT0587 | 41.85062566 | 28.30539764 | 66.91348976 | 74.85743371 | 2.043903765 | 1.031132727 | 5.7360115 | 0.001233898 | Rv0561c | Rv0561c | similar to squalene monooxygenase |
| MT0808 | 124.0788736 | 62.73088127 | 242.0890045 | 193.8743431 | 2.445094907 | 1.289890465 | 7.28607323 | 1.32E-07 | Rv0784 | Rv0784 | conserved hypothetical protein |
| MT1297 | 53.11476921 | 53.16824693 | 106.4280173 | 137.0368244 | 2.269378575 | 1.182297298 | 6.45526298 | 4.77E-07 | Rv1258c | Rv1258c | probable multidrug resistance pump |
| MT1608 | 59.44001905 | 67.57594933 | 351.6848531 | 540.0276521 | 6.868759212 | 2.780049511 | 7.99509155 | 2.41E-45 | Rv1557 | mmpL6 | conserved large membrane protein |
| MT2466 | 189.2376117 | 48.45068065 | 356.4088121 | 182.6207993 | 2.642643261 | 1.401981684 | 7.60444332 | 6.01E-07 | | | |
| MT2467 | 38.47138259 | 2.422534033 | 57.68787572 | 12.39314316 | 2.467509905 | 1.303055876 | 4.81690925 | 0.015975271 | | | |
| MT3110 | 24.34789572 | 13.26018628 | 44.12733461 | 30.12815838 | 2.016362166 | 1.011754779 | 4.82321562 | 0.006516259 | Rv3026c | Rv3026c | some similarity to acyltransferase Q59601 |
| MT3249 | 75.72970357 | 66.30093142 | 172.5634433 | 148.78892.29 | 2.261409078 | 1.177221992 | 6.86025793 | 1.61E-07 | Rv3160c | Rv3160c | putative transcriptional regulator |
| MT3250 | 221.9902752 | 251.4335322 | 561.7620884 | 554.9848939 | 2.363820532 | 1.241120506 | 8.63614257 | 1.87E-11 | Rv3161c | Rv3161c | putative dioxygenasesdiooxygenases |
| MT3591 | 87.60037792 | 32.51295675 | 185.7905285 | 63.03409023 | 2.032689675 | 1.02338998 | 6.53370648 | 9.07E-05 | Rv3487c | lipF | probable esterase |
| MT3933 | 406.8088767 | 230.7782421 | 917.61651407 | 560.9677906 | 2.340775278 | 1.226986438 | 9.04829852 | 8.04E-12 | Rv3825c | pks2 | polyketide synthase |

What is claimed is:

1. A method for inhibiting growth of one or more mycobacterial cells in which an at least two-component regulatory system is conserved, said two-component regulatory system comprises one or more sensor histidine kinase and a cognate response regulator, the method comprising contacting the one or more mycobacterial cells with an effective amount of a compound that inhibits the at least two component regulatory system to thereby inhibit the growth of the one or more mycobacterial cells;
   wherein the compound that inhibits the at least two-component regulatory system is an anti-virulence compound or analogs or derivatives thereof selected from the group consisting of HC101C, HC102A, HC103A, HC103B, HC104A, HC105A, and HC106A, or combinations thereof.

2. A method for treating a subject who is infected with mycobacterial cells in which an at least two-component regulatory system is conserved, said two-component regulatory system comprises one or more sensor histidine kinase and a cognate response regulator, the method comprising administering to the subject an effective amount of a compound that inhibits the at least two-component regulatory system to thereby treat the infection;
   wherein the compound that inhibits the at least two-component regulatory system is an anti-virulence compound or analogs or derivatives thereof selected from the group consisting of HC101C, HC102A, HC103A, HC103B, HC104A, HC105A, and HC106A, or combinations thereof.

3. The method according to claim 1, wherein the at least two-component regulatory system is a DosRST two-component regulatory system.

4. The method according to claim 1, wherein the at least two-component regulatory system regulon is a DosRST regulon.

5. The method according to claim 2, further comprising identifying the subject as having an infection with mycobacterial cells in which the two component regulatory system is conserved.

6. The method according to claim 1, wherein the mycobacteria or mycobacterial cells are *Mycobacterium tuberculosis*, or nontuberculosis mycobacterium (NTM).

7. The method according to claim 6, wherein the *Mycobacterium tuberculosis* is multi-drug resistant *Mycobacterium tuberculosis*.

8. A method for treating tuberculosis in a subject, the method comprising administering to the subject a compound that inhibits a DosRST two-component regulatory system and/or DosRST regulon in mycobacterial cells in an amount effective to treat tuberculosis;
   wherein the compound is an anti-virulence compound or analogs or derivatives thereof selected from the group consisting of HC101C, HC102A, HC103A, HC103B, HC104A, HC105A, and HC106A, or combinations thereof.

* * * * *